US009510802B2

(12) United States Patent
Barthe et al.

(10) Patent No.: US 9,510,802 B2
(45) Date of Patent: Dec. 6, 2016

(54) REFLECTIVE ULTRASOUND TECHNOLOGY FOR DERMATOLOGICAL TREATMENTS

(71) Applicant: GUIDED THERAPY SYSTEMS, LLC, Mesa, AZ (US)

(72) Inventors: Peter G. Barthe, Phoenix, AZ (US); Michael H. Slayton, Tempe, AZ (US); Charles D. Emery, Gilbert, AZ (US)

(73) Assignee: Guided Therapy Systems, LLC, Mesa, AZ (US)

( * ) Notice: Subject to any disclaimer, the term of this patent is extended or adjusted under 35 U.S.C. 154(b) by 0 days.

(21) Appl. No.: 14/225,189

(22) Filed: Mar. 25, 2014

(65) Prior Publication Data
US 2014/0276055 A1 Sep. 18, 2014

Related U.S. Application Data

(63) Continuation of application No. PCT/US2012/056730, filed on Sep. 21, 2012.

(51) Int. Cl.
*A61B 8/00* (2006.01)
*A61B 7/02* (2006.01)
(Continued)

(52) U.S. Cl.
CPC .............. *A61B 7/02* (2013.01); *A61B 8/4209* (2013.01); *A61B 8/4272* (2013.01);
(Continued)

(58) Field of Classification Search
CPC ......... A61B 5/682; A61B 8/08; A61B 8/0858; A61B 8/12; A61B 8/4483; A61B 8/483; A61B 8/546
(Continued)

(56) References Cited

U.S. PATENT DOCUMENTS 2,427,348 A 9/1947 Bond et al.
3,913,386 A 10/1975 Saglio
(Continued)

FOREIGN PATENT DOCUMENTS

CN 104027893 9/2014
DE 4029175 3/1992
(Continued)

OTHER PUBLICATIONS

Calderhead et al., "One Mechanism Behind LED Photo-Therapy for Wound Healing and Skin Rejuvenation: Key Role of the Mast Cell" Laser Therapy 17.3: 141-148 (2008).
(Continued)

*Primary Examiner* — Joel Lamprecht
(74) *Attorney, Agent, or Firm* — Knobbe, Martens, Olson & Bear, LLP

(57) ABSTRACT

Embodiments of a dermatological cosmetic treatment and imaging system and method can include use of transducer and a reflective surface to simultaneously produce multiple cosmetic treatment zones in tissue. The system can include a hand wand, a removable transducer module, a control module, a graphical user interface and/or a parabolic reflector. In some embodiments, the cosmetic treatment system may be used in cosmetic procedures, including brow lifts, fat reduction, sweat reduction, and treatment of the décolletage. Skin tightening, lifting and amelioration of wrinkles and stretch marks are provided.

20 Claims, 73 Drawing Sheets

(51) Int. Cl.
  *A61N 7/00*  (2006.01)
  *A61B 18/00*  (2006.01)
(52) U.S. Cl.
  CPC .......... *A61B 8/4281* (2013.01); *A61B 8/4411*
    (2013.01); *A61B 8/4427* (2013.01); *A61B*
    *8/4444* (2013.01); *A61B 8/4494* (2013.01);
    *A61B 8/461* (2013.01); *A61B 8/465* (2013.01);
    *A61B 8/467* (2013.01); *A61B 8/469* (2013.01);
    *A61B 8/54* (2013.01); *A61N 7/00* (2013.01);
    *A61B 8/468* (2013.01); *A61B 8/56* (2013.01);
    *A61B 2018/00023* (2013.01); *A61N 2007/0034*
    (2013.01); *A61N 2007/0052* (2013.01); *A61N*
    *2007/0082* (2013.01); *A61N 2007/0091*
    (2013.01); *A61N 2007/0095* (2013.01)
(58) Field of Classification Search
  USPC ....................... 600/407, 437, 441, 443; 601/2
  See application file for complete search history.

(56) References Cited

U.S. PATENT DOCUMENTS

| | | |
|---|---|---|
| 3,965,455 A | 6/1976 | Hurwitz |
| 3,992,925 A | 11/1976 | Perilhou |
| 4,039,312 A | 8/1977 | Patru |
| 4,059,098 A | 11/1977 | Murdock |
| 4,101,795 A | 7/1978 | Fukumoto |
| 4,166,967 A | 9/1979 | Benes et al. |
| 4,211,948 A | 7/1980 | Smith et al. |
| 4,211,949 A | 7/1980 | Brisken et al. |
| 4,213,344 A | 7/1980 | Rose |
| 4,276,491 A | 6/1981 | Daniel |
| 4,315,514 A | 2/1982 | Drewes et al. |
| 4,325,381 A | 4/1982 | Glenn |
| 4,343,301 A | 8/1982 | Indech |
| 4,372,296 A | 2/1983 | Fahim |
| 4,379,145 A | 4/1983 | Masuho et al. |
| 4,381,007 A | 4/1983 | Doss |
| 4,381,787 A | 5/1983 | Hottinger |
| 4,397,314 A | 8/1983 | Vaguine |
| 4,409,839 A | 10/1983 | Taenzer |
| 4,431,008 A | 2/1984 | Wanner et al. |
| 4,441,486 A | 4/1984 | Pounds |
| 4,452,084 A | 6/1984 | Taenzer |
| 4,484,569 A | 11/1984 | Driller |
| 4,507,582 A | 3/1985 | Glenn |
| 4,513,749 A | 4/1985 | Kino |
| 4,513,750 A | 4/1985 | Heyman et al. |
| 4,527,550 A | 7/1985 | Ruggera et al. |
| 4,528,979 A | 7/1985 | Marchenko |
| 4,534,221 A | 8/1985 | Fife et al. |
| 4,566,459 A | 1/1986 | Umemura et al. |
| 4,567,895 A | 2/1986 | Putzke |
| 4,586,512 A | 5/1986 | Do-Huu |
| 4,601,296 A | 7/1986 | Yerushalmi |
| 4,620,546 A | 11/1986 | Aida et al. |
| 4,637,256 A | 1/1987 | Sugiyama et al. |
| 4,646,756 A | 3/1987 | Watmough |
| 4,663,358 A | 5/1987 | Hyon |
| 4,668,516 A | 5/1987 | Duraffourd et al. |
| 4,672,591 A | 6/1987 | Breimesser et al. |
| 4,680,499 A | 7/1987 | Umemura et al. |
| 4,697,588 A | 10/1987 | Reichenberger |
| 4,754,760 A | 7/1988 | Fukukita et al. |
| 4,757,820 A | 7/1988 | Itoh |
| 4,771,205 A | 9/1988 | Mequio |
| 4,801,459 A | 1/1989 | Liburdy |
| 4,803,625 A | 2/1989 | Fu et al. |
| 4,807,633 A | 2/1989 | Fry |
| 4,817,615 A | 4/1989 | Fukukita et al. |
| 4,858,613 A | 8/1989 | Fry |
| 4,860,732 A | 8/1989 | Hasegawa et al. |
| 4,865,041 A | 9/1989 | Hassler |
| 4,865,042 A | 9/1989 | Umemura |
| 4,867,169 A | 9/1989 | Machida |
| 4,874,562 A | 10/1989 | Hyon |
| 4,875,487 A | 10/1989 | Seppi |
| 4,881,212 A | 11/1989 | Takeuchi |
| 4,891,043 A | 1/1990 | Zeimer et al. |
| 4,893,624 A | 1/1990 | Lele |
| 4,896,673 A | 1/1990 | Rose |
| 4,900,540 A | 2/1990 | Ryan et al. |
| 4,901,729 A | 2/1990 | Saitoh |
| 4,917,096 A | 4/1990 | Englehart |
| 4,973,096 A | 4/1990 | Jaworski |
| 4,932,414 A | 6/1990 | Coleman et al. |
| 4,938,216 A | 7/1990 | Lele |
| 4,938,217 A | 7/1990 | Lele |
| 4,947,046 A | 8/1990 | Kawabata et al. |
| 4,951,653 A | 8/1990 | Fry |
| 4,955,365 A | 9/1990 | Fry |
| 4,958,626 A | 9/1990 | Nambu |
| 4,976,709 A | 12/1990 | Sand |
| 4,979,501 A | 12/1990 | Valchanov |
| 4,992,989 A | 2/1991 | Watanabe et al. |
| 5,012,797 A | 5/1991 | Liang |
| 5,018,508 A | 5/1991 | Fry et al. |
| 5,030,874 A | 7/1991 | Saito et al. |
| 5,036,855 A | 8/1991 | Fry |
| 5,040,537 A | 8/1991 | Katakura |
| 5,054,310 A | 10/1991 | Flynn |
| 5,054,470 A | 10/1991 | Fry |
| 5,070,879 A | 12/1991 | Herres |
| 5,088,495 A | 2/1992 | Miyagawa |
| 5,115,814 A | 5/1992 | Griffith |
| 5,117,832 A | 6/1992 | Sanghvi |
| 5,123,418 A | 6/1992 | Saurel |
| 5,143,063 A | 9/1992 | Fellner |
| 5,143,074 A | 9/1992 | Dory |
| 5,149,319 A | 9/1992 | Unger |
| 5,150,711 A | 9/1992 | Dory |
| 5,150,714 A | 9/1992 | Green |
| 5,152,294 A | 10/1992 | Mochizuki et al. |
| 5,156,144 A | 10/1992 | Iwasaki |
| 5,158,536 A | 10/1992 | Sekins |
| 5,159,931 A | 11/1992 | Pini |
| 5,163,421 A | 11/1992 | Bernstein |
| 5,163,436 A | 11/1992 | Saitoh et al. |
| 5,178,135 A | 1/1993 | Uchiyama et al. |
| 5,190,518 A | 3/1993 | Takasu |
| 5,190,766 A | 3/1993 | Ishihara |
| 5,191,880 A | 3/1993 | McLeod |
| 5,205,287 A | 4/1993 | Erbel et al. |
| 5,209,720 A | 5/1993 | Unger |
| 5,212,671 A | 5/1993 | Fujii et al. |
| 5,215,680 A | 6/1993 | D'Arrigo |
| 5,224,467 A | 7/1993 | Oku |
| 5,230,334 A | 7/1993 | Klopotek |
| 5,230,338 A | 7/1993 | Allen et al. |
| 5,247,924 A | 9/1993 | Suzuki et al. |
| 5,255,681 A | 10/1993 | Ishimura et al. |
| 5,257,970 A | 11/1993 | Dougherty |
| 5,265,614 A | 11/1993 | Hayakawa |
| 5,267,985 A | 12/1993 | Shimada |
| 5,269,297 A | 12/1993 | Weng |
| 5,282,797 A | 2/1994 | Chess |
| 5,295,484 A | 3/1994 | Marcus |
| 5,295,486 A | 3/1994 | Wollschlager et al. |
| 5,304,169 A | 4/1994 | Sand |
| 5,305,756 A | 4/1994 | Entrekin et al. |
| 5,321,520 A | 6/1994 | Inga et al. |
| 5,323,779 A | 6/1994 | Hardy et al. |
| 5,327,895 A | 7/1994 | Hashimoto et al. |
| 5,348,016 A | 9/1994 | Unger et al. |
| 5,360,268 A | 11/1994 | Hayashi |
| 5,370,121 A | 12/1994 | Reichenberger |
| 5,371,483 A | 12/1994 | Bhardwaj |
| 5,375,602 A | 12/1994 | Lancee et al. |
| 5,379,773 A | 1/1995 | Hornsby |
| 5,380,280 A | 1/1995 | Peterson |
| 5,380,519 A | 1/1995 | Schneider et al. |
| 5,383,917 A | 1/1995 | Desai et al. |
| 5,391,140 A | 2/1995 | Schaetzle et al. |

(56) References Cited

U.S. PATENT DOCUMENTS

| | | |
|---|---|---|
| 5,391,197 A | 2/1995 | Burdette et al. |
| 5,392,259 A | 2/1995 | Bolorforosh |
| 5,396,143 A | 3/1995 | Seyed-Bolorforosh et al. |
| 5,398,689 A | 3/1995 | Connor et al. |
| 5,406,503 A | 4/1995 | Williams |
| 5,413,550 A | 5/1995 | Castel |
| 5,417,216 A | 5/1995 | Tanaka |
| 5,419,327 A | 5/1995 | Rohwedder |
| 5,423,220 A | 6/1995 | Finsterwald et al. |
| 5,435,311 A | 7/1995 | Umemura |
| 5,438,998 A | 8/1995 | Hanafy |
| 5,443,068 A | 8/1995 | Cline et al. |
| 5,458,596 A | 10/1995 | Lax |
| 5,460,179 A | 10/1995 | Okunuki et al. |
| 5,460,595 A | 10/1995 | Hall et al. |
| 5,469,854 A | 11/1995 | Unger et al. |
| 5,471,988 A | 12/1995 | Fujio et al. |
| 5,472,405 A | 12/1995 | Buchholtz et al. |
| 5,487,388 A | 1/1996 | Rello et al. |
| 5,492,126 A | 2/1996 | Hennige |
| 5,496,256 A | 3/1996 | Bock |
| 5,501,655 A | 3/1996 | Rolt |
| 5,503,152 A | 4/1996 | Oakley et al. |
| 5,503,320 A | 4/1996 | Webster et al. |
| 5,507,790 A | 4/1996 | Weiss |
| 5,511,296 A | 4/1996 | Dias et al. |
| 5,520,188 A | 5/1996 | Hennige |
| 5,522,869 A | 6/1996 | Burdette |
| 5,523,058 A | 6/1996 | Umemura et al. |
| 5,524,620 A | 6/1996 | Rosenschein |
| 5,524,624 A | 6/1996 | Tepper |
| 5,524,625 A | 6/1996 | Okazaki |
| 5,526,624 A | 6/1996 | Berg |
| 5,526,812 A | 6/1996 | Dumoulin et al. |
| 5,526,814 A | 6/1996 | Cline et al. |
| 5,526,815 A | 6/1996 | Granz |
| 5,529,070 A | 6/1996 | Augustine et al. |
| 5,540,235 A | 7/1996 | Wilson |
| 5,558,092 A | 9/1996 | Unger |
| 5,560,362 A | 10/1996 | Sliwa et al. |
| 5,575,291 A | 11/1996 | Hayakawa |
| 5,575,807 A | 11/1996 | Faller |
| 5,577,502 A | 11/1996 | Darrow et al. |
| 5,577,507 A | 11/1996 | Snyder et al. |
| 5,577,991 A | 11/1996 | Akui et al. |
| 5,580,575 A | 12/1996 | Unger et al. |
| 5,601,526 A | 2/1997 | Chapelon |
| 5,603,323 A | 2/1997 | Pflugrath et al. |
| 5,609,562 A | 3/1997 | Kaali |
| 5,615,091 A | 3/1997 | Palatnik |
| 5,617,858 A | 4/1997 | Taverna et al. |
| 5,618,275 A | 4/1997 | Bock |
| 5,620,479 A | 4/1997 | Diederich |
| 5,622,175 A | 4/1997 | Sudol et al. |
| 5,638,819 A | 6/1997 | Manwaring et al. |
| 5,643,179 A | 7/1997 | Fujimoto |
| 5,644,085 A | 7/1997 | Lorraine et al. |
| 5,647,373 A | 7/1997 | Paltieli |
| 5,655,535 A | 8/1997 | FrIemel et al. |
| 5,655,538 A | 8/1997 | Lorraine |
| 5,657,760 A | 8/1997 | Ying |
| 5,658,328 A | 8/1997 | Johnson |
| 5,660,836 A | 8/1997 | Knowlton |
| 5,662,116 A | 9/1997 | Kondo |
| 5,665,053 A | 9/1997 | Jacobs |
| 5,665,141 A | 9/1997 | Vago |
| 5,671,746 A | 9/1997 | Dreschel et al. |
| 5,673,699 A | 10/1997 | Trahey et al. |
| 5,676,692 A | 10/1997 | Sanghvi |
| 5,685,820 A | 11/1997 | Riek et al. |
| 5,690,608 A | 11/1997 | Watanabe |
| 5,694,936 A | 12/1997 | Fujimoto |
| 5,697,897 A | 12/1997 | Buchholtz |
| 5,701,900 A | 12/1997 | Shehada et al. |
| 5,704,361 A | 1/1998 | Seward et al. |
| 5,706,252 A | 1/1998 | Le Verrier et al. |
| 5,706,564 A | 1/1998 | Rhyne |
| 5,715,823 A | 2/1998 | Wood et al. |
| 5,720,287 A | 2/1998 | Chapelon et al. |
| 5,722,411 A | 3/1998 | Suzuki |
| 5,727,554 A | 3/1998 | Kalend et al. |
| 5,735,280 A | 4/1998 | Sherman et al. |
| 5,743,863 A | 4/1998 | Chapelon |
| 5,746,005 A | 5/1998 | Steinberg |
| 5,746,762 A | 5/1998 | Bass |
| 5,748,767 A | 5/1998 | Raab |
| 5,749,364 A | 5/1998 | Sliwa et al. |
| 5,755,228 A | 5/1998 | Wilson et al. |
| 5,755,753 A | 5/1998 | Knowlton |
| 5,762,066 A | 6/1998 | Law |
| 5,763,886 A | 6/1998 | Schulte |
| 5,769,790 A | 6/1998 | Watkins |
| 5,779,644 A | 7/1998 | Eberle et al. |
| 5,792,058 A | 8/1998 | Lee |
| 5,795,297 A | 8/1998 | Daigle |
| 5,795,311 A | 8/1998 | Wess |
| 5,810,009 A | 9/1998 | Mine et al. |
| 5,810,888 A | 9/1998 | Fenn |
| 5,814,599 A | 9/1998 | Mitragotri et al. |
| 5,817,013 A | 10/1998 | Ginn et al. |
| 5,817,021 A | 10/1998 | Reichenberger |
| 5,820,564 A | 10/1998 | Slayton |
| 5,823,962 A | 10/1998 | Schaetzle |
| 5,827,204 A | 10/1998 | Grandia et al. |
| 5,840,032 A | 11/1998 | Hatfield et al. |
| 5,844,140 A | 12/1998 | Seale |
| 5,853,367 A | 12/1998 | Chalek et al. |
| 5,869,751 A | 2/1999 | Bonin |
| 5,871,524 A | 2/1999 | Knowlton |
| 5,873,902 A | 2/1999 | Sanghvi |
| 5,876,341 A | 3/1999 | Wang et al. |
| 5,879,303 A | 3/1999 | Averkiou et al. |
| 5,882,557 A | 3/1999 | Hayakawa |
| 5,891,034 A | 4/1999 | Bucholz |
| 5,895,356 A | 4/1999 | Andrus et al. |
| 5,899,861 A | 5/1999 | Friemel et al. |
| 5,904,659 A | 5/1999 | Duarte |
| 5,919,219 A | 7/1999 | Knowlton |
| 5,923,099 A | 7/1999 | Bilir |
| 5,924,989 A | 7/1999 | Polz |
| 5,928,169 A | 7/1999 | Schatzle et al. |
| 5,931,805 A | 8/1999 | Brisken |
| 5,938,606 A | 8/1999 | Bonnefous |
| 5,938,612 A | 8/1999 | Kline-Schoder |
| 5,948,011 A | 9/1999 | Knowlton |
| 5,957,844 A | 9/1999 | Dekel |
| 5,957,882 A | 9/1999 | Nita et al. |
| 5,957,941 A | 9/1999 | Ream |
| 5,964,707 A | 10/1999 | Fenster et al. |
| 5,967,980 A | 10/1999 | Ferre et al. |
| 5,968,034 A | 10/1999 | Fullmer |
| 5,971,949 A | 10/1999 | Levin |
| 5,977,538 A | 11/1999 | Unger et al. |
| 5,984,881 A | 11/1999 | Ishibashi et al. |
| 5,984,882 A | 11/1999 | Rosenschein |
| 5,990,598 A | 11/1999 | Sudol et al. |
| 5,997,471 A | 12/1999 | Gumb et al. |
| 5,997,497 A | 12/1999 | Nita et al. |
| 5,999,843 A | 12/1999 | Anbar |
| 6,004,262 A | 12/1999 | Putz et al. |
| 6,007,499 A | 12/1999 | Martin et al. |
| 6,013,032 A | 1/2000 | Savord |
| 6,014,473 A | 1/2000 | Hossack et al. |
| 6,016,255 A | 1/2000 | Bolan et al. |
| 6,019,724 A | 2/2000 | Gronningsaeter et al. |
| 6,022,308 A | 2/2000 | Williams |
| 6,022,327 A | 2/2000 | Chang |
| 6,030,374 A | 2/2000 | McDaniel |
| 6,036,646 A | 3/2000 | Barthe |
| 6,039,048 A | 3/2000 | Silberg |
| 6,039,689 A | 3/2000 | Lizzi |
| 6,042,556 A | 3/2000 | Beach |
| 6,049,159 A | 4/2000 | Barthe |
| 6,050,943 A | 4/2000 | Slayton |

(56) References Cited

U.S. PATENT DOCUMENTS

| | | | |
|---|---|---|---|
| 6,059,727 A | 5/2000 | Fowlkes |
| 6,071,239 A | 6/2000 | Cribbs |
| 6,080,108 A | 6/2000 | Dunham |
| 6,083,148 A | 7/2000 | Williams |
| 6,086,535 A | 7/2000 | Ishibashi |
| 6,086,580 A | 7/2000 | Mordon et al. |
| 6,090,054 A | 7/2000 | Tagishi |
| 6,093,148 A | 7/2000 | Fujimoto |
| 6,093,883 A | 7/2000 | Sanghvi |
| 6,101,407 A | 8/2000 | Groezinger |
| 6,106,469 A | 8/2000 | Suzuki et al. |
| 6,113,558 A | 9/2000 | Rosenschein |
| 6,113,559 A | 9/2000 | Klopotek |
| 6,120,452 A | 9/2000 | Barthe |
| 6,123,081 A | 9/2000 | Durette |
| 6,126,619 A | 10/2000 | Peterson et al. |
| 6,135,971 A | 10/2000 | Hutchinson |
| 6,139,499 A | 10/2000 | Wilk |
| 6,159,150 A | 12/2000 | Yale et al. |
| 6,171,244 B1 | 1/2001 | Finger et al. |
| 6,176,840 B1 | 1/2001 | Nishimura |
| 6,183,426 B1 | 2/2001 | Akisada |
| 6,183,502 B1 | 2/2001 | Takeuchi |
| 6,183,773 B1 | 2/2001 | Anderson |
| 6,190,323 B1 | 2/2001 | Dias |
| 6,190,336 B1 | 2/2001 | Duarte |
| 6,193,658 B1 | 2/2001 | Wendelken |
| 6,210,327 B1 | 4/2001 | Brackett et al. |
| 6,213,948 B1 | 4/2001 | Barthe |
| 6,216,029 B1 | 4/2001 | Paltieli |
| 6,233,476 B1 | 5/2001 | Strommer et al. |
| 6,234,990 B1 | 5/2001 | Rowe et al. |
| 6,241,753 B1 | 6/2001 | Knowlton |
| 6,246,898 B1 | 6/2001 | Vesely et al. |
| 6,251,074 B1 | 6/2001 | Averkiou et al. |
| 6,251,088 B1 | 6/2001 | Kaufman et al. |
| 6,268,405 B1 | 7/2001 | Yao |
| 6,273,864 B1 | 8/2001 | Duarte |
| 6,280,402 B1 | 8/2001 | Ishibashi et al. |
| 6,287,257 B1 | 9/2001 | Matichuk |
| 6,287,304 B1 | 9/2001 | Eggers et al. |
| 6,296,619 B1 | 10/2001 | Brisken |
| 6,301,989 B1 | 10/2001 | Brown et al. |
| 6,307,302 B1 | 10/2001 | Toda |
| 6,309,355 B1 | 10/2001 | Cain et al. |
| 6,311,090 B1 | 10/2001 | Knowlton |
| 6,315,741 B1 | 11/2001 | Martin |
| 6,322,509 B1 | 11/2001 | Pan et al. |
| 6,322,532 B1 | 11/2001 | D'Sa |
| 6,325,540 B1 | 12/2001 | Lounsberry et al. |
| 6,325,758 B1 | 12/2001 | Carol et al. |
| 6,325,769 B1 | 12/2001 | Klopotek |
| 6,325,798 B1 | 12/2001 | Edwards et al. |
| 6,338,716 B1 | 1/2002 | Hossack et al. |
| 6,350,276 B1 | 2/2002 | Knowlton |
| 6,356,780 B1 | 3/2002 | Licato et al. |
| 6,361,531 B1 | 3/2002 | Hissong |
| 6,370,411 B1 | 4/2002 | Osadchy et al. |
| 6,375,672 B1 | 4/2002 | Aksan |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,390,982 B1 | 5/2002 | Bova et al. |
| 6,405,090 B1 | 6/2002 | Knowlton |
| 6,409,720 B1 | 6/2002 | Hissong |
| 6,413,216 B1 | 7/2002 | Cain et al. |
| 6,413,253 B1 | 7/2002 | Koop |
| 6,413,254 B1 | 7/2002 | Hissong |
| 6,419,648 B1 | 7/2002 | Vitek |
| 6,423,007 B2 | 7/2002 | Lizzi et al. |
| 6,425,865 B1 | 7/2002 | Salcudean |
| 6,425,867 B1 | 7/2002 | Vaezy |
| 6,425,912 B1 | 7/2002 | Knowlton |
| 6,428,477 B1 | 8/2002 | Mason |
| 6,428,532 B1 | 8/2002 | Doukas |
| 6,430,446 B1 | 8/2002 | Knowlton |
| 6,432,057 B1 | 8/2002 | Mazess et al. |
| 6,432,067 B1 | 8/2002 | Martin |
| 6,432,101 B1 | 8/2002 | Weber |
| 6,436,061 B1 | 8/2002 | Costantino |
| 6,438,424 B1 | 8/2002 | Knowlton |
| 6,440,071 B1 | 8/2002 | Slayton |
| 6,440,121 B1 | 8/2002 | Weber |
| 6,443,914 B1 | 9/2002 | Costantino |
| 6,447,443 B1 | 9/2002 | Keogh et al. |
| 6,451,013 B1 | 9/2002 | Bays et al. |
| 6,453,202 B1 | 9/2002 | Knowlton |
| 6,461,378 B1 | 10/2002 | Knowlton |
| 6,470,216 B1 | 10/2002 | Knowlton |
| 6,488,626 B1 | 12/2002 | Lizzi |
| 6,491,657 B2 | 12/2002 | Rowe |
| 6,500,121 B1 | 12/2002 | Slayton |
| 6,500,141 B1 | 12/2002 | Irion |
| 6,506,171 B1 | 1/2003 | Vitek et al. |
| 6,508,774 B1 | 1/2003 | Acker |
| 6,511,427 B1 | 1/2003 | Sliwa, Jr. et al. |
| 6,511,428 B1 | 1/2003 | Azuma |
| 6,514,244 B2 | 2/2003 | Pope |
| 6,517,484 B1 | 2/2003 | Wilk |
| 6,524,250 B1 | 2/2003 | Weber |
| 6,540,679 B2 | 4/2003 | Slayton |
| 6,540,685 B1 | 4/2003 | Rhoads et al. |
| 6,540,700 B1 | 4/2003 | Fujimoto et al. |
| 6,547,788 B1 | 4/2003 | Maguire et al. |
| 6,554,771 B1 | 4/2003 | Buil et al. |
| 6,569,099 B1 | 5/2003 | Babaev |
| 6,569,108 B2 | 5/2003 | Sarvazyan et al. |
| 6,572,552 B2 | 6/2003 | Fukukita |
| 6,575,956 B1 | 6/2003 | Brisken et al. |
| 6,595,934 B1 | 7/2003 | Hissong |
| 6,599,256 B1 | 7/2003 | Acker |
| 6,605,080 B1 | 8/2003 | Altshuler et al. |
| 6,607,498 B2 | 8/2003 | Eshel |
| 6,618,620 B1 | 9/2003 | Freundlich et al. |
| 6,623,430 B1 | 9/2003 | Slayton |
| 6,626,854 B2 | 9/2003 | Friedman |
| 6,626,855 B1 | 9/2003 | Weng |
| 6,638,226 B2 | 10/2003 | He et al. |
| 6,645,150 B2 | 11/2003 | Angelsen et al. |
| 6,645,162 B2 | 11/2003 | Friedman |
| 6,662,054 B2 | 12/2003 | Kreindel |
| 6,663,627 B2 | 12/2003 | Francischelli |
| 6,665,806 B1 | 12/2003 | Shimizu |
| 6,666,835 B2 | 12/2003 | Martin |
| 6,669,638 B1 | 12/2003 | Miller |
| 6,685,639 B1 | 2/2004 | Wang et al. |
| 6,685,640 B1 | 2/2004 | Fry |
| 6,692,450 B1 | 2/2004 | Coleman |
| 6,699,237 B2 | 3/2004 | Weber |
| 6,716,184 B2 | 4/2004 | Vaezy et al. |
| 6,719,449 B1 | 4/2004 | Laugharn, Jr. et al. |
| 6,719,694 B2 | 4/2004 | Weng |
| 6,726,627 B1 | 4/2004 | Lizzi et al. |
| 6,733,449 B1 | 5/2004 | Krishnamurthy et al. |
| 6,749,624 B2 | 6/2004 | Knowlton |
| 6,772,490 B2 | 8/2004 | Toda |
| 6,773,409 B2 | 8/2004 | Truckai et al. |
| 6,775,404 B1 | 8/2004 | Pagoulatos et al. |
| 6,790,187 B2 | 9/2004 | Thompson et al. |
| 6,824,516 B2 | 11/2004 | Batten et al. |
| 6,835,940 B2 | 12/2004 | Morikawa et al. |
| 6,846,290 B2 | 1/2005 | Lizzi et al. |
| 6,875,176 B2 | 4/2005 | Mourad |
| 6,882,884 B1 | 4/2005 | Mosk et al. |
| 6,887,239 B2 | 5/2005 | Elstrom |
| 6,889,089 B2 | 5/2005 | Behl |
| 6,896,657 B2 | 5/2005 | Willis |
| 6,902,536 B2 | 6/2005 | Manna |
| 6,905,466 B2 | 6/2005 | Salgo |
| 6,918,907 B2 | 7/2005 | Kelly |
| 6,920,883 B2 | 7/2005 | Bessette |
| 6,921,371 B2 | 7/2005 | Wilson |

(56) References Cited

U.S. PATENT DOCUMENTS

| | | |
|---|---|---|
| 6,932,771 B2 | 8/2005 | Whitmore |
| 6,932,814 B2 | 8/2005 | Wood |
| 6,936,044 B2 | 8/2005 | McDaniel |
| 6,936,046 B2 | 8/2005 | Hissong |
| 6,945,937 B2 | 9/2005 | Culp et al. |
| 6,948,843 B2 | 9/2005 | Laugharn et al. |
| 6,953,941 B2 | 10/2005 | Nakano et al. |
| 6,958,043 B2 | 10/2005 | Hissong |
| 6,971,994 B1 | 12/2005 | Young et al. |
| 6,974,417 B2 | 12/2005 | Lockwood |
| 6,976,492 B2 | 12/2005 | Ingle |
| 6,992,305 B2 | 1/2006 | Maezawa et al. |
| 6,997,923 B2 | 2/2006 | Anderson |
| 7,006,874 B2 | 2/2006 | Knowlton |
| 7,020,528 B2 | 3/2006 | Neev |
| 7,022,089 B2 | 4/2006 | Ooba |
| 7,058,440 B2 | 6/2006 | Heuscher et al. |
| 7,063,666 B2 | 6/2006 | Weng |
| 7,070,565 B2 | 7/2006 | Vaezy et al. |
| 7,074,218 B2 | 7/2006 | Washington et al. |
| 7,094,252 B2 | 8/2006 | Koop |
| 7,108,663 B2 | 9/2006 | Talish et al. |
| 7,115,123 B2 | 10/2006 | Knowlton |
| 7,122,029 B2 | 10/2006 | Koop et al. |
| 7,142,905 B2 | 11/2006 | Slayton |
| 7,165,451 B1 | 1/2007 | Brooks et al. |
| 7,179,238 B2 | 2/2007 | Hissong |
| 7,189,230 B2 | 3/2007 | Knowlton |
| 7,229,411 B2 | 6/2007 | Slayton |
| 7,235,592 B2 | 6/2007 | Muratoglu |
| 7,258,674 B2 | 8/2007 | Cribbs |
| 7,273,459 B2 | 9/2007 | Desilets |
| 7,294,125 B2 | 11/2007 | Phalen et al. |
| 7,297,117 B2 | 11/2007 | Trucco |
| 7,303,555 B2 | 12/2007 | Makin et al. |
| 7,311,679 B2 | 12/2007 | Desilets et al. |
| 7,327,071 B2 | 2/2008 | Nishiyama et al. |
| 7,331,951 B2 | 2/2008 | Eshel et al. |
| 7,332,985 B2 | 2/2008 | Larson et al. |
| 7,338,434 B1 | 3/2008 | Haarstad et al. |
| 7,347,855 B2 | 3/2008 | Eshel |
| RE40,403 E | 6/2008 | Cho et al. |
| 7,393,325 B2 | 7/2008 | Barthe |
| 7,398,116 B2 | 7/2008 | Edwards |
| 7,399,279 B2 | 7/2008 | Abend et al. |
| 7,491,171 B2 | 2/2009 | Barthe et al. |
| 7,507,235 B2 | 3/2009 | Keogh et al. |
| 7,510,536 B2 | 3/2009 | Foley et al. |
| 7,517,315 B2 | 4/2009 | Willis |
| 7,530,356 B2 | 5/2009 | Slayton |
| 7,530,958 B2 | 5/2009 | Slayton |
| 7,532,201 B2 | 5/2009 | Quistgaard et al. |
| 7,571,336 B2 | 8/2009 | Barthe |
| 7,601,120 B2 | 10/2009 | Moilanen et al. |
| 7,615,015 B2 | 11/2009 | Coleman |
| 7,615,016 B2 | 11/2009 | Barthe |
| 7,652,411 B2 | 1/2010 | Crunkilton et al. |
| 7,662,114 B2 | 2/2010 | Seip et al. |
| 7,674,257 B2 | 3/2010 | Pless et al. |
| 7,686,763 B2 | 3/2010 | Vaezy et al. |
| 7,694,406 B2 | 4/2010 | Wildes et al. |
| 7,695,437 B2 | 4/2010 | Quistgaard et al. |
| 7,713,203 B2 | 5/2010 | Lacoste et al. |
| 7,727,156 B2 | 6/2010 | Angelsen et al. |
| 7,758,524 B2 | 7/2010 | Barthe |
| 7,766,848 B2 | 8/2010 | Desilets et al. |
| 7,789,841 B2 | 9/2010 | Huckle et al. |
| 7,806,839 B2 | 10/2010 | Mast et al. |
| 7,815,570 B2 | 10/2010 | Eshel et al. |
| 7,819,826 B2 | 10/2010 | Diederich et al. |
| 7,824,348 B2 | 11/2010 | Barthe |
| 7,828,734 B2 | 11/2010 | Azhari et al. |
| 7,833,162 B2 | 11/2010 | Hasegawa et al. |
| 7,841,984 B2 | 11/2010 | Cribbs et al. |
| 7,846,096 B2 | 12/2010 | Mast et al. |
| 7,857,773 B2 | 12/2010 | Desilets et al. |
| 7,875,023 B2 | 1/2011 | Eshel et al. |
| 7,901,359 B2 | 3/2011 | Mandrusov et al. |
| 7,905,007 B2 | 3/2011 | Calisti et al. |
| 7,905,844 B2 | 3/2011 | Desilets et al. |
| 7,914,453 B2 | 3/2011 | Slayton et al. |
| 7,914,469 B2 | 3/2011 | Torbati |
| 7,931,611 B2 | 4/2011 | Novak et al. |
| 7,955,262 B2 | 6/2011 | Rosenberg |
| 7,955,281 B2 | 6/2011 | Pedersen et al. |
| 7,967,764 B2 | 6/2011 | Lidgren et al. |
| 7,967,839 B2 | 6/2011 | Flock et al. |
| 7,993,289 B2 | 8/2011 | Quistgaard et al. |
| 8,057,389 B2 | 11/2011 | Barthe et al. |
| 8,057,465 B2 | 11/2011 | Sliwa, Jr. et al. |
| 8,066,641 B2 | 11/2011 | Barthe et al. |
| 8,123,707 B2 | 2/2012 | Huckle et al. |
| 8,128,618 B2 | 3/2012 | Gliklich et al. |
| 8,133,180 B2 | 3/2012 | Slayton et al. |
| 8,133,191 B2 | 3/2012 | Rosenberg et al. |
| 8,142,200 B2 | 3/2012 | Crunkilton et al. |
| 8,152,904 B2 | 4/2012 | Slobodzian et al. |
| 8,162,858 B2 | 4/2012 | Manna et al. |
| 8,166,332 B2 | 4/2012 | Barthe et al. |
| 8,182,428 B2 | 5/2012 | Angelsen et al. |
| 8,197,409 B2 | 6/2012 | Foley et al. |
| 8,206,299 B2 | 6/2012 | Foley et al. |
| 8,208,346 B2 | 6/2012 | Crunkilton |
| 8,211,017 B2 | 7/2012 | Foley et al. |
| 8,262,591 B2 | 9/2012 | Pedersen et al. |
| 8,262,650 B2 | 9/2012 | Zanelli et al. |
| 8,264,126 B2 | 9/2012 | Toda et al. |
| 8,273,037 B2 | 9/2012 | Kreindel et al. |
| 8,282,554 B2 | 10/2012 | Makin et al. |
| 8,292,835 B1 | 10/2012 | Cimino |
| 8,298,163 B1 | 10/2012 | Cimino |
| 8,333,700 B1 | 12/2012 | Barthe et al. |
| 8,334,637 B2 | 12/2012 | Crunkilton et al. |
| 8,337,407 B2 | 12/2012 | Quistgaard et al. |
| 8,343,051 B2 | 1/2013 | Desilets et al. |
| 8,366,622 B2 | 2/2013 | Slayton et al. |
| 8,388,535 B2 | 3/2013 | Weng et al. |
| 8,409,097 B2 | 4/2013 | Slayton et al. |
| 8,425,435 B2 | 4/2013 | Wing et al. |
| 8,444,562 B2 | 5/2013 | Barthe et al. |
| 8,454,540 B2 | 6/2013 | Eshel et al. |
| 8,460,193 B2 | 6/2013 | Barthe et al. |
| 8,480,585 B2 | 7/2013 | Slayton et al. |
| 8,506,486 B2 | 8/2013 | Slayton et al. |
| 8,512,250 B2 | 8/2013 | Quistgaard et al. |
| 8,523,775 B2 | 9/2013 | Barthe et al. |
| 8,535,228 B2 | 9/2013 | Slayton et al. |
| 8,570,837 B2 | 10/2013 | Toda et al. |
| 8,573,392 B2 | 11/2013 | Bennett et al. |
| 8,583,211 B2 | 11/2013 | Salomir et al. |
| 8,585,618 B2 | 11/2013 | Hunziker et al. |
| 8,604,672 B2 | 12/2013 | Toda et al. |
| 8,622,937 B2 | 1/2014 | Weng et al. |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,708,935 B2 | 4/2014 | Barthe et al. |
| 8,715,186 B2 | 5/2014 | Slayton et al. |
| 8,726,781 B2 | 5/2014 | Eckhoff et al. |
| 8,728,071 B2 | 5/2014 | Lischinsky et al. |
| 8,753,295 B2 | 6/2014 | Thierman |
| 8,758,253 B2 | 6/2014 | Sano et al. |
| 8,836,203 B2 | 9/2014 | Nobles et al. |
| 8,857,438 B2 | 10/2014 | Barthe et al. |
| 8,858,471 B2 | 10/2014 | Barthe et al. |
| 8,915,853 B2 | 12/2014 | Barthe et al. |
| 8,915,854 B2 | 12/2014 | Slayton et al. |
| 8,915,870 B2 | 12/2014 | Barthe et al. |
| 8,920,320 B2 | 12/2014 | Stecco et al. |
| 8,920,324 B2 | 12/2014 | Slayton et al. |

(56) References Cited

U.S. PATENT DOCUMENTS

| | | |
|---|---|---|
| 8,926,533 B2 | 1/2015 | Bockenstedt et al. |
| 8,932,224 B2 | 1/2015 | Barthe et al. |
| 8,932,238 B2 | 1/2015 | Wing et al. |
| 8,968,205 B2 | 3/2015 | Zeng et al. |
| 9,011,336 B2 | 4/2015 | Slayton et al. |
| 9,039,617 B2 | 5/2015 | Slayton et al. |
| 9,039,619 B2 | 5/2015 | Barthe et al. |
| 9,095,697 B2 | 8/2015 | Barthe et al. |
| 9,114,247 B2 | 8/2015 | Barthe et al. |
| 9,272,162 B2 | 3/2016 | Slayton et al. |
| 9,283,409 B2 | 3/2016 | Slayton et al. |
| 9,283,410 B2 | 3/2016 | Slayton et al. |
| 9,320,537 B2 | 4/2016 | Slayton et al. |
| 2001/0009997 A1 | 7/2001 | Pope |
| 2001/0009999 A1 | 7/2001 | Kaufman et al. |
| 2001/0014780 A1 | 8/2001 | Martin |
| 2001/0014819 A1 | 8/2001 | Ingle |
| 2001/0031922 A1 | 10/2001 | Weng |
| 2001/0039380 A1 | 11/2001 | Larson et al. |
| 2001/0041880 A1 | 11/2001 | Brisken |
| 2002/0000763 A1 | 1/2002 | Jones |
| 2002/0002345 A1 | 1/2002 | Marlinghaus |
| 2002/0040199 A1 | 4/2002 | Klopotek |
| 2002/0040442 A1 | 4/2002 | Ishidera |
| 2002/0055702 A1 | 5/2002 | Atala |
| 2002/0062077 A1 | 5/2002 | Emmenegger |
| 2002/0062142 A1 | 5/2002 | Knowlton |
| 2002/0072691 A1 | 6/2002 | Thompson et al. |
| 2002/0082528 A1 | 6/2002 | Friedman |
| 2002/0082529 A1 | 6/2002 | Suorsa et al. |
| 2002/0082589 A1 | 6/2002 | Friedman |
| 2002/0087080 A1 | 7/2002 | Slayton |
| 2002/0095143 A1 | 7/2002 | Key |
| 2002/0099094 A1 | 7/2002 | Anderson |
| 2002/0115917 A1 | 8/2002 | Honda et al. |
| 2002/0128639 A1 | 9/2002 | Pless et al. |
| 2002/0128648 A1 | 9/2002 | Weber |
| 2002/0143252 A1 | 10/2002 | Dunne et al. |
| 2002/0156400 A1 | 10/2002 | Babaev |
| 2002/0161357 A1 | 10/2002 | Anderson |
| 2002/0165529 A1 | 11/2002 | Danek |
| 2002/0168049 A1 | 11/2002 | Schriever |
| 2002/0169394 A1 | 11/2002 | Eppstein et al. |
| 2002/0169442 A1 | 11/2002 | Neev |
| 2002/0173721 A1 | 11/2002 | Grunwald et al. |
| 2002/0193784 A1 | 12/2002 | McHale et al. |
| 2002/0193831 A1 | 12/2002 | Smith |
| 2003/0009153 A1 | 1/2003 | Brisken et al. |
| 2003/0014039 A1 | 1/2003 | Barzell et al. |
| 2003/0018255 A1 | 1/2003 | Martin |
| 2003/0018270 A1 | 1/2003 | Makin et al. |
| 2003/0023283 A1 | 1/2003 | McDaniel |
| 2003/0028111 A1 | 2/2003 | Vaezy et al. |
| 2003/0028113 A1 | 2/2003 | Gilbert et al. |
| 2003/0032900 A1 | 2/2003 | Ella |
| 2003/0036706 A1 | 2/2003 | Slayton et al. |
| 2003/0040739 A1 | 2/2003 | Koop |
| 2003/0050678 A1 | 3/2003 | Sierra |
| 2003/0055417 A1 | 3/2003 | Truckai et al. |
| 2003/0060736 A1 | 3/2003 | Martin et al. |
| 2003/0040442 A1 | 4/2003 | Ishidera |
| 2003/0065313 A1 | 4/2003 | Koop |
| 2003/0073907 A1 | 4/2003 | Taylor |
| 2003/0074023 A1 | 4/2003 | Kaplan |
| 2003/0083536 A1 | 5/2003 | Eshel |
| 2003/0092988 A1 | 5/2003 | Makin |
| 2003/0097071 A1 | 5/2003 | Halmann et al. |
| 2003/0099383 A1 | 5/2003 | Lefebvre |
| 2003/0125629 A1 | 7/2003 | Ustuner |
| 2003/0135135 A1 | 7/2003 | Miwa et al. |
| 2003/0139790 A1 | 7/2003 | Ingle et al. |
| 2003/0153961 A1 | 8/2003 | Babaev |
| 2003/0171678 A1 | 9/2003 | Batten et al. |
| 2003/0171701 A1 | 9/2003 | Babaev |
| 2003/0176790 A1 | 9/2003 | Slayton |
| 2003/0191396 A1 | 10/2003 | Sanghvi |
| 2003/0200481 A1 | 10/2003 | Stanley |
| 2003/0212129 A1 | 11/2003 | Liu et al. |
| 2003/0212351 A1 | 11/2003 | Hissong |
| 2003/0212393 A1 | 11/2003 | Knowlton |
| 2003/0216648 A1 | 11/2003 | Lizzi et al. |
| 2003/0216795 A1 | 11/2003 | Harth |
| 2003/0220536 A1 | 11/2003 | Hissong |
| 2003/0220585 A1 | 11/2003 | Hissong |
| 2003/0229331 A1 | 12/2003 | Brisken et al. |
| 2003/0233085 A1 | 12/2003 | Giammarusti |
| 2003/0236487 A1 | 12/2003 | Knowlton |
| 2004/0000316 A1 | 1/2004 | Knowlton |
| 2004/0001809 A1 | 1/2004 | Brisken |
| 2004/0002705 A1 | 1/2004 | Knowlton |
| 2004/0010222 A1 | 1/2004 | Nunomura et al. |
| 2004/0015079 A1 | 1/2004 | Berger et al. |
| 2004/0015106 A1 | 1/2004 | Coleman |
| 2004/0030227 A1 | 2/2004 | Littrup |
| 2004/0039312 A1 | 2/2004 | Hillstead |
| 2004/0039418 A1 | 2/2004 | Elstrom |
| 2004/0041563 A1 | 3/2004 | Lewin et al. |
| 2004/0041880 A1 | 3/2004 | Ikeda et al. |
| 2004/0042168 A1 | 3/2004 | Yang et al. |
| 2004/0044375 A1 | 3/2004 | Diederich et al. |
| 2004/0049134 A1 | 3/2004 | Tosaya et al. |
| 2004/0049734 A1 | 3/2004 | Simske |
| 2004/0059266 A1 | 3/2004 | Fry |
| 2004/0068186 A1 | 4/2004 | Ishida et al. |
| 2004/0073079 A1 | 4/2004 | Altshuler et al. |
| 2004/0073113 A1 | 4/2004 | Salgo |
| 2004/0073115 A1 | 4/2004 | Horzewski et al. |
| 2004/0073116 A1 | 4/2004 | Smith |
| 2004/0073204 A1 | 4/2004 | Ryan et al. |
| 2004/0077977 A1 | 4/2004 | Ella et al. |
| 2004/0082857 A1 | 4/2004 | Schonenberger |
| 2004/0082859 A1 | 4/2004 | Schaer |
| 2004/0102697 A1 | 5/2004 | Evron |
| 2004/0105559 A1 | 6/2004 | Aylward et al. |
| 2004/0106867 A1 | 6/2004 | Eshel et al. |
| 2004/0122323 A1 | 6/2004 | Vortman et al. |
| 2004/0122493 A1 | 6/2004 | Ishibashi et al. |
| 2004/0143297 A1 | 7/2004 | Ramsey |
| 2004/0152982 A1 | 8/2004 | Hwang et al. |
| 2004/0158150 A1 | 8/2004 | Rabiner et al. |
| 2004/0186535 A1 | 9/2004 | Knowlton |
| 2004/0189155 A1 | 9/2004 | Funakubo |
| 2004/0206365 A1 | 10/2004 | Knowlton |
| 2004/0210214 A1 | 10/2004 | Knowlton |
| 2004/0217675 A1 | 11/2004 | Desilets |
| 2004/0249318 A1 | 12/2004 | Tanaka |
| 2004/0254620 A1 | 12/2004 | Lacoste |
| 2004/0267252 A1 | 12/2004 | Washington et al. |
| 2005/0033201 A1 | 2/2005 | Takahashi |
| 2005/0033316 A1 | 2/2005 | Kertz |
| 2005/0038340 A1 | 2/2005 | Vaezy et al. |
| 2005/0055018 A1 | 3/2005 | Kreindel |
| 2005/0055073 A1 | 3/2005 | Weber |
| 2005/0061834 A1 | 3/2005 | Garcia et al. |
| 2005/0070961 A1 | 3/2005 | Maki |
| 2005/0074407 A1 | 4/2005 | Smith |
| 2005/0080469 A1 | 4/2005 | Larson |
| 2005/0091770 A1 | 5/2005 | Mourad et al. |
| 2005/0096542 A1 | 5/2005 | Weng et al. |
| 2005/0104690 A1 | 5/2005 | Larson et al. |
| 2005/0113689 A1 | 5/2005 | Gritzky |
| 2005/0131302 A1 | 6/2005 | Poland |
| 2005/0137656 A1 | 6/2005 | Malak |
| 2005/0143677 A1 | 6/2005 | Young et al. |
| 2005/0154313 A1 | 7/2005 | Desilets |
| 2005/0154314 A1 | 7/2005 | Quistgaard |
| 2005/0154332 A1 | 7/2005 | Zanelli |
| 2005/0154431 A1 | 7/2005 | Quistgaard |
| 2005/0187495 A1 | 8/2005 | Quistgaard |
| 2005/0191252 A1 | 9/2005 | Mitsui |
| 2005/0193451 A1 | 9/2005 | Quistgaard |
| 2005/0197681 A1 | 9/2005 | Barolet et al. |
| 2005/0228281 A1 | 10/2005 | Nefos |
| 2005/0240170 A1 | 10/2005 | Zhang et al. |

(56) References Cited

U.S. PATENT DOCUMENTS

| | | |
|---|---|---|
| 2005/0251120 A1 | 11/2005 | Anderson et al. |
| 2005/0251125 A1 | 11/2005 | Pless et al. |
| 2005/0256406 A1 | 11/2005 | Barthe |
| 2005/0261584 A1 | 11/2005 | Eshel |
| 2005/0261585 A1 | 11/2005 | Makin et al. |
| 2005/0267454 A1 | 12/2005 | Hissong |
| 2005/0288748 A1 | 12/2005 | Li et al. |
| 2006/0004306 A1 | 1/2006 | Altshuler |
| 2006/0020260 A1 | 1/2006 | Dover et al. |
| 2006/0025756 A1 | 2/2006 | Francischelli |
| 2006/0042201 A1 | 3/2006 | Curry |
| 2006/0058664 A1 | 3/2006 | Barthe |
| 2006/0058671 A1 | 3/2006 | Vitek et al. |
| 2006/0058707 A1 | 3/2006 | Barthe |
| 2006/0058712 A1 | 3/2006 | Altshuler et al. |
| 2006/0074309 A1 | 4/2006 | Bonnefous |
| 2006/0074313 A1 | 4/2006 | Slayton et al. |
| 2006/0074314 A1 | 4/2006 | Slayton |
| 2006/0074355 A1 | 4/2006 | Slayton |
| 2006/0079816 A1 | 4/2006 | Barthe |
| 2006/0079868 A1 | 4/2006 | Makin |
| 2006/0084891 A1 | 4/2006 | Barthe |
| 2006/0089632 A1 | 4/2006 | Barthe |
| 2006/0089688 A1 | 4/2006 | Panescu |
| 2006/0094988 A1 | 5/2006 | Tosaya |
| 2006/0111744 A1 | 5/2006 | Makin |
| 2006/0116583 A1 | 6/2006 | Ogasawara et al. |
| 2006/0116671 A1 | 6/2006 | Slayton |
| 2006/0122508 A1 | 6/2006 | Slayton |
| 2006/0122509 A1 | 6/2006 | Desilets |
| 2006/0161062 A1 | 7/2006 | Arditi et al. |
| 2006/0184069 A1 | 8/2006 | Vaitekunas |
| 2006/0184071 A1 | 8/2006 | Klopotek |
| 2006/0189972 A1 | 8/2006 | Grossman |
| 2006/0206105 A1 | 9/2006 | Chopra |
| 2006/0229514 A1 | 10/2006 | Wiener |
| 2006/0241440 A1 | 10/2006 | Eshel |
| 2006/0241442 A1 | 10/2006 | Barthe |
| 2006/0241470 A1 | 10/2006 | Novak et al. |
| 2006/0241576 A1 | 10/2006 | Diederich et al. |
| 2006/0250046 A1 | 11/2006 | Koizumi et al. |
| 2006/0282691 A1 | 12/2006 | Barthe |
| 2006/0291710 A1 | 12/2006 | Wang et al. |
| 2007/0032784 A1 | 2/2007 | Gilklich et al. |
| 2007/0035201 A1 | 2/2007 | Desilets |
| 2007/0055154 A1 | 3/2007 | Torbati |
| 2007/0055155 A1 | 3/2007 | Owen et al. |
| 2007/0055156 A1 | 3/2007 | Desilets et al. |
| 2007/0065420 A1 | 3/2007 | Johnson |
| 2007/0083120 A1 | 4/2007 | Cain et al. |
| 2007/0087060 A1 | 4/2007 | Dietrich |
| 2007/0088245 A1 | 4/2007 | Babaev et al. |
| 2007/0088346 A1 | 4/2007 | Mirizzi et al. |
| 2007/0161902 A1 | 7/2007 | Dan |
| 2007/0166357 A1 | 7/2007 | Shaffer et al. |
| 2007/0167709 A1 | 7/2007 | Slayton |
| 2007/0208253 A1 | 9/2007 | Slayton |
| 2007/0219604 A1 | 9/2007 | Yaroslavsky et al. |
| 2007/0219605 A1 | 9/2007 | Yaroslavsky et al. |
| 2007/0238994 A1 | 10/2007 | Stecco et al. |
| 2007/0239075 A1 | 10/2007 | Rosenberg |
| 2007/0239077 A1 | 10/2007 | Azhari et al. |
| 2007/0239079 A1 | 10/2007 | Manstein et al. |
| 2007/0239142 A1 | 10/2007 | Altshuler |
| 2008/0027328 A1 | 1/2008 | Klopotek |
| 2008/0039724 A1 | 2/2008 | Seip et al. |
| 2008/0071255 A1 | 3/2008 | Barthe |
| 2008/0086054 A1 | 4/2008 | Slayton |
| 2008/0086056 A1 | 4/2008 | Chang et al. |
| 2008/0097214 A1 | 4/2008 | Meyers et al. |
| 2008/0097253 A1 | 4/2008 | Pedersen et al. |
| 2008/0114251 A1 | 5/2008 | Weymer et al. |
| 2008/0139974 A1 | 6/2008 | Da Silva |
| 2008/0146970 A1 | 6/2008 | Litman et al. |
| 2008/0167556 A1 | 7/2008 | Thompson |
| 2008/0183077 A1 | 7/2008 | Moreau-Gobard et al. |
| 2008/0183110 A1 | 7/2008 | Davenport et al. |
| 2008/0188745 A1 | 8/2008 | Chen et al. |
| 2008/0194964 A1 | 8/2008 | Randall et al. |
| 2008/0195000 A1 | 8/2008 | Spooner et al. |
| 2008/0200810 A1 | 8/2008 | Buchalter |
| 2008/0200813 A1 | 8/2008 | Quistgaard |
| 2008/0214966 A1 | 9/2008 | Slayton |
| 2008/0221491 A1 | 9/2008 | Slayton |
| 2008/0223379 A1 | 9/2008 | Stuker et al. |
| 2008/0242991 A1 | 10/2008 | Moon et al. |
| 2008/0243035 A1 | 10/2008 | Crunkilton |
| 2008/0269608 A1 | 10/2008 | Anderson et al. |
| 2008/0275342 A1 | 11/2008 | Barthe |
| 2008/0281206 A1 | 11/2008 | Bartlett et al. |
| 2008/0281236 A1 | 11/2008 | Eshel et al. |
| 2008/0281237 A1 | 11/2008 | Slayton |
| 2008/0281255 A1 | 11/2008 | Slayton |
| 2008/0294073 A1 | 11/2008 | Barthe |
| 2008/0319356 A1 | 12/2008 | Cain |
| 2009/0005680 A1 | 1/2009 | Jones et al. |
| 2009/0012394 A1 | 1/2009 | Hobelsberger et al. |
| 2009/0043198 A1 | 2/2009 | Milner et al. |
| 2009/0043293 A1 | 2/2009 | Pankratov et al. |
| 2009/0048514 A1 | 2/2009 | Azhari et al. |
| 2009/0069677 A1 | 3/2009 | Chen et al. |
| 2009/0093737 A1 | 4/2009 | Chomas et al. |
| 2009/0156969 A1 | 6/2009 | Santangelo |
| 2009/0171252 A1 | 7/2009 | Bockenstedt et al. |
| 2009/0177122 A1 | 7/2009 | Peterson |
| 2009/0177123 A1 | 7/2009 | Peterson |
| 2009/0182231 A1 | 7/2009 | Barthe et al. |
| 2009/0198157 A1 | 8/2009 | Babaev et al. |
| 2009/0216159 A1 | 8/2009 | Slayton et al. |
| 2009/0226424 A1 | 9/2009 | Hsu |
| 2009/0227910 A1 | 9/2009 | Pedersen et al. |
| 2009/0253988 A1 | 10/2009 | Slayton et al. |
| 2009/0281463 A1 | 11/2009 | Chapelon et al. |
| 2009/0312693 A1 | 12/2009 | Thapliyal et al. |
| 2009/0318909 A1 | 12/2009 | Debenedictis et al. |
| 2009/0326420 A1 | 12/2009 | Moonen et al. |
| 2010/0011236 A1 | 1/2010 | Barthe et al. |
| 2010/0022919 A1 | 1/2010 | Peterson |
| 2010/0022921 A1 | 1/2010 | Seip et al. |
| 2010/0022922 A1 | 1/2010 | Barthe et al. |
| 2010/0030076 A1 | 2/2010 | Vortman et al. |
| 2010/0042020 A1 | 2/2010 | Ben-Ezra |
| 2010/0049178 A1 | 2/2010 | Deem et al. |
| 2010/0056925 A1 | 3/2010 | Zhang et al. |
| 2010/0100014 A1 | 4/2010 | Eshel et al. |
| 2010/0113983 A1 | 5/2010 | Heckerman et al. |
| 2010/0130891 A1 | 5/2010 | Taggart et al. |
| 2010/0160782 A1 | 6/2010 | Slayton et al. |
| 2010/0160837 A1 | 6/2010 | Hunziker et al. |
| 2010/0168576 A1 | 7/2010 | Poland et al. |
| 2010/0191120 A1 | 7/2010 | Kraus et al. |
| 2010/0241035 A1 | 9/2010 | Barthe et al. |
| 2010/0249602 A1 | 9/2010 | Buckley et al. |
| 2010/0249669 A1 | 9/2010 | Ulric et al. |
| 2010/0256489 A1 | 10/2010 | Pedersen et al. |
| 2010/0274161 A1 | 10/2010 | Azhari et al. |
| 2010/0280420 A1 | 11/2010 | Barthe et al. |
| 2010/0286518 A1 | 11/2010 | Lee et al. |
| 2010/0312150 A1 | 12/2010 | Mast et al. |
| 2011/0040171 A1 | 2/2011 | Foley et al. |
| 2011/0040190 A1 | 2/2011 | Jahnke et al. |
| 2011/0066084 A1 | 3/2011 | Desilets et al. |
| 2011/0087099 A1 | 4/2011 | Eshel et al. |
| 2011/0087255 A1 | 4/2011 | McCormack et al. |
| 2011/0112405 A1 | 5/2011 | Barthe et al. |
| 2011/0144490 A1 | 6/2011 | Davis et al. |
| 2011/0178444 A1 | 7/2011 | Slayton et al. |
| 2011/0178541 A1 | 7/2011 | Azhari |
| 2011/0190745 A1 | 8/2011 | Uebelhoer et al. |
| 2011/0251524 A1 | 10/2011 | Azhari et al. |
| 2011/0251527 A1 | 10/2011 | Kushculey et al. |
| 2011/0270137 A1 | 11/2011 | Goren et al. |
| 2011/0319793 A1 | 12/2011 | Hynynen |
| 2012/0004549 A1 | 1/2012 | Barthe et al. |

(56) References Cited

U.S. PATENT DOCUMENTS

| | | |
|---|---|---|
| 2012/0016239 A1 | 1/2012 | Barthe et al. |
| 2012/0029353 A1 | 2/2012 | Slayton et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0111339 A1 | 5/2012 | Barthe et al. |
| 2012/0123304 A1 | 5/2012 | Rybyanets et al. |
| 2012/0136280 A1 | 5/2012 | Rosenberg et al. |
| 2012/0136282 A1 | 5/2012 | Rosenberg et al. |
| 2012/0143056 A1 | 6/2012 | Slayton et al. |
| 2012/0143100 A1 | 6/2012 | Jeong et al. |
| 2012/0165668 A1 | 6/2012 | Slayton et al. |
| 2012/0165848 A1 | 6/2012 | Slayton et al. |
| 2012/0191020 A1 | 7/2012 | Vitek et al. |
| 2012/0197120 A1 | 8/2012 | Makin et al. |
| 2012/0197121 A1 | 8/2012 | Slayton et al. |
| 2012/0209150 A1 | 8/2012 | Zeng et al. |
| 2012/0215105 A1 | 8/2012 | Slayton et al. |
| 2012/0271202 A1 | 10/2012 | Wisdom |
| 2012/0271294 A1 | 10/2012 | Barthe et al. |
| 2012/0296240 A1 | 11/2012 | Azhari et al. |
| 2012/0302883 A1 | 11/2012 | Kong et al. |
| 2012/0316426 A1 | 12/2012 | Foley et al. |
| 2012/0330197 A1 | 12/2012 | Makin et al. |
| 2012/0330222 A1 | 12/2012 | Makin et al. |
| 2012/0330223 A1 | 12/2012 | Makin et al. |
| 2012/0330283 A1 | 12/2012 | Hyde et al. |
| 2012/0330284 A1 | 12/2012 | Hyde et al. |
| 2013/0012755 A1 | 1/2013 | Slayton |
| 2013/0012816 A1 | 1/2013 | Slayton et al. |
| 2013/0012838 A1 | 1/2013 | Jaeger et al. |
| 2013/0012842 A1 | 1/2013 | Barthe |
| 2013/0018285 A1 | 1/2013 | Park et al. |
| 2013/0018286 A1 | 1/2013 | Slayton et al. |
| 2013/0046209 A1 | 2/2013 | Slayton et al. |
| 2013/0051178 A1 | 2/2013 | Rybyanets |
| 2013/0060170 A1 | 3/2013 | Lee et al. |
| 2013/0066208 A1 | 3/2013 | Barthe et al. |
| 2013/0066237 A1 | 3/2013 | Smotrich et al. |
| 2013/0072826 A1 | 3/2013 | Slayton et al. |
| 2013/0096471 A1 | 4/2013 | Slayton et al. |
| 2013/0190659 A1 | 7/2013 | Slayton et al. |
| 2013/0211293 A1 | 8/2013 | Auboiroux et al. |
| 2013/0225994 A1 | 8/2013 | Hsu et al. |
| 2013/0268032 A1 | 10/2013 | Neev |
| 2013/0274603 A1 | 10/2013 | Barthe et al. |
| 2013/0281853 A1 | 10/2013 | Slayton et al. |
| 2013/0281891 A1 | 10/2013 | Slayton et al. |
| 2013/0296697 A1 | 11/2013 | Slayton et al. |
| 2013/0296700 A1 | 11/2013 | Slayton et al. |
| 2013/0303904 A1 | 11/2013 | Barthe et al. |
| 2013/0303905 A1 | 11/2013 | Barthe et al. |
| 2013/0310714 A1 | 11/2013 | Eshel et al. |
| 2013/0310863 A1 | 11/2013 | Makin et al. |
| 2013/0345562 A1 | 12/2013 | Barthe et al. |
| 2014/0024974 A1 | 1/2014 | Slayton et al. |
| 2014/0050054 A1 | 2/2014 | Toda et al. |
| 2014/0081300 A1 | 3/2014 | Melodelima et al. |
| 2014/0082907 A1 | 3/2014 | Barthe et al. |
| 2014/0117814 A1 | 5/2014 | Toda et al. |
| 2014/0142430 A1 | 5/2014 | Slayton et al. |
| 2014/0148834 A1 | 5/2014 | Barthe et al. |
| 2014/0180174 A1 | 6/2014 | Slayton et al. |
| 2014/0187944 A1 | 7/2014 | Slayton et al. |
| 2014/0188015 A1 | 7/2014 | Slayton et al. |
| 2014/0188145 A1 | 7/2014 | Slayton et al. |
| 2014/0194723 A1 | 7/2014 | Herzog et al. |
| 2014/0208856 A1 | 7/2014 | Schmid |
| 2014/0221823 A1 | 8/2014 | Keogh et al. |
| 2014/0236049 A1 | 8/2014 | Barthe et al. |
| 2014/0236061 A1 | 8/2014 | Lee et al. |
| 2014/0243713 A1 | 8/2014 | Slayton et al. |
| 2014/0257145 A1 | 9/2014 | Emery |
| 2015/0000674 A1 | 1/2015 | Barthe et al. |
| 2015/0080723 A1 | 3/2015 | Barthe et al. |
| 2015/0080771 A1 | 3/2015 | Barthe et al. |
| 2015/0080874 A1 | 3/2015 | Slayton et al. |
| 2015/0088182 A1 | 3/2015 | Slayton et al. |
| 2015/0164734 A1 | 6/2015 | Slayton et al. |
| 2015/0165238 A1 | 6/2015 | Slayton et al. |
| 2015/0165243 A1 | 6/2015 | Slayton et al. |
| 2015/0174388 A1 | 6/2015 | Slayton |
| 2015/0202468 A1 | 7/2015 | Slayton et al. |
| 2015/0217141 A1 | 8/2015 | Barthe et al. |
| 2015/0360058 A1 | 12/2015 | Barthe et al. |
| 2015/0374333 A1 | 12/2015 | Barthe et al. |
| 2015/0375014 A1 | 12/2015 | Slayton et al. |
| 2016/0027994 A1 | 1/2016 | Toda et al. |

FOREIGN PATENT DOCUMENTS

| | | |
|---|---|---|
| DE | 10140064 A1 | 3/2003 |
| DE | 10219297 | 11/2003 |
| DE | 10219217 | 12/2004 |
| DE | 20314479 | 12/2004 |
| EP | 0142215 | 5/1984 |
| EP | 0344773 A2 | 12/1989 |
| EP | 1479412 A1 | 11/1991 |
| EP | 0473553 | 4/1992 |
| EP | 670147 | 2/1995 |
| EP | 0661029 A1 | 7/1995 |
| EP | 724894 | 2/1996 |
| EP | 763371 | 11/1996 |
| EP | 1044038 | 10/2000 |
| EP | 1050322 A1 | 11/2000 |
| EP | 1234566 | 8/2002 |
| EP | 1262160 | 12/2002 |
| EP | 1283690 | 2/2003 |
| EP | 1374944 | 1/2004 |
| EP | 1028660 | 1/2008 |
| EP | 1874241 | 1/2008 |
| EP | 1362223 | 5/2008 |
| EP | 1750804 | 7/2008 |
| EP | 1811901 | 4/2009 |
| EP | 1785164 | 8/2009 |
| EP | 2230904 | 9/2010 |
| EP | 1501331 | 6/2011 |
| EP | 2066405 | 11/2011 |
| EP | 2474050 | 7/2012 |
| FR | 2532851 | 9/1983 |
| FR | 2685872 | 1/1992 |
| FR | 2672486 | 8/1992 |
| FR | 2703254 | 3/1994 |
| GB | 2113099 | 8/1983 |
| IL | 102516 | 1/1996 |
| IL | 112369 | 8/1999 |
| IL | 120079 | 3/2001 |
| JP | 63036171 | 2/1988 |
| JP | 03048299 | 3/1991 |
| JP | 3123559 | 5/1991 |
| JP | 03136642 | 6/1991 |
| JP | 4089058 | 3/1992 |
| JP | 4-150847 | 5/1992 |
| JP | 04150847 | 5/1992 |
| JP | 7080087 | 3/1995 |
| JP | 07505793 | 6/1995 |
| JP | 2007505793 | 6/1995 |
| JP | 7184907 | 7/1995 |
| JP | 7222782 | 8/1995 |
| JP | 09047458 | 2/1997 |
| JP | 9108288 | 4/1997 |
| JP | 9503926 | 4/1997 |
| JP | 11-505440 | 5/1999 |
| JP | 11123226 | 5/1999 |
| JP | 11-506636 | 6/1999 |
| JP | 2000166940 | 6/2000 |
| JP | 2001170068 | 6/2001 |
| JP | 2002505596 | 2/2002 |
| JP | 2002078764 | 3/2002 |
| JP | 2002515786 | 5/2002 |
| JP | 2002521118 | 7/2002 |
| JP | 2002-537939 | 11/2002 |
| JP | 2003050298 | 7/2003 |

(56) References Cited

FOREIGN PATENT DOCUMENTS

| | | |
|---|---|---|
| JP | 2003204982 | 7/2003 |
| JP | 2004-507280 | 3/2004 |
| JP | 2004-509671 | 4/2004 |
| JP | 2004-512856 | 4/2004 |
| JP | 2004-147719 | 5/2004 |
| JP | 2005503388 | 2/2005 |
| JP | 2005527336 | 9/2005 |
| JP | 2005323213 | 11/2005 |
| JP | 2006520247 | 9/2006 |
| JP | 2008515559 | 5/2008 |
| JP | 2009518126 | 5/2009 |
| JP | 2010517695 | 5/2010 |
| KR | 1020010024871 | 3/2001 |
| KR | 100400870 | 10/2003 |
| KR | 1020060113930 | 11/2006 |
| KR | 1020070065332 | 6/2007 |
| KR | 1020070070161 | 7/2007 |
| KR | 1020070098856 | 10/2007 |
| KR | 1020070104878 | 10/2007 |
| KR | 1020070114105 | 11/2007 |
| KR | 1020000059516 | 4/2012 |
| WO | WO93/12742 | 7/1993 |
| WO | WO95/24159 | 9/1995 |
| WO | WO 96/25888 | 8/1996 |
| WO | WO9634568 | 11/1996 |
| WO | WO 96/39079 | 12/1996 |
| WO | WO 9735518 | 10/1997 |
| WO | WO 9832379 | 7/1998 |
| WO | WO9852465 | 11/1998 |
| WO | WO 9933520 | 7/1999 |
| WO | WO 9949788 | 10/1999 |
| WO | WO 0006032 | 2/2000 |
| WO | WO 0015300 | 3/2000 |
| WO | WO 0021612 | 4/2000 |
| WO | WO 0053113 | 9/2000 |
| WO | WO 0128623 | 4/2001 |
| WO | WO0145550 | 6/2001 |
| WO | WO0180709 | 11/2001 |
| WO | WO 0182777 | 11/2001 |
| WO | WO 0182778 | 11/2001 |
| WO | WO 0187161 | 11/2001 |
| WO | WO0187161 | 11/2001 |
| WO | WO 0209813 | 2/2002 |
| WO | WO0215768 | 2/2002 |
| WO | WO 0224050 | 3/2002 |
| WO | WO02054018 | 7/2002 |
| WO | WO 02092168 | 11/2002 |
| WO | WO 03/053266 | 7/2003 |
| WO | WO 03065347 | 8/2003 |
| WO | WO 03070105 | 8/2003 |
| WO | WO 03077833 | 9/2003 |
| WO | WO 03086215 | 10/2003 |
| WO | WO 03/096883 A2 | 11/2003 |
| WO | WO 03/099382 | 12/2003 |
| WO | WO 03099177 | 12/2003 |
| WO | WO 03101530 | 12/2003 |
| WO | WO 2004000116 | 12/2003 |
| WO | WO 2004080147 | 9/2004 |
| WO | WO 2004110558 | 12/2004 |
| WO | WO 2005011804 | 2/2005 |
| WO | WO 2005065408 | 7/2005 |
| WO | WO 2005090978 | 9/2005 |
| WO | WO2005113068 | 12/2005 |
| WO | WO 2006036870 | 4/2006 |
| WO | WO 2006042163 | 4/2006 |
| WO | WO 2006042168 | 4/2006 |
| WO | WO 2006042201 | 4/2006 |
| WO | WO 2006065671 | 6/2006 |
| WO | WO 2006082573 | 8/2006 |
| WO | WO 2007067563 | 6/2007 |
| WO | WO 2008036622 | 3/2008 |
| WO | WO2008036479 | 11/2008 |
| WO | WO2008144274 | 11/2008 |
| WO | WO 2009013729 | 1/2009 |
| WO | WO2009/149390 | 10/2009 |
| WO | WO2012134645 | 10/2012 |
| WO | WO2014045216 | 3/2014 |
| WO | WO2014/055708 | 4/2014 |
| WO | WO2014057388 | 4/2014 |

OTHER PUBLICATIONS

Alster, Tinas S., Tanzi, Elizabeth L., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.

Arthur et al., "Non-invasive estimation of hyperthermia temperatures with ultrasound," Int. J. Hyperthermia, Sep. 2005, 21(6), pp. 589-600.

Barthe et al., "Ultrasound therapy system and ablation results utilizing miniature imaging/therapy arrays," Ultrasonics Symposium, 2004 IEEE, Aug. 23, 2004, pp. 1792-1795, vol. 3.

Chen, L. et al., "Effect of Blood Perfusion on the ablation of liver parenchyma with high intensity focused ultrasound," Phys. Med. Biol; 38:1661-1673; 1993b.

Coon, Joshua et al., "Protein identification using sequential ion/ion reactions and tandem mass spectrometry" Proceedings of the National Academy of Sciences of the USA, vol. 102, No. 27, Jul. 27, 2005, pp. 9463-9468.

Corry, Peter M., et al., "Human Cancer Treatment with Ultrasound", IEEE Transactions on Sonics and Ultrasonics, vol. SU-31, No. 5, Sep. 1984, pp. 444, 456.

Damianou et al., "Application of the Thermal Dose Concept for Predicting the Necrosed Tissue Volume During Ultrasound Surgery," 1993 IEEE Ultrasound Symposium, pp. 1199-1202.

Daum et al., Design and Evaluation of a Feedback Based Phased Array System for Ultrasound Surgery, IEEE Transactions on Ultrasonics, Ferroelectrics, and Frequency Control, vol. 45, No. 2, Mar. 1998, pp. 431-438.

Davis, Brian J., et al., "An Acoustic Phase Shift Technique for the Non-Invasive Measurement of Temperature Changes in Tissues", 1985 Ultrasonics Symposium, pp. 921-924.

Decision of the Korean Intellectual Property Tribunal dated Jun. 28, 2013 regarding Korean Patent No. 10-1142108, which is related to the pending application and/or an application identified in the Table on pp. 1-4 of the Information Disclosure Statement herein (English translation, English translation certification, and Korean decision included).

Fry, W.J. et al., "Production of Focal Destructive Lesions in the Central Nervous System with Ultrasound," J. Neurosurg., 11:471-478; 1954.

Gliklich et al., Clinical Pilot Study of Intense Ultrasound therapy to Deep Dermal Facial Skin and Subcutaneous Tissues, Arch Facial Plastic Surgery, Mar. 1, 2007, vol. 9, No. 1.

Haar, G.R. et al., "Tissue Destruction with Focused Ultrasound in Vivo," Eur. Urol. 23 (suppl. 1):8-11; 1993.

Hassan et al., "Structure and Applications of Poly(vinyl alcohol) Hydrogels Produced by Conventional Crosslinking or by Freezing/Thawing Methods," advanced in Polymer Science, 2000, pp. 37-65, vol. 153.

Hassan et al., "Structure and Morphology of Freeze/Thawed PVA Hydrogels," Macromolecules, Mar. 11, 2000, pp. 2472-2479, vol. 33, No. 7.

Husseini et al, "The Role of Cavitation in Acoustically Activated Drug Delivery," J. Control Release, Oct. 3, 2005, pp. 253-261, vol. 107(2).

Husseini et al. "Investigating the mechanism of acoustically activated uptake of drugs from Pluronic micelles," BMD Cancer 2002, 2:20k, Aug. 30, 2002, pp. 1-6.

Jeffers et al., "Evaluation of the Effect of Cavitation Activity on Drug-Ultrasound Synergisms," 1993 IEEE Ultrasonics Symposium, pp. 925-928.

Jenne, J., et al., "Temperature Mapping for High Energy US-Therapy", 1994 Ultrasonics Symposium, pp. 1879-1882.

Johnson, S.A., et al., "Non-Intrusive Measurement of Microwave and Ultrasound-Induced Hyperthermia by Acoustic Temperature Tomography", Ultrasonics Symposium Proceedings, pp. 977-982. (1977).

(56) References Cited

OTHER PUBLICATIONS

Madersbacher, S. et al., "Tissue Ablation in Benign Prostatic Hyperplasia with High Intensity Focused Ultrasound," Dur. Urol., 23 (suppl. 1):39-43; 1993.
Makin et al, "B-Scan Imaging and Thermal Lesion Monitoring Using Miniaturized Dual-Functionality Ultrasound Arrays," Ultrasonics Symposium, 2004 IEEE, Aug. 23, 2004, pp. 1788-1791, vol. 3.
Makin et al, "Confirmed Bulk Ablation and Therapy Monitoring Using Intracorporeal Image-Treat Ultrasound Arrays," 4th International Symposium on Therapeutic Ultrasound, Sep. 19, 2004.
Makin et al., "Miniaturized Ultrasound Arrays for Interstitial Ablation and Imaging," UltraSound Med. Biol. 2005, Nov. 1, 2005, pp. 1539-1550, vol. 31(11).
Manohar et al, "Photoacoustic mammography laboratory prototype: imaging of breast tissue phantoms," Journal of Biomedical Optics, Nov./Dec. 2004, pp. 1172-1181, vol. 9, No. 6.
Mast et al, "Bulk Ablation of Soft Tissue with Intense Ultrasound; Modeling and Experiments," J. Acoust. Soc. Am., Oct. 1, 2005, pp. 2715-2724, vol. 118(4).
Mitragotri, S., "Healing sound: the use of ultrasound in drug delivery and other therapeutic applications," Nature Reviews; Drug Delivery, pp. 255-260, vol. 4 (Mar. 2005).
Paradossi et al., "Poly(vinyl alcohol) as versatile biomaterial for potential biomedical applications," Journal of Materials Science: Materials in Medicine, 2003, pp. 687-691, vol. 14.
Reid, Gavin, et al., "Tandem Mass spectrometry of ribonuclease A and B: N-linked glycosylation site analysis of whole protein ions," Analytical Chemistry. Feb. 1, 2002, vol. 74, No. 3, pp. 577-583.
Righetti et al, "Elastographic Characterization of HIFU-Induced Lesions in Canine Livers," 1999, Ultrasound in Med & Bio, vol. 25, No. 7, pp. 1099-1113.
Saad et al., "Ultrasound-Enhanced Effects of Adriamycin Against Murine Tumors," Ultrasound in Med. & Biol. vol. 18, No. 8, pp. 715-723 (1992).
Sanghvi, N.T., et al., "Transrectal Ablation of Prostrate Tissue Using Focused Ultrasound," 1993 Ultrasonics Symposium, IEEE, pp. 1207-1210.
Sassen, Sander, "ATI's R520 architecture, the new king of the hill?" http://www.hardwareanalysis.com/content/article/1813, Sep. 16, 2005, 2 pages.
Seip, Ralf, et al., "Noninvasive Detection of Thermal Effects Due to Highly Focused Ultrasonic Fields," IEEE Symposium, pp. 1229-1232, vol. 2, Oct. 3-Nov. 1993.
Seip, Ralf, et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.
Simon et al., "Applications of Lipid-Coated Microbubble Ultrasonic Contrast to Tumor Therapy," Ultrasound in Med. & Biol. vol. 19, No. 2, pp. 123-125 (1993).
Smith, Nadine Barrie, et al., "Non-invasive In Vivo Temperature Mapping of Ultrasound Heating Using Magnetic Resonance Techniques", 1994 Ultrasonics Symposium, pp. 1829-1832, vol. 3.
Surry et al., "Poly(vinyl alcohol) cryogel phantoms for use in ultrasound and MR imaging," Phys. Med. Biol., Dec. 6, 2004, pp. 5529-5546, vol. 49.
Syka J. E. P. et al., "Peptide and Protein Sequence Analysis by Electron Transfer Dissociation Mass Spectrometry," Proceedings of the National Academy of Sciences of USA, National Academy of Science, Washington, DC, vol. 101, No. 26, Jun. 29, 2004, pp. 9528-9533.
Talbert, D. G., "An Add-On Modification for Linear Array Real-Time Ultrasound Scanners to Produce 3D Displays," UTS Int'l 1977 Brighton, England (Jun. 28-30, 1977) pp. 57-67.
Tata et al., "Interaction of Ultrasound and Model Membrane Systems: Analyses and Predictions," American Chemical Society, Phys. Chem. 1992, 96, pp. 3548-3555.
Ueno, S., et al., "Ultrasound Thermometry in Hyperthermia", 1990 Ultrasonic Symposium, pp. 1645-1652.
Wang, H., et al., "Limits on Focused Ultrasound for Deep Hyperthermia", 1994 Ultrasonic Symposium, Nov. 1-4, 1994, pp. 1869-1872, vol. 3.
Wasson, Scott, "NVIDIA's GeForce 7800 GTX graphics processor Power MADD," http://techreport.com/reviews/2005q2/geforce-7800gtx/index.x?pg=1, Jun. 22, 2005, 4 pages.
White et al "Selective Creating of Thermal Injury Zones in the Superficial Musculoaponeurotic System Using Intense Ultrasound Therapy," Arch Facial Plastic Surgery, Jan./Feb. 2007, vol. 9, No. 1.
Chapelon et al., "Effects of Cavitation in the High Intensity Therapeutic Ultrasound", Ultrasonics Symposium—1357 (1991).
Chapelon, et al., "Thresholds for Tissue Ablation by Focused Ultrasound" (1990).
Fujimoto, et al., "A New Cavitation Suppression Technique for Local Ablation Using High-Intensity Focused Ultrasound" Ultrasonics Symposium—1629 (1995).
Hynynen et al., Temperature Distributions During Local Ultrasound Induced Hyperthermia In Vivo, Ultrasonics Symposium—745 (1982).
Agren, Magnus S. et al., Collagenase in Wound Healing: Effect of Wound Age and Type. The Journal of Investigative Dermatology, vol. 99/No. 6, (Dec. 1992).
Alam, M., "The future of noninvasive procedural dermatology". Semin Cutan Med Surg. Mar. 2013; 32(1):59-61.
Alam, M., et al., "Ultrasound tightening of facial and neck skin: a rater-blinded prospective cohort study". J Am Acad Dermatol, 2010. 62(2): p. 262-9.
Alexiades-Armenakas, M., "Ultrasound Technologies for Dermatologic Techniques". J Drugs Derm. 2014. 12 (11): p. 1305.
Alster, T.S., et. al., "Noninvasive lifting of arm, thigh, and knee skin with transcutaneousintense focused ultrasound". Dermatol Surg, 2012. 38(5): p. 754-9.
Arosarena, O., "Options and Challenges for Facial Rejuvenation in Patients With Higher Fitzpatrick Skin Phototypes". JAMA Facial Plastic Surgery, 2015.
Bozec, Laurent et al., Thermal Denaturation Studies of Collagen by Microthermal Analysis and Atomic Force Microscopy, Biophysical Journal, vol. 101, pp. 228-236. (Jul. 2001).
Brobst, R.W., et. al., "Noninvasive Treatment of the Neck". Facial Plast Surg Clin North Am, 2014. 22(2): p. 191-202.
Brobst, R.W., et., al., "Ulthera: initial and six month results". Facial Plast Surg Clin North Am, 2012. 20(2): p. 163-76.
Casabona, G., et. al., "Microfocused Ultrasound With Visualization and Fillers for Increased Neocollagenesis: Clinical and Histological Evaluation". Dermatol Surg 2014;40:S194-S198.
Chan, N.P., et al., "Safety study of transcutaneous focused ultrasound for non-invasive skin tightening in Asians". Lasers Surg Med, 2011. 43(5): p. 366-75.
Dayan, S.H., et al., "Prospective, Multi-Center, Pivotal Trial Evaluating the Safety and Effectiveness of Micro-Focused Ultrasound with Visualization (MFU-V) for Improvement in Lines and Wrinkles of the Décolletage". Plast Reconstr Surg. Oct. 2014; 134(4 Suppl 1):123-4.
Dierickx, Christine C., "The Role of Deep Heating for Noninvasive Skin Rejuvenation" Lasers in Surgery and Medicine 38:799-807 (2006).
Dobke, M.K., et al., "Tissue restructuring by energy-based surgical tools". Clin Plast Surg, 2012. 39(4): p. 399-408.
Dong, Yuan-Lin et al., "Effect of Ibuprofen on the Inflammatory Response to Surgical Wounds" The Journal of Trauma, vol. 35, No. 3. (1993).
Dvivedi, Sanjay, et al. "Effect of Ibuprofen and diclofenac sodium on experimental wound healing" Indian Journal of Experimental Biology, vol. 35, pp. 1243-1245. (Nov. 1997).
Fabi, S.G., "Microfocused Ultrasound With Visualization for Skin Tightening and Lifting: My Experience and a Review of the Literature". Dermatol Surg. Dec. 2014; 40 Suppl 12:S164-7.
Fabi, S.G., "Noninvasive skin tightening: focus on new ultrasound techniques". Clin Cosmet Investig Dermatol. Feb. 5, 2015; 8:47-52.
Fabi, S.G., et. al., "A prospective multicenter pilot study of the safety and efficacy of microfocused ultrasound with visualization for improving lines and wrinkles of the décolleté". Dermatol Surg. Mar. 2015; 41(3):327-35.

(56) References Cited

OTHER PUBLICATIONS

Fabi, S.G., et. al., "Evaluation of microfocused ultrasound with visualization for lifting, tightening, and wrinkle reduction of the decolletage". J Am Acad Dermatol, 2013. 69(6): p. 965-71.
Fabi, S.G., et. al., "Future directions in cutaneous laser surgery". Dermatol Clin, 2014. 32(1): p. 61-9.
Fabi, S.G., et al., "Retrospective Evaluation of Micro-focused Ultrasound for Lifting and Tightening the Face and Neck". Dermatol Surg, 2014.
Friedmann D.P., "Comments on evaluation of microfocused ultrasound system for improving skin laxity and tightening in the lower face". Aesthet Surg J. Mar. 2015;35(3):NP81-2.
Friedmann, D.P., et. al., "Combination of intense pulsed light, Sculptra, and Ultherapy for treatment of the aging face". J Cosmet Dermatol, 2014. 13(2): p. 109-18.
Gold, M.H., et. al., "Use of Micro-Focused Ultrasound with Visualization to Lift and Tighten Lax Knee Skin". J Cosmet Laser Ther, 2014: p. 1-15.
Goldberg, D.J., et. al., "Safety and Efficacy of Microfocused Ultrasound to Lift, Tighten, and Smooth the Buttocks". Dermatol Surg 2014; 40:1113-1117.
Greene, R.M., et al., "Skin tightening technologies". Facial Plast Surg. Feb. 2014; 30(1):62-7.
Greenhalgh, David G., "Wound healing and diabetes mellitus" Clinics in Plastic Surgery 30; 37-45. (2003).
Guo, S. et al., "Factors Affecting Wound Healing" Critical Reviews in Oral Biology & Medicine, J Dent Res 89(3), pp. 219-229. (2010).
Hantash, Basil M. et al., "Bipolar Fractional Radiofrequency Treatment Induces Neoelastogenesis and Neocollagenesis" Lasers in Surgery and Medicine 41:1-9 (2009).
Hantash, Basil M. et al., "In Vivo Histological Evaluation of a Novel Ablative Fractional Resurfacing Device" Lasers in Surgery and Medicine 39:96-107 (2007).
Harris, M.O., "Safety of Microfocused Ultrasound With Visualization in Patients With Fitzpatrick Skin Phototypes III to VI". JAMA Facial Plast. Surg, 2015.
Hart, et. al., "Current Concepts in the Use of PLLA:Clinical Synergy Noted with Combined Use of Microfocused Ultrasound and Poly-l-Lactic Acid on the Face, Neck, and Décolletage". Amer. Soc. Plast. Surg. 2015. 136; 180-187S.
Hitchcock, T.M. et al., "Review of the safety profile for microfocused ultrasound with Visualization". Journal of Cosmetic Dermatology, 13, 329-335. (2014).
Jeong, K.H., et al., "Neurologic complication associated with intense focused ultrasound". J Cosmet Laser Ther, 2013.
Kim, H.J., et al., "Coagulation and ablation patterns of high-intensity focused ultrasound on a tissue mimicking phantom and cadaveric skin". Laser Med Sci. Sep. 4, 2015.
Kornstein, A.N., "Ulthera for silicone lip correction". Plast Reconstr Surg, 2012. 129(6): p. 1014e-1015e.
Kornstein, A.N., "Ultherapy shrinks nasal skin after rhinoplasty following failure of conservative measures". Plast Reconstr Surg, 2013. 131(4): p. 664e-6e.
Krischak, G.D., et al., "The effects of non-steroidal anti-inflammatory drug application on incisional wound healing in rats" Journal of Wound Care, vol. 6, No. 2, (Feb. 2007).
Laubach, H.J., et. al., "Confined Thermal Damage with Intense Ultrasound (IUS)" [abstr.] American Society for Laser Medicine and Surgery Abstracts, p. 15 #43 (Apr. 2006).
Laubach, H.J., et. al., "Intense focused ultrasound: evaluation of a new treatment modality for precise microcoagulation within the skin". Dermatol Surg, 2008. 34(5): p. 727-34.
Lee, H.J., et. al., "The efficacy and safety of intense focused ultrasound in the treatment of enlarged facial pores in Asian skin". J Dermatolog Treat, 2014.
Lee, H.S., et. al., "Multiple Pass Ultrasound Tightening of Skin Laxity of the Lower Face and Neck". Dermatol Surg, 2011.
Lin, Sung-Jan, et al., "Monitoring the thermally induced structural transitions of collagen by use of second-harmonic generation microscopy" Optics Letters, vol. 30, No. 6, (Mar. 15, 2005).

MacGregor J.L., et. al., "Microfocused Ultrasound for Skin Tightening". Semin Cutan Med Surg 32:18-25. (2013).
Meshkinpour, Azin, et al., "Treatment of Hypertrophic Scars and Keloids With a Radiofrequency Device: A Study of Collagen Effects" Lasers in Surgery and Medicine 37:343-349 (2005).
Minkis, K., et. al., "Ultrasound skin tightening". Dermatol Clin, 2014. 32(1): p. 71-7.
Mosser, David M. et al., "Exploring the full spectrum of macrophage activation" Nat Rev Immunol; 8(12): 958-969. (Dec. 2008).
Murota, SEI-ITSU, et al., "Stimulatory Effect of Prostaglandins on the Production of Hexosamine-Containing Substances by Cultured Fibroblasts (3) Induction of Hyaluronic Acid Synthetase by Prostaglandin" Department of Pharmacology, Tokyo Metropolitan Institute of Gerontology, Itabashiku, Tokyo-173, Japan. (Nov. 1977, vol. 14, No. 5).
Murota, SEI-ITSU, et al., "The Stimulatory Effect of Prostaglandins on Production of Hexosamine-Containing Substances by Cultured Fibroblasts" Department of Pharmacology, Tokyo Metropolitan Institute of Gerontology, Itabashiku, Tokyo-173, Japan. (Aug. 1976, vol. 12, No. 2).
Nestor, M.S. et. al., "Safety and Efficacy of Micro-focused Ultrasound Plus Visualization for the Treatment of Axillary Hyperhidrosis". J Clin Aesthet Dermatol, 2014. 7(4): p. 14-21.
Oni, G., et. al. "Response to 'comments on evaluation of microfocused ultrasound system for improving skin laxity and tightening in the lower face'". Aesthet Surg J. Mar. 2015;35(3):NP83-4.
Oni, G., et. al., "Evaluation of a Microfocused Ultrasound System for Improving Skin Laxity and Tightening in the Lower Face". Aesthet Surg J, 2014. 38:861-868.
Pak, C.S., et. al., "Safety and Efficacy of Ulthera in the Rejuvenation of Aging Lower Eyelids: A Pivotal Clinical Trial". Aesthetic Plast Surg, 2014.
Pritzker, R.N., et. al, "Updates in noninvasive and minimally invasive skin tightening". Semin Cutan Med Surg. Dec. 2014;33(4):182-7.
Pritzker, R.N., et. al., "Comparison of different technologies for noninvasive skin tightening". Journal of Cosmetic Dermatology, 13, 315-323. (2014).
Rappolee, Daniel A., et al., "Wound Macrophages Express TGF and Other Growth Factors in Vivo: Analysis by mRNA Phenotyping" Science, vol. 241, No. 4866 (Aug. 1988).
Rokhsar, C., et. al., "Safety and efficacy of microfocused ultrasound in tightening of lax elbow skin". Dermatol Surg. 2015; 41(7):821-6.
Rosenberg, Carol S. "Wound Healing in the Patient with Diabetes Mellitus" Nursing Clinics of North America, vol. 25, No. 1, (Mar. 1990).
Sabet-Peyman, E.J. et. al., "Complications Using Intense Ultrasound Therapy to TreatDeep Dermal Facial Skin and Subcutaneous Tissues". Dermatol Surg 2014; 40:1108-1112.
Sandulache, Vlad C. et al., "Prostaglandin E2 inhibition of keloid fibroblast migration, contraction, and transforming growth factor (TGF)-B1-induced collagen synthesis" Wound Rep Reg 15 122-133, 2007. (2007).
Sasaki, G.H. et. al., "Clinical Efficacy and Safety of Focused-Image Ultrasonography: A 2-Year Experience". Aesthet Surg J, 2012.
Sasaki, G.H. et. al., "Microfocused Ultrasound for Nonablative Skin and Subdermal Tightening to the Periorbitum and Body Sites: Preliminary Report on Eighty-Two Patients". Journal of Cosmetics, Dermatological Sciences and Applications, 2012, 2, 108-116.
Sklar, L.R., et. al., "Use of transcutaneous ultrasound for lipolysis and skin tightening: a review". Aesthetic Plast Surg, 2014. 38(2): p. 429-41.
Suh, D.H., et. al., "A intense-focused ultrasound tightening for the treatment of infraorbital laxity". J Cosmet Laser Ther, 2012. 14(6): p. 290-5.
Suh, D.H., et. al., "Comparative histometric analysis of the effects of high-intensity focused ultrasound and radiofrequency on skin". J Cosmet Laser Ther. Mar. 24, 2015:1-7.
Suh, D.H., et. al., "Intense Focused Ultrasound Tightening in Asian Skin: Clinical and Pathologic Results" American Society for Dermatologic Surgery, Inc.; 37:1595-1602. (2011).

(56) References Cited

OTHER PUBLICATIONS

Suh, D.H., et. al., "Intense focused ultrasound tightening in asian skin: clinical and pathologic results". Dermatol Surg, 2011. 37(11): p. 1595-602.
Verhofstad, Michiel H.J. et al., "Collagen Synthesis in rat skin and ileum fibroblasts is affected differently by diabetes-related factors" Int. J. Exp. Path. (1998), 79, 321-328.
Weiss, M., "Commentary: noninvasive skin tightening: ultrasound and other technologies: where are we in 2011?" Dermatol Surg, 2012. 38(1): p. 28-30.
White, W. M., et al., "Selective Transcutaneous Delivery of Energy to Facial Subdermal Tissues Using the Ultrasound Therapy System" [abstr]. American Society for Laser Medicine and Surgery Abstracts, p. 37 #113 (Apr. 2006).
White, W. Matthew, et al., "Selective Transcutaneous Delivery of Energy to Porcine Soft Tissues Using Intense Ultrasound (IUS)" Lasers in Surgery and Medicine 40:67-75 (2008).
Woodward, J.A., et. al. "Safety and Efficacy of Combining Microfocused Ultrasound With Fractional CO2 Laser Resurfacing for Lifting and Tightening the Face and Neck". Dermatol Surg, Dec. 2014 40:S190-S193.
Zelickson, Brian D. et al., "Histological and Ultrastructural Evaluation of the Effects of a Radiofrequency-Based Nonablative Dermal Remodeling Device, A Pilot Study" Arch Dermatol, vol. 140, (Feb. 2004).
U.S. Appl. No. 12/966,616, filed Jan. 12, 2011, Hand Wand for Ultrasonic Cosmetic Treatment and Imaging.
U.S. Appl. No. 13/245,822, filed Sep. 26, 2011, System and Method for Cosmetic Treatment.
U.S. Appl. No. 13/245,852, filed Sep. 26, 2011, Systems for Cosmetic Treatment.
U.S. Appl. No. 13/245,864, filed Sep. 27, 2011, Methods for Non-Invasive Cosmetic Treatment of the Eye Region.
U.S. Appl. No. 13/246,117, filed Sep. 27, 2011, Methods for Non-Invasive Lifting and Tightening of the Lower Face and Neck.
U.S. Appl. No. 13/246,112, filed Sep. 27, 2011, Tissue Imaging and Treatment Method.
U.S. Appl. No. 14/193,234, filed Feb. 28, 2014, Devices and Methods for Multi-Focus Ultrasound Therapy.
U.S. Appl. No. 08/950,353, filed Oct. 14, 1997, Imaging, Therapy and Temperature Monitoring Ultrasonic System.
U.S. Appl. No. 09/502,174, filed Feb. 10, 2000, Imaging, Therapy and Temperature Monitoring Ultrasonic System.
U.S. Appl. No. 10/193,419, filed Jul. 10, 2002, Imaging, Therapy and Temperature Monitoring Ultrasonic System.
U.S. Appl. No. 10/944,499, filed Sep. 16, 2004, Method and System for Ultrasound Treatment With a Multi-Directional Transducer.
U.S. Appl. No. 11/163,177, filed Oct. 7, 2005, Method and System for Treating Acne and Sebaceous Glands.
U.S. Appl. No. 10/950,112, filed Sep. 24, 2004, Method and System for Combined Ultrasound Treatment.
U.S. Appl. No. 11/163,178, filed Oct. 7, 2005, Method and System for Treating Stretch Marks.
U.S. Appl. No. 11/245,999, filed Oct. 6, 2005, System and Method for Ultra-High Frequency Ultrasound Treatment.
U.S. Appl. No. 10/944,500, filed Sep. 16, 2004, System and Method for Variable Depth Ultrasound Treatment.
U.S. Appl. No. 11/744,655, filed May 4, 2007, Imaging, Therapy and Temperature Monitoring Ultrasonic System.
U.S. Appl. No. 13/937,190, filed Jul. 8, 2013, Imaging, Therapy and Temperature Monitoring Ultrasonic System.
U.S. Appl. No. 12/135,962, filed Jun. 9, 2008, Method and System for Ultrasound Treatment With a Multi-Directional Transducer.
U.S. Appl. No. 12/792,934, filed Jun. 3, 2010, System and Method for Ultra-High Frequency Ultrasound Treatment.
U.S. Appl. No. 13/914,945, filed Jun. 11, 2013, System and Method for Ultra-High Frequency Ultrasound Treatment.
U.S. Appl. No. 12/834,754, filed Jul. 12, 2010, System and Method for Variable Depth Ultrasound Treatment.
U.S. Appl. No. 14/264,732, filed Apr. 29, 2014, System and Method for Variable Depth Ultrasound Treatment.
U.S. Appl. No. 11/126,760, filed May 11, 2005, Method and System for Three-Dimensional Scanning and Imaging.
U.S. Appl. No. 13/564,552, filed Aug. 1, 2012, Method and System for Controlled Scanning, Imaging and/or Therapy.
U.S. Appl. No. 12/437,726, filed May 8, 2009, Method and System for Combined Ultrasound Treatment.
U.S. Appl. No. 11/163,148, filed Oct. 6, 2005, Method and System for Controlled Thermal Injury of Human Superficial Tissue.
U.S. Appl. No. 13/444,688, filed Apr. 11, 2012, Customized Cosmetic Treatment.
U.S. Appl. No. 11/163,152, filed Oct. 6, 2005, Method and System for Treatment of Sweat Glands.
U.S. Appl. No. 13/444,485, filed Apr. 11, 2012, Methods for Treatment of Sweat Glands.
U.S. Appl. No. 13/603,159, filed Sep. 4, 2012, Methods for Treatment of Hyperhidrosis.
U.S. Appl. No. 13/603,279, filed Sep. 4, 2012, Energy Based Hyperhidrosis Treatment.
U.S. Appl. No. 13/950,728, filed Jul. 25, 2013, Energy Based Hyperhidrosis Treatment.
U.S. Appl. No. 14/571,835, filed Dec. 16, 2014, Energy Based Hyperhidrosis Treatment.
U.S. Appl. No. 11/163,151, filed Oct. 6, 2005, Method and System for Noninvasive Face Lifts and Deep Tissue Tightening.
U.S. Appl. No. 13/444,336, filed Apr. 11, 2012, Treatment of Sub-Dermal Regions for Cosmetic Effects.
U.S. Appl. No. 13/679,430, filed Nov. 16, 2012, Ultrasound Treatment of Sub-Dermal Tissue for Cosmetic Effects.
U.S. Appl. No. 13/924,376, filed Jun. 21, 2013, Noninvasive Tissue Tightening for Cosmetic Effects.
U.S. Appl. No. 13/924,355, filed Jun. 21, 2013, Noninvasive Aesthetic Treatment for Tightening Tissue.
U.S. Appl. No. 13/924,323, filed Jun. 21, 2013, Energy-Based Tissue Tightening.
U.S. Appl. No. 14/200,852, filed Mar. 7, 2014, Noninvasive Tissue Tightening System.
U.S. Appl. No. 14/200,961, filed Mar. 7, 2014, Energy-Based Tissue Tightening System.
U.S. Appl. No. 12/028,636, filed Feb. 8, 2008, Method and System for Noninvasive Face Lifts and Deep Tissue Tightening.
U.S. Appl. No. 13/964,820, filed Aug. 12, 2013, Methods for Noninvasive Skin Tightening.
U.S. Appl. No. 14/201,256, filed Mar. 7, 2014, System for Noninvasive Skin Tightening.
U.S. Appl. No. 15/098,139, filed Apr. 13, 2016, System and Method for Noninvasive Skin Tightening.
U.S. Appl. No. 14/685,390, filed Apr. 13, 2015, Energy-Based Tissue Tightening System.
U.S. Appl. No. 11/163,150, filed Oct. 6, 2005, Method and System for Photoaged Tissue.
U.S. Appl. No. 13/230,498, filed Sep. 12, 2011, Method and System for Photoaged Tissue.
U.S. Appl. No. 14/169,709, filed Jan. 31, 2014, Methods for Treating Skin Laxity.
U.S. Appl. No. 14/692,114, filed Apr. 21, 2015, Systems for Treating Skin Laxity.
U.S. Appl. No. 11/163,176, filed Oct. 7, 2005, Method and System for Treating Blood Vessel Disorders.
U.S. Appl. No. 13/601,742, filed Aug. 31, 2012, Method and System for Treating Blood Vessel Disorders.
U.S. Appl. No. 12/574,512, filed Oct. 6, 2009, Method and System for Treating Stretch Marks.
U.S. Appl. No. 14/554,668, filed Nov. 26, 2014, Method and System for Treating Stretch Marks.
U.S. Appl. No. 11/857,989, filed Sep. 19, 2007, Method and System for Treating Muscle, Tendon, Ligament and Cartilage Tissue.
U.S. Appl. No. 13/494,856, filed Jun. 12, 2012, Method and System for Treating Muscle, Tendon, Ligament and Cartilage Tissue.
U.S. Appl. No. 13/835,635, filed Mar. 15, 2013, Methods for Face and Neck Lifts.

(56) References Cited

OTHER PUBLICATIONS

U.S. Appl. No. 13/965,741, filed Aug. 13, 2013, Methods for Preheating Tissue for Cosmetic Treatment of the Face and Body.
U.S. Appl. No. 14/740,092, filed Jun. 15, 2015, Methods for Rejuvenating Skin by Heating Tissue for Cosmetic Treatment of the Face and Body.
U.S. Appl. No. 14/628,198, filed Feb. 20, 2015, System and Method for Treating Cartilage and Injuries to Joints and Connective Tissue.
U.S. Appl. No. 14/554,571, filed Nov. 26, 2014, Methods for Face and Neck Lifts.
U.S. Appl. No. 12/954,484, filed Nov. 24, 2010, Methods and Systems for Generating Thermal Bubbles for Improved Ultrasound Imaging and Therapy.
U.S. Appl. No. 12/350,383, filed Jan. 8, 2009, Method and System for Treating Acne and Sebaceous Glands.
U.S. Appl. No. 12/116,845, filed May 7, 2008, Method and System for Combined Energy Profile.
U.S. Appl. No. 14/643,749, filed Mar. 10, 2015, Method and System for Combined Energy Profile.
U.S. Appl. No. 08/766,083, filed Dec. 16, 1996, Method and Apparatus for Surface Ultrasound Imaging.
U.S. Appl. No. 09/113,227, filed Jul. 10, 1998, Method and Apparatus for Three Dimensional Ultrasound Imaging.
U.S. Appl. No. 08/944,261, filed Oct. 6, 1997, Wideband Acoustic Transducer.
U.S. Appl. No. 09/434,078, filed Nov. 5, 1999, Method and Apparatus for Three Dimensional Ultrasound Imaging.
U.S. Appl. No. 09/523,890, filed Mar. 13, 2000, Method and Apparatus for Three Dimensional Ultrasound Imaging.
U.S. Appl. No. 09/419,543, filed Oct. 18, 1999, Peripheral Ultrasound Imaging System.
U.S. Appl. No. 09/750,816, filed Dec. 28, 2000, Visual Imaging System for Ultrasonic Probe.
U.S. Appl. No. 10/358,110, filed Feb. 4, 2003, Visual Imaging System for Ultrasonic Probe.
U.S. Appl. No. 11/380,161, filed Apr. 25, 2006, Method and System for Enhancing Computer Peripheral Safety.
U.S. Appl. No. 11/554,272, filed Oct. 30, 2006, Visual Imaging System for Ultrasonic Probe.
U.S. Appl. No. 13/071,298, filed Mar. 24, 2011, Visual Imaging System for Ultrasonic Probe.
U.S. Appl. No. 13/854,936, filed Mar. 25, 2013, Visual Imaging System for Ultrasonic Probe.
U.S. Appl. No. 12/509,254, filed Jul. 24, 2009, Method and System for Enhancing Computer Peripheral Safety.
U.S. Appl. No. 13/453,847, filed Apr. 23, 2012, Method and System for Enhancing Computer Peripheral Safety.
U.S. Appl. No. 11/538,794, filed Oct. 4, 2006, Ultrasound System and Method for Imaging and/or Measuring Displacement of Moving Tissue and Fluid.
U.S. Appl. No. 09/502,175, filed Feb. 10, 2000, Method and Apparatus for Safely Delivering Medicants to a Region of Tissue, Using Imaging, Therapy and Temperature Monitoring.
U.S. Appl. No. 08/943,728, filed Oct. 3, 1997, Method and Apparatus for Safely Delivering Medicants to a Region of Tissue Using Ultrasound.
U.S. Appl. No. 12/415,945, filed Mar. 31, 2009, Method and System for Noninvasive Mastopexy.
U.S. Appl. No. 11/163,155, filed Oct. 6, 2005, Method and System for Noninvasive Mastopexy.
U.S. Appl. No. 11/163,154, filed Oct. 6, 2005, Method and System for Treatment of Cellulite.
U.S. Appl. No. 13/356,405, filed Jan. 23, 2012, Method and System for Treatment of Cellulite.
U.S. Appl. No. 13/789,562, filed Mar. 7, 2013, Method and System for Ultrasound Treatment of Fat.
U.S. Appl. No. 14/164,598, filed Jan. 27, 2013, Method for Fat and Cellulite Reduction.
U.S. Appl. No. 14/550,720, filed Nov. 21, 2014, System and Method for Fat and Cellulite Reduction.
U.S. Appl. No. 15/041,829, filed Feb. 11, 2016, System and Method for Fat and Cellulite Reduction.
U.S. Appl. No. 11/738,682, filed Apr. 23, 2007, Method and System for Non-Ablative Acne Treatment and Prevention.
U.S. Appl. No. 12/116,810, filed May 7, 2008, Methods and Systems for Modulating Medicants Using Acoustic Energy.
U.S. Appl. No. 12/116,828, filed May 7, 2008, Methods and Systems for Coupling and Focusing Acoustic Energy Using a Coupler Member.
U.S. Appl. No. 12/646,609, filed Dec. 23, 2009, Methods and System for Fat Reduction and/or Cellulite Treatment.
U.S. Appl. No. 14/192,520, filed Feb. 27, 2014, Energy Based Fat Reduction.
U.S. Appl. No. 14/550,772, filed Nov. 21, 2014, Energy Based Fat Reduction.
U.S. Appl. No. 15/401,804, filed Feb. 11, 2016, Energy Based Fat Reduction.
U.S. Appl. No. 13/291,312, filed Nov. 11, 2011, Devices and Methods for Acoustic Shielding.
U.S. Appl. No. 14/487,504, filed Sep. 16, 2014, Devices and Methods for Acoustic Shielding.
U.S. Appl. No. 13/136,538, filed Aug. 2, 2011, Systems and Methods for Treating Acute and/or Chronic Injuries in Soft Tissue.
U.S. Appl. No. 13/136,542, filed Aug. 2, 2011, System and Method for Treating Cartilage.
U.S. Appl. No. 13/163,541, filed Aug. 2, 2011, Methods and Systems for Treating Plantar Fascia.
U.S. Appl. No. 13/136,544, filed Aug. 2, 2011, Systems and Methods for Ultrasound Treatment.
U.S. Appl. No. 13/547,023, filed Jul. 11, 2012, Systems and Methods for Coupling an Ultrasound Source to Tissue.
U.S. Appl. No. 13/545,931, filed Jul. 10, 2012, Methods and Systems for Controlling Acoustic Energy Deposition Into a Medium.
U.S. Appl. No. 13/545,953, filed Jul. 10, 2012, Systems and Methods for Accelerating Healing of Implanted Material and/or Native Tissue.
U.S. Appl. No. 13/547,011, filed Jul. 11, 2012, Systems and Methods for Monitoring and Controlling Ultrasound Power Output and Stability.
U.S. Appl. No. 13/545,954, filed Jul. 10, 2012, Systems and Methods for Improving an Outside Appearance of Skin Using Ultrasound as an Energy Source.
U.S. Appl. No. 13/545,945, filed Jul. 10, 2012, Systems and Methods for Treating Injuries to Joints and Connective Tissue.
U.S. Appl. No. 13/545,929, filed Jul. 10, 2012, Methods and Systems for Ultrasound Treatment.
U.S. Appl. No. 13/863,249, filed Apr. 15, 2013, Systems for Cosmetic Treatment.
U.S. Appl. No. 13/863,281, filed Apr. 15, 2013, Methods for Non-invasive Cosmetic Treatment.
U.S. Appl. No. 14/847,626, filed Sep. 8, 2015, Systems for Cosmetic Treatment.
U.S. Appl. No. 13/863,362, filed Apr. 15, 2013, Thick Film Transducer Arrays.
U.S. Appl. No. 14,217,110, filed Mar. 17, 2014, Ultrasound Treatment Device and Method of Use.
U.S. Appl. No. 14/217,382, filed Mar. 17, 2014, Ultrasound Treatment Device and Method of Use.
U.S. Appl. No. 14/225,189, filed Mar. 25, 2014, Reflective Ultrasound Technology for Dermatological Treatments.
U.S. Appl. No. 14/270,859, filed May 6, 2014, Methods and Systems for Generating Thermal Bubbles for Improved Ultrasound Imaging and Therapy.
U.S. Appl. No. 14/679,494, filed Apr. 6, 2015, Methods and Systems for Generating Thermal Bubbles for Improved Ultrasound Imaging and Therapy.
U.S. Appl. No. 14/405,368, filed Dec. 3, 2014, Devices and Methods for Ultrasound Focal Depth Control.
U.S. Appl. No. 14/568,954, filed Dec. 12, 2014, System and Method for Cosmetic Enhancement of Lips.
U.S. Appl. No. 14/569,001, filed Dec. 12, 2014, System and Method for Non-Invasive Treatment With Improved Efficiency.

(56) References Cited

OTHER PUBLICATIONS

U.S. Appl. No. 14/600,782, filed Jan. 20, 2015, Methods and Systems for Controlling and Acoustic Energy Deposition in Various Media.
U.S. Appl. No. 14/738,420, filed Jun. 12, 2015, Systems and Methods for Fast Ultrasound Treatment.
U.S. Appl. No. 14/751,349, filed Jun. 26, 2015, Methods and Systems for Tattoo Removal.

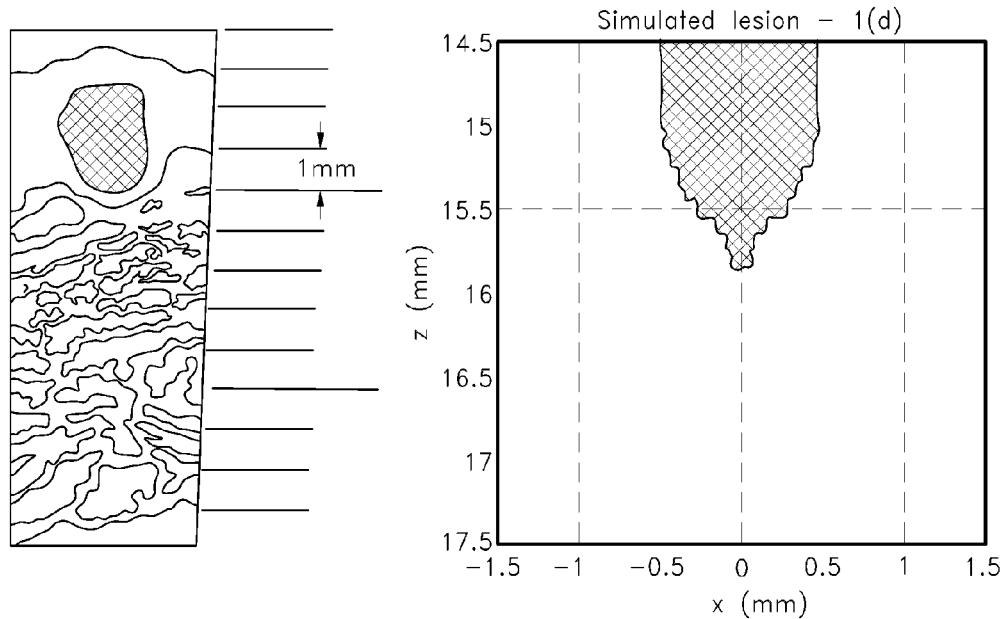
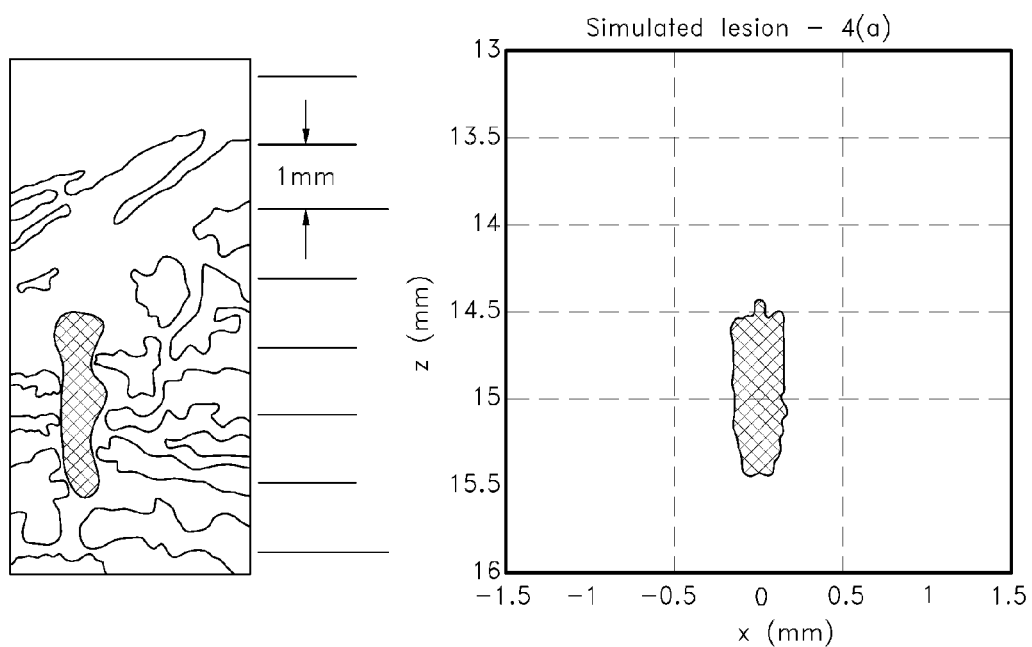
FIG. 38

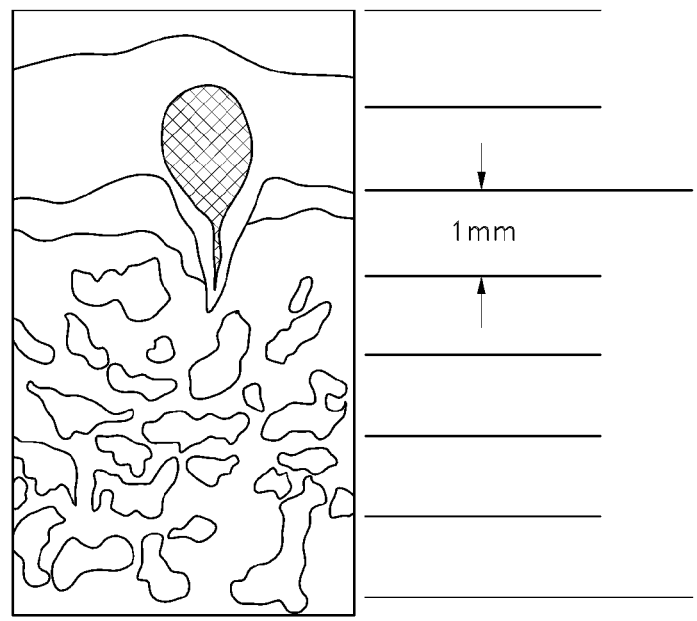
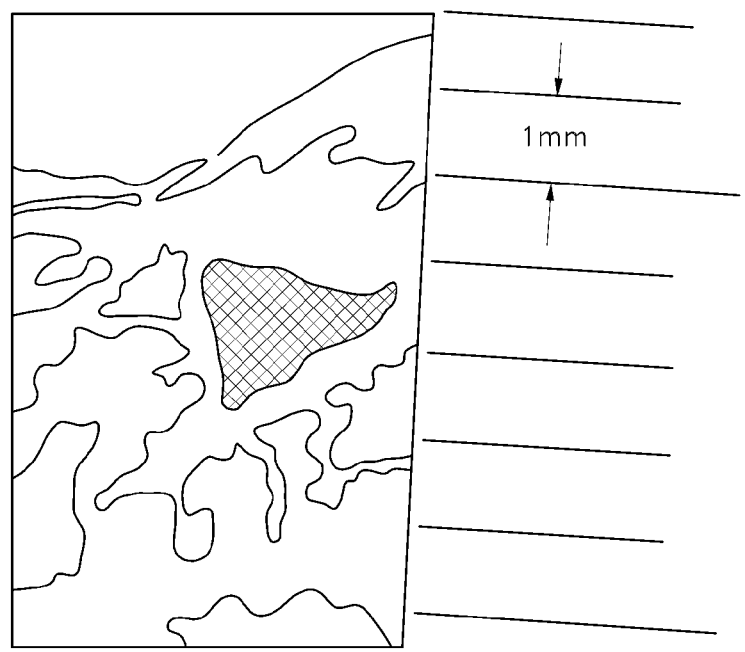
FIG. 39

ANNULAR ARRAY
(PLAIN VIEW)
PLANAR, FOCUSED
OR DEFOCUSED

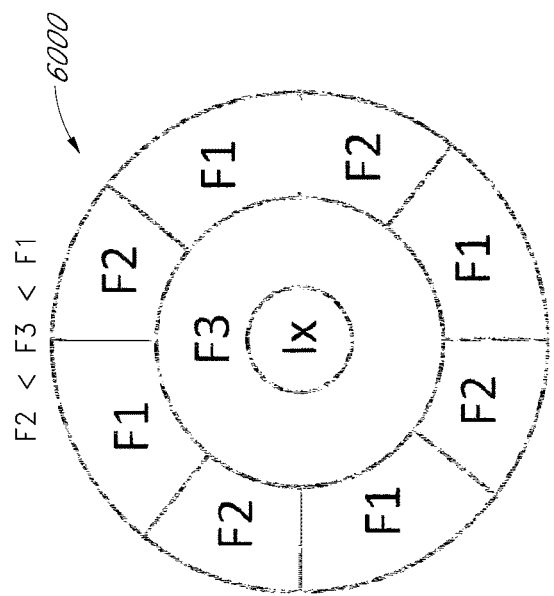
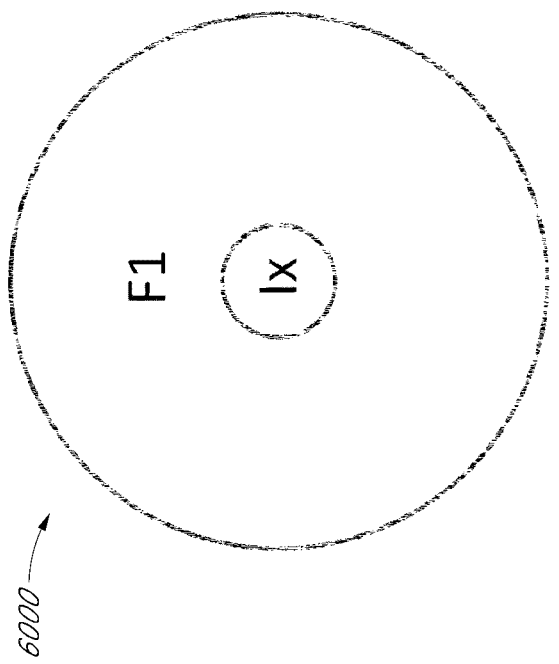

| s | xs (mm) | ys (mm) |
|---|---|---|
| 0 | 0.0000 | 10.0000 |
| 1 | 0.0050 | 9.9985 |
| 2 | 0.0100 | 9.9970 |
| 3 | 0.0150 | 9.9955 |
| 4 | 0.0200 | 9.9939 |
| 5 | 0.0250 | 9.9924 |
| 6 | 0.0300 | 9.9909 |
| 7 | 0.0350 | 9.9894 |
| 8 | 0.0400 | 9.9879 |
| 9 | 0.0450 | 9.9864 |
| 10 | 0.0500 | 9.9849 |

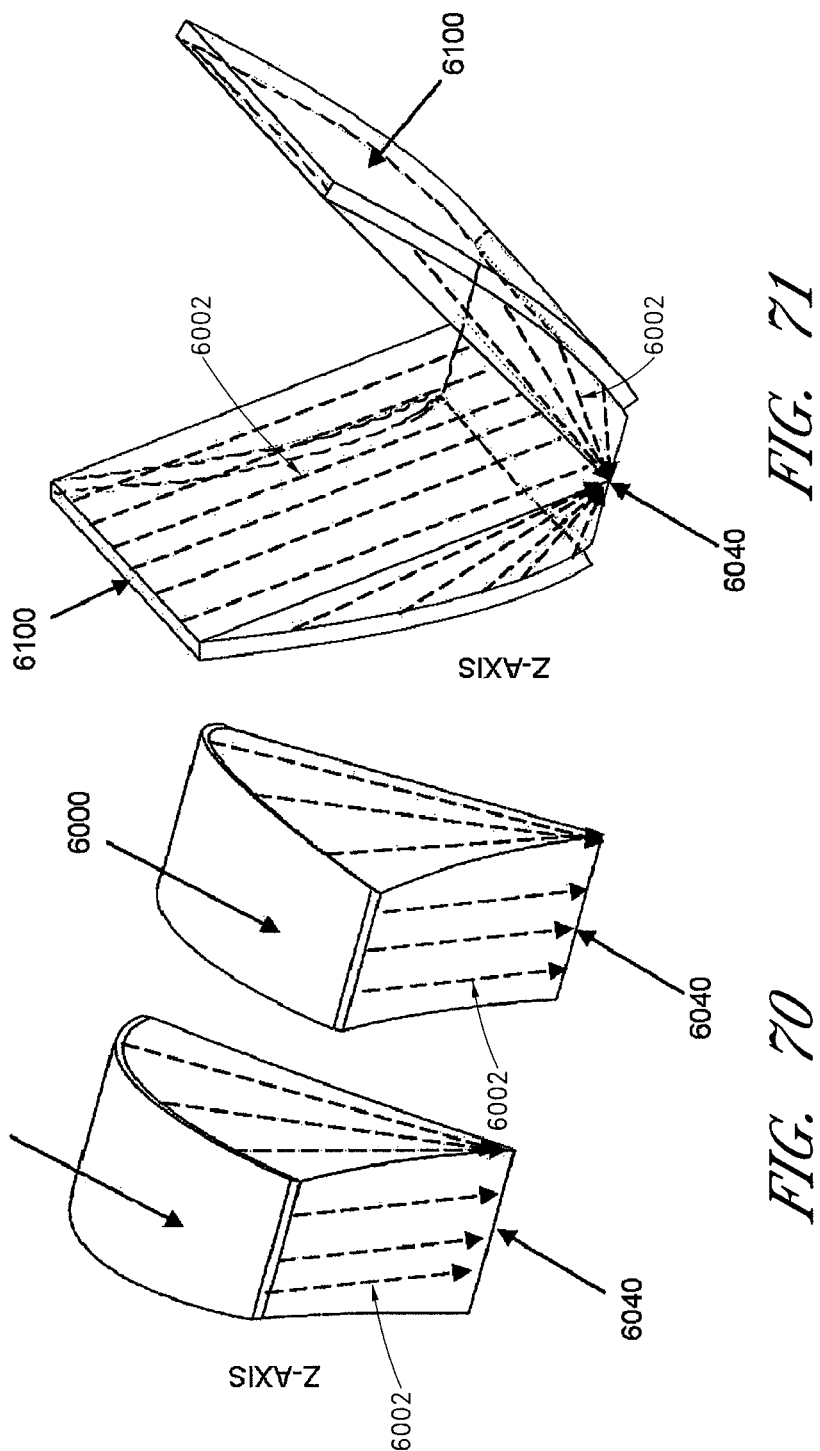

REFLECTIVE ULTRASOUND TECHNOLOGY FOR DERMATOLOGICAL TREATMENTS

CROSS-REFERENCE TO RELATED APPLICATIONS

This application is a continuation of Application No. PCT/US2012/056730, filed on Sep. 21, 2012, which is incorporated in its entirety by reference, herein. Any and all priority claims identified in the Application Data Sheet, or any correction thereto, are hereby incorporated by reference under 37 CFR 1.57.

BACKGROUND

Field

Several embodiments of the present invention generally relate to noninvasive energy-based treatments to achieve cosmetic effects. For example, several embodiments disclose ultrasound treatment and/or imaging devices for use on any part of the body, and more specifically relate to ultrasound devices having a transducer probe operable to emit and receive ultrasound energy for cosmetic and/or medical treatment and/or imaging. In particular, reflective technologies are used in some embodiments to focus energy to achieve unexpected enhanced results.

Related Art

Many cosmetic procedures involve invasive procedures that require surgery. Patients not only have to endure weeks of recovery time, but also are frequently required to undergo risky anesthetic procedures for aesthetic treatments.

Although energy-based treatments have been disclosed for cosmetic and medical purposes, no procedures are known to Applicant, other that Applicant's own work, that successfully achieve an aesthetic effect using targeted and precise ultrasound to cause a visible and effective cosmetic result via a thermal pathway.

SUMMARY

In several embodiments disclosed herein, non-invasive ultrasound is used to achieve one or more of the following effects: a face lift, a brow lift, a chin lift, an eye treatment, a wrinkle reduction, a scar reduction, a burn treatment, a tattoo removal, a vein removal, a vein reduction, a treatment on a sweat gland, a treatment of hyperhidrosis, sun spot removal, an acne treatment, and a pimple removal. Treatment of the décolletage is provided in several embodiments. In another embodiment, the device may be used on adipose tissue (e.g., fat). In another embodiment the system, device and/or method may be applied in the genital area (e.g., vaginal rejuvenation and/or vaginal tightening, such as for tightening the supportive tissue of the vagina).

In accordance with various embodiments, a cosmetic ultrasound treatment system and/or method can non-invasively produce single or multiple cosmetic treatment zones in different locations in a region of treatment in tissue under a skin surface. Some systems and methods provide cosmetic treatment at different locations in tissue, such as at different depths, heights, widths, and/or positions. In one embodiment, a method and system comprise a multiple depth transducer system configured for providing ultrasound treatment to more than one region of interest, such as between at least two of a deep treatment region of interest, a superficial region of interest, and/or a subcutaneous region of interest. Some embodiments can be configured for spatial control, such as by changing the distance from a transducer to a reflecting surface, or changing the angles of energy focused or unfocused to the region of interest, and/or configured for temporal control, such as by controlling changes in the frequency, drive amplitude and timing of the transducer. As a result, changes in the location of the treatment region, the number, shape, size and/or volume of spots or cosmetic treatment zones in a region of interest, as well as the thermal conditions, can be dynamically controlled over time.

In various embodiments, a reflective surface can be used to reflect or refract energy from an energy source to create one or more focus points for the energy. In one embodiment, energy can be ultrasound energy from any embodiment of a transducer. In one embodiment, a reflective surface can be used in conjunction with a flat, concave, cylindrical, curved, or other shaped transducer and/or element. In one embodiment, a reflective surface can be a parabolic reflector configured to focus acoustic energy at one or more cosmetic treatment zones in tissue. In various embodiments, one or more reflective surfaces can be used with one or more transducers with one or more therapy elements. In one embodiment, a reflective surface can be radially symmetric about an axis of rotation. In one embodiment, a reflective surface can have a cross sectional shape that is extended along an axis. In one embodiment, a reflective surface can vary. In one embodiment, a reflective surface can be parabolic.

In one embodiment, a treatment system includes a controlling device operably controlling an ultrasonic treatment function for providing an ultrasonic treatment and a hand wand configured to direct ultrasonic treatment in a sequence of individual thermal cosmetic treatment zones. In one embodiment, the hand wand includes a transducer and a parabolic reflective surface configured to direct ultrasound energy from the transducer to a cosmetic treatment zone at a depth from a skin surface. In one optional embodiment, the transducer can include a flat portion and a concave portion. In one embodiment, a parabolic reflective surface is configured to direct ultrasound energy from the flat portion to a first cosmetic treatment zone at a first depth from a skin surface. The concave portion is configured to direct ultrasound energy to a second cosmetic treatment zone at a second depth from the skin surface.

In one embodiment, an aesthetic imaging and treatment system for use in cosmetic treatment includes an ultrasonic probe and a control module. The ultrasonic probe includes a transducer module with an ultrasound transducer and a reflective surface. The probe can also include a first switch operably controlling an ultrasonic imaging function for providing an ultrasonic imaging, a second switch operably controlling an ultrasonic treatment function for providing an ultrasonic treatment, and a movement mechanism configured to direct ultrasonic treatment in at least one sequence of individual thermal cosmetic treatment zones. The transducer module can be configured for both ultrasonic imaging and ultrasonic treatment and interchangeable coupling to the ultrasonic probe. The ultrasound transducer can be configured to apply ultrasonic therapy to tissue at least at a cosmetic treatment zone at a first depth. The reflective surface, in one embodiment, is configured to reflect energy from the ultrasound transducer to apply ultrasonic therapy to tissue at least at cosmetic treatment zone at a second depth. The transducer module can be configured to be operably coupled to at least one of the first switch, the second switch and the movement mechanism. The control module includes, in one embodiment, a processor and a display for controlling the transducer module. In various embodiments, the first depth and the second depth are located at different depths below a single region of a skin surface to increase the overall volume of tissue treated below the skin surface, thereby providing an enhanced overall cosmetic result.

In one embodiment, the reflective surface is a parabolic reflector. In one embodiment, the reflective surface optionally includes an absorber configured to reduce the amount of re-radiation of ultrasound energy that is transmitted into the reflective surface. The reflective surface can include a membrane and a reflective surface cavity. The reflective surface cavity, in one embodiment, includes a coupling medium configured for transmission of the ultrasound energy between the transducer, reflective surface, and the membrane. In one embodiment, the transducer optionally includes a flat portion (which may be configured to direct energy to the reflective surface). In one embodiment, the transducer includes a concave portion configured to focus ultrasound energy to the first depth in tissue. In one embodiment, the transducer module is configured to provide an acoustic power in a range of between about 1 W to about 100 W and a frequency of about 1 MHz to about 10 MHz to thermally heat the tissue to cause coagulation. In one embodiment, the movement mechanism is configured to move the transducer to change a treatment depth. In one embodiment, the movement mechanism is configured to move the reflective surface to change a treatment depth. The movement mechanism can be configured to be programmed to provide variable spacing between the individual thermal cosmetic treatment zones. In one embodiment, the movement mechanism is configured for travel through a liquid-tight seal. The thermal cosmetic treatment zones (such as points or lines, whether linear or not) can be discrete or overlapping. In one embodiment, the linear sequence of individual thermal cosmetic treatment zones has a treatment spacing in a range from about 0.01 mm to about 25 mm. The first and second switches can include user operated buttons or keys. In one embodiment, at least one of the first switch and the second switch is activated by the control module.

In several embodiments, an aesthetic imaging and treatment system includes an ultrasonic probe with at least one ultrasound transducer configured for ultrasonic treatment, at least one reflective surface acoustically coupled to the at least one ultrasound transducer, and a movement mechanism operable to move at least one of the ultrasound transducer and the reflective surface within the ultrasonic probe. The system can also include a control module coupled to the ultrasonic probe and comprising a graphical user interface for controlling the at least one ultrasound transducer and the movement mechanism. The ultrasound transducer is configured to apply ultrasonic therapy to tissue at least at a first cosmetic treatment zone at a first depth. In one embodiment, the reflective surface is configured to reflect energy from the ultrasound transducer to apply ultrasonic therapy to tissue at least at a second cosmetic treatment zone at a second depth. In one embodiment, the first depth is different from the second depth.

In one embodiment, a method of performing a cosmetic procedure includes coupling a transducer module with an ultrasonic probe. The transducer module includes an ultrasound transducer and a parabolic reflective surface. The ultrasonic probe includes a first switch to control acoustic imaging, a second switch to control acoustic therapy for causing a plurality of individual cosmetic treatment zones, and a movement mechanism to provide desired spacing between the individual cosmetic treatment zones. The method includes contacting the transducer module with a subject's skin surface and activating the first switch on the ultrasonic probe to acoustically image, with the transducer module, a region below the skin surface. The method includes activating the second switch on the ultrasonic probe to acoustically treat, with the transducer module, the region below the skin surface in a desired sequence of individual cosmetic treatment zones that is controlled by the movement mechanism. The ultrasound energy is reflected from the ultrasound transducer off the parabolic reflective surface to focus at an individual cosmetic treatment zone to heat a tissue to cause a cosmetic effect.

In various embodiments, the method also includes ultrasonically imaging a target region on the subject with the transducer module. In various embodiments, the method also includes ultrasonically treating the target region on the subject with the transducer module at a tissue depth, where the treatment includes multiple treatment lines across the target region that is controlled by the movement mechanism. In various embodiments, the method also includes collecting data based on the acoustic imaging and performing the acoustic therapy based on the data. In one embodiment, the acoustic therapy includes tightening the region below the skin surface to produce a desired cosmetic effect on a face, a head, a neck area or a body of the subject. In one embodiment, the cosmetic procedure is at least one of a face lift, a brow lift, a chin lift, an eye treatment, a wrinkle reduction, a scar reduction, a burn treatment, a tattoo removal, a skin tightening, a vein removal, a vein reduction, a treatment on a sweat gland, a treatment of hyperhidrosis, a sun spot removal, a fat treatment, a vaginal rejuvenation, and an acne treatment.

In several of the embodiments described herein, the procedure is entirely cosmetic and not a medical act. For example, in one embodiment, the methods described herein need not be performed by a doctor, but at a spa or other aesthetic institute. In some embodiments, a system can be used for the non-invasive cosmetic treatment of skin.

Further areas of applicability will become apparent from the description provided herein. It should be understood that the description and specific examples are intended for purposes of illustration only and are not intended to limit the scope of the embodiments disclosed herein.

BRIEF DESCRIPTION OF THE DRAWINGS

The drawings described herein are for illustration purposes only and are not intended to limit the scope of the present disclosure in any way. Features from one illustration can be combined with features in one or more other illustrations. Embodiments of the present invention will become more fully understood from the detailed description and the accompanying drawings wherein:

FIG. 38 illustrates a diagram of simulation results of a pair of lesioning and simulation results in accordance with an embodiment;

FIG. 39 illustrates another diagram of simulation results of a pair of lesioning results in accordance with an embodiment

FIG. 57 illustrates a schematic bottom view of a transducer with a single focal distance according to an embodiment;

FIG. 58 illustrates a schematic bottom view of a transducer with a multiple focal distances according to an embodiment;

FIG. 70 illustrates a schematic isometric side view of the two cylindrical transducers of FIG. 69;

FIG. 71 illustrates a schematic isometric side view of the two parabolic reflective surfaces of FIG. 69;

DETAILED DESCRIPTION

Figure 1:
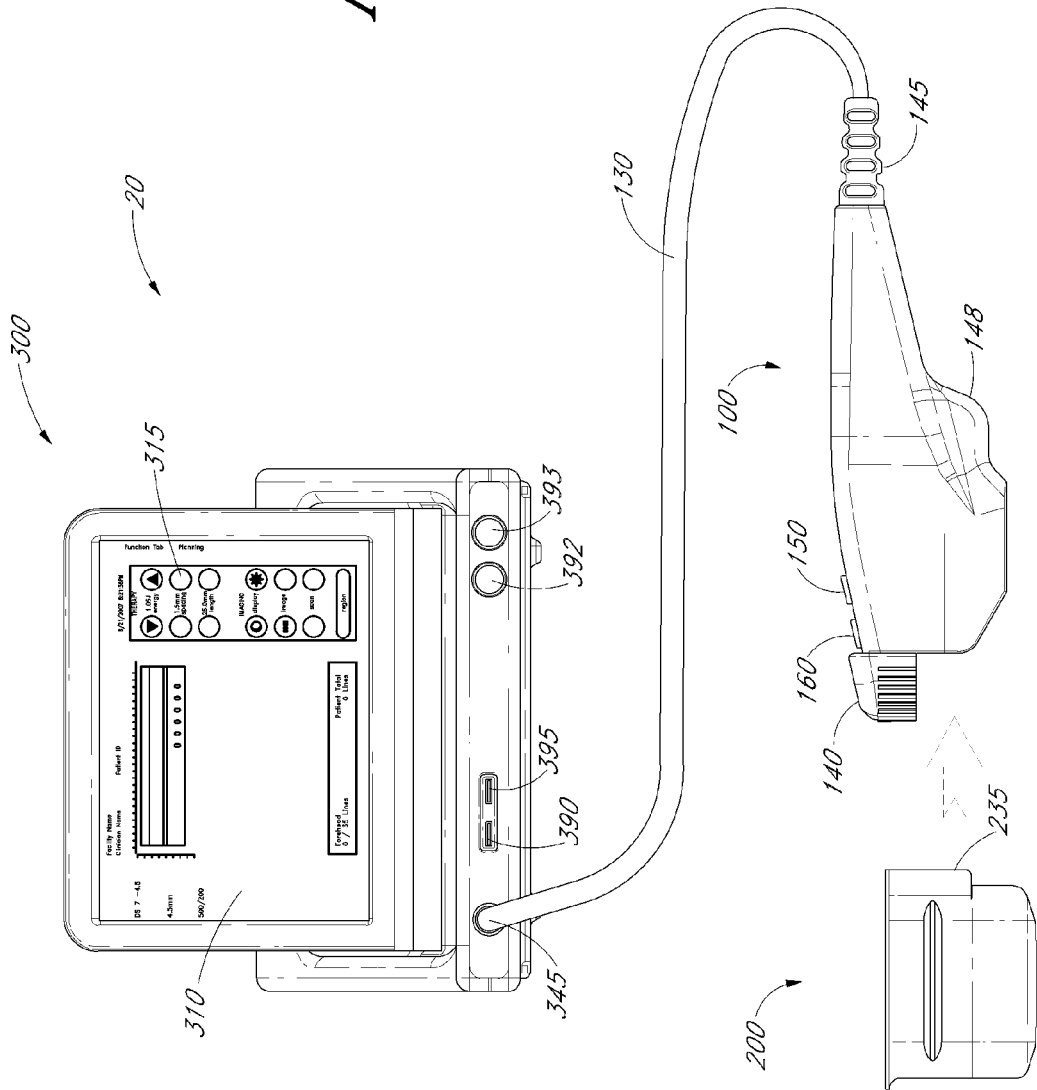
FIG. 1 is an illustration depicting a cosmetic treatment system according to various embodiments of the present invention.

The following description sets forth examples of embodiments, and is not intended to limit the present invention or its teachings, applications, or uses thereof. It should be understood that throughout the drawings, corresponding reference numerals indicate like or corresponding parts and features. The description of specific examples indicated in various embodiments of the present invention are intended for purposes of illustration only and are not intended to limit the scope of the invention disclosed herein. Moreover, recitation of multiple embodiments having stated features is not intended to exclude other embodiments having additional features or other embodiments incorporating different combinations of the stated features. Further, features in one embodiment (such as in one figure) may be combined with descriptions (and figures) of other embodiments.

In various embodiments, systems and methods for ultrasound treatment of tissue are configured to provide cosmetic treatment. In various embodiments, tissue below or even at a skin surface such as epidermis, dermis, fascia, and superficial muscular aponeurotic system ("SMAS"), are treated non-invasively with ultrasound energy. The ultrasound energy can be focused at one or more treatment points, can be unfocused and/or defocused, and can be applied to a region of interest containing at least one of epidermis, dermis, hypodermis, fascia, and SMAS to achieve a cosmetic and/or therapeutic effect. In various embodiments, systems and/or methods provide non-invasive dermatological treatment to tissue through thermal treatment, coagulation, ablation, and/or tightening. In several embodiments disclosed herein, non-invasive ultrasound is used to achieve one or more of the following effects: a face lift, a brow lift, a chin lift, an eye treatment, a wrinkle reduction, a scar reduction, a burn treatment, a tattoo removal, a vein removal, a vein reduction, a treatment on a sweat gland, a treatment of hyperhidrosis, sun spot removal, an acne treatment, and a pimple removal. In one embodiment, fat reduction is achieved. In one embodiment, décolletage is treated. In some embodiments, two, three or more beneficial effects are achieved during the same treatment session, and may be achieved simultaneously. In another embodiment, the device may be used on adipose tissue (e.g., fat). In another embodiment the system, device and/or method may be applied in the genital area (e.g., a vagina for vaginal rejuvenation and/or vaginal tightening, such as for tightening the supportive tissue of the vagina).

Reflective Surfaces for Production of Multiple Cosmetic Treatment Zones

In accordance with various embodiments, a cosmetic ultrasound treatment system and/or method can produce multiple cosmetic treatment zones in different locations in a region of treatment under a skin surface. Some systems and methods provide cosmetic treatment simultaneously at different locations in tissue, such as at different depths, heights, and/or positions. In one embodiment, a method and system comprise a variable depth transducer system configured for providing ultrasound treatment to more than one region of interest, such as between at least two of a deep treatment region of interest, a superficial region of interest, and/or a subcutaneous region of interest. Some embodiments can be configured for spatial control, such as by changing the distance from a transducer to a reflecting surface, or changing the angles of energy focused or unfocused to the region of interest. In various embodiments, a reflective surface can be used to reflect or refract energy from an energy source to create one or more focus points for the energy. In one embodiment, energy can be ultrasound energy from any embodiment of a transducer. In one embodiment, a reflective surface can be used in conjunction with a flat, concave, cylindrical, or other shaped transducer and/or element. In one embodiment, a reflective surface can be a parabolic reflector configured to focus acoustic energy at one or more cosmetic treatment zones in tissue. In various embodiments, one or more reflective surfaces can be used with one or more transducers with one or more therapy elements.

The reflective technology described herein is particularly advantageous in several embodiments. For example, transducers with reflective portions offer simplified and cheaper manufacturing, compared to other manufacturing processes (such as with a lens or machining a ceramic transducer). In one embodiment, the use of reflective regions results in to the ability to simultaneously produce a plurality of cosmetic treatment zones with a reduction in the overall power (as compared to a non-reflective system). In one embodiment, an increase by a factor of 2, 3, 4, 6, 8, 10 and higher is achieved in power/time. In one embodiment, placement of multiple foci on the same beam axis allows energy from the proximal focus to contribute to the distal focus. Another advantage, according to one embodiment, of a transducer configured to simultaneously produce a plurality of cosmetic treatment zones includes the use of a single transmitter to drive the transducer. For example, in one embodiment, a single RF transmission channel can be used to control a therapy transducer. Another advantage, according to one embodiment, includes the ability to adjust areas on the transducer to properly balance the focus intensity and account for focal gain, attenuation and dosing differences. Adjustability of the energy delivered to a focus by modifying the number of segments, facets, portions, and/or elements in the transducer is advantageously provided in some embodiments. The reduction in the amount of water or acoustic coupling media in a probe, which can decrease the weight of a probe, hand wand, and/or system, is yet another advantage that is provided in several embodiments using a reflective surface. Other advantages of reflective surfaces, in accordance with some embodiments, include one or more of the following: (i) the ability to achieve various unique distributions of acoustic energy with a parabolic reflector (such as, but not limited to, foci as a function of angle, foci as a function of radial position, etc.); (ii) the ability to produce two or more foci at different positions or locations in tissue, such as at different heights, depths, widths, etc.; (iii) an increase in the amount of tissue that is therapeutically affected; and/or (iv) the reduction in time it takes to treat a region of tissue. In one embodiment, the use of reflective regions results in to the ability to simultaneously produce a plurality of cosmetic treatment zones to reduce pain in a treatment through reduced treatment time, and/or or dispersion of energy across multiple treatment points. Additional details on reflective surfaces are provided below.

Aesthetic Indications

Several embodiments of the invention provide systems and methods for achieving aesthetic effects. For example, a method of performing a brow lift is provided. In one embodiment, the method includes coupling a probe to a brow region of the patient and imaging at least a portion of subcutaneous tissue of the brow region to determine a target area in the subcutaneous tissue. In one embodiment, the method includes administering ultrasound energy into the target area in the subcutaneous tissue to ablate or coagulate the subcutaneous tissue in the target area, which causes tightening of a dermal layer above or below the subcutaneous tissue of the brow region. The ultrasound system disclosed herein may be used to treat the brow region. In one embodiment, the transducer is shaped and dimensioned to overly the eyebrow region. In some embodiments, desired eyebrow arching is achieved by targeting ultrasound in an arch-shaped pattern or other pattern configured to achieve an arch. In several embodiments, reflective surfaces can be used to provide multiple simultaneous treatment points, which can increase the speed of a brow treatment.

A system and method of tightening the décolletage area are provided in several embodiments. In one embodiment, the method includes coupling a probe to the chest area of the patient and imaging at least a portion of subcutaneous tissue of the chest region to determine a target area in the subcutaneous tissue. In one embodiment, the method includes administering ultrasound energy into the target area in the subcutaneous tissue to ablate or coagulate the subcutaneous tissue in the target area, which causes tightening of a dermal layer above or below the subcutaneous tissue of the chest region. The ultrasound system disclosed herein may be used to treat the chest region. In one embodiment, treatment results in a tightening of the décolletage area and/or a reduction in wrinkles in the area. In one embodiment, the treatment facilitates the natural formation of collagen and elastin on the chest (just as with the face and neck) giving the ultrasound technology described herein the ability to lift tissue. In several embodiments, reflective surfaces can be used to provide multiple treatment points, which can treat a larger region on a body (e.g., a chest) in a more efficient manner.

In several embodiments, a method of treating the lower face and neck area (e.g., the submental area) is provided. In several embodiments, a method of treating (e.g., softening) mentolabial folds is provided. In other embodiments, a method of blepharoplasty and/or treating the eye region is provided. Upper lid laxity improvement and periorbital lines and texture improvement will be achieved by several embodiments by treating at variable depths. In one embodiment, a subject is treated with about 40-50 lines at depths of 4.5 and 3 mm. The subject is optionally treated with about 40-50 lines at a depth of about 1.5-2 mm. The subject is optionally treated with about 40-50 lines at a depth of about 6 mm. By treating at varied depths in a single treatment session, optimal clinical effects (e.g., softening, tightening) can be achieved. In several embodiments, reflective surfaces can be used to provide multiple simultaneous treatment points, which can reduce the amount of pain associated with a treatment by spreading energy or power dissipation across a wider cosmetic treatment area.

In several embodiments, a method of treating fat is provided. In one embodiment, a system is used to visualize and/or treat areas of fat with a hand-held applicator using a thermal treatment for cosmetic results. Fat can be treated at depths between 1-40 mm below a skin surface, or in any range therein, including but not limited to 2-30 mm, 3-20 mm, 4.5-15 mm, 5-10 mm, etc. In various embodiments, a fat treatment frequency can be 2-12 MHz, 3-10 MHz, 3.5-4.5 MHz, or other ranges. In various embodiments, a fat treatment can delivery energy at 1 joule, 2 joules, 3 joules or more. In various embodiments, a fat treatment can comprise thermal coagulation and/or ablation in a treatment point of 1 cubic millimeter or more. In several embodiments, reflective surfaces can be used to provide multiple simultaneous treatment points, which can increase the speed and total volume and/or area of a fat treatment. In one embodiment, a fat treatment will treat a relatively large volume of tissue, so the provision of multiple simultaneous treatment points can improve the fat treatment.

Another treatment that can be effectively accomplished by the systems disclosed herein involves the efficacious treatment of sweat glands. The sweat glands may be overactive, such as in hyperhidrosis, or may function normally. In the latter case, the subject may wish to reduce the amount of sweat produced for cosmetic reasons. Various embodiments of procedures involving sweat glands or treatment of hyperhidrosis are disclosed in U.S. application Ser. No. 11/163, 152 and/or Ser. No. 13/444,485, which is incorporated in its entirety by reference, herein. In various embodiments, a non-invasive method and system for using therapeutic ultrasound energy for the treatment of conditions resulting from sweat gland disorders. In various embodiments, an ultrasound system and method comprises a transducer probe and control system configured to deliver ultrasound energy to the regions of the superficial tissue (e.g., skin) such that the energy can be deposited at the particular depth at which the sweat gland population is located below the skin surface.

In one embodiment, a non-invasive method and system for the treatment of sweat glands includes an ultrasound transducer probe and control system are configured to deliver ultrasound energy to a targeted/specified depth and zone where the sweat gland population is required to be treated. The ultrasound beam from the transducer probe can be spatially and/or temporally adjusted, modified or otherwise controlled to match the adequate treatment of the sweat glands in the region of interest. For example, in one embodiment, a treatment system configured to treat a region of interest (ROI) with one or more sweat glands comprises a control system, an imaging/therapy probe with acoustic coupling, and a display system. In accordance with some embodiments, imaging transducers may operate at frequencies from approximately 2 MHz-75 MHz or more (e.g., 5 MHz-50 MHz, 10 MHz-40 MHz, etc.) while therapy energy can be delivered at frequencies from approximately 500 kHz-25 MHz (e.g., 500 kHz-15 MHz, 2 MHz-25 MHz, 1 MHz-10 MHz, 2-12 MHz, 3-10 MHz, 3.5-4.5 MHz, 4-5 MHz, 4.2-4.9 MHz, 4.3-4.7 MHz, 4.3 MHz, 4.7 MHz, 7-8 MHz, 7.2-7.8 MHz, 7.3-7.7 MHz, 7.3 MHz, 7.5 MHz, 8-12 MHz, 9-11 MHz, 9.5-10.5 MHz, or other frequencies). Sweat glands are generally located within a dermis layer at a depth close to hair bulbs. In various embodiments, a treatment of sweat glands can be directed to, but not limited to, the axillary region (armpit), the palms and soles, a forehead, the back, or other areas of sweat. In one embodiment, a treatment method and system are configured for initially imaging a region within a region of interest and displaying that region on a display to facilitate localization of the treatment area and surrounding structures, e.g., identification of sweat glands, such as within the axillary region (armpit), the palms and soles or any other tissue or skin surrounding sweat glands. In one embodiment, delivery of ultrasound energy at a depth, distribution, timing, and energy level to achieve the desired therapeutic effect of thermal ablation to treat a sweat gland is provided. Before, during, and/or after therapy, e.g., before, during and/or after delivery of ultrasound energy, monitoring of the treatment area and surrounding structures can be conducted to further planning and assessing of the results and/or providing feedback to control system and a system operator. Optionally, sweat glands can be seen lying along hair follicles and bulbs and their image may be further enhanced via signal and image processing. Imaging may be used to avoid injuring vital structures, such as nerve endings or other structures. In several embodiments, imaging is not used. In accordance with other embodiments, localization can also be accomplished without imaging region, but instead can be based, for example, on prior known depths of sweat glands or other target regions, and thus be configured geometrically and/or electronically to selectively deposit energy at a particular known depth below skin surface to a target region. In one embodiment, an ultrasound beam from a probe can be spatially and/or temporally controlled by changing the spatial parameters of the transducer, such as the placement, distance, treatment depth and transducer structure, as well as by changing the temporal parameters of transducer, such as the frequency, drive amplitude, and timing, with such control handled via control system. For example, in one embodiment, the temporal energy exposure at one location may range from approximately to 40 ms to 40 seconds, while the corresponding source frequency can suitably range from approximately 500 kHz to 15 MHz (e.g., 500 kHz-15 MHz, 2 MHz-25 MHz, 1 MHz-10 MHz, 2-12 MHz, 3-10 MHz, 3.5-4.5 MHz, 4-5 MHz, 4.2-4.9 MHz, 4.3-4.7 MHz, 4.3 MHz, 4.7 MHz, 7-8 MHz, 7.2-7.8 MHz, 7.3-7.7 MHz, 7.3 MHz, 7.5 MHz, 8-12 MHz, 9-11 MHz, 9.5-10.5 MHz, or other frequencies). Such spatial and temporal parameters can also be suitably monitored and/or utilized in open-loop and/or closed-loop feedback systems within treatment system. Various cosmetic treatment zones may be produced. In one embodiment, a cosmetic treatment zone is a lesion. In one embodiment, a lesion is a type of cosmetic treatment zone. In various embodiments, cosmetic treatment zones and/or lesions of various, specifically targeted, shapes, sizes and orientations can be configured within target region. In some embodiments, at least 10%, 20%, 30%, 40%, 50% or 75% of sweat glands in the target area are ablated or otherwise deactivated (e.g., physically rendered inactive or reduction in neurotransmission). In some embodiments, specific sweat glands are deactivated, while in other embodiments, multiple sweat glands in a target region are deactivated. The embodiments described herein with ultrasound may also be used in conjunction with, and or replaced by, other energy or therapeutic modalities. For example, electromagnetic, radio frequency, intense pulsed light, laser, infrared laser, microwave, or other suitable energy source may be used instead of, or along with, ultrasound at powers and frequencies sufficient to deactivate (e.g., ablate) sweat glands. In several embodiments, reflective surfaces can be used to provide multiple simultaneous treatment points, which can increase the efficiency of a plurality of sweat glands, which can be spread out in a tissue region. In one embodiment, a sweat treatment will treat a relatively large number of individual sweat glands, so the provision of multiple simultaneous treatment points can improve the coverage and reduce the time of a sweat treatment.

In one embodiment, the invention comprises treatment of hyperhidrosis (e.g., >50 mg/sweat production per axilla within 5 minutes by gravimetric method). A single treatment is performed, or two treatments are performed (e.g., weeks apart). In one embodiment, dual depth treatment using 3.0 mm and 4.5 mm transducers is used. In one embodiment, eccrine glands, found between 3-5 mm in axilla, are treated. In one embodiment, 240 lines per transducer is used, 480 lines total. In several embodiments, sweat is reduced by, e.g., more than 25%, 50%, 75%, 90% and 95%. In one embodiment, all sweat glands in the target area are affected and/or sweat is completely reduced. In several embodiments, the results are permanent. In several embodiments, the use of ultrasound therapy is minimally invasive and accompanied by low pain scores and out-patient procedures. In one embodiment, pain is substantially removed by using the reflective embodiments described herein. For example, by permitting two, three, four, or more points to be delivered simultaneously, pain is reduced by significantly reducing the treatment time, and/or simultaneous dispersal of power or energy through multiple spaced points.

In one embodiment, a whole contiguous sheet of treatment area can be achieved, whereby all the sweat glands within the area are ablated. In addition to selective treatment of sweat gland regions, in accordance with another embodiment, the treatment system could be configured to carpet bomb the fat layer at 1-7 mm depth. In one embodiment, non-thermal effects from an acoustic field can also shock the sweat producing apocrine and eccrine cells in to reduced activity. These effects mentioned here as examples are, but not limited to, acoustic cavitation, acoustic streaming, intercellular shear effects, cell resonant effects, and the like. In one embodiment, focused or directive ultrasound energy can be used for the treatment of sweat glands in the armpit (without the combination of pharmacological formulations). In one embodiment, Hidradenitis suppurativa is treated. In one embodiment, ultrasound energy deposited at a selective depth can also be used in combination with a number of pharmaceutical formulations that are currently prescribed for the treatment of sweat gland hyperactivity in the axillary region, palms and soles. The energy (e.g., ultrasound energy) delivered to the target region in combination with the pharmaceutical agents such as botulin, beta blockers, retinoids and anticholinergic drugs can help synergistically treat the sweat gland region by, for example (1) increasing activity of the agents due to the thermal and non-thermal mechanisms, (2) reduced requirement of overall drug dosage, as well as reducing the drug toxicity, and/or (3) increase local effect of drug in a site selective manner. Several embodiment of energy-based treatment described herein may also act synergistically topical formulations (e.g., antiperspirants). In some embodiments, primary hyperhidrosis is treated. In other embodiments, secondary hyperhidrosis (hyperhidrosis due to other conditions) is treated. Excessive perspiration on the face, back, chest, underarms, palms, and soles of the feet are treated in some embodiments. In one embodiment, excessive perspiration as a result of other treatments is treated (e.g., compensatory sweating). In several embodiments, energy-based treatments disclosed herein (ultrasound or non-acoustic energy-based treatments) are used to effectively treat (e.g., hyperhidrosis) without compensatory sweating, which is particularly advantageous as compared to other treatments such as sympathectomy.

Cosmetic Treatment Systems Using Multiple Cosmetic Treatment Zones

In various embodiments, certain cosmetic procedures that are traditionally performed through invasive techniques are accomplished by targeting energy, such as ultrasound energy, at specific subcutaneous tissues. In several embodiments, methods and systems for non-invasively treating subcutaneous tissues to perform a cosmetic treatment are provided; however, various other cosmetic treatment applications, such as face lifts, acne treatment and/or any other cosmetic treatment application, can also be performed with the cosmetic treatment system. In one embodiment, a system integrates the capabilities of high resolution ultrasound imaging with that of ultrasound therapy, providing an imaging feature that allows the user to visualize the skin and sub-dermal regions of interest before treatment. In one embodiment, the system allows the user to place a transducer module at optimal locations on the skin and provides feedback information to assure proper skin contact. In one embodiment, the therapeutic system provides an ultrasonic transducer module that directs acoustic waves to a cosmetic treatment zone in the treatment area. This acoustic energy heats tissue, in one embodiment, as a result of frictional losses during energy absorption, producing a discrete zone, area, region, line or point of coagulation and/or ablation.

In various embodiments, an ultrasound system is provided that includes a removable transducer module interfaced to a hand enclosure having at least one controller button such that the transducer module and the controller button is operable using only one hand. In some embodiments, the transducer module provides ultrasound energy for an imaging function and/or a treatment function. In another aspect of the embodiments, the device includes a controller coupled to the hand-held enclosure and interfaced to the transducer module. In some embodiments, the controller controls the ultrasound energy and receives a signal from the transducer module. The controller can have a power supply and driver circuits providing power for the ultrasound energy. In several embodiments, the device is used in cosmetic imaging and treatment of a patient, or simply treatment of the patient.

Moreover, several embodiments of the present invention provide a method of tightening a portion of a dermal and/or a subdermal layer of a patient. In various embodiments, the method includes inserting a transducer module into a hand controller and then coupling the transducer module to the skin of the patient. In one embodiment, the method includes activating a first switch on the hand to initiate an imaging sequence of a portion of tissue below a dermal layer, then collecting data from the imaging sequence. In these embodiments, the method includes calculating a treatment sequence from the collected data, and then activating a second switch on the hand to initiate the treatment sequence. In an aspect of the embodiments, the method can be useful on a portion of a face, head, neck and/or other part of the body of a patient. In several embodiments, the invention comprises a method for treating damaged skin, including undesired features in the dermal or subdermal portions, (e.g., wrinkles, stretch marks, scars, overactive sweat glands, acne, rosacea, spider veins, or other disfiguration or undesired quality), wherein the method comprises imaging a treatment region, selecting a probe configuration based on at least one of a spatial parameter and a temporal parameter based on the imaging results, verifying at least one of a spatial parameter and a temporal parameter of the probe; confirming acoustic coupling of the probe to the treatment region, and applying ultrasound energy using the selected probe configuration to ablate a portion of the treatment region.

Several embodiments of the present invention provide a hand wand. In some embodiments, the system includes a hand wand with at least one finger activated controller, and a removable transducer module having an ultrasound transducer. In one embodiment, the system includes a control module that is coupled to the hand wand and has a graphic user interface for controlling the removable transducer module with an interface coupling the hand wand to the control module. In one embodiment, the interface provides power to the hand wand. In one embodiment, the interface transfers at least one signal between the hand wand and the control module. In some embodiments, the hand wand includes a first controlling device operably controlling an imaging function, a second controlling device operably controlling a treatment function, a status indicator, an input for power, an output for at least one signal, and a movement mechanism. A removable transducer module can be coupled to the hand wand. The removable transducer module can be interfaced with the first controlling device, the second controlling device and/or the movement mechanism. In one embodiment, the hand wand is used in cosmetic procedures on a face, head, neck and/or other part of the body of a patient.

Several embodiments of the present invention provide a combined imaging and treatment system. In accordance with one embodiment, the aesthetic imaging system includes a hand wand, a removable transducer module, a control module, and an interface coupling the hand wand and the control module. The hand wand includes at least one finger activated controller. The removable transducer module includes an ultrasound transducer and at least one interface coupleable to the hand wand. The control module is coupled to the hand wand and includes a graphical user interface for controlling the removable transducer module.

In one embodiment, the interface couples the hand wand to the control module, and provides at least power to the hand wand. In one embodiment, the interface transfers one or more signals between the hand wand and the control module. In one embodiment, at least one signal (e.g., 1, 2, 3, 4, 5 or more signals) is communicated from the wand to the control module. In another embodiment, at least one signal (e.g., 1, 2, 3, 4, 5 or more signals) is communicated from the control module to the wand. In several embodiments, at least one signal (e.g., 1, 2, 3, 4, 5 or more signals) is communicated to, from, or between the wand and control module. In one embodiment, the aesthetic imaging system also includes a printer coupled to the control module and the control module provides an output signal and power to the printer. In one embodiment, the aesthetic imaging system also includes a key operable to unlock the control module for controlling the removable transducer module. In one embodiment of an aesthetic imaging system, the hand wand includes a movement mechanism, operable to move the ultrasound transducer within the transducer module. In one embodiment, the aesthetic imaging system also includes at least one sensor coupled to the hand wand and/or the removable transducer module.

In accordance with one embodiment, the device includes a removable transducer module and a controller. In one embodiment, the transducer module is not removable. In one embodiment, the transducer module is integrated, or permanently attached. The removable transducer module is interfaced to a hand enclosure having at least one controller button such that the transducer module and button is operable using one hand. The transducer module provides ultrasound energy for at least one of an imaging function and a treatment function. The controller is coupled to the hand enclosure and is interfaced to the transducer module. The controller controls the ultrasound energy and receives at least one signal from the transducer module. The controller has a power supply operably providing power for at least the ultrasound energy. In one embodiment, the device also includes a graphical user interface for controlling the transducer module and for viewing the at least one signal from the transducer module. In one embodiment, the device has a hand enclosure that also includes a movement mechanism operably moving a transducer in the transducer module, where the movement mechanism is controlled by the controller. In one embodiment, the device has at least one controller button as a first controller button controlling the imaging function and a second controlling button controlling the treatment function.

In accordance with one embodiment, the method includes inserting a transducer module into a hand controller, coupling the transducer module to the subject, activating a first switch on the hand controller operably initiating an imaging sequence of a portion of tissue below the dermal layer, collecting data from the imaging sequence, calculating a treatment sequence from the data, and activating a second switch on the hand controller operably initiating the treatment sequence. In one embodiment, the method also includes emitting a first ultrasound energy from a first transducer in the transducer module operably providing a source for the imaging sequence. In one embodiment, the method also includes emitting a second ultrasound energy from a second transducer in the transducer module operably providing a source for the treatment sequence. In one embodiment, the method also includes tightening a portion of the dermal layer on a facial area of a subject. In one embodiment, the method provides for the transducer module to permit the treatment sequence at a fixed depth below the dermal layer.

In accordance with one embodiment of a hand wand, the wand includes a first controlling device operably controlling an ultrasonic imaging function, a second controlling device operably controlling an ultrasonic treatment function, a movement mechanism configured for travel through a liquid-tight seal, and a fluid-filled transducer module. In one embodiment, the fluid-filled transducer module is operably coupled to at least one of the first controlling, the second controlling device and the movement mechanism. In one embodiment, the fluid-filled transducer module is mechanically and electrically separable from at least one of the first controlling, the second controlling device and the movement mechanism. In one embodiment, the fluid-filled transducer module includes an acoustic liquid. In one embodiment, the fluid-filled transducer module includes a gel adapted to enhance transmission of an ultrasonic signal. In one embodiment, a gel adapted to enhance transmission of an ultrasonic signal is placed between the transducer and the patient's skin.

In one embodiment, the linear sequence of individual thermal lesions has a treatment spacing in a range from about 0.01 mm to about 25 mm (e.g., including, but not limited to 0.1 mm-20 mm, 0.5 mm-15 mm, 0.01 mm-1 mm, 1 mm-5 mm, 1 mm-2 mm, 1 mm, 1.5 mm, 2 mm, 2.5 mm, 3 mm, 5 mm, etc.). In one embodiment, the linear sequence of individual thermal lesions has a treatment spacing in a range from about 0.1 mm to about 35 mm. In one embodiment, the movement mechanism is configured to be programmed to provide variable spacing between the individual thermal lesions. In one embodiment the individual thermal lesions are discrete. In one embodiment the individual thermal lesions are overlapping.

In accordance with one embodiment of a variable ultrasonic parameter ultrasonic system for use in cosmetic treatment, the system includes a movement mechanism and one or more removable transducer modules. In various embodiments, the one or more removable transducer modules includes two, three, four, five, six, or more removable transducer modules. In various embodiments, the different numbers of removable transducer modules can be configured for different or variable ultrasonic parameters. For example, in various non-limiting embodiments, the ultrasonic parameter can relate to transducer geometry, size, timing, spatial configuration, frequency, variations in spatial parameters, variations in temporal parameters, coagulation formation, controlled necrosis areas or zones, depth, width, absorption coefficient, refraction coefficient, tissue depths, and/or other tissue characteristics. In various embodiments, a variable ultrasonic parameter may be altered, or varied, in order to effect the formation of a lesion for the desired cosmetic approach. In various embodiments, a variable ultrasonic parameter may be altered, or varied, in order to effect the formation of a lesion for the desired clinical approach. By way of example, one variable ultrasonic parameter relates to aspects of configurations associated with tissue depth. For example, some non-limiting embodiments of removable transducer modules can be configured for a tissue depth of 3 mm, 4.5 mm, 6 mm, less than 3 mm, between 3 mm and 4.5 mm, more than more than 4.5 mm, more than 6 mm, and anywhere in the ranges of 0-3 mm, 0-4.5 mm, 0-25 mm, 0-100 mm, and any depths therein. In one embodiment, an ultrasonic system is provided with two transducer modules, in which the first module applies treatment at a depth of about 4.5 mm and the second module applies treatment at a depth of about 3 mm. An optional third module that applies treatment at a depth of about 1.5-2 mm is also provided. In some embodiments, a system and/or method comprises the use of removable transducers that treat at different depths is provided (e.g., a first depth in the range of about 1-4 mm below the skin surface and a second depth at about 4-7 mm below the skin surface). A combination of two or more treatment modules is particularly advantageous because it permits treatment of a patient at varied tissue depths, thus providing synergistic results and maximizing the clinical results of a single treatment session. For example, treatment at multiple depths under a single surface region permits a larger overall volume of tissue treatment, which results in enhanced collagen formation and tightening. Additionally, treatment at different depths affects different types of tissue, thereby producing different clinical effects that together provide an enhanced overall cosmetic result. For example, superficial treatment may reduce the visibility of wrinkles and deeper treatment may induce formation of more collagen growth. In some embodiments, treatment of different depths is used to treat different layers of tissue, e.g., epidermal tissue, the superficial dermal tissue, the mid-dermal tissue, and the deep dermal tissue. In another embodiment, treatment at different depths treats different cell types (e.g., dermal cells, fat cells). The combined treatment of different cell types, tissue types or layers, in, for example, a single therapeutic session, are advantageous in several embodiments.

Although treatment of a subject at different depths in one session may be advantageous in some embodiments, sequential treatment over time may be beneficial in other embodiments. For example, a subject may be treated under the same surface region at one depth in week 1, a second depth in week 2, etc. The new collagen produced by the first treatment may be more sensitive to subsequent treatments, which may be desired for some indications. Alternatively, multiple depth treatment under the same surface region in a single session may be advantageous because treatment at one depth may synergistically enhance or supplement treatment at another depth (due to, for example, enhanced blood flow, stimulation of growth factors, hormonal stimulation, etc.).

In several embodiments, different transducer modules provide treatment at different depths. In several embodiments, a system comprising different transducers, each having a different focal depth, is particularly advantageous because it reduces the risk that a user will inadvertently select an incorrect depth. In one embodiment, a single transducer module can be adjusted or controlled for varied depths. Safety features to minimize the risk that an incorrect depth will be selected can be used in conjunction with the single module system.

In several embodiments, the treatment methods described herein are non-invasive cosmetic procedures. In some embodiments, the methods can be used in conjunction with invasive procedures, such as surgical facelifts or liposuction, where skin tightening is desired. In several embodiments, the systems and methods do not cavitate or produce shock waves. In one embodiment, treatment destroys fat cells, while leaving other types of tissue intact. In some embodiments, cooling is not necessary and not used. In some embodiments, cell necrosis is promoted (rather than reduced) via ablation. In some embodiments, treatment does not irritate or scar a dermis layer, but instead affects tissue subdermally. In several embodiments, the transducer has a single emitter. In other embodiments, a plurality of emitters is used. In several embodiments, treatment is performed without puncturing the skin (e.g., with needles) and without the need to suction, pinch or vacuum tissue. In other embodiments, suctioning, pinching or vacuuming is performed. In several embodiments, the lesions that are formed do not overlap. In several embodiments, the treatment employs a pulse duration of 10-60 milliseconds (e.g., about 15-50 ms, 20-40 ms, 10 ms, 15 ms, 20 ms, 25 ms, 30 ms, 40 ms, etc.) and emits between about 1,000-5,000 W/cm$^2$ (e.g., 1,500-4,500 W/cm$^2$, 2,000-4,000 W/cm$^2$, 2,500 W/cm$^2$). In several embodiments, the energy flux is about 1.5-5.0 J/cm$^2$ (e.g., 2.0 J/cm$^2$, 2.5 J/cm$^2$, 3.0 J/cm$^2$, 3.5 J/cm$^2$, 4.0 J/cm$^2$, 4.5 J/cm$^2$). In several embodiments, efficacy is produced using 20-500 lines of treatment (e.g., 30-450, 50-300, 100-250 lines, etc.). In one embodiment, each line takes about 0.1 to 2 seconds to deliver (e.g., 0.2, 0.3, 0.4, 0.5, 1, 1.5, etc.). In one embodiment, each line contains multiple individual lesions which may or may not overlap.

A method of performing a cosmetic procedure on a subject using a hand wand as described herein is provided in several embodiments. In one embodiment, the method comprises ultrasonically imaging a first target region on the subject with the first transducer module and ultrasonically treating the first target region on the subject with the first transducer module at the first tissue depth. The treatment comprises multiple treatment lines across the first target region that are automatically selected (e.g., programmed, pre-set, etc.) by the movement mechanism. In one embodiment, the method further comprises exchanging the first transducer module with the second transducer module; ultrasonically imaging a second target region on the subject with the second transducer module; and ultrasonically treating the second target region on the subject with the second transducer module at the second tissue depth. The treatment comprises multiple treatment lines across the second target region that are automatically selected (e.g., programmed, pre-set, etc.) by the movement mechanism. In one embodiment, the first and second target regions are located under a single surface of the subject.

In several embodiments, the invention comprises a hand wand for use in cosmetic treatment. In accordance with one embodiment, the hand wand comprises a first controlling device, a second controlling device, a movement mechanism, and a transducer module. The first controlling device operably controls an ultrasonic imaging function for providing ultrasonic imaging. The second controlling device operably controls an ultrasonic treatment function for providing ultrasonic treatment. The movement mechanism is configured to direct ultrasonic treatment in a sequence of individual thermal lesions. The removable transducer module is configured for both ultrasonic imaging and ultrasonic treatment. The removable transducer module is configured for interchangeable coupling to the hand wand. The removable transducer module is configured to be operably coupled to at least one of the first controlling device, second controlling device and movement mechanism. The removable transducer module is configured to apply ultrasonic therapy to at a first variable ultrasonic parameter to tissue.

In one embodiment, the hand wand is configured to apply ultrasonic therapy to at a second variable ultrasonic parameter to tissue. In one embodiment, the removable transducer module is configured to apply ultrasonic therapy to at a second variable ultrasonic parameter to tissue. In one embodiment, the hand wand further comprises a second removable transducer module, wherein the second removable transducer module is configured to apply ultrasonic therapy to at the second variable ultrasonic parameter to tissue. In one embodiment, the variable ultrasonic parameter is tissue depth. In one embodiment, the variable ultrasonic parameter is frequency. In one embodiment, the variable ultrasonic parameter is timing. In one embodiment, the variable ultrasonic parameter is geometry.

System Components

To further explain in more detail various aspects of embodiments of the present invention, several examples of a cosmetic treatment system as used with a control system and an ultrasonic probe system will be provided. However, it should be noted that the following embodiments are for illustrative purposes, and that embodiments of the present invention can comprise various other configurations for a cosmetic treatment. In addition, although not illustrated in the drawing figures, the cosmetic treatment system can further include components associated with imaging, diagnostic, and/or treatment systems, such as any required power sources, system control electronics, electronic connections, and/or additional memory locations. The features described below are, in several embodiments, employed to treat the brow area, the décolletage, sweat glands, fat, and to cause tightening and reduce wrinkles, as described herein. Although ultrasound embodiments are described, other energy-based modalities are encompassed herein.

With reference to the illustration in FIG. 1, an embodiment of the present invention is depicted as a cosmetic treatment system 20. In various embodiments of the present invention, the cosmetic treatment system 20 (hereinafter "CTS 20") includes a hand wand 100, an emitter-receiver module 200, and a controller 300. The hand wand 100 can be coupled to the controller 300 by an interface 130. In one embodiment the interface is a cord. In one embodiment, the cord is a two way interface between the hand wand 100 and the controller 300. In various embodiments the interface 130 can be, for example, any multi-conductor cable or wireless interface. In one embodiment, the interface 130 is coupled to the hand wand 100 by a flexible connection 145. In one embodiment, the flexible connection 145 is a strain relief. The distal end of the interface 130 is connected to a controller connector on a flex circuit 345. In various embodiments the flexible connector 145 can be rigid or may be flexible, for example, including a device such as an elastomeric sleeve, a spring, a quick connect, a reinforced cord, a combination thereof, and the like. In one embodiment, the flexible connection 145 and the controller connection on the flex circuit 345 can include an antenna and receiver for communications wirelessly between the hand wand 100 and the controller 300. In one embodiment, the interface 130 can transmit controllable power from the controller 300 to the hand wand 100.

In various embodiments, the controller 300 can be configured for operation with the hand wand 100 and the emitter-receiver module 200, as well as the overall CTS 20 functionality. In various embodiments, multiple controllers 300, 300', 300", etc. can be configured for operation with multiple hand wands 100, 100', 100", etc. and or multiple emitter-receiver modules 200, 200', 200", etc. In various embodiments, a second embodiment of a reference can be indicated with a reference number with one or more primes ('). For example, in one embodiment a first module 200 may be used with or as an alternative to a second module 200', third module 200", fourth module 200'", etc. Likewise, in various embodiments, any part with multiples can have a reference number with one or more primes attached to the reference number in order to indicate that embodiment. For example, in one embodiment a first transducer 280 can be indicated with the 280 reference number, and a second transducer 280' uses the prime. In one embodiment, controller 300 houses an interactive graphical display 310, which can include a touch screen monitor and Graphic User Interface (GUI) that allows the user to interact with the CTS 20. In various embodiments, this display 310 sets and displays the operating conditions, including equipment activation status, treatment parameters, system messages and prompts and ultrasound images. In various embodiments, the controller 300 can be configured to include, for example, a microprocessor with software and input/output devices, systems and devices for controlling electronic and/or mechanical scanning and/or multiplexing of transducers and/or multiplexing of transducer modules, a system for power delivery, systems for monitoring, systems for sensing the spatial position of the probe and/or transducers and/or multiplexing of transducer modules, and/or systems for handling user input and recording treatment results, among others. In various embodiments, the controller 300 can comprise a system processor and various digital control logic, such as one or more of microcontrollers, microprocessors, field-programmable gate arrays, computer boards, and associated components, including firmware and control software, which may be capable of interfacing with user controls and interfacing circuits as well as input/output circuits and systems for communications, displays, interfacing, storage, documentation, and other useful functions. System software may be capable of controlling all initialization, timing, level setting, monitoring, safety monitoring, and all other system functions required to accomplish user-defined treatment objectives. Further, the controller 300 can include various control switches that may also be suitably configured to control operation of the CTS 20. In one embodiment, the controller 300 includes an interactive graphical display 310 for conveying information to user. In one embodiment, the controller 300 includes one or more data ports 390. In one embodiment, the data port 390 is a USB port, and can be located on the front, side, and/or back of the controller 300 for access to storage, a printer 391, devices, or be used for other purposes. In various embodiments the CTS 20 includes a lock 395, and in one embodiment the lock 395 can be connectable to the controller 300 via a USB port. In one embodiment, in order to operate CTS 20, lock 395 must be unlocked so that power switch 393 may be activated. In another embodiment lock 395 must be unlocked insertion of USB access key or hardware dongle and associated software so that the interactive graphical display 310 can execute. In one embodiment, an emergency stop button 392 is readily accessible for emergency de-activation.

In various embodiments, an aesthetic imaging system or CTS 20 includes a hand wand 100 with at least one finger activated controller (150 and/or 160), and a removable emitter-receiver module 200 having an ultrasound transducer. Other embodiments may include non-removable emitter-receiver modules, imaging-only emitter-receiver modules, treatment-only emitter-receiver modules, and imaging-and-treatment emitter-receiver modules. In one embodiment, the CTS 20 includes a control module 300 that is coupled to the hand wand 100 and has a graphic user interface 310 for controlling the removable transducer module 200 with an interface 130, such as in one embodiment, a cord coupling the hand wand 100 to the control module 300. In one embodiment, the interface 130 provides power to the hand wand 100. In one embodiment, the interface 130 transfers at least one signal between the hand wand 100 and the control module 300. In an aspect of this embodiment, the aesthetic imaging system of CTS 20 is used in aesthetic procedures on a portion of a head of a patient. In one embodiment, the CTS 20 is used in aesthetic procedures on a portion of a face, head, neck and/or other part of the body of a patient.

In addition, certain embodiments of the present invention provide a hand wand 100 for use in aesthetic treatment. In some embodiments, the hand wand 100 includes a first controlling device 150 operably controlling an imaging function, a second controlling device 160 operably controlling a treatment function, a status indicator 155, an input for power, an output for at least one signal (for example to a controller 300), a movement mechanism 400, and a removable transducer module 200 in communication with the first controlling device 150, the second controlling device 160 and/or the movement mechanism 400. In an aspect of the embodiments, the hand wand 100 is used in cosmetic procedures on a face, head, neck and/or other part of the body of a patient.

In accordance to various embodiments of the present invention, an emitter-receiver module 200 can be coupled to the hand wand 100. In some embodiments an emitter-receiver module 200 can emit and receive energy, such as ultrasonic energy. In one embodiment, an emitter-receiver module 200 can be configured to only emit energy, such as ultrasonic energy. In one embodiment, the emitter-receiver module 200 is permanently attachable to the hand wand 100. In one embodiment, the emitter-receiver module 200 is attachable to and detachable from the hand wand 100. The emitter-receiver module 200 can be mechanically coupled to the hand wand 100 using a latch or coupler 140. An interface guide 235 can be useful in assisting the coupling of the emitter-receiver module 200 to the hand wand 100. In addition, the emitter-receiver module 200 can be electronically coupled to the hand wand 100 and such coupling may include an interface which is in communication with the controller 300. In one embodiment, an electric coupler at the interface guide 235, located at a proximal end of an emitter-receiver module 200 provides for electronic communication between the emitter-receiver module 200 and the hand wand 100, which can both be in electric communication with a controller 300. The emitter-receiver module 200 can comprise various probe and/or transducer configurations. For example, the emitter-receiver module 200 can be configured for a combined dual-mode imaging/therapy transducer, coupled or co-housed imaging/therapy transducers, or simply a separate therapy probe and an imaging probe. In one embodiment, the hand wand 100 includes a handle with an integrated receptacle for insertion of an emitter-receiver module 200 containing at least a transducer on one end and an electrical cable for attachment to the controller 200 on the other end.

Figure 2:
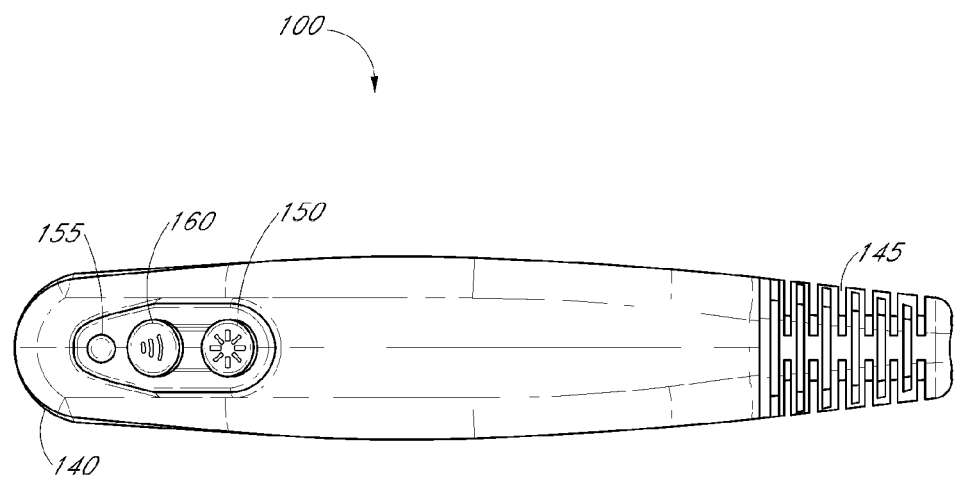
FIG. 2 is a top view illustrating a hand wand according to various embodiments.
Figure 3:
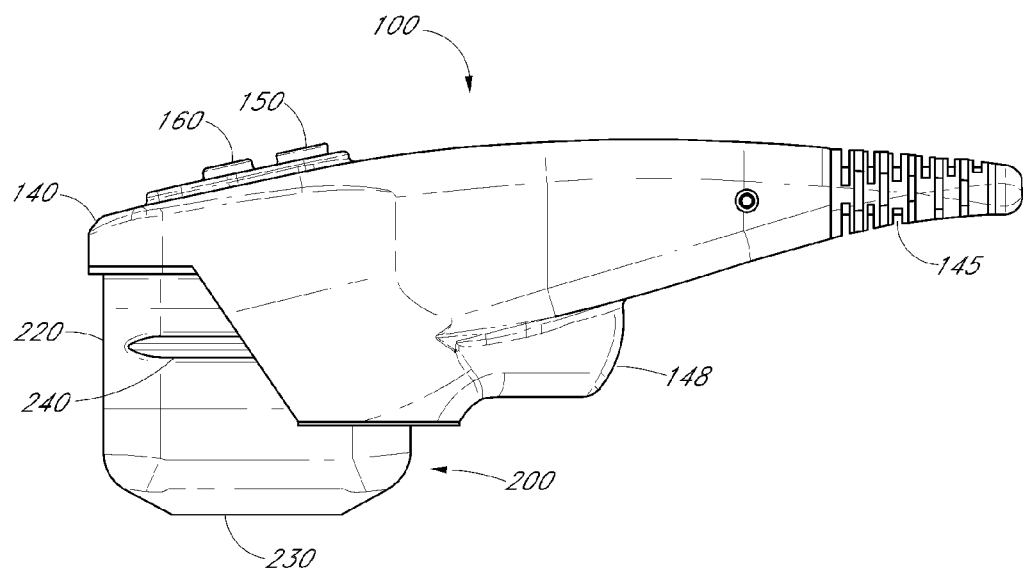
FIG. 3 is a side view illustrating a hand wand according to various embodiments.

With additional reference to the illustrations in FIGS. 2 and 3, the hand wand 100 can be designed for ergonomic considerations to improve comfort, functionality and/or ease of use of the hand wand 100 by a user, such as, for example, a practitioner or medical professional. The hand wand 100 can be designed to be used ambidextrously. In one embodiment, the use of the hand wand 100 is not diminished by whether it is in a right hand or a left hand. In one embodiment, of the hand wand 100 includes an imaging button 150, a treatment button 160, and an indicator 155 on a top portion of the hand wand 100. Other arrangements of buttons and/or indicators are possible in various embodiments. In one embodiment the hand wand 100 includes a hand rest 148 on a bottom portion and a coupler 140 distal to the flexible connector 145. In one embodiment, the hand rest 148 includes a clearance pocket molded into the hand wand 100 housing which allows a magnet-tipped clutch rod (433 and 432 of FIG. 7) to move back and forth to drive the transducer module's rectilinear motion without hitting the hand wand's housing. According to these aspects, the hand wand 100 can be operated by the user either in a right hand or a left hand. Further to these aspects, the user can control the imaging button 150 and the treatment button 160 with a thumb or finger, such as an index finger. An interior portion of the hand wand 100 can include electronics as well as software, connections, and/or couplings for interfacing to and from the electronics. In one embodiment, the hand wand 100 contains an electronic interface 175 (not illustrated here, but see other figures) in communication with at least one of the imaging button 150 and the treatment button 160. In accordance with one embodiment, the electronic interface 175 can interface with an outside source such as, for example, the controller 300. In various embodiments, the indictor 145 can be an LED, a light, an audio signal, and combinations thereof. In one aspect of the embodiments, the indicator 155 is a LED which can change colors based on different states of the CTS 20. For example the indicator 155 can be one color (or off) in a standby mode, a second color in an imaging mode and a third color in a treatment mode.

In one embodiment, the emitter-receiver module 200 is configured to removably attach both electronically and mechanically with a hand wand 100. In one embodiment, a motion mechanism 400 (see FIG. 7) is configured to move an ultrasonic transducer 280 in an emitter-receiver module 200 such as is illustrated in various embodiments in FIGS. 4-6. A user can remove the indicated transducer module from its protective, resealable pouch, setting aside the pouch for storing the transducer module between procedures, if necessary. In one embodiment, a hand wand 100 and an emitter-receiver module 200 can be connected by pushing the coupler 140 upwards and sliding the emitter-receiver module 200 into the hand wand 100 as shown in FIG. 1. In one embodiment, when the emitter-receiver module 200 is inserted, the controller 300 automatically detects it and updates the interactive graphical display 310. In one embodiment, the emitter-receiver module 200 locked into the hand wand 100 once the emitter-receiver module 200 is fully inserted and the coupler 140 at the tip of the hand wand 100 is pushed down. To disconnect the emitter-receiver module 200, the user can lift the coupler 140 at the tip of the hand wand 100 and slide the emitter-receiver module 200 out of the hand wand 100.

Figure 4:
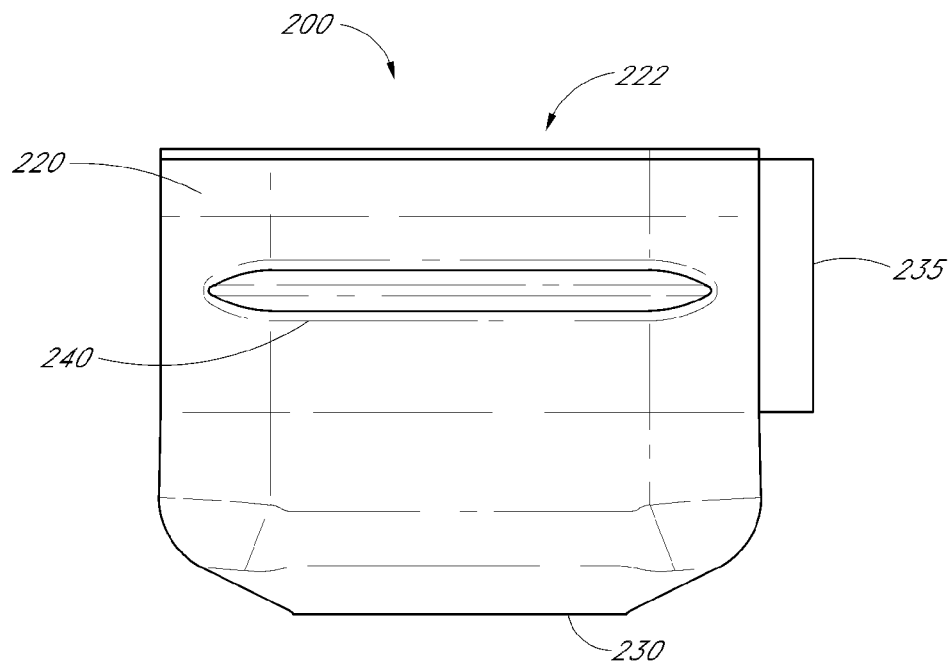
FIG. 4 is a side view illustrating an emitter-receiver module according to various embodiments.
Figure 5:
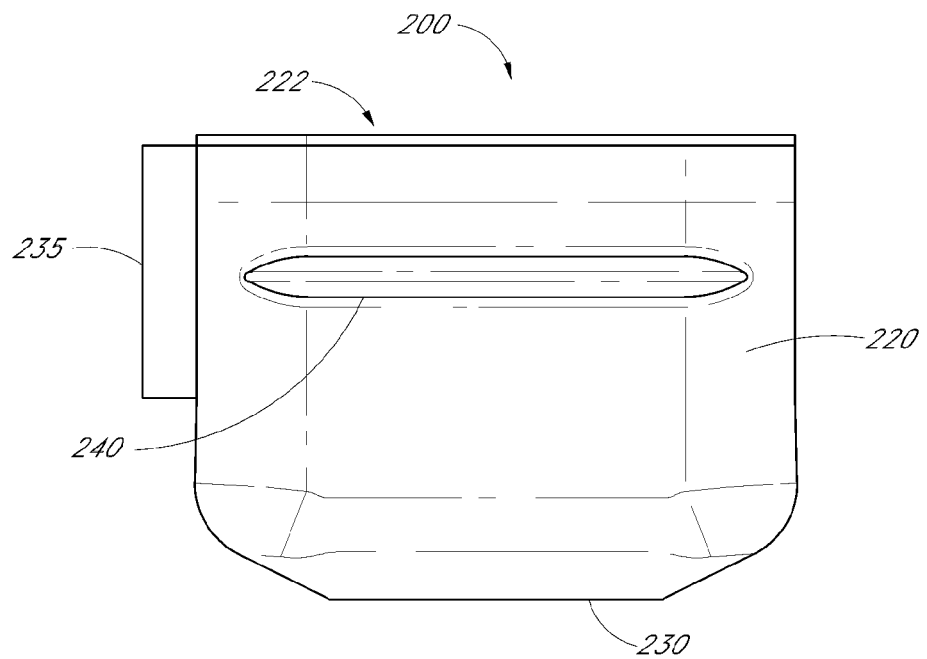
FIG. 5 is another side view illustrating an emitter-receiver module according to various embodiments.

FIGS. 4 and 5 illustrate two opposing side views of an embodiment of an emitter-receiver module 200 comprising a housing 220 and an acoustically transparent member 230. In one embodiment, the housing 220 may include a cap 222 that is removable or permanently attachable to the housing 220. In one embodiment, the emitter-receiver module 200 includes an interface guide 235 and/or one or more side guides 240 that can be useful in assisting the coupling of the emitter-receiver module 200 to the hand wand 100. The emitter-receiver module 200 can include a transducer 280 which can emit energy through an acoustically transparent member 230. The acoustically transparent member 230 can be a window, a filter and/or a lens. The acoustically transparent member 230 can be made of any material that is transparent to the energy that is that is emitted by the transducer 280. In one embodiment, the acoustically transparent member 230 is transparent to ultrasound energy.

Figure 6:
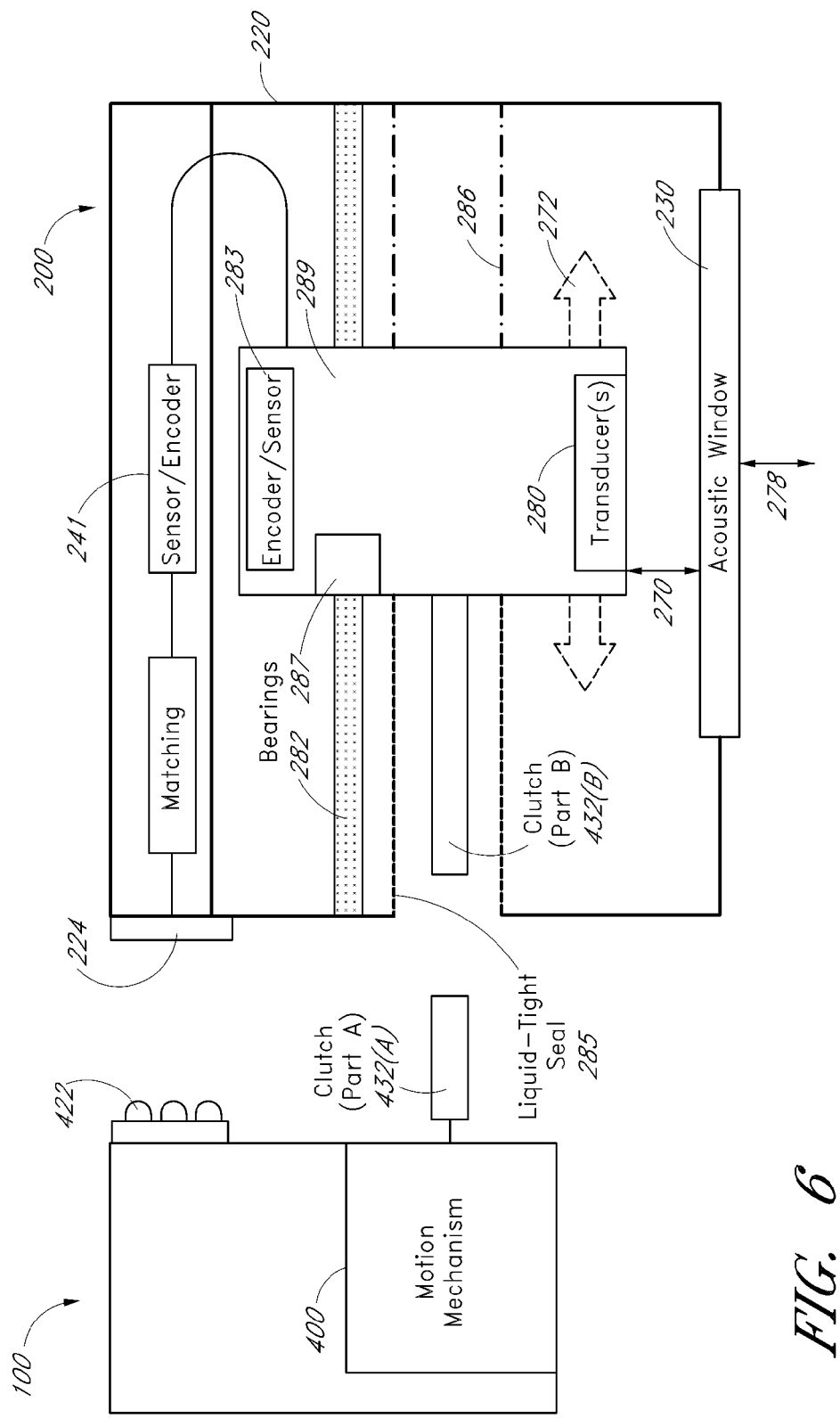
FIG. 6 is a block diagram illustrating an emitter-receiver module according to various embodiments.

In various embodiments, the transducer 280 is in communication with the controller 300. In one embodiment, the transducer 280 is electronically coupled to the hand wand 100 and/or the controller 300. In one embodiment, the housing 220 is sealed by the cap 222 and the structure of the combination of the housing 220 and the cap 222 can hold a liquid (not shown). As illustrated in FIG. 6, an embodiment of the emitter-receiver module 200 housing 220 can have a port 275 which allows interfacing from the hand wand 100 into the transducer module 200 without affecting the integrity of the sealed structure of the housing 220 and the cap 222. Further, the cap 222 can include one or more ports. For example, a first port 292, a second port 293 and a third port 294. The ports in the cap 222 can be useful for electronically coupling the transducer 280 to the hand wand 100 and/or the controller 300. In one embodiment, at least one of the ports in the cap 222 may be used to interface a sensor 201 that may be useful in the emitter-receiver module 200. The sensor 201 can be in communication with the controller 300. More than one sensor 201 is used in some embodiments.

In various embodiments, as illustrated in the block diagram of FIG. 6, the transducer 280 is movable within the emitter-receiver module 200. The transducer 280 is held by a transducer holder 289. In one embodiment, the transducer holder 289 includes a sleeve 287 which is moved along motion constraining bearings, such as linear bearings, namely, a bar (or shaft) 282 to ensure a repeatable linear movement of the transducer 280. In one embodiment, sleeve 287 is a spline bushing which prevents rotation about a spline shaft 282, but any guide to maintain the path of motion is appropriate. In one embodiment, the transducer holder 289 is driven by a motion mechanism 400, which may be located in the hand wand 100 or in the emitter-receiver module 200. The motion mechanism 400, as is discussed below in relation to FIG. 7, includes a scotch yoke 403 with a movement member 432 and a magnetic coupling 433 on a distal end of the movement member 432. The magnet coupling 433 helps move the transducer 280. One benefit of a motion mechanism such as motion mechanism 400 is that it provides for a more efficient, accurate and precise use of an ultrasound transducer 280, for both imaging and for therapy purposes. One advantage this type of motion mechanism has over conventional fixed arrays of multiple transducers fixed in space in a housing is that the fixed arrays are a fixed distance apart. By placing transducer 280 on a linear track under controller 300 control, embodiments of the system and device provide for adaptability and flexibility in addition to the previously mentioned efficiency, accuracy and precision. Real time and near real time adjustments can be made to imaging and treatment positioning along the controlled motion by the motion mechanism 400. In addition to the ability to select nearly any resolution based on the incremental adjustments made possible by the motion mechanism 400, adjustments can be made if imaging detects abnormalities or conditions meriting a change in treatment spacing and targeting.

In one embodiment, one or more sensors 201 may be included in the emitter-receiver module 200. In one embodiment, one or more sensors 201 may be included in the emitter-receiver module 200 to ensure that a mechanical coupling between the movement member 432 and the transducer holder 289 is indeed coupled. In one embodiment, an encoder 283 may be positioned on top of the transducer holder 289 and a sensor 201 may be located in a dry portion of the emitter-receiver module 200, or vice versa (swapped). In various embodiments the sensor 201 is a magnetic sensor, such as a giant magnetoresistive effect (GMR) or Hall Effect sensor, and the encoder a magnet, collection of magnets, or multi-pole magnetic strip. The sensor may be positioned as a transducer module home position. In one embodiment, the sensor 201 is a contact pressure sensor. In one embodiment, the sensor 201 is a contact pressure sensor on a surface of the device to sense the position of the device or the transducer on the patient. In various embodiments, the sensor 201 can be used to map the position of the device or a component in the device in one, two, or three dimensions. In one embodiment the sensor 201 is configured to sense the position, angle, tilt, orientation, placement, elevation, or other relationship between the device (or a component therein) and the patient. In one embodiment, the sensor 201 comprises an optical sensor. In one embodiment, the sensor 201 comprises a roller ball sensor. In one embodiment, the sensor 201 is configured to map a position in one, two and/or three dimensions to compute a distance between areas or lines of treatment on the skin or tissue on a patient. Motion mechanism 400 can be any motion mechanism that may be found to be useful for movement of the transducer 280. Other embodiments of motion mechanisms useful herein can include worm gears and the like. In various embodiments of the present invention, the motion mechanism is located in the emitter-receiver module 200. In various embodiments, the motion mechanism can provide for linear, rotational, multi-dimensional motion or actuation, and the motion can include any collection of points and/or orientations in space. Various embodiments for motion can be used in accordance with several embodiments, including but not limited to rectilinear, circular, elliptical, arc-like, spiral, a collection of one or more points in space, or any other 1-D, 2-D, or 3-D positional and attitudinal motional embodiments. The speed of the motion mechanism 400 may be fixed or may be adjustably controlled by a user. One embodiment, a speed of the motion mechanism 400 for an image sequence may be different than that for a treatment sequence. In one embodiment, the speed of the motion mechanism 400 is controllable by the controller 300.

Transducer 280 can have a travel distance 272 such that an emitted energy 50 is able to be emitted through the acoustically transparent member 230. In one embodiment, the travel 272 is described as end-to-end range of travel of the transducer 280. In one embodiment, the travel 272 of the transducer 280 can be between about 100 mm and about 1 mm. In one embodiment, the length of the travel 272 can be about 30 mm. In one embodiment, the length of the travel 272 can be about 25 mm. In one embodiment, the length of the travel 272 can be about 15 mm. In one embodiment, the length of the travel 272 can be about 10 mm. In various embodiments the length of the travel 272 can be about between 0-25 mm, 0-15 mm, 0-10 mm.

The transducer 280 can have an offset distance 270, which is the distance between the transducer 280 and the acoustically transparent member 230. In various embodiments of the present invention, the transducer 280 can image and treat a region of interest of about 25 mm and can image a depth less than about 10 mm. In one embodiment, the emitter-receiver module 200 has an offset distance 270 for a treatment at a depth 278 of about 4.5 mm below the skin surface 501 (see FIG. 15).

In various embodiments, transducer modules 200 can be configured for different or variable ultrasonic parameters. For example, in various non-limiting embodiments, the ultrasonic parameter can relate to aspects of the transducer 280, such as geometry, size, timing, spatial configuration, frequency, variations in spatial parameters, variations in temporal parameters, coagulation formation, depth, width, absorption coefficient, refraction coefficient, tissue depths, and/or other tissue characteristics. In various embodiments, a variable ultrasonic parameter may be altered, or varied, in order to effect the formation of a lesion for the desired cosmetic approach. In various embodiments, a variable ultrasonic parameter may be altered, or varied, in order to effect the formation of a lesion for the desired clinical approach. By way of example, one variable ultrasonic parameter relates to configurations associated with tissue depth 278. In several embodiments, the transducer module 200 is configured for both ultrasonic imaging and ultrasonic treatment and is operably coupled to at least one controlling device 150, 160 and a movement mechanism 400. The transducer module 200 is configured to apply ultrasonic therapy at a first ultrasonic parameter and a second ultrasonic parameter. In various embodiments, the first and second ultrasonic parameters are selected from the group consisting of: variable depth, variable frequency, and variable geometry. For example, in one embodiment, a single transducer module 200 delivers ultrasonic therapy at two or more depths 278, 278'. In another embodiment, two or more interchangeable transducer modules 200 each provide a different depth 278 (e.g., one module treats at 3 mm depth while the other treats at a 4.5 mm depth). In yet another embodiment, a single transducer module 200 delivers ultrasonic therapy at two or more frequencies, geometries, amplitudes, velocities, wave types, and/or wavelengths. In other embodiments, two or more interchangeable transducer modules 200 each provide a different parameter value. In one embodiment, a single transducer module 200 may provide at least two different depths 278, 278' and at least two different frequencies (or other parameter). Variable parameter options are particularly advantageous in certain embodiments because they offer enhanced control of tissue treatment and optimize lesion formation, tissue coagulation, treatment volume, etc.

Figure 15:
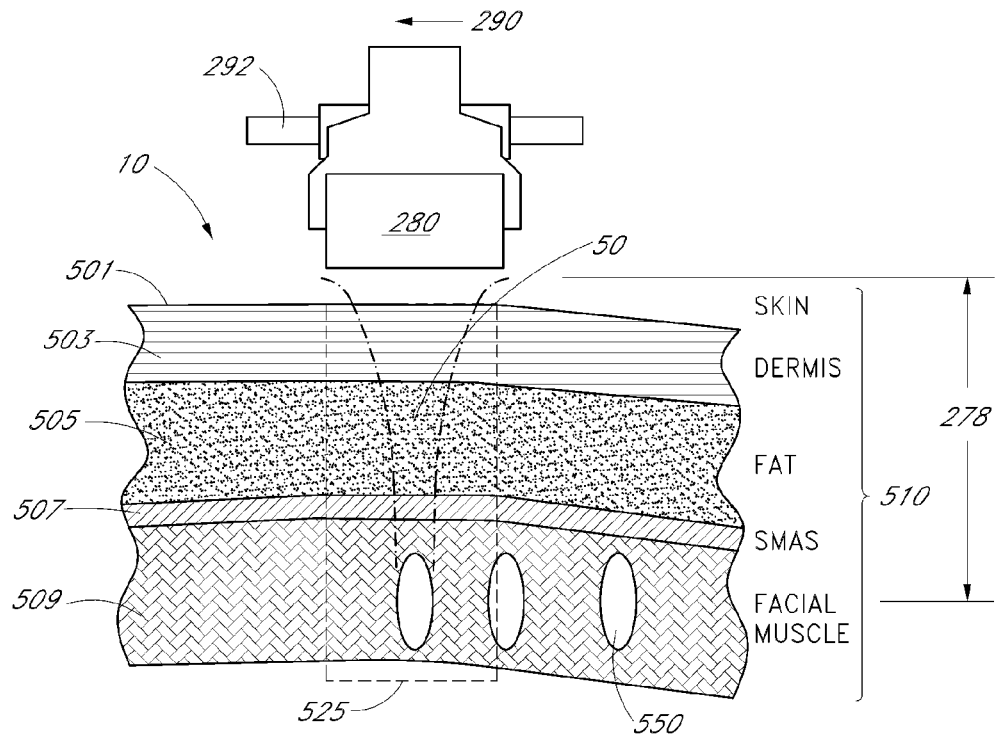
FIG. 15 is a cross-sectional illustration depicting an apparatus and a method according to one embodiment.

FIG. 15 illustrates one embodiment of a depth 278 that corresponds to a muscle depth. In various embodiments, the depth 278 can correspond to any tissue, tissue layer, skin, dermis, fat, SMAS, muscle, or other tissue. In some embodiments, different types of tissue are treated to provide synergistic effects, thus optimizing clinical results. In another embodiment, the emitter-receiver module has an offset distance 270 for a treatment at a depth 278 of about 3.0 mm below the surface 501. In various embodiments, this offset distance may be varied such that the transducer 280 can emit energy to a desired depth 278 below a surface 501. In various embodiments, in a treatment mode, bursts of acoustic energy from the transducer 280 can create a linear sequence of individual thermal lesions 550. In one embodiment the individual thermal lesions 550 are discrete. In one embodiment the individual thermal lesions 550 are overlapping. In various embodiments, the transducer 280 can image to a depth roughly between 1 and 100 mm. In one embodiment, the transducer imaging depth can be approximately 20 mm. In one embodiment, the transducer 280 can treat to a depth of between about zero (0) to 25 mm. In one embodiment, the transducer treatment depth can be approximately 4.5 mm.

In any of the embodiments described herein, the transducer treatment depth can be approximately 0.5 mm, 1 mm, 1.5 mm, 2 mm, 3 mm, 4 mm, 4.5 mm, 5 mm, 6 mm, 10 mm 15 mm, 20 mm, 25 mm, or any other depth in the range of 0-100 mm. Varied depth treatment, including treatment of the same tissue at different depths or treatment of different tissues, can increase clinical results by providing synergistic effects.

In various embodiments of the present invention, a transducer 280 is capable of emitting ultrasound energy for imaging, diagnostics, or treating and combinations thereof. In one embodiment, the transducer 280 is configured to emit ultrasound energy at a specific depth in a region of interest to target a region of interest of a specific tissue such as a corrugator supercilii muscle as described below. In this embodiment, the transducer 280 may be capable of emitting unfocused or defocused ultrasound energy over a wide area of the region of interest 65 for treatment purposes (see FIGS. 12 and 22). In one embodiment, the emitter-receiver module 200 contains a transducer 280 that can image and treat a region of tissue up to 25 mm long and can image a depth of up to 8 millimeters. Treatment occurs along a line less than or equal to the transducer's active length, which is indicated in one embodiment by guide marks (not illustrated here) on the sides of the emitter-receiver module 200 near a acoustically transparent member 230 along the surface adjacent to the patient's skin. In one embodiment, a marked guide at the front tip of the transducer 280 represents the center of the treatment line. In one embodiment of a treatment mode, bursts of sound energy create a linear sequence of individual cosmetic treatment zones. In some embodiments, the cosmetic treatment zones are thermal coagulation zones. In one embodiment the individual thermal coagulation zones are discrete. In one embodiment the individual thermal coagulation zones are overlapping. A label (not illustrated here) may be applied or etched on a side or top surface of the emitter-receiver module 200 to provide the transducer 280 type, expiration date, and other information. In one embodiment, an emitter-receiver module 200 can be configured with a label for tracking the type transducer 280 used, treatment frequency and treatment depth, a unique serial number, a part number, and date of manufacture. In one embodiment, the emitter-receiver modules 200 are disposable. In one embodiment, the system tracks use of the emitter-receiver modules 200 in order to determine the remaining life of the emitter-receiver module 200 as transducer life diminishes over time and/or usage. Once a transducer 280 has diminished capacity, the emitter-receiver module 200 may work less effectively in performing its functions. In one embodiment, the emitter-receiver module 200 or controller 300 will track usage and prevent additional usage of an emitter-receiver module 200 beyond a recommended usage life in order to preserve the safety and effectiveness of the device. This safety feature can be configured based on test data.

In one embodiment, an emitter-receiver module 200 is configured with a treatment frequency of approximately 4 MHz, a treatment depth of approximately 4.5 mm and an imaging depth range of roughly 0-8 mm. In various embodiments, the treatment frequencies can be in the range of 4-5 MHz, 4.2-4.9 MHz, 4.3-4.7 MHz, 4.3 MHz, 4.7 MHz, or other frequencies. In various embodiments, the treatment depth can be in the range of approximately 4-5 mm, 4.3 mm-4.7 mm, and/or 4.4 mm-4.6 mm. In one embodiment, an emitter-receiver module 200 is configured with a treatment frequency of approximately 7 MHz, a treatment depth of approximately 3.0 mm and an imaging depth range of roughly 0-8 mm. In various embodiments, the treatment frequencies can be in the range of 7-8 MHz, 7.2-7.8 MHz, 7.3-7.7 MHz, 7.3 MHz, 7.5 MHz, or other frequencies. In various embodiments, the treatment depth can be in the range of approximately 4-5 mm, 4.3 mm-4.7 mm, and/or 4.4 mm-4.6 mm. In one embodiment, an emitter-receiver module 200 is configured with a treatment frequency of approximately 7 MHz, a treatment depth of approximately 4.5 mm and an imaging depth range of roughly 0-8 mm. In various embodiments, the treatment frequencies can be in the range of 7-8 MHz, 7.2-7.8 MHz, 7.3-7.7 MHz, 7.3 MHz, 7.5 MHz, or other frequencies. In various embodiments, the treatment depth can be in the range of approximately 4-5 mm, 4.3 mm-4.7 mm, and/or 4.4 mm-4.6 mm. In one embodiment, an emitter-receiver module 200 is configured with a treatment frequency of approximately 10 MHz, a treatment depth of approximately 1.5 mm and an imaging depth range of roughly 0-8 mm. In various embodiments, the treatment frequencies can be in the range of 8-12 MHz, 9-11 MHz, 9.5-10.5 MHz, or other frequencies. In various embodiments, the treatment depth can be in the range of approximately 1-2 mm, 1.25 mm-1.75 mm, and/or 1.4 mm-1.6 mm.

Transducer 280 may comprise one or more transducers for facilitating imaging and/or treatment. The transducer 280 may comprise a piezoelectrically active material, such as, for example, lead zirconante titanate, or other piezoelectrically active materials such as, but not limited to, a piezoelectric ceramic, crystal, plastic, and/or composite materials, as well as lithium niobate, lead titanate, barium titanate, and/or lead metaniobate, including piezoelectric, electrically conductive, and plastic film layers deposited on spherically focused backing material. In addition to, or instead of, a piezoelectrically active material, the transducer 280 may comprise any other materials configured for generating radiation and/or acoustical energy. The transducer 280 may also comprise one or more matching and/or backing layers coupled to the piezoelectrically active material. The transducer 280 may also be configured with single or multiple damping elements.

In one embodiment, the thickness of a transduction element of the transducer 280 may be configured to be uniform. That is, the transduction element may be configured to have a thickness that is generally substantially the same throughout. In another embodiment, the transduction element may also be configured with a variable thickness, and/or as a multiple damped device. For example, the transduction element of the transducer 280 may be configured to have a first thickness selected to provide a center operating frequency of a lower range, for example from about 1 MHz to about 10 MHz. The transduction element may also be configured with a second thickness selected to provide a center operating frequency of a higher range, for example from about 10 MHz to greater than 100 MHz.

In yet another embodiment, the transducer 280 is configured as a single broadband transducer excited with two or more frequencies to provide an adequate output for raising a temperature within a treatment area of the region of interest to the desired level as discussed herein. The transducer 280 may be configured as two or more individual transducers, such that each transducer 280 may comprise a transduction element. The thickness of the transduction elements may be configured to provide center-operating frequencies in a desired treatment range. For example, in one embodiment, the transducer 280 may comprise a first transducer configured with a first transduction element having a thickness corresponding to a center frequency range of about 1 MHz to about 10 MHz, and a second transducer configured with a second transduction element having a thickness corresponding to a center frequency range of about 10 MHz to greater than 100 MHz. Various other combinations and ranges of thickness for a first and/or second transduction element can be designed to focus at specific depths below a surface 501, for specific frequency ranges, and/or specific energy emissions.

The transduction elements of the transducer 280 can be configured to be concave, convex, and/or planar. In one embodiment, the transduction elements are configured to be concave in order to provide focused energy for treatment of the region of interest. Additional embodiments of transducers are disclosed in U.S. application Ser. No. 10/944,500, which is incorporated in its entirety herein by reference.

Moreover, the transducer 280 can be any distance from the surface 501. In that regard, it can be far away from the surface 501 disposed within a long transducer or it can be just a few millimeters from the surface 501. This distance can be determined by design using the offset distance 270 as described herein. In certain embodiments, positioning the transducer 280 closer to the surface 501 is better for emitting ultrasound at higher frequencies. Moreover, both two and three dimensional arrays of elements can be used in the present invention. Furthermore, the transducer 280 may comprise a reflective surface, tip, or area at the end of the transducer 280 that emits ultrasound energy. This reflective surface may enhance, magnify, or otherwise change ultrasound energy emitted from the CTS 20.

In various embodiments any set of one or more transducers 280 can be used for various functions, such as separate treat/image or dual-mode (both treat/image) transducers or a treat-only version. In various embodiments the imaging element(s) can be on the side (adjacent to) or at any relative position, attitude, and/or height, or even within the therapy element(s). One or more therapy depths and frequencies can be used and one or more imaging elements or one or more dual-mode elements. In various embodiments any controllable means of moving the active transduction element(s) within the emitter-receiver module 200 housing constitute viable embodiments.

In various embodiments, the emitter-receiver module 200 can also be configured in various manners and comprise a number of reusable and/or disposable components and parts in various embodiments to facilitate its operation. For example, the emitter-receiver module 200 can be configured within any type of transducer probe housing or arrangement for facilitating the coupling of the transducer 280 to a tissue interface, with such housing comprising various shapes, contours and configurations. The emitter-receiver module 200 can comprise any type of matching, such as for example, electric matching, which may be electrically switchable, multiplexer circuits and/or aperture/element selection circuits, and/or probe identification devices, to certify probe handle, electric matching, transducer usage history and calibration, such as one or more serial EEPROM (memories).

In various embodiments, the emitter-receiver module 200 may also comprise cables and connectors, motion mechanisms, motion sensors and encoders, thermal monitoring sensors, and/or user control and status related switches, and indicators such as LEDs. In one embodiment, a motion mechanism similar to the motion mechanism 400 described in the hand wand 100 may be used to drive the emitter-receiver module 200 from within the emitter-receiver module 200. In one embodiment, a hand wand 100 is electrically connectable to the emitter-receiver module 200 to drive the emitter-receiver module 200 from within itself. In various embodiments, a motion mechanism (in any of the embodiments described herein) may be used to controllably create multiple lesions, or sensing of probe motion itself may be used to controllably create multiple lesions and/or stop creation of lesions 550, as discussed herein. For example in one embodiment, for safety reasons if the emitter-receiver module 200 is suddenly jerked or is dropped, a sensor can relay this action to the controller 300 to initiate a corrective action or shut down the emitter-receiver module 200. In addition, an external motion encoder arm may be used to hold the probe during use, whereby the spatial position and attitude of the emitter-receiver module 200 is sent to the controller 300 to help controllably create lesions 550. Furthermore, other sensing functionality such as profilometers or other imaging modalities may be integrated into the emitter-receiver module 200 in accordance with various embodiments. In one embodiment, pulse-echo signals to and from the emitter/receiver module 200 are utilized for tissue parameter monitoring of the treatment region 550.

Coupling components can comprise various devices to facilitate coupling of the emitter-receiver module 200 to a region of interest. For example, coupling components can comprise cooling and acoustic coupling system configured for acoustic coupling of ultrasound energy and signals. Acoustic cooling/coupling system with possible connections such as manifolds may be utilized to couple sound into the region-of-interest, control temperature at the interface and deeper into tissue, provide liquid-filled lens focusing, and/or to remove transducer waste heat. The coupling system may facilitate such coupling through use of one or more coupling mediums, including air, gases, water, liquids, fluids, gels, solids, and/or any combination thereof, or any other medium that allows for signals to be transmitted between the transducer 280 and a region of interest. In one embodiment one or more coupling media is provided inside a transducer. In one embodiment a fluid-filled emitter-receiver module 200 contains one or more coupling media inside a housing. In one embodiment a fluid-filled emitter-receiver module 200 contains one or more coupling media inside a sealed housing, which is separable from a dry portion of an ultrasonic device.

In addition to providing a coupling function, in accordance with one embodiment, the coupling system can also be configured for providing temperature control during the treatment application. For example, the coupling system can be configured for controlled cooling of an interface surface or region between the emitter-receiver module 200 and a region of interest and beyond by suitably controlling the temperature of the coupling medium. The suitable temperature for such coupling medium can be achieved in various manners, and utilize various feedback systems, such as thermocouples, thermistors or any other device or system configured for temperature measurement of a coupling medium. Such controlled cooling can be configured to further facilitate spatial and/or thermal energy control of the emitter-receiver module 200.

Figure 7:
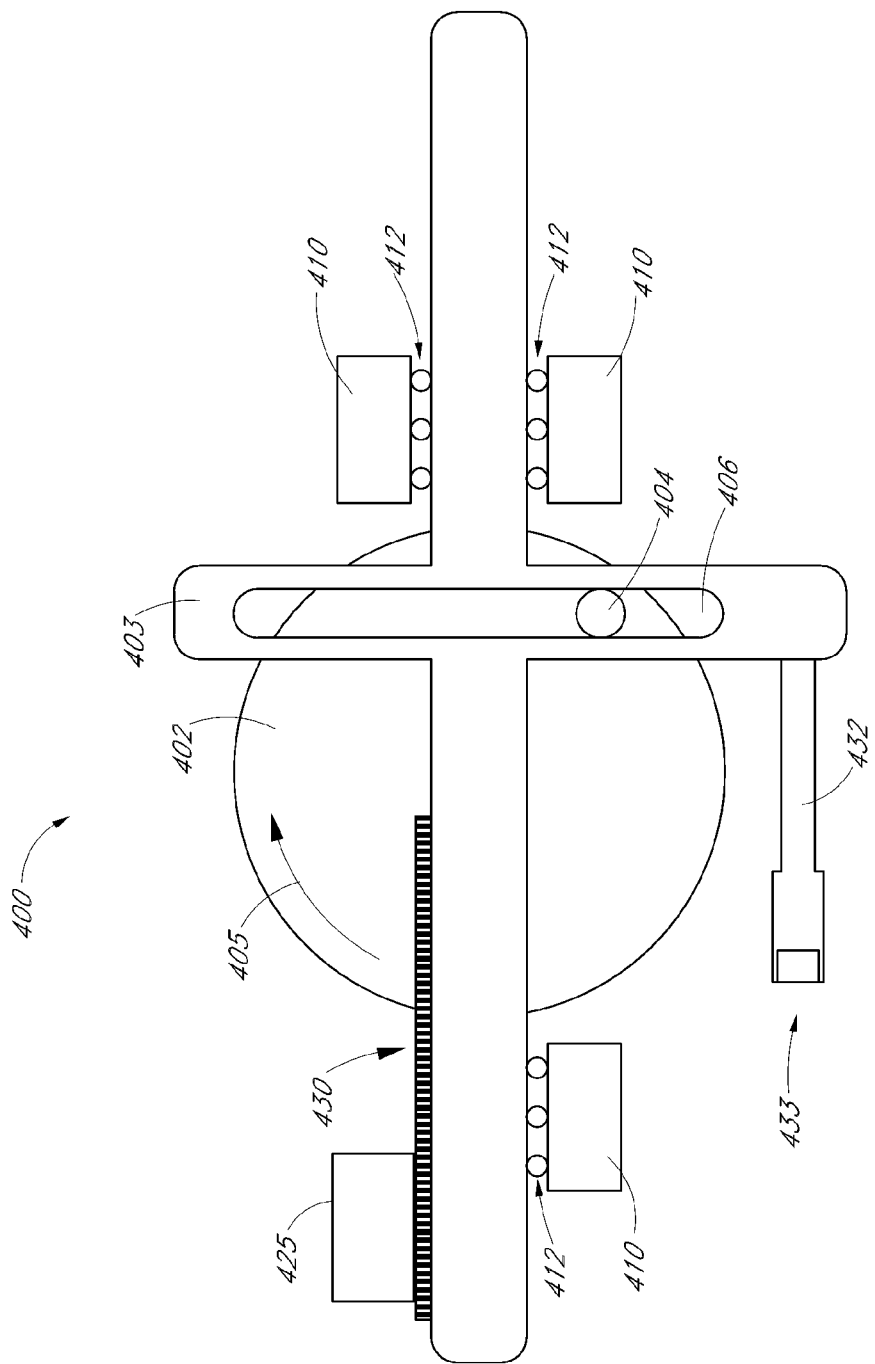
FIG. 7 is an illustration depicting a movement mechanism according to various embodiments.

In one embodiment, the emitter-receiver module 200 is connected to a motion mechanism 400 in the hand wand 100. In one embodiment, the motion mechanism 400 may be in the emitter-receiver module 200. One embodiment of a motion mechanism 400 is illustrated in FIG. 7, which depicts a two phase stepper motor 402 and a scotch yoke 403 to produce a linear motion. The stepper motor 402 rotates as indicated by arrow 405 which moves a pin 404 in a circular path. The pin 404 slides in a slot 406 of the scotch yoke 403. This causes the scotch yoke 403 to move in a linear fashion. The scotch yoke 403 is held by guides 410 and glide members 412 may be between the scotch yoke 403 and guide 410. In one embodiment, a guide 410 is a shoulder screw. Embodiments of the glide member 412 may include any material or mechanical device that lowers a coefficient of friction between the guide 410 and the scotch yoke 403, or any linear bearings. For example, in various embodiments the glide member 412 can be at least one of an elastomeric material, a lubricant, ball bearings, a polished surface, a magnetic device, pressurized gas, or any other material or device useful for gliding.

A sensor 425 operates as one embodiment of a position sensor by reading an encoder 430 which is mounted on the scotch yoke 403. In one embodiment, the encoder strip 430 is an optical encoder which has a pitch in a range from about 1.0 mm to about 0.01 mm. In one embodiment, the pitch may be about 0.1 mm. The encoder strip 430 can include index marks at each end of its travel. The direction of travel of the encoder strip 430 can be determined by comparing phases of two separate channels in the optical sensor 425. In one embodiment, the encoder strip 430 has one, two or more home positions which may be useful in calibrating for a position and travel of the scotch yoke 403.

In one embodiment, the movement of the scotch yoke 403 is transferred through the movement mechanism 432 such that the transducer 280 moves in a linear fashion inside of the emitter-receiver module 200. In one embodiment, the scotch yoke 403 includes a movement member 432 and a magnetic coupling 433 on a distal end of the movement member 432. The movement member 432 can be sized to travel through or within a liquid-tight seal.

Figure 8:
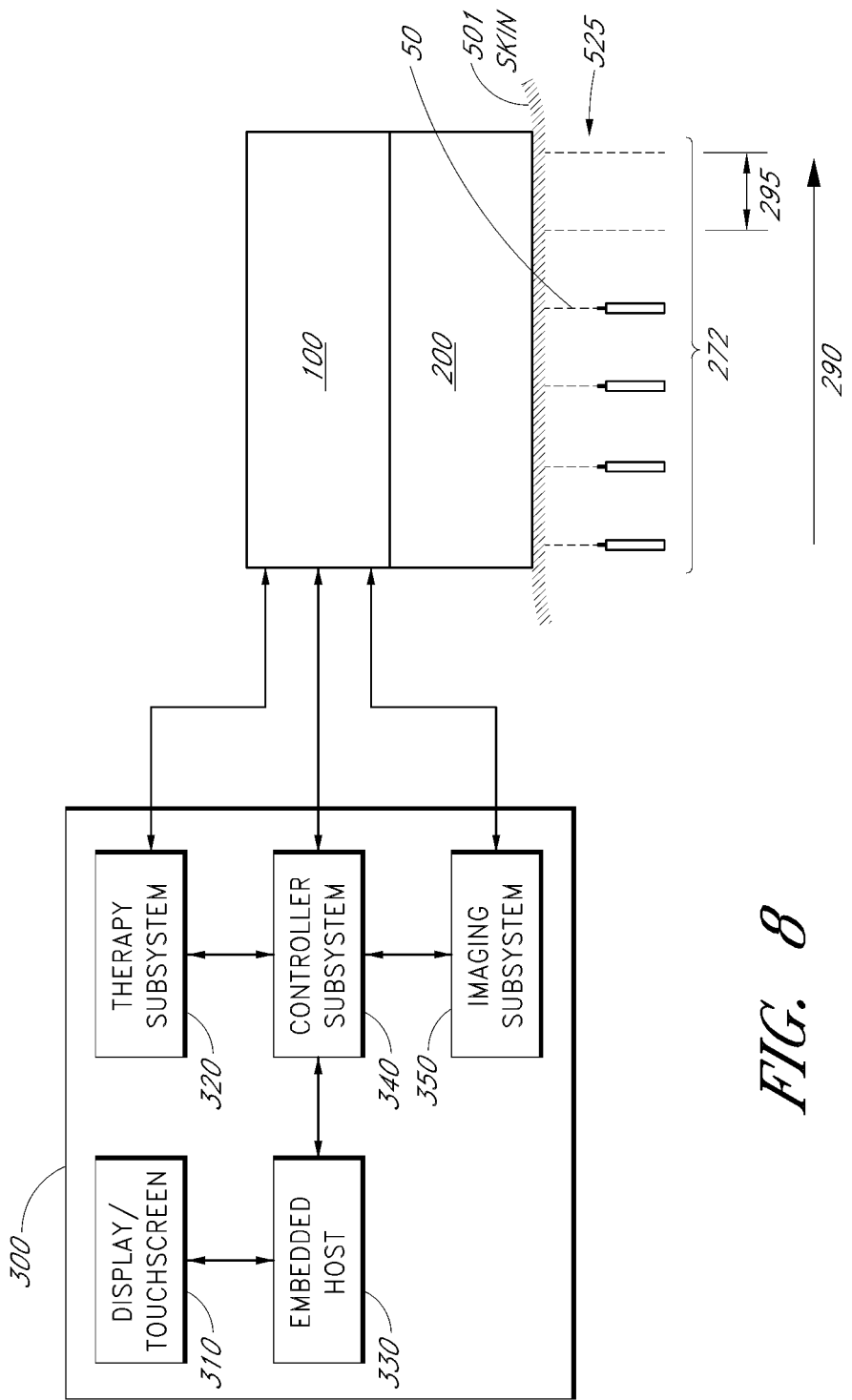
FIG. 8 is a block diagram illustrating a cosmetic treatment system according to various embodiments.

Transducer 280 can have a travel distance 272 The coupling system may facilitate such coupling With reference to FIG. 8, a block diagram illustrates various embodiments of the CTS 20. In one embodiment, the controller 300 includes a controller subsystem 340, a therapy subsystem 320, an imaging subsystem 350, an embedded host 330 (with software) and an interactive graphical display 310. In one embodiment, the therapy subsystem 320, the controller subsystem 340, and/or the imaging subsystem 350 is interfaced with the hand wand 100 and/or the emitter-receiver module 200. In various embodiments, the CTS 20 has built into the controller 300 limits as to an amount of energy 50 that can be emitted from the emitter-receiver module 200. These limits can be determined by time of emission, frequency of the energy emitted, power of energy, a temperature, and/or combinations thereof. The temperature may be from monitoring the surface 501 and/or monitoring the emitter-receiver module 200. According to one embodiment the limits may be preset and cannot be changed by the user.

According to various embodiments, when the emitter-receiver module 200 is coupled to the surface 501, which may be a skin surface of the subject, the CTS 20 can image and/or treat a treatment area 272. In some aspects of these embodiments, the imaging by the CTS 20 can be over essentially the entire treatment area 272 at specified depths 278 below the surface 501. In some aspects of these embodiments, the treatment can include discrete energy emissions 50 to create lesion 550 at intervals along the treatment area 272 and at specified depths 278. In one embodiment the intervals are discrete. In one embodiment the intervals are overlapping.

In various embodiments the imaging subsystem 350 may be operated in a B-mode. The imaging subsystem 350 can provide support to the emitter-receiver module 200 such that the emitter-receiver module 200 can have emission energy 50 from a frequency of about 10 MHz to greater than 100 MHz. In one embodiment, the frequency is about 18 MHz.

In one embodiment, the frequency is about 25 MHz. The imaging subsystem 350 can support any frame rate that may be useful for the applications. In some embodiments, the frame rate may be in a range from about 1 frames per second (hereinafter "FPS") to about 100 FPS, or from about 5 FPS to about 50 FPS or from about 5 FPS to about 20 FPS nominal. An image field of view may be controlled by the image area of the transducer 280 in a focus of the transducer 280 at a specific depth 278 below the surface 501 as discussed herein. In various embodiments, the field of view can be less than 20 mm in depth and 100 mm in width or less than 10 mm in depth and less than 50 mm in width. In one embodiment, a particularly useful image field of view is about 8 mm in depth by about 25 mm in width.

A resolution of the field of view can be controlled by the graduation of the movement mechanism 400. As such, any pitch may be useful based on the graduation of the motion mechanism 400. In one embodiment, the resolution of the field of view may be controlled by the resolution of an encoder 430 and sensor 425. In one embodiment the image field of view can have a pitch in the range of 0.01 mm to 0.5 mm or from about 0.05 mm to about 0.2 mm. In one embodiment, a particularly useful line pitch for the image field of view is about 0.1 mm.

According to various embodiments, the imaging subsystem 350 can include one or more functions. In one embodiment, the one or more functions can include any of the following B-mode, scan image, freeze image, image brightness, distance calipers, text annotation for image, save image, print image, and/or combinations thereof. In various embodiments of the present invention, the imaging subsystem 350 contains pulse echo imaging electronics.

Various embodiments of the therapy subsystem 320 comprise a radio frequency (hereinafter "RF") driver circuit which can deliver and/or monitor power going to the transducer 280. In one embodiment, the therapy subsystem 320 can control an acoustic power of the transducer 280. In one embodiment, the acoustic power can be from a range of 1 watt (hereinafter "W") to about 100 W in a frequency range from about 1 MHz to about 10 MHz, or from about 10 W to about 50 W at a frequency range from about 3 MHz to about 8 MHz. In one embodiment, the acoustic power and frequencies are about 40 W at about 4.3 MHz and about 30 W at about 7.5 MHz. An acoustic energy produced by this acoustic power can be between about 0.01 joule (hereinafter "J") to about 10 J or about 2 J to about 5 J. In one embodiment, the acoustic energy is in a range less than about 3 J. In various embodiments, the acoustic energy is approximately 0.2 J-2.0 J, 0.2 J, 0.4 J, 1.2 J, 2.0 J or other values. In one embodiment, the amount of energy deliverable is adjustable.

In various embodiments the therapy subsystem 320 can control a time on for the transducer 280. In one embodiment, the time on can be from about 1 millisecond (hereinafter "ms") to about 100 ms or about 10 ms to about 50 ms. In one embodiment, time on periods can be about 30 ms for a 4.3 MHz emission and about 30 ms for a 7.5 MHz emission.

In various embodiments, the therapy subsystem 320 can control the drive frequency of the transducer 280 moving across the travel 272. In various embodiments, the frequency of the transducer 280 is based on the emitter/receiver 200 connected to the hand wand 100. According to some embodiments, the frequency of this movement may be in a range from about 1 MHz to about 10 MHz, or about 4 MHz to about 8 MHz. In one embodiment, the frequencies of this movement are about 4.3 MHz or about 7.5 MHz. As discussed herein, the length of the travel 272 can be varied, and in one embodiment, the travel 272 has a length of about 25 mm.

According to various embodiments, the therapy subsystem 320 can control the line scan along the travel 272 and this line scan can range from 0 to the length of the distal of the travel 272. In one embodiment, the line scan can be in a range from about 0 to about 25 mm. According to one embodiment, the line scan can have incremental energy emissions 50 having a treatment spacing 295 and this treatment spacing can range from about 0.01 mm to about 25 mm or from 0.2 mm to about 2.0 mm. In one embodiment, treatment spacing 295 is about 1.5 mm. In various embodiments, the treatment spacing 295 can be about 0.5 mm, 1 mm, 1.5 mm, 2 mm, 2.5 mm, 3 mm, or more. In various embodiments, the treatment spacing 295 can be predetermined, constant, variable, programmable, and/or changed at any point before, during or after a treatment line. In various embodiments, steps between treatment spacing 295 can vary by fixed or variable amounts, such as 0.1 mm, 0.5 mm, 1 mm, or other amounts. The resolution of the line scan is proportional to the resolution of the motion mechanism 400. In various embodiments, the resolution that is controllable by the therapy subsystem 320 is equivalent to the resolution controllable by the imaging subsystem 350 and, as such, can be in the same range as discussed for the imaging subsystem 350.

In various embodiments, the therapy subsystem 320 can have one or more functions. In one embodiment, the one or more functions can include any of the following: emission energy control, treatment spacing, travel length, treatment ready, treatment, treatment stop, save record, print record, display treatment, and/or combinations thereof.

In various embodiments, the control subsystem 340 includes electronic hardware which mechanically scans the transducer 280 for one or more functions. In one embodiment, one or more functions that can be scanned by the controller subsystem 340 can include scanning the transducer 280 for imaging, a position of the transducer 280 for imaging, scan slip positions of the transducer 280 at locations for therapy, controls therapy hardware settings, provides other control functions, interfacing with the embedded host 330, and/or combinations thereof. In one embodiment the locations are discrete. In one embodiment the locations are overlapping.

In various embodiments, an embedded host 330 is in two-way communication with the controller 340 and the graphical interface 310. In one embodiment, data from the controller 340 can be converted to a graphical format by the embedded host 330 and then transferred to the graphical interface 310 for displaying imaging and/or treatment data.

In one embodiment, commands can be entered by a user employing the graphical interface 310. The commands entered by use of the graphical interface 310 can be communicated to embedded host 330 and then communicated to controller 340 for control and operation of the therapy subsystem 320, the imaging subsystem 350, the hand wand 100, and/or the emitter-receiver module 200. In various embodiments, the embedded host 330 can include a processing unit, memory, and/or software.

In various embodiments, when the imaging button 150 is pressed the CTS 20 enters an imaging sequence in which the imaging subsystem 350 acquires scan lines which are transferred to the embedded host 330 for data conversion and/or graphical conversion which is then communicated to the graphical interface 310. While the system is operating in the imaging sequence, the imaging button 150 may be pressed again which puts the CTS 20 into a ready state. In an aspect of this embodiment, an audio warning or visual display such as the indicator 155 may be initiated to alert the user that the CTS 20 is in the ready state. In the ready state, the controller subsystem 340 communicates with the embedded host 330 to acquire users entered treatment settings. These treatment settings can be checked and can be verified and converted to hardware parameter in the controller subsystem 340. In one embodiment, such set hardware parameters can include treatment timing, cadence, time on, time off, RF driver power, voltage levels, acoustic power output, oscillator frequency, therapy transducer frequency, treatment spacing, travel, motion mechanism speed, and/or combinations thereof. The CTS 20 may remain in the ready state indefinitely or may be timed out after a set time period.

In various embodiments of the present invention, when the CTS 20 is in the ready state, the treatment button 160 may be activated. This activation of the treatment button 160 commences a treatment sequence. The treatment sequence is controllable by the therapy subsystem 320 which executes the treatment sequence along with the controller subsystem 340 and independently of the embedded host 330. The treatment sequence is delivered in real time and last one of the length of the activating of the treatment button 160 or a programmed time downloaded from the embedded host 330 into the controller subsystem 340 and/or the therapy subsystem 320.

In various embodiments, safety features can be designed in the CTS 20 to ensure safe use, imaging, and treatment. In various embodiments, the embedded host 330 is in communication with data port 390 which can comprise either one-way or two-way communication between the data port 390 and the embedded host 330. The data port 390 can interface any electronic storage device, for example, the data port 390 can be interfaced for one or more of a USB drive, a compact flash drive, a secured digital card, a compact disc, and the like. In one embodiment, a storage device through data port 390 to the embedded host 330 can download treatment records or software updates. In another aspect of these embodiments, the storage device can be a two-way communication through data port 390 to the embedded host 330 such that a treatment protocol can be downloaded to the embedded host 330 and CTS 20. A treatment protocol can include parameters, imaging data, treatment data, date/time, treatment duration, subject information, treatment location, and combinations thereof, and the like which can be uploaded by and/or downloaded from the embedded host 330 to the storage device via the data port 390. In one embodiment, a second data port (not shown) may be located on the back of the controller. The second data port may provide power and/or data to a printer.

In various embodiments, the CTS 20 includes a lock 395. In one embodiment, in order to operate CTS 20, lock 395 must be unlocked so that power switch 393 may be activated. In one embodiment, the power may remain on as the lock 395 is unlocked and locked successively and different parameters are entered. A key 396 (not illustrated) may be needed to unlock the lock 395. Examples of keys 396 useful herein include a standard metal tooth and groove key, or an electronic key. In some embodiments, an electronic key 396 may be digitally encoded to include user information and collect data and/or time usage of CTS 20. In one embodiment, an electronic key is particularly useful with CTS 20 may be a USB drive with encryption such that inserting the USB drive key into lock 395 the CTS 20 may be activated. In various embodiments, a software key can be configured to indicate a condition or status to the user, lock the system, interrupt the system, or other feature.

Figure 9:
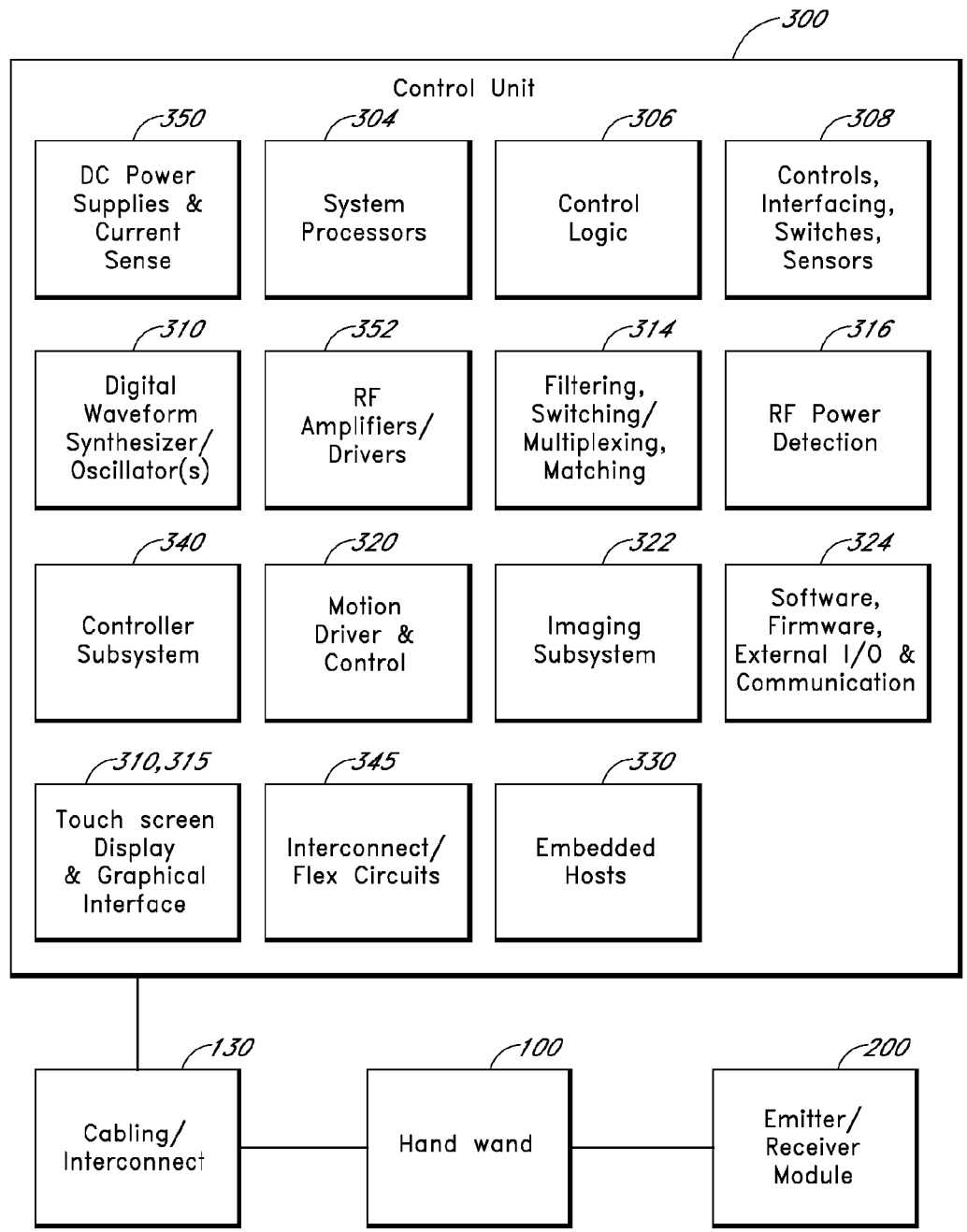
FIG. 9 is an electronic block diagram illustrating a cosmetic treatment system according to various embodiments.

With reference to FIG. 9, a CTS 20 layout block diagram is illustrated according to various embodiments of the present invention. In accordance with the aspects of these embodiments, the controller 300 can include several electronic sections. Included in these electronic sections can be a power supply 350 which provides power to CTS 20 including the controller 300, the hand wand 100, and/or the emitter-receiver module 200. In one embodiment, the power supply 350 can supply power to a printer or other data output device. The controller 300 can include the controller subsystem 340 as described herein, the host 330, a graphical interface 310, an RF driver 352 and a front panel flex circuit 345. The RF driver 352 can provide power to the transducer 280. The embedded host 330 can be a host computer which may be used collecting user input, transferring it to the controller subsystem 340 and for displaying images and system statuses on the graphical interface 310. The power supply 350 can be convertible for use internationally based on different voltage inputs and typically is a medical grade power supply. The power supply may be plugged into a standard wall socket to draw power or may draw power from a battery or any other alternative source that may be available.

The graphical interface 310 displays images and systems status as well as facilitates the user interface for entering commands to control the CTS 20. The controller subsystem 340 can control the imaging subsystem 350, the therapy subsystem 320, as well as interfacing and communicating treatment protocol to the hand wand 100 and the emitter-receiver module 200, as described herein. In one embodiment, the controller subsystem 340 not only sets treatment parameters but also monitors the status of such treatment and transfers such status to the host 330 for display on display/touch screen 310. The front panel flex circuit 345 can be a printed circuit cable that connects the controller 300 to the interface cable 130.

In one embodiment, the cable 130 can include a quick connect or release, multi-pin connector plug which interfaces to the front panel flex circuit 345 as described herein. The cable 130 allows for interfacing of the controller 300 with the hand wand 100 and the emitter-receiver module 200 as described herein.

Figure 10:
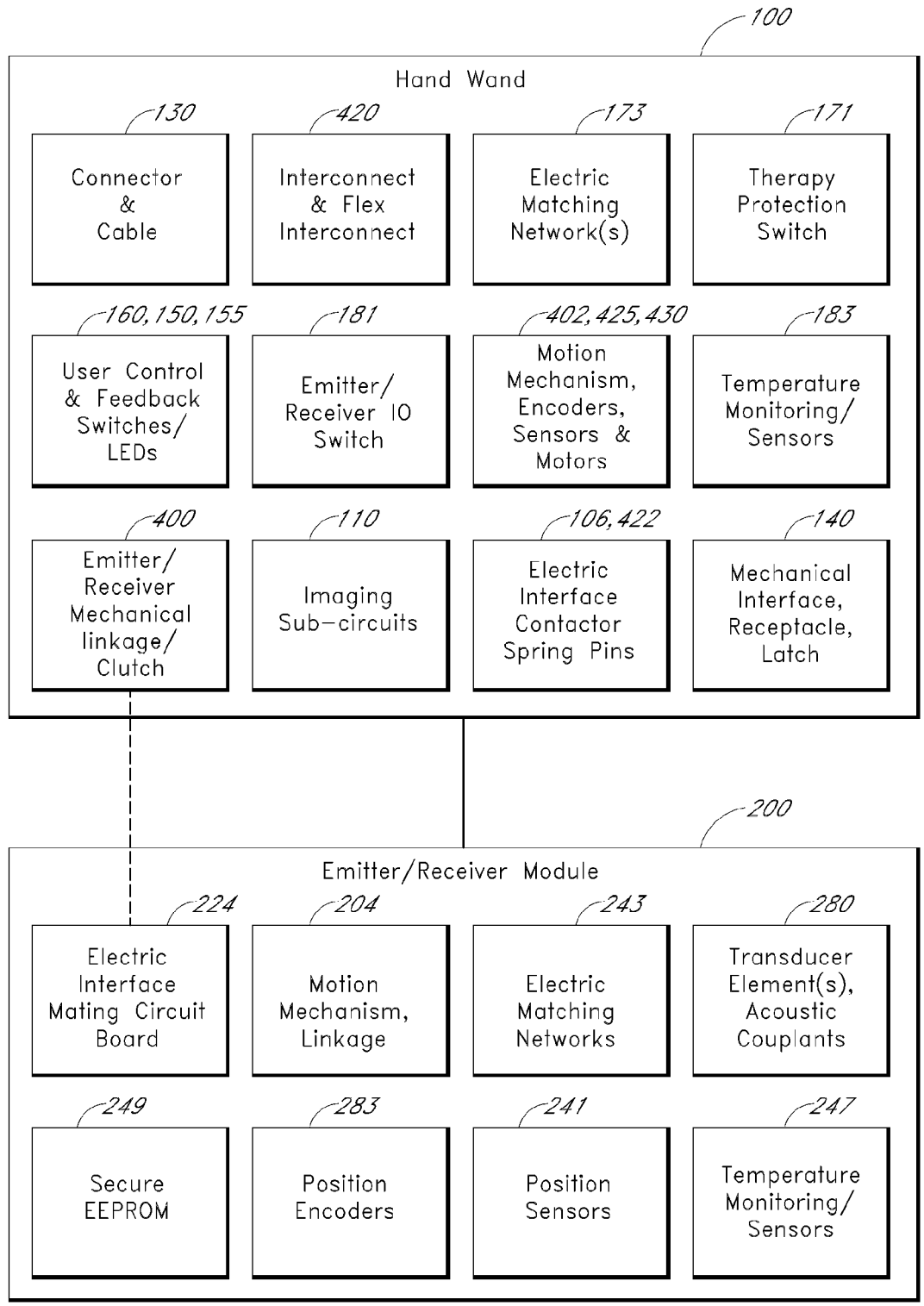
FIG. 10 is a schematic illustration of a hand wand and an emitter-receiver module according to various embodiments.

Now with reference to FIG. 10, the hand wand 100 includes the hand piece imaging sub-circuits 110, encoder 420, sensor 425, image 150 and treat 160 switches, motor 402, status light 155, and interconnect and flex interconnect 420. The hand wand 100 interfaces with spring pin flex 106 and spring pin connector 422 which can be used for hardware, software and/or power interface from the hand wand 100 to the emitter-receiver module 200.

In various embodiments of the present invention, the emitter-receiver module 200 can include a probe ID and connector PCB 224. The probe ID and connector PCB can include a secure EEPROM. The probe ID and connector PCB 224 can be interfaced with a PCB located in a dry portion of the emitter-receiver module 200 and interfaced with the transducer 280 The transducer 280 is typically located in the liquid portion of the emitter-receiver module 200. In one embodiment, the emitter-receiver module 200 can be connected to the hand wand 100 via the spring pin flex 106 and spring pin connector 422 which can be a twelve contact spring pin connector that is recessed in the hand wand 100. The spring pin flex 106 with its twelve contact spring pin connector can be connected to the probe ID and connector PCB 224 which can include gold plated contacts.

In one embodiment, the probe ID and connector PCB 224 can include a usage counter that disables the emitter-receiver module 200 after a pre-set usage. In various embodiments, the pre-set usage can range from a single treatment sequence to multiple treatment sequences. In one embodiment, the pre-set usage is determined by a pre-set time on of the transducer 280. In one embodiment, the pre-set usage is a single cycle of treatment sequences. In this aspect, essentially the emitter-receiver module 200 is disposable after each use. In one embodiment, the system automatically shuts off or otherwise indicates to a user that the emitter-receiver module 200 should be replaced. The system may be programmed to shut off or otherwise indicate replacement based on at least one of usage time, energy delivered, shelf time, or a combination thereof.

With further reference to FIG. 10, a block diagram illustrates an interconnection of the hand wand 100 and the emitter-receiver module 200. The hand wand 100 can include a therapy protection switch which can provide an electric isolation between treat and image functions. A transducer pulse generated by the controller subsystem 340 can be received by matching network 173. In one embodiment, a single transducer 280 can be used for therapy without imaging. In another embodiment one dual-mode transducer can be used for therapy and imaging. In another embodiment, two transducers 280 can be used for therapy and imaging. In yet another embodiment, therapy is done at relatively low frequencies (such as, in one embodiment, nominally 4 and 7 MHz) with a first transducer 280, and a second higher frequency transducer for imaging (such as, in one embodiment, 18-40 MHz or more).

The imaging sub-circuits 110 can include a time gain control amplifier and tunable bypass filter which can receive echoes produced by the imaging portion of the transducer 280. The imaging can be controlled by imaging switch 150. Power can be transferred from the controller 300 via cable 130. Such power can be directed to the imaging sub-circuits 110, the image switch 150 and the treatment switch 160. Such power can also be provided to the stepper motor 402, the encoder 425, the probe 10 switch 181, the hand wand temperature sensor 183, and a hand wand ID EEPROM 169. All of the electronics described in FIG. 10 for the hand wand 100 can be mounted on the circuit board with an interface to cable 130 and/or an interface to the emitter-receiver module 200.

The emitter-receiver module 200 includes an interface connectable to the hand wand 100 as described in FIG. 9. The emitter-receiver module 200 can include any type of storage device 249. In one embodiment, the storage device 249 is part of the electric interface mating circuit board 224 and electric matching 243 circuit board. In one embodiment, the storage device 249 is a permanent storage device. In one embodiment, the storage device 249 is a non-volatile member. In one embodiment, the storage device 249 is an EEPROM. In one embodiment, the storage device 249 is a secure EEPROM. In one embodiment, a transducer PCB can contain calibration data and information storage in the secure EEPROM. Further in this aspect, the emitter-receiver module 200 includes a sensor which measures a fluid temperature of the fluid portion of the emitter-receiver module 200, a matching network 243 interfaced to the treatment portion of the transducer 280. In various embodiments, the storage device 249 can contain digital security information, build date, transducer focus depth, transducer power requirements, and the like. In one embodiment, the storage device 249 can include a timer which inactivates the emitter-receiver module 200 for use with CTS 20 after a predetermined shelf life has expired. The emitter-receiver module 200 can include a position encoder 283, such as a magnet, connected to the transducer 280 and a sensor 241, such as a Hall sensor, connected to the stationary emitter/receiver housing 220 via circuit board. The position encoder 283 and the position sensor 241 can act as a sensor for determining a transducer 280 home position and/or movement as described herein. The imaging portion of the transducer 280 can receive a transducer RF signal from the controller 300.

Since it is possible for a user to potentially touch the spring pin flex contacts 422 when an emitter-receiver module 200 is not attached, the current must be able to be turned off in this situation to provide safety to the user. To provide such safety, contact pins 422 on opposite ends of the spring pin flex 106 can be used to detect an attachment of the emitter-receiver module 200 to the hand wand 100. As discussed above, motion mechanism 400 can be connected to the transducer 280 to provide linear movement of the transducer along the travel 272.

In various embodiments, the CTS 20 can include various safety features to provide a safe environment for the user and/or the subject that receives treatment. One embodiment, the CTS 20 can include at least one of calibration data, safe operating area, high mismatch detect, high current detect, RF driver supply voltage monitoring, forward and reverse electric power monitoring, acoustic coupling detection, acoustic coupling complete, treatment position sensing, and combinations thereof.

For example, calibration data can include certain characteristics for a given emitter-receiver module 200 that reside on the storage device 249. Such characteristics can include but are not limited to unique and traceable serial numbers, probe identification, frequency setting, acoustic power versus voltage lookup table, electric power versus voltage lookup table, maximum power levels, date codes, usage, other information, and/or combinations thereof. For example, a safe operating area safety feature limits energy output for a given emitter-receiver module 200 is limited to a safe operating area. Such a limitation may include for a given emitter-receiver module 200, the acoustic power level supplied by the power supply voltage and the time On may be limited in the hardware and/or software of the controller 300 and/or the emitter-receiver module 200.

An example of a high mismatch detect safety feature can include if a fault occurs in reflective power from the load of the emitter-receiver module 200 is large as compared a forward power such as the emitter-receiver module 200 failure, open circuit, or high reflective energy, then a system Stop state would automatically and indefinitely be invoked by comparator circuit latched in the hardware of the controller 300 and a notification of such fault would appear on the display/touch screen 310 to alert the user. An example of a high current detect safety feature can include if a driver fault or load fault occurs such that a large current draw is detected such as for example a short circuit or electrical component failure, then a Stop state would be automatically and immediately invoked as located in the hardware of the controller 300 and a notice would be displayed on the display/touch screen 310 to alert the user.

An example of RF driver supply voltage monitoring safety feature can include the CTS 20 measuring the RF driver power supply voltage setting before, during and after treatment to assure that the voltage is at the correct level. If it is determined that the voltage is outside the correct level, then a Stop state would be automatically and immediately invoked and a notice would be displayed on the display/touch screen 310 to alert the user. An example of a safety feature includes monitoring the stepper motor 402 during treatment and determining if it is in an acceptable range such that the transducer 280 is properly moving along the travel 272 at a predetermined rate or frequency. If it is determined that the stepper motor 402 is not at an expected position, a notification is issued to alert the user.

An example of an acoustic coupling safety feature includes an imaging sequence that indicates to the user that the emitter-receiver module 200 is acoustically coupled to the surface 501 before and after treatment. An image sequence confirms that the transducer 280 is scanning a treatment area.

Still further, other safety features may be included such as thermal monitoring, use of a stop switch, a probe sensor, or a combination thereof. An example of thermal monitoring can include monitoring the temperature of the liquid portion of the emitter-receiver module 200, monitoring the temperature of the hand wand 100, monitoring the temperature of the controller 300, monitoring the temperature of the controller subsystem 340 and/or monitoring the temperature of the RF driver 352. Such temperature monitoring assures that the devices described operate within temperatures that are acceptable and will provide notification if a temperature is outside an acceptable range thus alerting the user.

A stop switch can be included in CTS 20 such that when a user hits the stop switch the system moves to a safe and inactive state upon activation of the stop switch. An example of a probe sense fail safe can include immediately stopping imaging and/or treatment if the emitter-receiver module 200 is disconnected from the hand wand 100 while in use. In one embodiment, the CTS 20 can include a system diagnostic which can include software checks for errors, unexpected events and usage. The system diagnostics may also include maintenance indicator that tracks the usage of the CTS 20 and notifies the user that maintenance is needed for the system. Other safety features may be included in the CTS 20 that are well known in the art such as fuses, system power supply over voltage and over current limiting, as well as standardized protections such as fire safety ratings, electrical safety ratings, ISO\EN 60601 compliance and the like.

In various embodiments, the CTS 20 includes a removable transducer module 200 interfaced to a hand enclosure 100 having at least one controller button (150 and/or 160) such that the transducer module 200 and the controller button (150 and/or 160) is operable using only one hand. In an aspect of the embodiments, the transducer module 200 provides ultrasound energy for an imaging function and/or a treatment function. In another aspect of the embodiments, the device includes a controller 300 coupled to the hand-held enclosure 100 and interfaced to the transducer module 200. In a further aspect of these embodiments, the controller 300 controls the ultrasound energy of and receives a signal from the transducer module 200. The controller 300 can have a power supply providing power for the ultrasound energy. In still another aspect of the embodiments, the device is used in aesthetic imaging and treatment on a brow of a patient.

Figure 11:
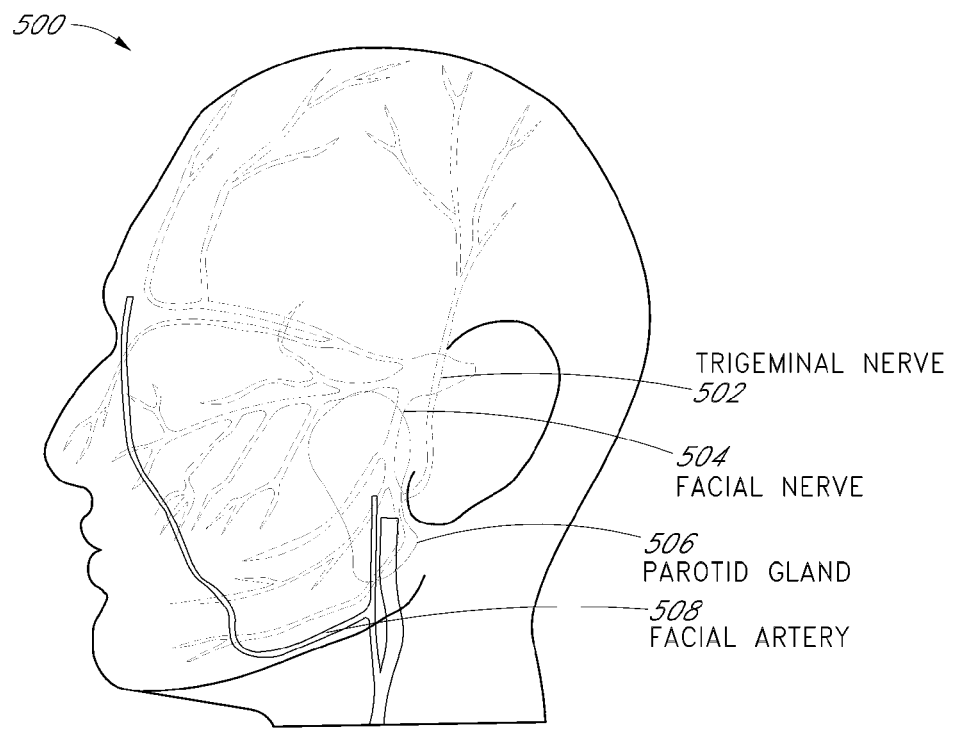
FIG. 11 is an illustration depicting one possible area of interest of a subject according to various embodiments.
Figure 12:
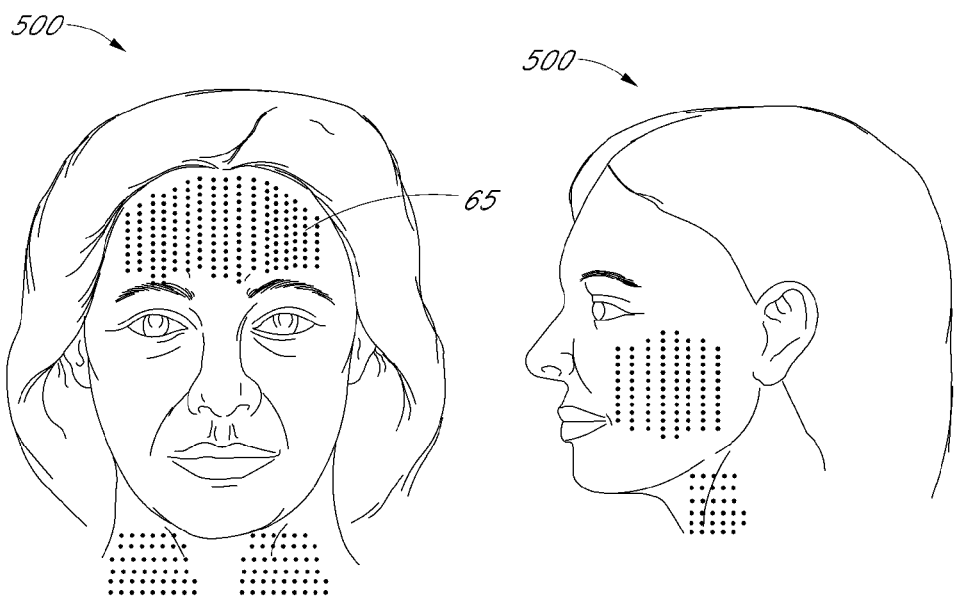
FIG. 12 is an illustration depicting one possible area of interest of a subject according to various embodiments.
Figure 13:
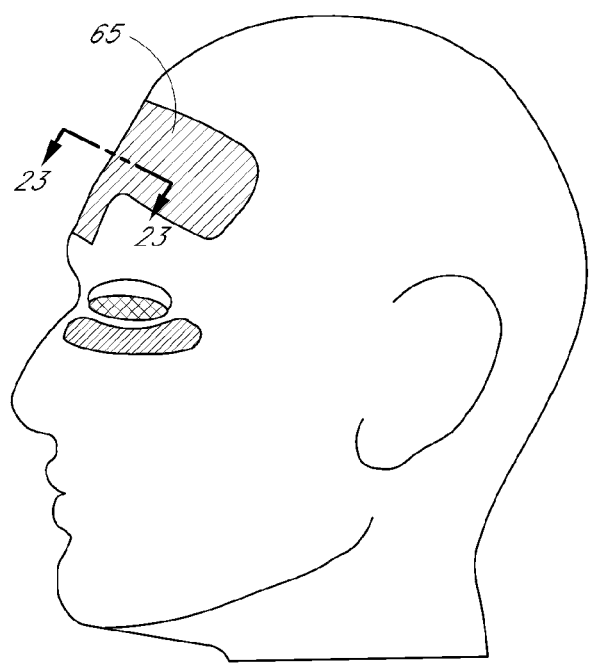
FIG. 13 is an illustration depicting an area of interest of a subject according to various embodiments.
Figure 14:
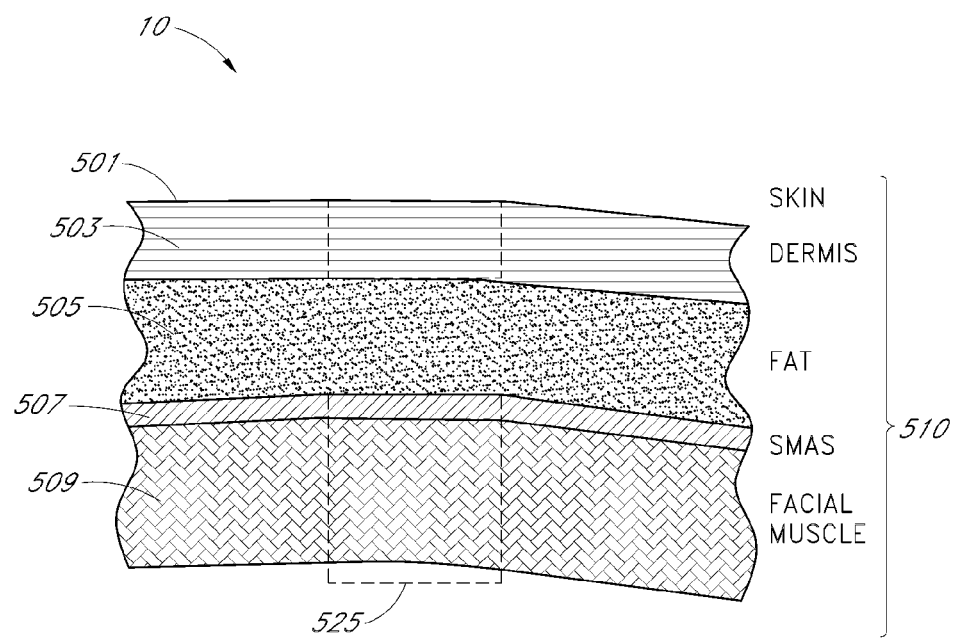
FIG. 14 is a cross-sectional illustration of a portion of an area of interest according to various embodiments.

FIG. 11 illustrates a schematic drawing of anatomical features of interest in the head and face region of a patient 500, including a trigeminal nerve 502, a facial nerve 504, a parotid gland 506 and a facial artery 508. In one embodiment, the anatomical features of interest are areas to be treated with care or to be noted, treated with care, or even avoided during treatment. FIGS. 12-14 illustrate one region of interest 65 (hereinafter "ROI 65") and a cross-sectional tissue portion 10 along the line 23-23 of the ROI 65 on a subject 500, such as may be used for example when performing a brow lift. This cross-sectional tissue portion 10 can be located anywhere in the ROI 65 and can in any direction or of any length with in the ROI 65. Of course, the subject 500 can be a patient that may be treated with a brow lift. The cross-sectional portion tissue 10 includes a surface 501 in a dermal layer 503, a fat layer 505, a superficial muscular aponeurotic system 507 (hereinafter "SMAS 507"), and a facial muscle layer 509. The combination of these layers in total may be known as subcutaneous tissue 510. Also illustrated in FIG. 14 is a treatment zone 525 which is below the surface 501. In one embodiment, the surface 501 can be a surface of the skin of a subject 500. Although the term facial muscle may be used herein as an example, the inventors have contemplated application of the device to any tissue in the body. In various embodiments, the device and/or methods may be used on muscles (or other tissue) of the face, neck, head, torso, chest, abdomen, buttocks, arms, legs, genitals, or any other location in the body. For example, in one embodiment the system and methods can be applied to genital tissue, such as for vaginal rejuvenation and/or vaginal tightening.

Application of the embodiments of the invention can be applied to any part of the body. For example, in some embodiments the system and methods are applied to a face or neck. Facial muscle tissue is capable of contraction and expansion. Skeletal muscle is a fibrous tissue used to generate stress and strain. For example, skeletal muscles in the forehead region can produce frowning and wrinkles. There are several facial muscles within the brow or forehead including the epicranius muscle, the corrugator supercilii muscle, and the procerus muscle. These facial muscles are responsible for movement of the forehead and various facial expressions. Besides facial muscles, other tissues exist in the brow region that also can lead to wrinkles on the brow.

In accordance with one embodiment of the present invention, methods for ultrasound cosmetic treatment of tissue using one cosmetic treatment system are provided. The ultrasound energy can be focused, unfocused or defocused and is applied to a ROI 65 containing one of facial muscle tissue or dermal layers or fascia to achieve a therapeutic effect, such as a tighten of a brow of a subject 500.

In various embodiments, certain cosmetic procedures that are traditionally performed through invasive techniques are accomplished by targeting energy such as ultrasound energy at specific subcutaneous tissues 510. In one embodiment, methods for non-invasively treating subcutaneous tissues 510 to perform a brow life are provided. In one embodiment, a non-invasive brow lift is performed by applying ultrasound energy at specific depths 278 along the brow to ablatively cut, cause tissue to be reabsorbed into the body, coagulate, remove, manipulate, or paralyze subcutaneous tissue 510 such as the facial muscle 509, for example, the corrugator supercilii muscle, the epicranius muscle, and the procerus muscle within the brow to reduce wrinkles.

In some embodiments, ultrasound energy is applied at a ROI 65 along a patient's forehead. The ultrasound energy can be applied at specific depths and is capable of targeting certain subcutaneous tissues within the brow such as with reference to FIGS. 12-14, SMAS 507 and/or facial muscle 509. The ultrasound energy targets these tissues and cuts, ablates, coagulates, micro-ablates, manipulates and/or causes the subcutaneous tissue 510 to be reabsorbed into the subject's body which effectuates a brow lift non-invasively.

For example, the corrugator supercilii muscle in a target zone 525, can be targeted and treated by the application of ultrasound energy at specific depths 278. This facial muscle 509 or other subcutaneous facial muscles can be ablated, coagulated, micro-ablated, shaped or otherwise manipulated by the application of ultrasound energy in a non-invasive manner. Specifically, instead of cutting a corrugator supercilii muscle during a classic or endoscopic brow lift, the targeted muscle 509 such as the corrugator supercilii can be ablated, micro-ablated, or coagulated by applying ultrasound energy at the forehead without the need for traditional invasive techniques.

One method is configured for targeted treatment of subcutaneous tissue 510 in the forehead region 65 in various manners such as through the use of therapy only, therapy and monitoring, imaging and therapy, or therapy, imaging and monitoring. Targeted therapy of tissue can be provided through ultrasound energy delivered at desired depths 278 and locations via various spatial and temporal energy settings. In one embodiment, the tissues of interest are viewed in motion in real time by utilizing ultrasound imaging to clearly view the moving tissue to aid in targeting and treatment of a ROI 65 on the patient's forehead. Therefore, the practitioner or user performing the non-invasive brow lift can visually observe the movement and changes occurring to the subcutaneous tissue 510 during treatment.

Figure 16:
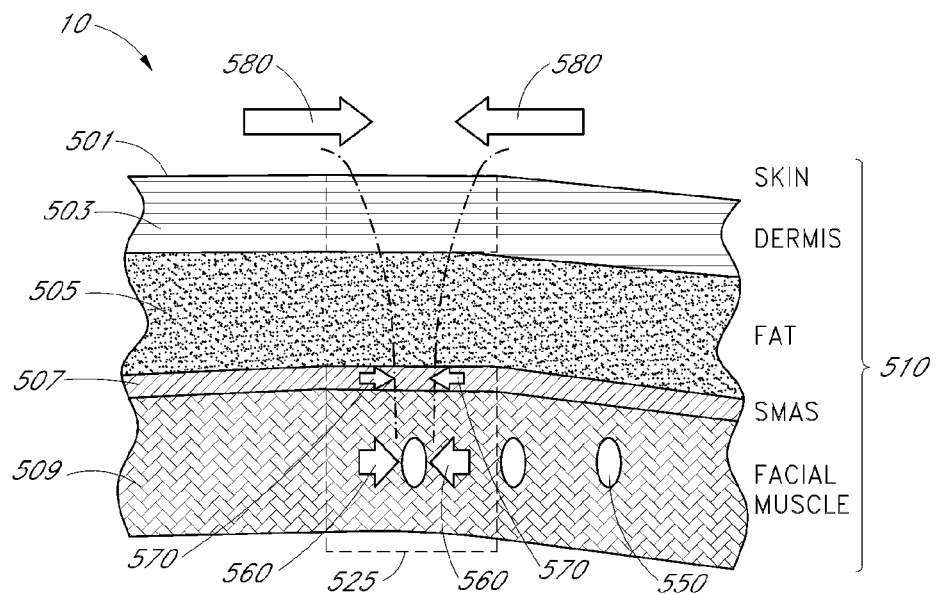
FIG. 16 is a cross-sectional illustration depicting a treatment region according to various embodiments.
Figure 17:
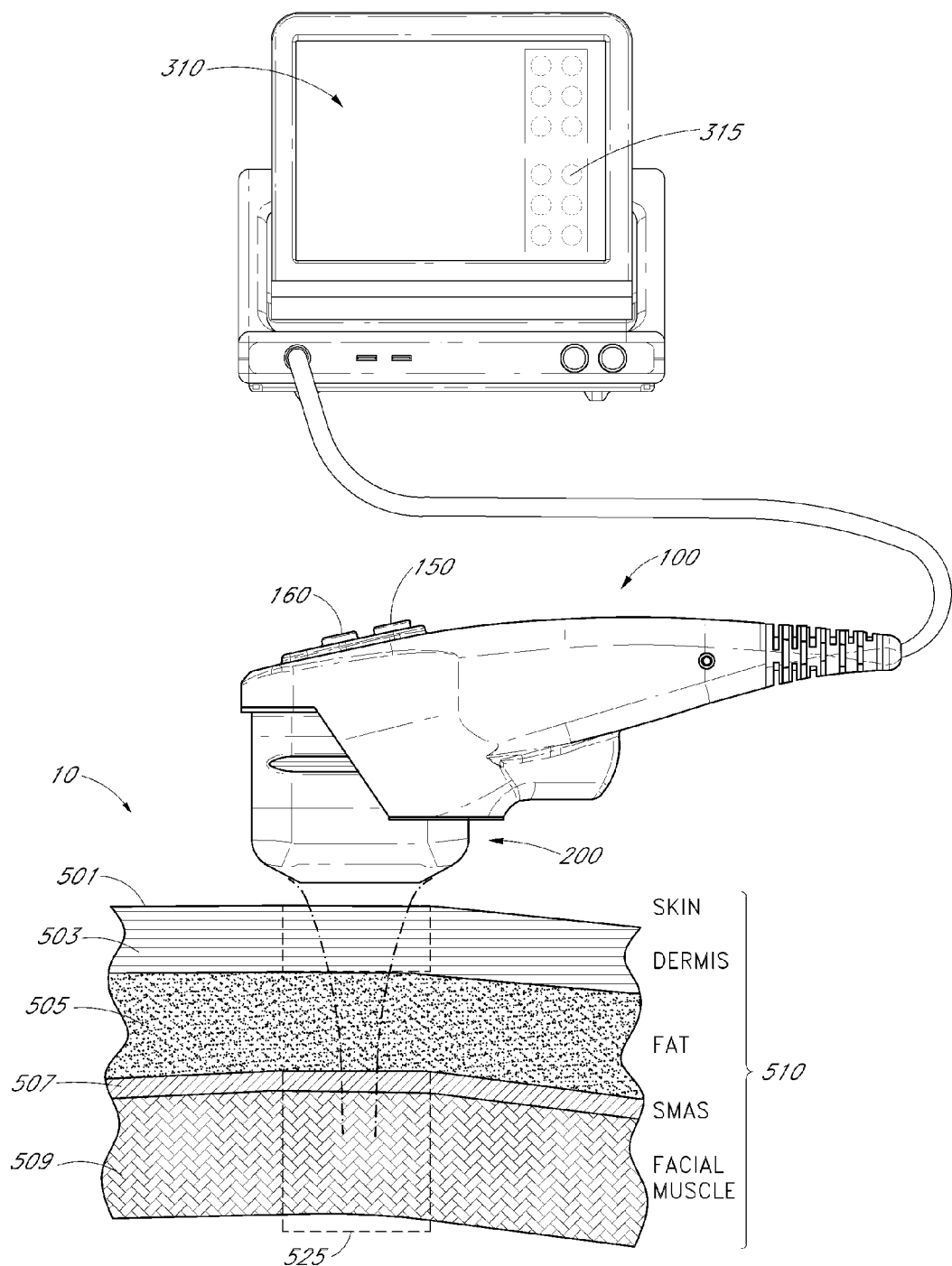
FIG. 17 is an illustration depicting the cosmetic treatment system coupled to the region of interest according to various embodiments.

FIGS. 15-17 illustrate an embodiment of a method of administering a brow lift. Other embodiments include multiple treatment depths, three dimensional (3-D) treatment, and use of multiple treatment sessions over time. The CTS 20 can be coupled to a tissue portion 10 of the ROI 65 that is to be treated. In one embodiment, a treatment zone 525 is first imaged and then treated. In one embodiment, a user activates the imaging button 150 to initiate the imaging sequence. Imaging can be displayed on the graphical interface 310. In one embodiment, the imaging sequence can be controlled on a touchscreen 315 that is part of the graphical interface 310. After the imaging sequence is started, the treatment sequence can be initiated at any time. The user can activate treatment button 160 at any time to initiate the treatment sequence. Treatment and imaging can occur simultaneously or occur sequentially. For example, a user can image, treat, image, treat, etc. As schematically illustrated in FIG. 15, the treatment sequence activates the treatment portion of the transducer 280 to create voids or lesions 550 below the surface 105. Note that FIG. 15 illustrates one embodiment of a depth 278 that corresponds to a muscle depth. In various embodiments, the depth 278 can correspond to any tissue, tissue layer, skin, dermis, fat, SMAS, muscle, or other tissue. Note that as illustrated, the energy 50 represented is for illustration purposes only. Certain figures including FIGS. 15-17 show energy 50 emanating from the entire length of the transducer housing (its entire opening such as corresponding to travel distance 272); however the actual energy is emitted from a sub-length of that, e.g., the actual transduction element of the transducer 280. In one embodiment, the transduction element of the transducer 280 is scanned in a linear motion to cover the region of interest, such that at any time the energy is not coming out of the entire transducer housing's length at once.

In one embodiment, CTS 20 generates ultrasound energy which is directed to and focused below the surface 501. This controlled and focused ultrasound energy creates the lesion 550 which may be a thermally coagulated zone or void in subcutaneous tissue 510. In one embodiment, the emitted energy 50 raises a temperature of the tissue at a specified depth 278 below the surface 501. The temperature of the tissue can be raised from about 1° C. to about 100° C. above an ambient temperature of the tissue, or about 5° C. to about 60° C. above an ambient temperature of the tissue or above 10° C. to about 50° C. above the ambient temperature of the tissue. In some embodiments, the emitted energy 50 targets the tissue below the surface 501 which cuts, ablates, coagulates, micro-ablates, manipulates, and/or causes a lesion 550 in the tissue portion 10 below the surface 501 at a specified depth 278. In one embodiment, during the treatment sequence, the transducer 280 moves in a direction denoted by the arrow marked 290 at specified intervals 295 to create a series of treatment zones 254 each of which receives an emitted energy 50 to create a lesion 550. For example, the emitted energy 50 creates a series of lesions 550 in the facial muscle layer 509 of tissue portion 10.

In various embodiments, delivery of emitted energy 50 at a suitable depth 278, distribution, timing, and energy level is provided by the emitter-receiver module 200 through controlled operation by the control system 300 to achieve the desired therapeutic effect of controlled thermal injury to treat at least one of the dermis layer 503, fat layer 505, the SMAS layer 507 and the facial muscle layer 509. During operation, the emitter-receiver module 200 and/or the transducer 280 can also be mechanically and/or electronically scanned along the surface 501 to treat an extended area. In addition, spatial control of a treatment depth 278 can be suitably adjusted in various ranges, such as between a wide range of about 0 mm to about 25 mm, suitably fixed to a few discrete depths, with an adjustment limited to a fine range, for example, approximately between about 3 mm to about 9 mm, and/or dynamically adjusted during treatment, to treat at least one of the dermis layer 503, fat layer 505, the SMAS layer 507 and the facial muscle layer 509. Before, during, and after the delivery of ultrasound energy 50 to at least one of the dermis layer 503, fat layer 505, the SMAS layer 507 and the facial muscle layer 509, monitoring of the treatment area and surrounding structures can be provided to plan and assess the results and/or provide feedback to the controller 300 and the user via the graphical interface 310.

As to the treatment of the SMAS layer 507 and similar fascia, connective tissue can be permanently tightened by thermal treatment to temperatures about 60° C. or higher. Upon ablating, collagen fibers shrink immediately by approximately 30% of their length. The shrunken fibers can produce tightening of the tissue, wherein the shrinkage should occur along the dominant direction of the collagen fibers. Throughout the body, collagen fibers are laid down in connective tissues along the lines of chronic stress (tension). On the aged face, the collagen fibers of the SMAS 507 region are predominantly oriented along the lines of gravitational tension. Shrinkage of these fibers results in tightening of the SMAS 507 in the direction desired for correction of laxity and sagging due to aging. The treatment includes the ablation of specific regions of the SMAS 507 region and similar suspensory connective tissues.

In addition, the SMAS layer 507 varies in depth and thickness at different locations, for example from about 0.5 mm to about 5 mm or more. On the face, important structures such as nerves, parotid gland, arteries and veins are present over, under or near the SMAS 507 region. Treating through localized heating of regions of the SMAS 507 layer or other suspensory subcutaneous tissue 510 to temperatures of about 50° C. to about 100° C., and/or 60° C. to about 90° C. (e.g., 65, 70, 75, 80, 85° C.), without significant damage to overlying or distal/underlying tissue, or proximal tissue, as well as the precise delivery of therapeutic energy to the SMAS layer 507, and obtaining feedback from the region of interest before, during, and after treatment can be suitably accomplished through the CTS 20.

In various embodiments, a method is provided for performing a brow lift on a patient. In some embodiments, the method includes coupling a probe 200 to a brow region 65 of the patient 60 and imaging at least a portion of subcutaneous tissue 510 of the brow region to determine a target area in the subcutaneous tissue 510. In an aspect of the embodiment, the method includes administering ultrasound energy 50 into the target area 525 in the subcutaneous tissue 510 to ablate the subcutaneous tissue 510 in the target area 525, which causes tightening of a dermal layer 503 above the subcutaneous tissue 510 of the brow region 65.

In various embodiments, a method is provided for tightening a portion of a dermal layer 503 on a facial area of a patient 60. In some embodiments, the method includes inserting a transducer module 200 into a hand controller 100 and then coupling the transducer module 200 to a facial area of the patient 60. In one embodiment, the method includes activating a first switch 150 on the hand controller 100 to initiate an imaging sequence of a portion of tissue 10 below the dermal layer 503, then collecting data from the imaging sequence. In this embodiment, the method includes calculating a treatment sequence from the collected data, and activating a second switch 160 on the hand controller 100 to initiate the treatment sequence. In an aspect of the embodiments, the method can be useful on a portion of a face, head, neck and/or other part of the body of a patient 60.

With reference to FIG. 16, after the emitted energy has created lesions 550, healing and/or tightening of the portion of tissue 10 begins. In one embodiment, the void or lesion 550 can dissipate in the facial muscle layer 509 of the portion of tissue 10. For example, the facial muscle layer 509 has movement 560 around the lesion 550 to shrink the lesion 550. Eventually, the body essentially eliminates the lesion 550 through resorption, and can enhance the growth of tissue. This movement 560 causes upper layers such as the SMAS 507 to have movement 570 above where the lesion 550 was located. This in turn causes movement 580 at the surface 501 which tightens surface 501. This surface movement 580 at the surface 501 is the goal of any brow lift. The surface movement 580 creates a tightening effect across the skin surface 501 which can provide a more youthful look for the subject 500. In various embodiments, a medicant can be applied during the coupling of the CTS 20 to the portion of tissue 10. This medicant can be activated in the target zone 525 by the emitted energy 50 and can assist, accelerate, and/or treat the void or lesion 550 during the dissipation and/or healing of the void or lesion 550. In various embodiments, medicants include, but are not limited to, hyaluronic acid, retinol, vitamins (e.g., vitamin c), minerals (e.g., copper) and other compounds or pharmaceuticals that can be activated by energy and/or would benefit from deeper penetration into the skin.

Figure 18:
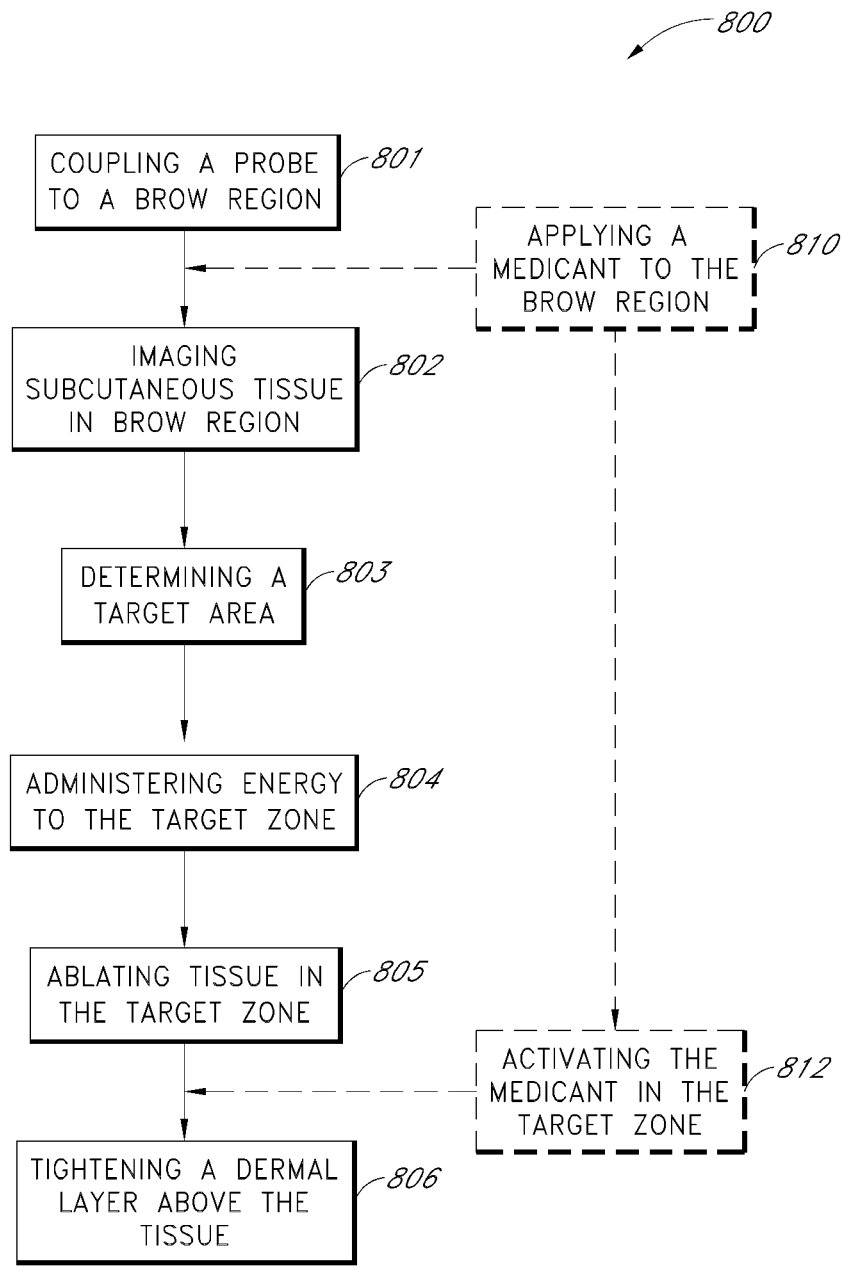
FIG. 18 is a flow chart depicting a method according to various embodiments.

Turning to FIG. 18, a flow chart illustrates a method according to various embodiments of the present invention. A method 800 can include a first step 801 which is a coupling of a probe to a brow region. For example, step 801 can include the coupling of the emitter-receiver module 200 to a portion of tissue 10 in a ROI 65 of the subject 500. This step 801 can include a gel located between the emitter-receiver module 200 and the portion of tissue 10 that assists in the coupling of a probe to the brow region. Step 801 can move to step 802 which is imaging subcutaneous tissue 510 in the brow region. Step 802 can include imaging the portion of tissue 10 using the CTS 20 as discussed herein. Optionally, a step 810 can be included between steps 801 and 802. Step 810 is the applying a medicant to the brow region. The medicant can be any substance or material that has an active ingredient that may be helpful in the tightening of the surface 501 and/or in the healing and/or dissipation of the void or lesion 550 in a portion of tissue 10 below the surface 501. In one embodiment, the medicant can also act as a coupling gel useful in step 801. Step 802 moves to step 803 which is determining a target zone 525. Step 803 can include reviewing an image that was created in step 802 to help determine the target zone 525.

Step 803 moves to step 804 which is the administering of energy to the target zone 525. For example, step 804 can be illustrated in, for example, FIG. 15. Note that FIG. 15 illustrates one embodiment of a depth 278 that corresponds to a muscle depth. In various embodiments, the depth 278 can correspond to any tissue, tissue layer, skin, dermis, fat, SMAS, muscle, or other tissue. Step 804 moves to step 805 which is ablating the tissue in the target zone 525. In various embodiments, this "ablating" may be coagulation instead of ablation. Ablation is more or less instantaneous physical removal, analogous to sublimation or vaporization, while thermal coagulation is milder in that it is killing tissue but leaving it in place. As used herein, "ablation" shall be given its ordinary meaning and shall include the stronger and the milder forms described herein. Step 805 is illustrated in FIG. 15. Note that FIG. 15 illustrates one embodiment of a depth 278 that corresponds to a muscle depth. In various embodiments, the depth 278 can correspond to any tissue, tissue layer, skin, dermis, fat, SMAS, muscle, or other tissue. In step 805, the void or lesion 550 is created in a portion of tissue 10 below the surface 501. Step 805 moves to step 806 which is tightening a dermal layer 503 above or below the treated tissue. In the illustrated embodiment, step 806 is merely tightening a dermal layer above the tissue, but the broader step described is possible in various embodiments. Step 806 is illustrated in FIG. 17. For example, one of the surface 501 in the dermal layer 503 is tightened due to the void or lesion 505 being dissipated or healed. Between step 505 and 506, an optional step 812 may be used. Typically, for step 812 to be used, optional step 810 must also be used. In step 812, the medicant is activated in the target zone 525. This activation of the medicant can allow active ingredient to assist in tightening the dermal layer 503 above the ablate tissue. For example, the active ingredient may assist in the healing or dissipating of the void or lesion 550. In another example, the medicant may be activated at the surface 501 or in the dermal layer 503 to assist tightening.

Figure 19:
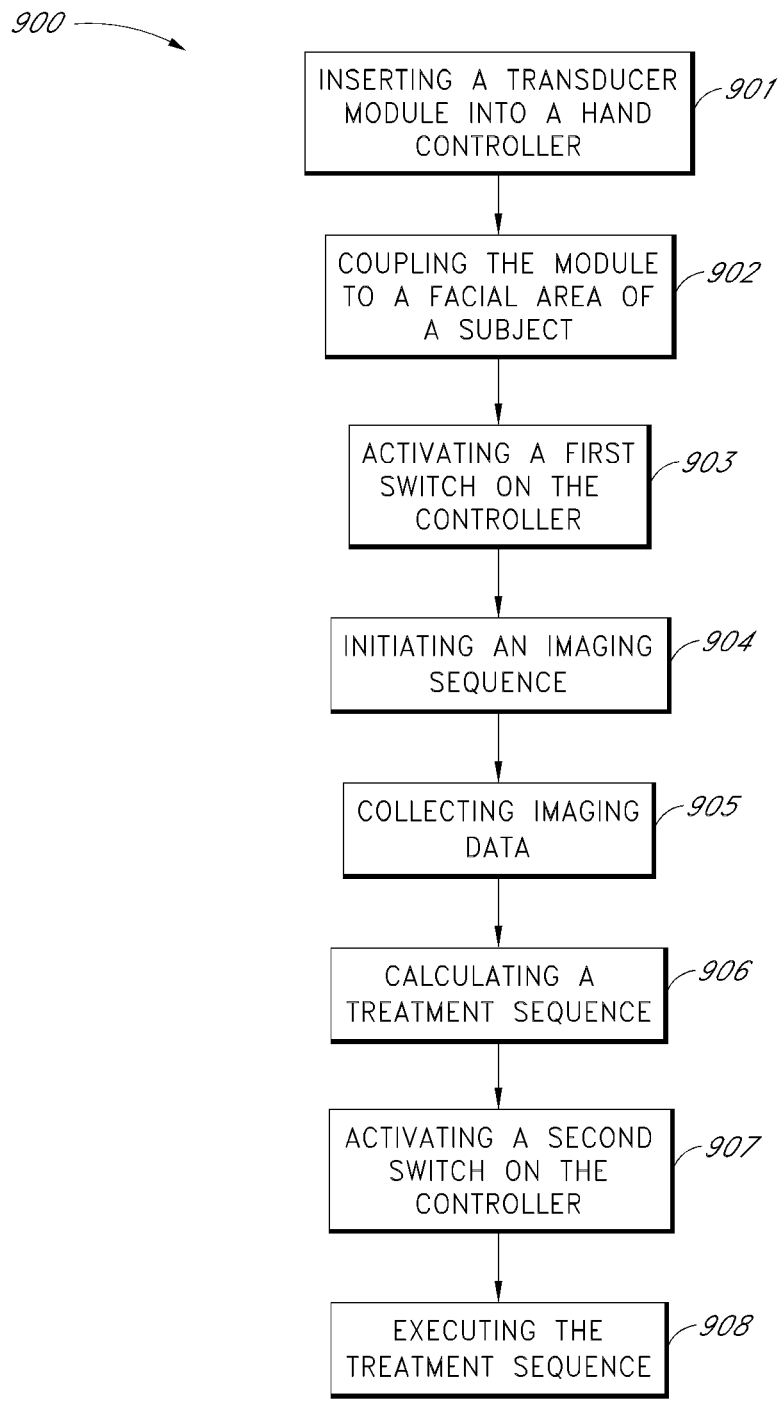
FIG. 19 is a flow chart depicting another method according to various embodiments.

With reference to FIG. 19 a method 900 is illustrated according to various embodiments of the present invention. Method 900 begins with inserting a transducer module to the hand controller. For example, method 900 can include the inserting of the emitter-receiver module 200 into the hand wand 100. Step 901 moves to step 902 which is the coupling of the module to a facial area of the subject. For example, step 902 can include coupling the emitter-receiver module 200 to a region of interest 65 of a subject 63. Step 902 moves to step 903 which is activating a first switch on the hand controller. For example, step 903 can include activating an imaging button 150 on the hand wand 100. Step 903 moves to step 904 which is initiating the imaging sequence. For example, step 904 can include imaging sequence that can be collected by the CTS 20 as discussed herein. Step 904 moves to step 905 which is collecting imaging data. Step 905 moves to step 906 which is calculating a treatment sequence. In various embodiments, "calculating" as used with respect to step 906 can be determining, selecting, selecting a predetermined treatment sequence, and/or selecting a desired treatment sequence. For example, step 906 can include the controller 300 downloading a treatment sequence to the hand wand 100 and the emitter-receiver module 200. Step 906 moves to step 907 which is the activating of a second switch on the hand controller. For example, step 907 can be the activating of the treatment button 160 on the hand wand 100. Step 907 moves to step 908 which is executing the treatment sequence. For example, step 908 can be any treatment sequence as discussed herein. In other embodiments, the illustrated method may be broader to include generalized activating of switches anywhere and anyhow, such as with foot switches or switches on the controller 300, in various non-limiting embodiments.

Figure 20:
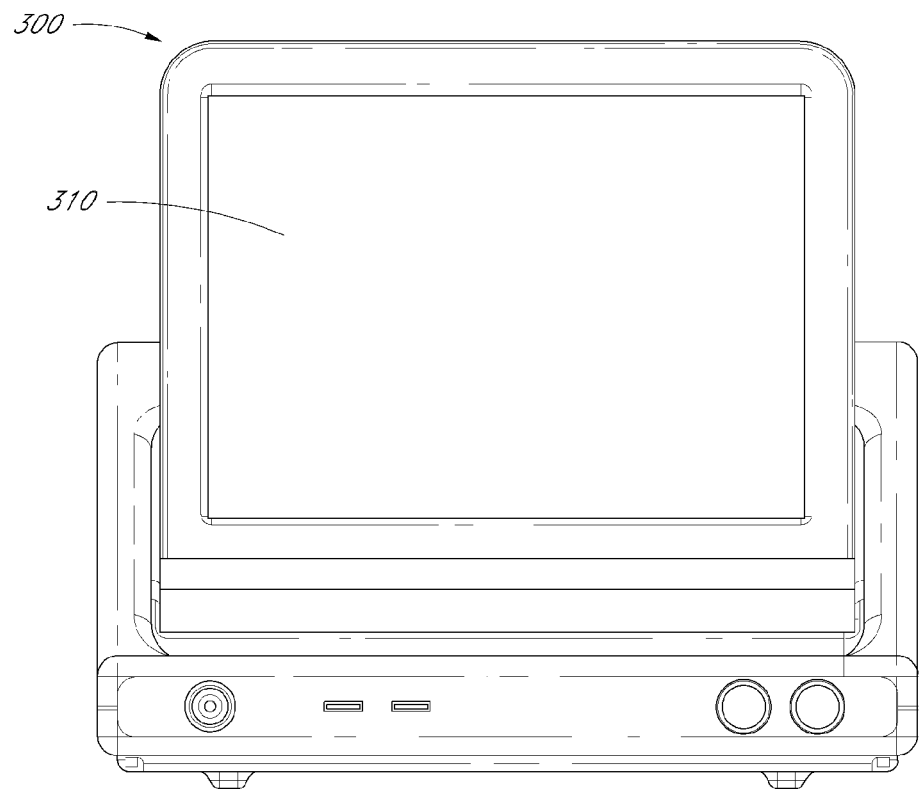
FIG. 20 is a front view illustrating a controller according to various embodiments.
Figure 21:
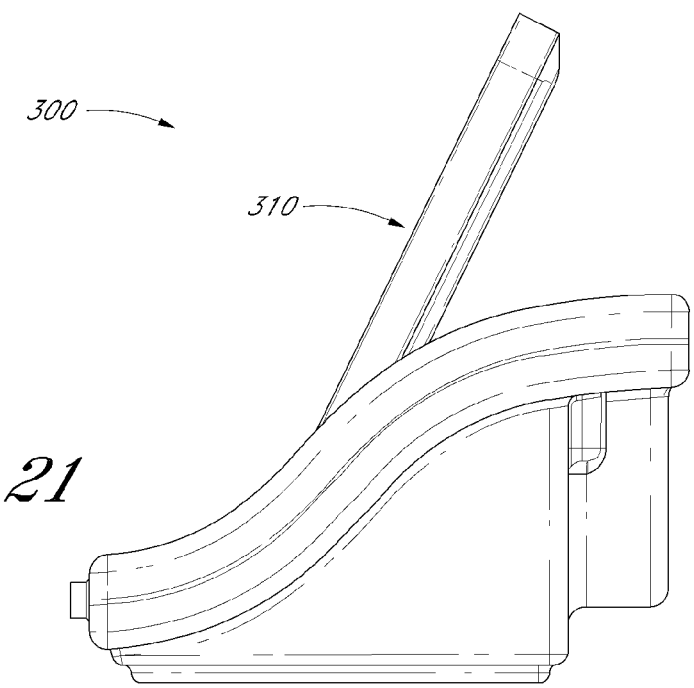
FIG. 21 is a side view illustrating a controller according to various embodiments.
Figure 22:
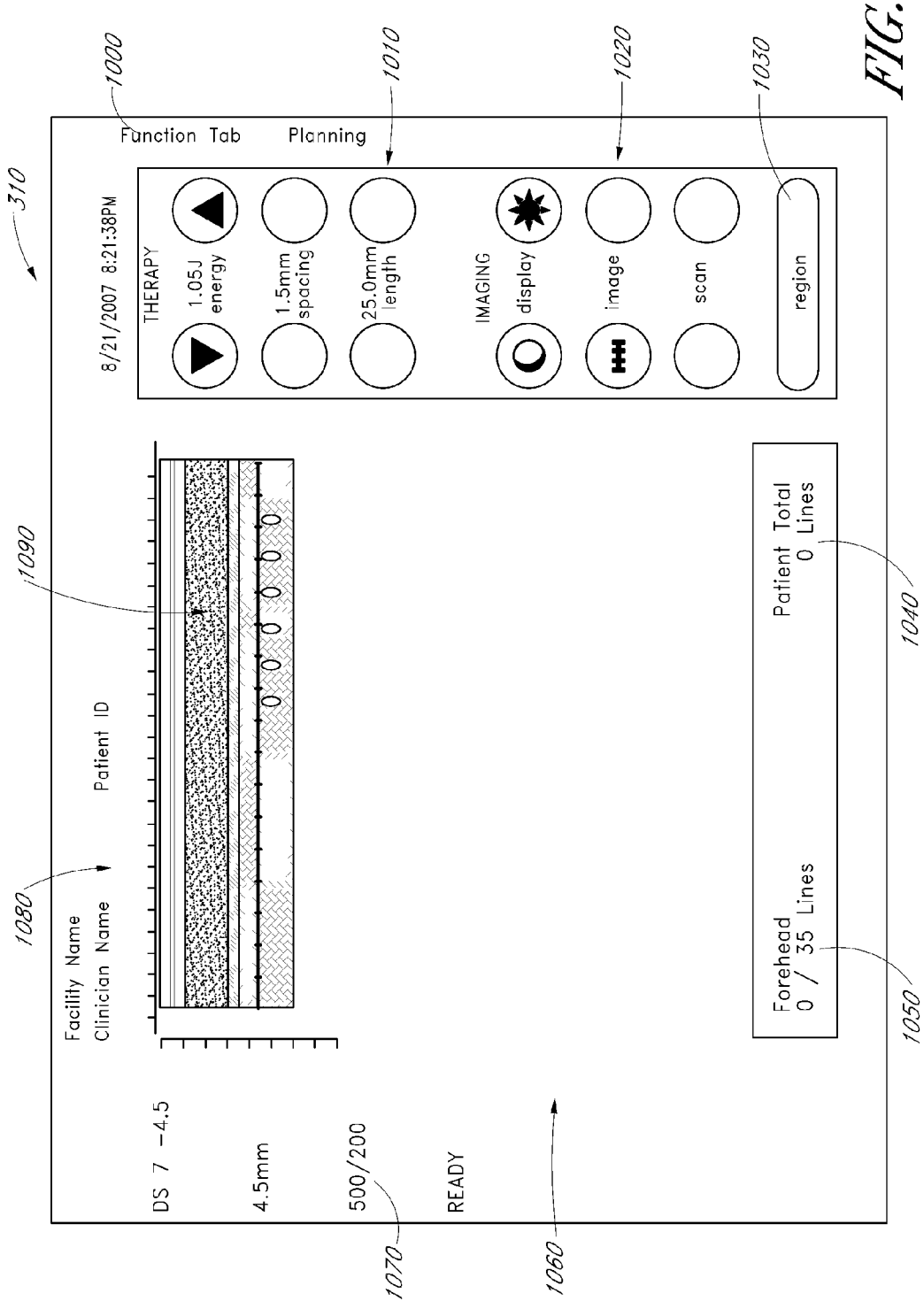
FIG. 22 is a representation of an interactive graphical display on a controller according one embodiment.

FIGS. 20-21 illustrate a front and side view of one embodiment of a controller 300 as previously described herein. FIG. 22 illustrates one embodiment of an interactive graphical display 310, which can include a touch screen monitor and Graphic User Interface (GUI) that allows the user to interact with the CTS 20. FIG. 22 illustrates a general example of an embodiment of an interactive graphical display 310, which may include system function tabs 1000, therapy controls 1010, imaging controls 1020, region control 1030, patient total line count 1040, treat zone line count 1050, system status 1060, probe information area 1070, header information 1080 and/or image-treat region 1090.

The system function tabs 1000 reflect aspects of the system function. In one embodiment, the interactive graphical display 310 has one or more general functions. In various embodiments the interactive graphical display 310 has two, three, four or more general functions. In one embodiment, an interactive graphical display 310 has three general functions: a planning function, a imaging/treatment function, and a settings function. In one embodiment, the planning function contains the controls and information instrumental in planning a treatment, which can automatically set therapy controls. In one embodiment, the planning function can display an overview of the various treatment regions with recommended treatment parameters for each. For example, parameters for treating such regions as the forehead, left or right temple, left or right preauricular, left or right neck, submental, and left or right cheek can show a recommended emitter-receiver module 200 listing energy levels and recommended numbers of lines of treatment. Certain areas can include a protocol listing for selection of treatment protocols, a protocol allowed treat regions listing, and disallowed regions that cannot be selected due to an incorrect transducer, which can be grayed out. In one embodiment, the imaging/treatment function contains the controls and protocol information needed for imaging soft tissue and for treating pertinent soft tissue. In various embodiments, a start up screen can include patient and/or facility data. In one embodiment the imaging/treatment function can include a main startup screen. In one embodiment a imaging/treatment function can be configured for a forehead. The settings function allows the user to input, track, store and/or print patient treatment information outside the scanning function, and can include such information as patient and facility information, end treatment, treatment records, images, help, volume, and system shutdown controls and dialogs.

The therapy controls 1010 can set acoustic energy level, spacing for setting the distance between micro-coagulative zones, and length which can set the maximum distance of the treatment line and similar information.

The imaging controls 1020 can include marker (not scanning), display (scanning), image and scan information. The marker can include a distance icon to show calipers and text for annotation. The display can increase or decrease brightness or other display related characteristics. The image icon can toggle a treat ruler, or save an image. The scan buttons can start or stop scanning for imaging purposes and similar information.

The region control 1030 launches a dialog below the image to select tissue region. The patient total line count 1040 keeps track of the cumulative number of treatment lines delivered and similar information. The treat zone line count 1050 indicates a zone of treatment, such as forehead or submental, etc. and can display the lines delivered to a zone or a protocol for recommended lines and similar information. The system status 1060 can display that the system is ready, treating, or other mode-dependent system messages and similar information. The probe information area 1070 can display the name of the attached transducer, the treatment depth of the transducer, and the number of lines spent/(vs.) total line capacity of transducer and similar information. The header information 1080 can include the facility, clinician, patient name and patient identification, date and time and similar information. The image-treat region 1090 can include an ultrasound image, horizontal and vertical (depth) rulers with 1 mm tick marks or other measuring dimensions, a treatment ruler indicating spacing, length and depth of treatment, and other similar information.

One benefit or advantage of using a treatment system that also allows imaging is that a user can verify that there sufficient coupling between the transducer and the skin (such as by applying coupling gel between the emitter-receiver module 200 and skin) by ensuring there are not dark, vertical bars, as indicative of air pockets between the face of the transducer and patient. A lack of coupling may result in a region that is improperly treated. Corrective action might include placing more coupling ultrasound gel to ensure proper contact and communication between the device and the patient.

Therapeutic treatment can be initiated by pressing the treatment button 160 on the hand wand 100. In one embodiment, an indicator 155 will display a yellow light to indicate the system is in the "treating" state. As the energy 50 is delivered a continuous tone is sounded and a yellow 'treating' line will advance over the green 'ready' treatment line on the screen. To deliver the next line of energy in the same treatment area, the user can advance the transducer roughly 1-6 mm, or roughly 2-3 mm (depending on the treatment, region, etc.) to adjacent tissue and press the treatment button 160 again. In various embodiments, a time period can elapse between delivering a previous line of energy 50. In various embodiments, the time period can be 1 second, 5 seconds, 10 seconds, or any other duration. In one embodiment, if five or ten seconds (or some other duration) have elapsed between delivering the previous line of energy 50, the user can press the imaging button 150 on the hand wand 100 to restore the "ready" state, and then press the treatment button 160 next to it. Treatment can continue in this fashion until the recommended number of lines (as shown on the bottom/ center of the screen) has been delivered. In one embodiment, when the correct number of lines is delivered, the line count color turns from orange to white.

In one embodiment, the settings function allows a user to export images. Stored images are listed in the bottom dialog box and the most recently user-selected image is displayed above it. If an external storage device and/or printer is attached then image file export and/or printing is enabled, respectively. In one embodiment, the settings function allows a user to export records.

In certain embodiments, the interactive graphical display 310 can display error messages to direct appropriate user responses, such as in one embodiment of an error message.

Embodiments of the present invention may be described herein in terms of various functional components and processing steps. It should be appreciated that such components and steps may be realized by any number of hardware components configured to perform the specified functions. For example, embodiments of the present invention may employ various medical and/or cosmetic treatment devices, visual imaging and display devices, input terminals and the like, which may carry out a variety of functions under the control of one or more control systems or other control devices. In addition, embodiments of the present invention may be practiced in any number of medical and/or cosmetic contexts and that some embodiments relating to a method and system for noninvasive face lift and deep tissue tightening as described herein are merely indicative of some applications for the invention. For example, the principles, features and methods discussed may be applied to any tissue, such as in one embodiment, a SMAS-like muscular fascia, such as platysma, temporal fascia, and/or occipital fascia, or any other medical and/or cosmetic application.

Thermal Cosmetic Treatment Zones

Further, various aspects of embodiments of the present invention may be suitably applied to other applications. Some embodiments of the system and method of the present invention may also be used for controlled thermal application of energy to various tissues and/or noninvasive facelifts and deep tissue tightening. Certain embodiments of systems and methods are disclosed in U.S. application Ser. No. 12/028,636, which is incorporated herein by reference in its entirety. Certain embodiments of systems and methods for controlled thermal application to various tissues are disclosed in U.S. application Ser. No. 11/163,148 and/or Ser. No. 13/444,688, which are incorporated herein by reference their entirety. Certain embodiments of systems and methods for non-invasive facelift and deep tissue tightening are disclosed in U.S. application Ser. No. 11/163,151 and/or Ser. No. 13/494,856, each of which is incorporated herein by reference in its entirety.

In accordance with some embodiments of the present invention, a method and system for noninvasive face lifts and deep tissue tightening are provided. For example, in accordance with an embodiment, with reference to FIG. 23, a treatment system 2100 (or 20 as shown in FIG. 1 or otherwise referred to as a cosmetic treatment system or CTS) configured to treat a region of interest 2106 (or 525 as shown in FIG. 14 or otherwise referred to as a treatment zone) comprises a control system 2102 (or 300 as shown in FIGS. 1 and 9 or otherwise referred to as a control module or control unit), an imaging/therapy probe with acoustic coupling 2104 (or 100 and/or 200 as shown in FIGS. 1-10 or otherwise referred to as a probe, probe system, hand wand, emitter/receiver module, removable transducer module), and a display system 2108 (or 310 as shown in FIGS. 1, 8-10, and 22 or otherwise referred to as display or interactive graphical display). Control system 2102 and display system 2108 can comprise various configurations for controlling probe 2102 and overall system 2100 functionality, such as, for example, a microprocessor with software and a plurality of input/output devices, system and devices for controlling electronic and/or mechanical scanning and/or multiplexing of transducers, a system for power delivery, systems for monitoring, systems for sensing the spatial position of the probe and/or transducers, and/or systems for handling user input and recording treatment results, among others. Imaging/therapy probe 2104 can comprise various probe and/or transducer configurations. For example, probe 2104 can be configured for a combined dual-mode imaging/therapy transducer, coupled or co-housed imaging/therapy transducers, or simply a separate therapy probe and an imaging probe.

In accordance with an embodiment, treatment system 2100 is configured for treating tissue above, below and/or in the SMAS region by imaging of region of interest 2106 for localization of the treatment area and surrounding structures, delivery of ultrasound energy at a depth, distribution, timing, and energy level to achieve the desired therapeutic effect, and optionally monitoring the treatment area before, during, and/or after therapy to plan and assess the results and/or provide feedback. According to another embodiment of the present invention, treatment system 2100 is configured for controlled thermal application of cosmetic treatment zones to human superficial tissue based on treatment system 2100's ability to controllably create thermal points of conformally variable shape, size, and depth through precise spatial and temporal control of acoustic energy deposition.

As to the treatment of the SMAS region (or SMAS 507), connective tissue can be permanently tightened by thermal treatment to temperatures about 60 degrees Celsius or higher. Upon ablating, collagen fibers shrink immediately by approximately 30% of their length. The shrunken fibers can produce tightening of the tissue, wherein the shrinkage should occur along the dominant direction of the collagen fibers. Throughout the body, collagen fibers are laid down in connective tissues along the lines of chronic stress (tension). On the aged face, neck and/or body, the collagen fibers of the SMAS region are predominantly oriented along the lines of gravitational tension. Shrinkage of these fibers results in tightening of the SMAS in the direction desired for correction of laxity and sagging due to aging. The treatment, in one embodiment, comprises the ablation of specific regions of the SMAS region and similar suspensory connective tissues.

In addition, the SMAS region varies in depth and thickness at different locations, e.g., between 0.5 mm to 5 mm or more. On the face and other parts of the body, important structures such as nerves, parotid gland, arteries and veins are present over, under or near the SMAS region. Tightening of the SMAS in certain locations, such as the preauricular region associated with sagging of the cheek to create jowls, the frontal region associated with sagging brows, mandibular region associated with sagging neck, can be conducted. Treating through localized heating of regions of the SMAS or other suspensory subcutaneous connective tissue structures to temperatures of about 60-90° C., without significant damage to overlying or distal/underlying tissue, e.g., proximal tissue, as well as the precise delivery of therapeutic energy to SMAS regions, and obtaining feedback from the region of interest before, during, and after treatment can be suitably accomplished through treatment system 2100.

To further illustrate an embodiments of a method and system 2200, with reference to FIGS. 24A-24F, imaging of a region of interest 2206, such as by imaging a region 2222 and displaying images 2224 of the region of interest 2206 on a display 2208, to facilitate localization of the treatment area and surrounding structures can initially be conducted. Next, delivery of ultrasound energy 2220 at a suitably depth, distribution, timing, and energy level to achieve the desired therapeutic effect of thermal injury or ablation to treat SMAS region 2216 (or 507 as shown in FIG. 14 or otherwise referred to as SMAS) can be suitably provided by probe 2204 (or 200 as shown in FIGS. 1-10 or otherwise referred to as module, or emitter-receiver module) through control by control system 2202. Monitoring of the treatment area and surrounding structures before, during, and after therapy, e.g., before, during, and after the delivery of ultrasound energy to SMAS region 2216, can be provided to plan and assess the results and/or provide feedback to control system 2202 and a system user.

Ultrasound imaging and providing of images 2224 can facilitate safe targeting of the SMAS layer 2216. For example, with reference to FIG. 24B, specific targeting for the delivery of energy can be better facilitated to avoid heating vital structures such as the facial nerve (motor nerve) 2234 (or 504 as shown in FIG. 11), parotid gland (which makes saliva) 2236 (or 506 as shown in FIG. 11), facial artery 2238, and trigeminal nerve (for sensory functions) 2232 (or 502 as shown in FIG. 11) among other regions. Further, use of imaging with targeted energy delivery to provide a limited and controlled depth of treatment can minimize the chance of damaging deep structures, such as for example, the facial nerve that lies below the parotid, which is typically 10 mm thick.

Figure 24A:
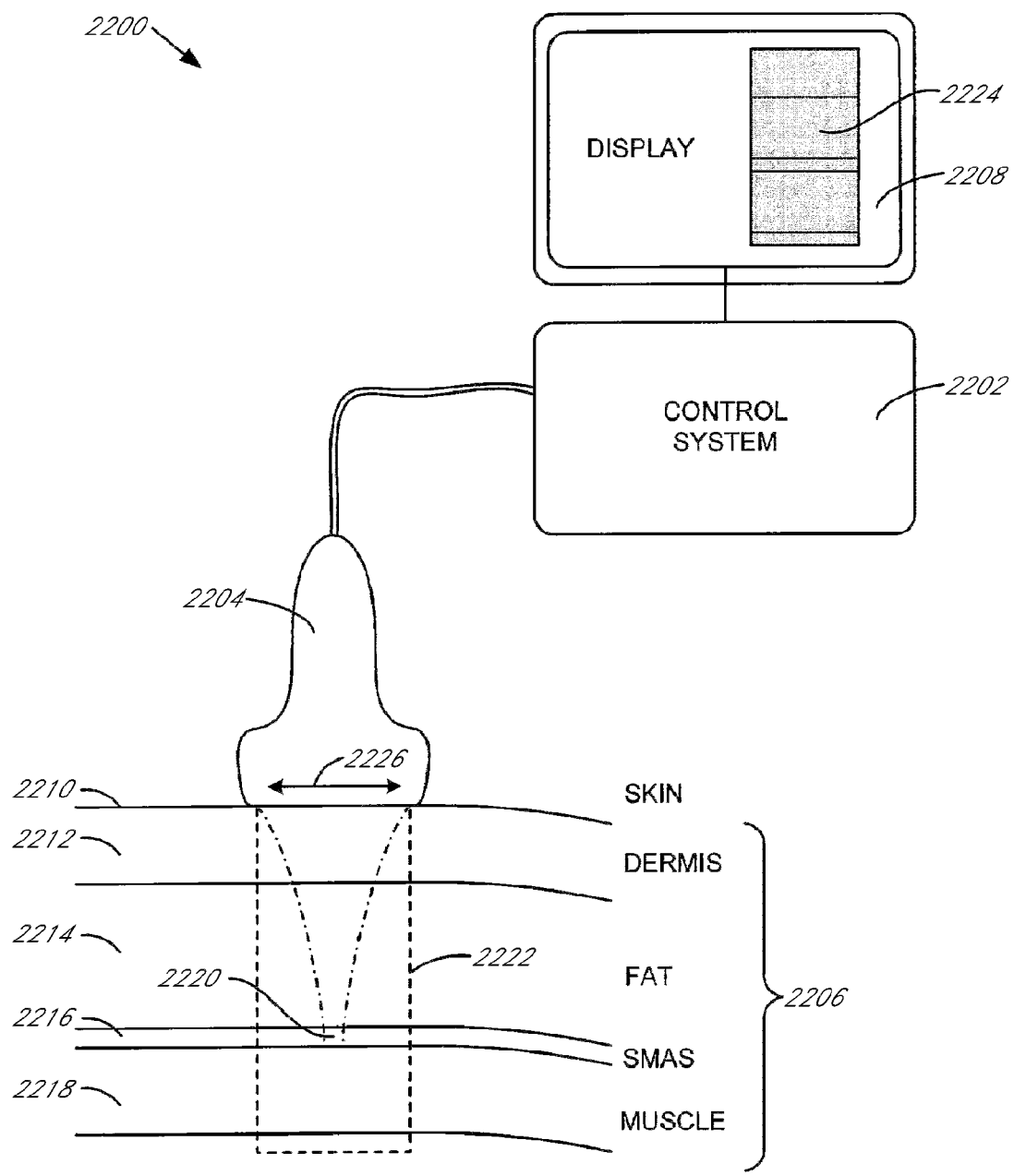
FIGS. 24A-24F illustrates schematic diagrams of an ultrasound imaging/therapy and monitoring system for treating the SMAS layer in accordance with various embodiments.
Figure 24B:
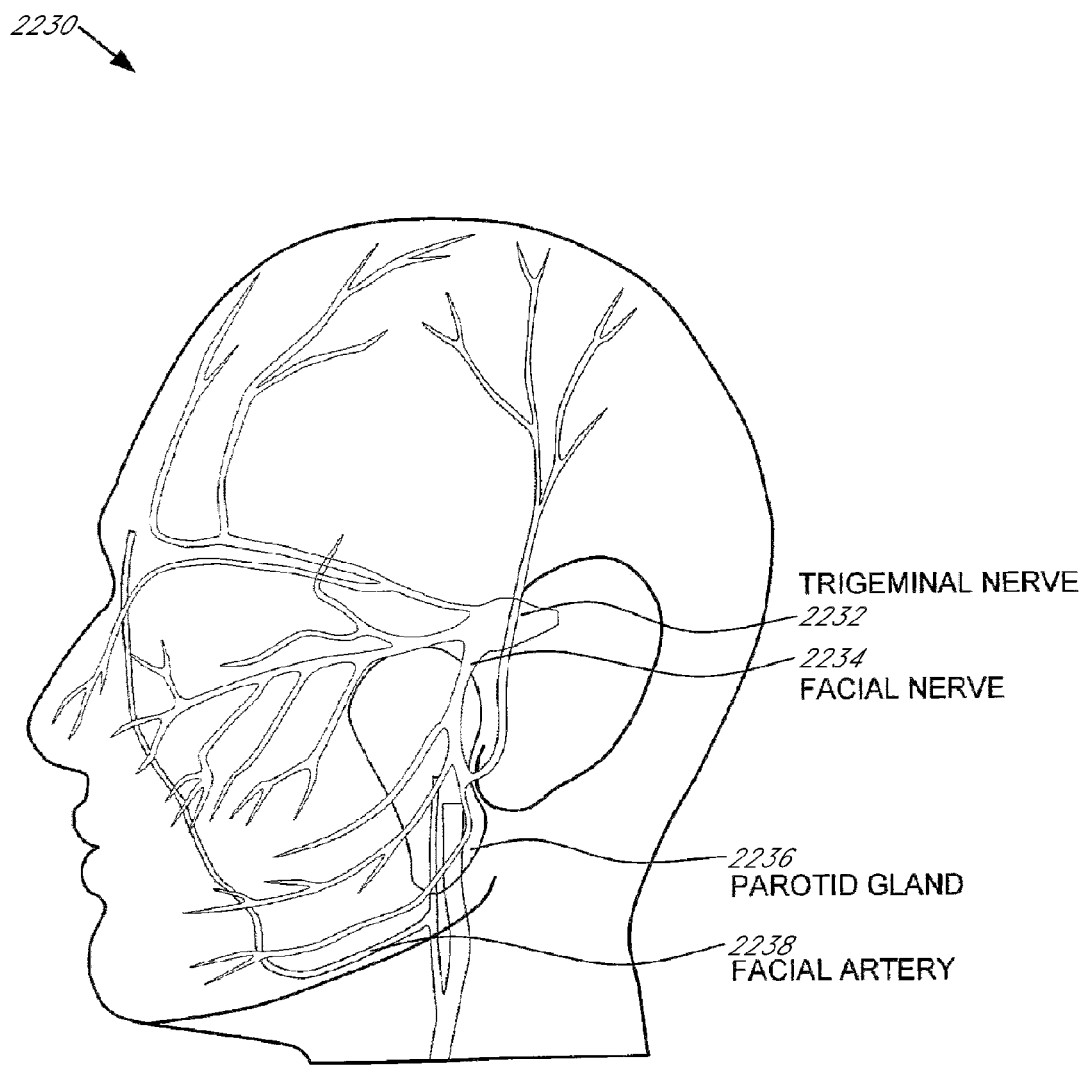
Figure 24C:
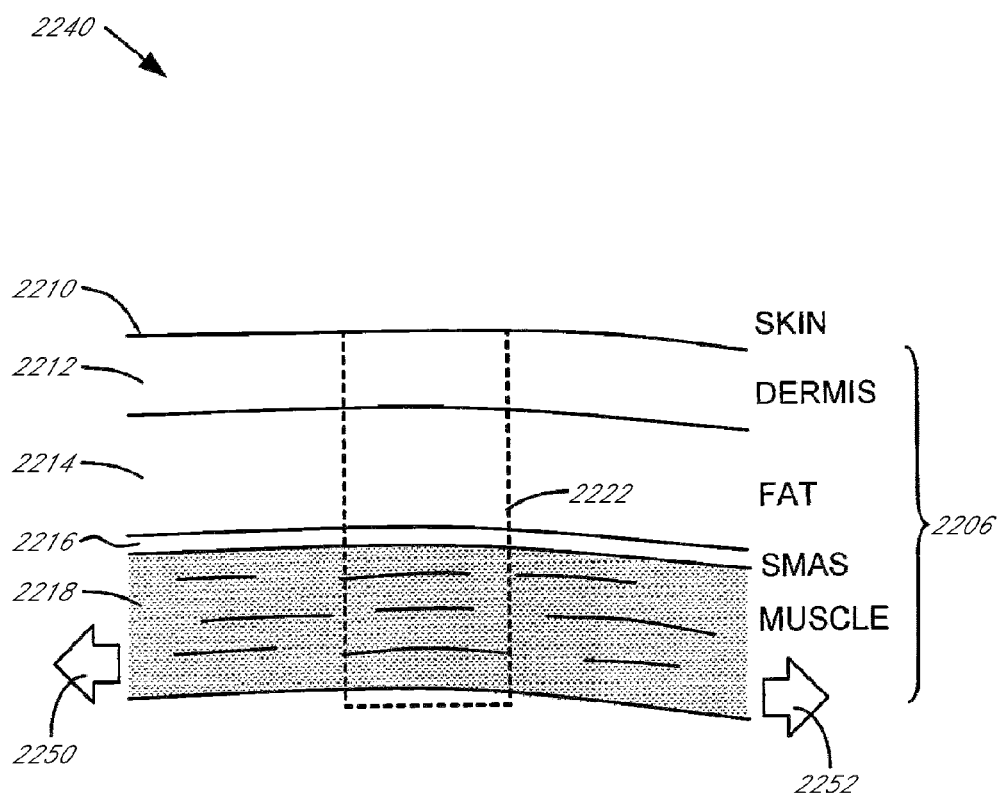

In accordance with an embodiment, with reference to FIG. 24C, ultrasound imaging of region 2222 of the region of interest 2206 can also be used to delineate SMAS layer 2216 as the superficial, echo-dense layer overlying facial muscles 2218 (or 509 as shown in FIG. 14-16). Such muscles can be seen via imaging region 2222 by moving muscles 2218, for example by extensional flexing of muscle layer 2218 generally towards directions 2250 and 2252. Such imaging of region 2222 may be further enhanced via signal and image processing. Once SMAS layer 2216 is localized and/or identified, SMAS layer 2216 is ready for treatment.

The delivery of ultrasound energy 2220 at a suitably depth, distribution, timing, and energy level is provided by probe 2204 through controlled operation by control system 2202 to achieve the desired therapeutic effect of thermal injury to treat SMAS region 2216. During operation, probe 2204 can also be mechanically and/or electronically scanned within tissue surface region 2226 to treat an extended area. In addition, spatial control of a treatment depth 2220 (or 278 as shown in FIG. 15 or otherwise referred to as depth) can be suitably adjusted in various ranges, such as between a wide range of approximately 0 to 15 mm, suitably fixed to a few discrete depths, with an adjustment limited to a fine range, e.g. approximately between 3 mm to 9 mm, and/or dynamically adjusted during treatment, to treat SMAS layer 2216 that typically lies at a depth between approximately 5 mm to 7 mm. Before, during, and after the delivery of ultrasound energy to SMAS region 2216, monitoring of the treatment area and surrounding structures can be provided to plan and assess the results and/or provide feedback to control system 2202 and a system user.

Figure 24D:
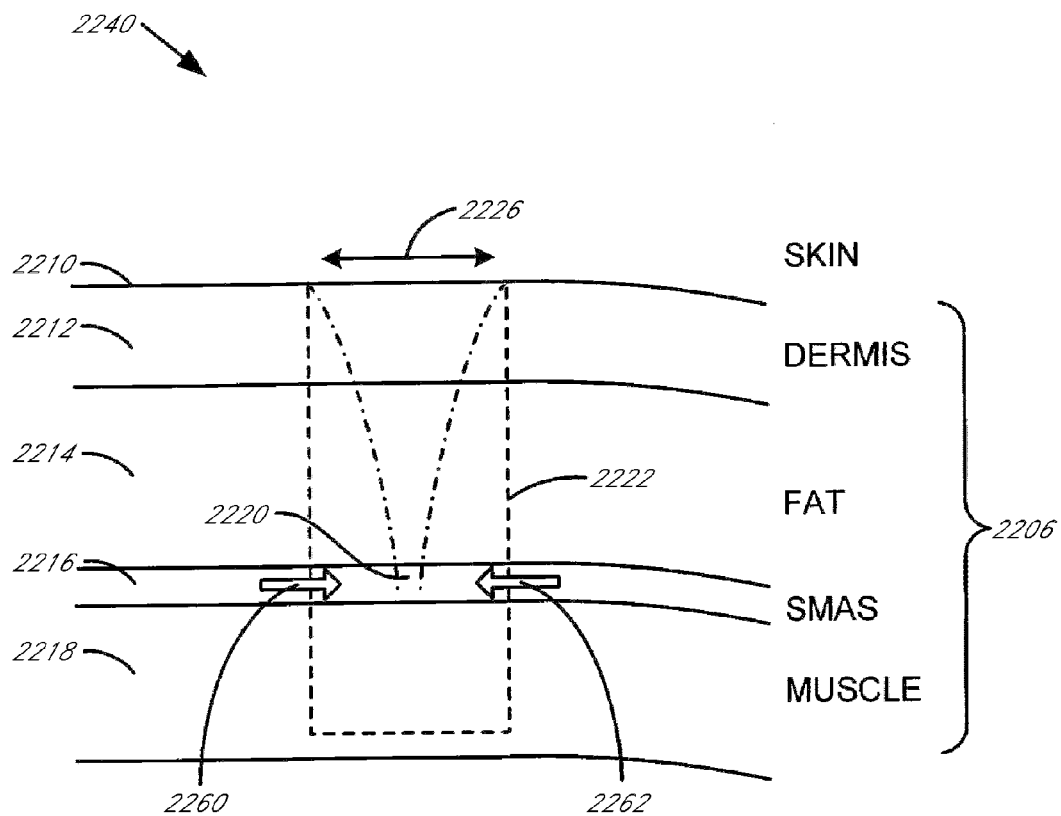

For example, in accordance with an embodiment, with additional reference to FIG. 24D, ultrasound imaging of region 2222 can be used to monitor treatment by watching the amount of shrinkage of SMAS layer 2216 in direction of areas 2260 and 2262, such as in real time or quasi-real time, during and after energy delivery to region 2220. The onset of substantially immediate shrinkage of SMAS layer 2216 is detectable by ultrasound imaging of region 2222 and may be further enhanced via image and signal processing. In one embodiment, the monitoring of such shrinkage can be advantageous because it can confirm the intended therapeutic goal of noninvasive lifting and tissue tightening; in addition, such monitoring may be used for system feedback. In addition to image monitoring, additional treatment parameters that can be suitably monitored in accordance with various other embodiments may include temperature, video, profilometry, strain imaging and/or gauges or any other suitable spatial, temporal and/or other tissue parameters, or combinations thereof.

Figure 24E:
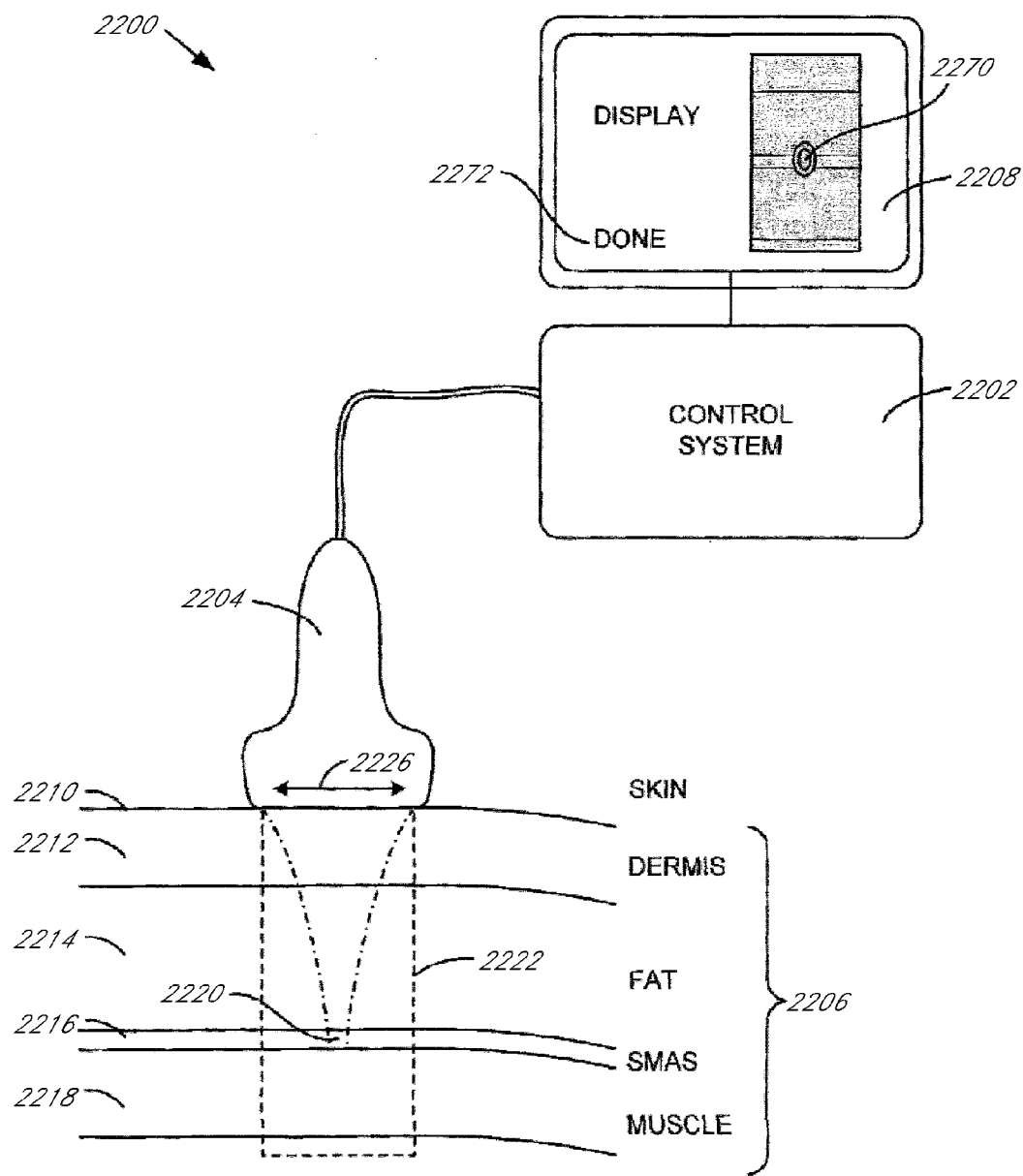

For example, in accordance with an embodiment of the present invention, with additional reference to FIG. 24E, an embodiment of a monitoring method and system 2200 may suitably monitor the temperature profile or other tissue parameters of the region of interest 2206, such as attenuation or speed of sound of treatment region 2222 and suitably adjust the spatial and/or temporal characteristics and energy levels of ultrasound therapy transducer probe 2204. The results of such monitoring techniques may be indicated on display 2208 in various manners, such as, for example, by way of one-, two-, or three-dimensional images of monitoring results 2270, or may comprise an indicator 2272, such as a success, fail and/or completed/done type of indication, or combinations thereof.

Figure 24F:
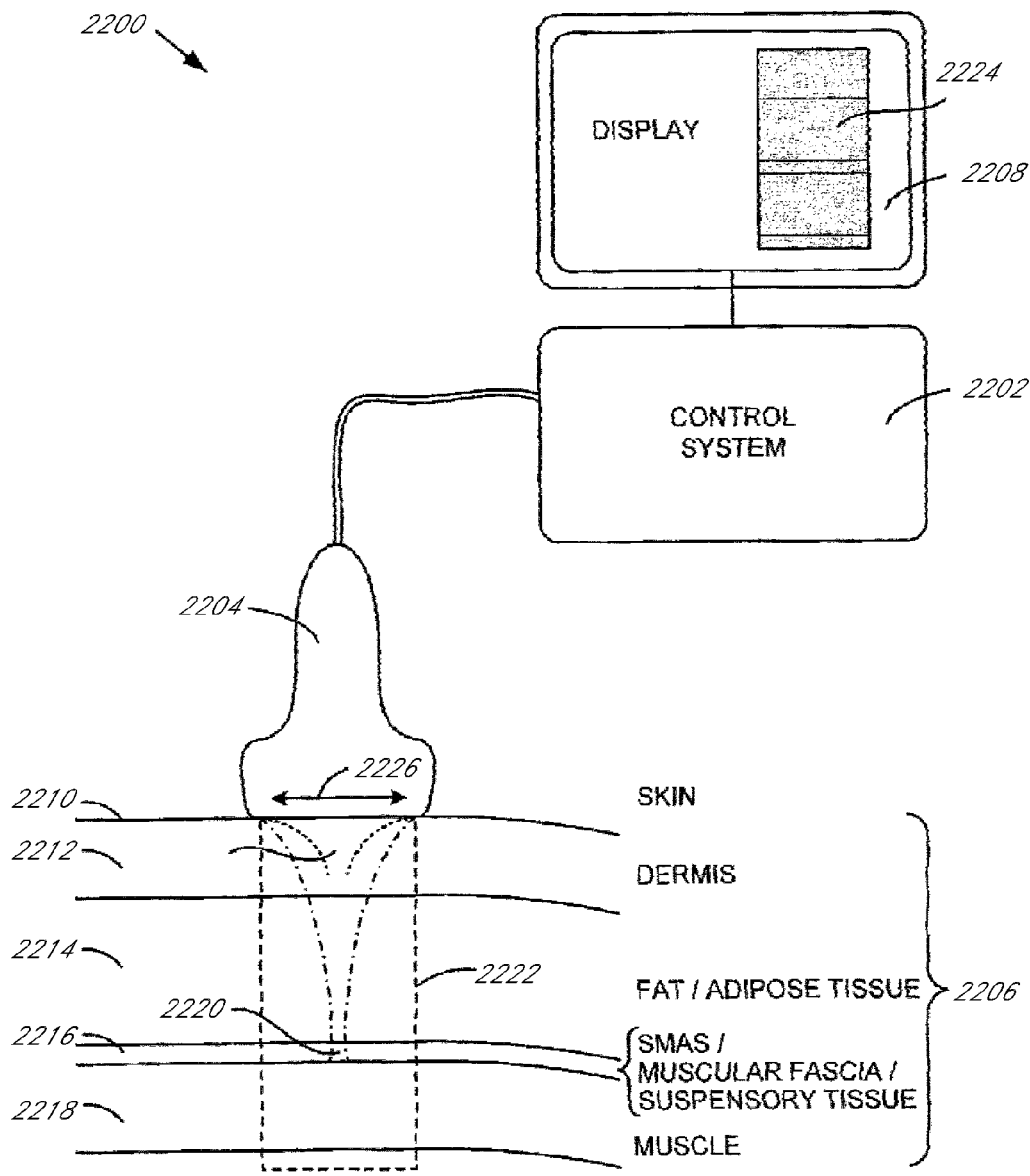

In accordance with another embodiment, with reference to FIG. 24F, the targeting of particular region 2220 within SMAS layer 2216 can be suitably be expanded within region of interest 2206 to include a combination of tissues, such as skin 2210 (or 501 as shown in FIGS. 14-16), dermis 2212 2210 (or 503 as shown in FIGS. 14-16), fat/adipose tissue 2214 2210 (or 505 as shown in FIGS. 14-16), SMAS/muscular fascia/and/or other suspensory tissue 2216 2210 (or 507 as shown in FIGS. 14-16), and muscle 2218 2210 (or 509 as shown in FIGS. 14-16). Treatment of a combination of such tissues and/or fascia may be treated including at least one of SMAS layer 2216 or other layers of muscular fascia in combination with at least one of muscle tissue, adipose tissue, SMAS and/or other muscular fascia, skin, and dermis, can be suitably achieved by treatment system 2200. For example, treatment of SMAS layer 2216 may be performed in combination with treatment of dermis 2280 by suitable adjustment of the spatial and temporal parameters of probe 2204 within treatment system 2200.

Figure 23:
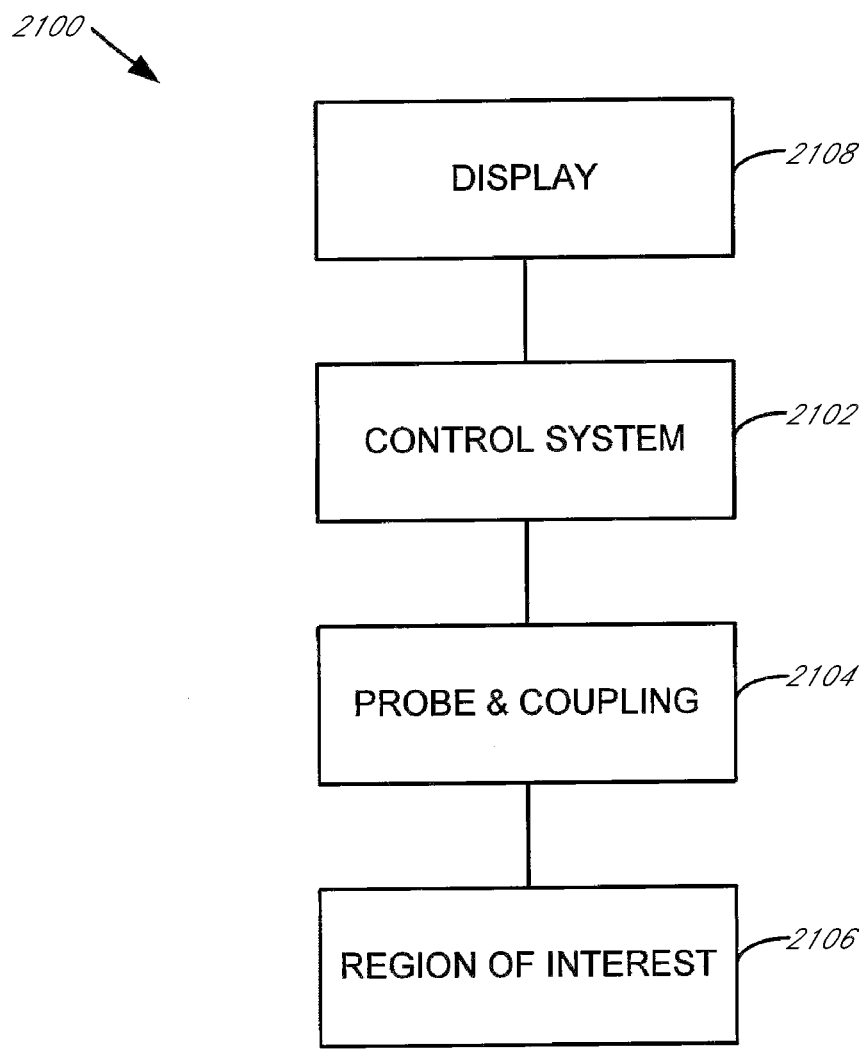
FIG. 23 illustrates a block diagram of a treatment system in accordance with an embodiment.

In accordance with various aspects of the present invention, a therapeutic treatment method and system for controlled thermal injury of human superficial tissue to effectuate face lifts, deep tissue tightening, and other procedures is based on the ability to controllably create thermal lesions of conformally variable shape, size, and depth through precise spatial and temporal control of acoustic energy deposition. With reference to FIG. 23, in accordance with an embodiment, a therapeutic treatment system 2200 includes a control system 2102 and a probe system 2104 that can facilitate treatment planning, controlling and/or delivering of acoustic energy, and/or monitoring of treatment conditions to a region of interest 2106. Region-of-interest 2106 is configured within the human superficial tissue comprising from just below the tissue outer surface to approximately 30 mm or more in depth.

Therapeutic treatment system 2100 is configured with the ability to controllably produce conformal lesions of thermal injury in superficial human tissue within region of interest 2106 through precise spatial and temporal control of acoustic energy deposition, e.g., control of probe 2104 is confined within selected time and space parameters, with such control being independent of the tissue. In accordance with an embodiment, control system 2102 and probe system 2104 can be suitably configured for spatial control of the acoustic energy by controlling the manner of distribution of the acoustical energy. For example, spatial control may be realized through selection of the type of one or more transducer configurations insonifying region of interest 2106, selection of the placement and location of probe system 2104 for delivery of acoustical energy relative to region-of-interest 2106, e.g., probe system 2104 being configured for scanning over part or whole of region-of-interest 2106 to produce contiguous thermal injury having a particular orientation or otherwise change in distance from region-of-interest 2106, and/or control of other environment parameters, e.g., the temperature at the acoustic coupling interface can be controlled, and/or the coupling of probe 2104 to human tissue. In addition to the spatial control parameters, control system 2102 and probe system 2104 can also be configured for temporal control, such as through adjustment and optimization of drive amplitude levels, frequency/waveform selections, e.g., the types of pulses, bursts or continuous waveforms, and timing sequences and other energy drive characteristics to control thermal ablation of tissue. The spatial and/or temporal control can also be facilitated through open-loop and closed-loop feedback arrangements, such as through the monitoring of various spatial and temporal characteristics. As a result, control of acoustical energy within six degrees of freedom, e.g., spatially within the X, Y and Z domain, as well as the axis of rotation within the XY, YZ and XZ domains, can be suitably achieved to generate conformal lesions of variable shape, size and orientation. For example, control of energy can be provided in any one or more of an x-axis, y-axis, z-axis, in a direction or axis parallel to X, Y, and/or Z, for linear motion, and/or rotational motion. In one embodiment, control of energy is provided through varying characteristics of the energy. In one embodiment, control of energy is provided through spatial motion of the energy emitter, such as in one example, through a motion mechanism moving a transducer.

Figure 36:
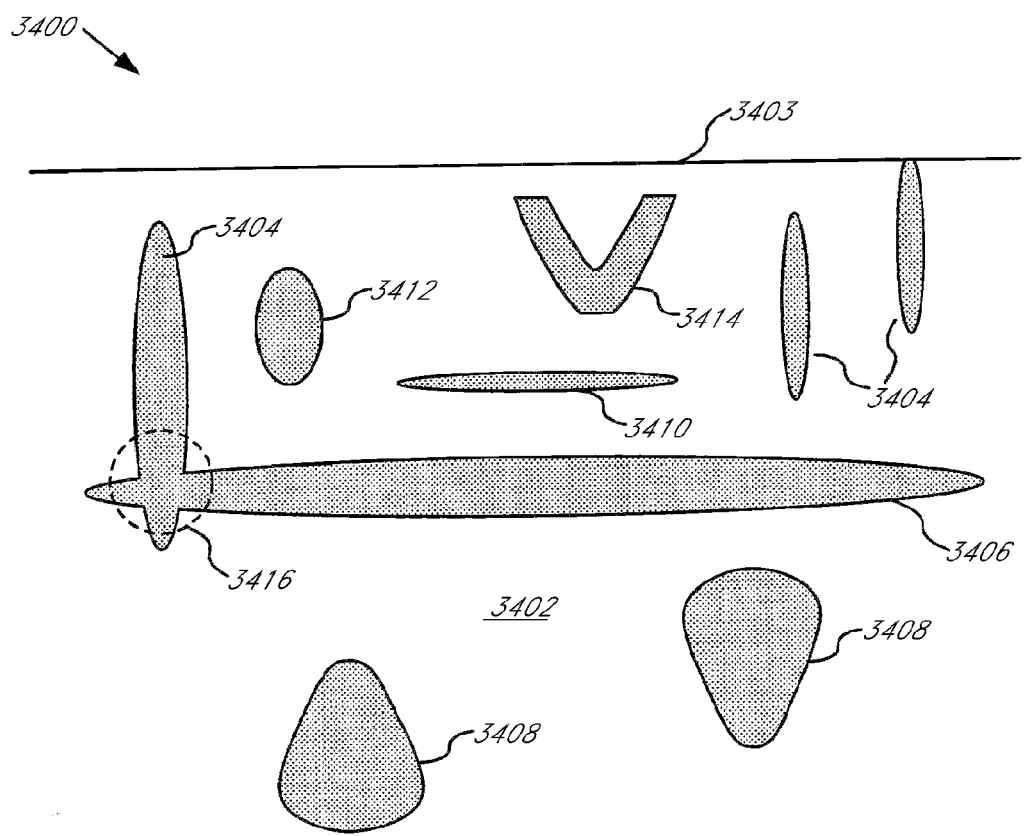
FIG. 36 illustrates a cross sectional diagram of a human superficial tissue region of interest including a plurality of lesions of controlled thermal injury in accordance with an embodiment.

For example, through such spatial and/or temporal control, an embodiment of a treatment system 2100 can enable the regions of thermal injury to possess arbitrary shape and size and allow the tissue to be destroyed (ablated) in a controlled manner. With reference to FIG. 36, one or more thermal lesions may be created within a tissue region of interest 3400, with such thermal lesions having a narrow or wide lateral extent, long or short axial length, and/or deep or shallow placement, including up to a tissue outer surface 3403. For example, cigar shaped lesions may be produced in a vertical disposition 3404 and/or horizontal disposition 3406. In addition, raindrop-shaped lesions 3408, flat planar lesions 3410, round lesions 3412 and/or other v-shaped/ellipsoidal lesions 3414 may be formed, among others. For example, mushroom-shaped lesion 3420 may be provided, such as through initial generation of an initial round or cigar-shaped lesion 3422, with continued application of ablative ultrasound resulting in thermal expansion to further generate a growing lesion 3424, such thermal expansion being continued until raindrop-shaped lesion 3420 is achieved. The plurality of shapes can also be configured in various sizes and orientations, e.g., lesions 3408 could be rotationally oriented clockwise or counterclockwise at any desired angle, or made larger or smaller as selected, all depending on spatial and/or temporal control. Moreover, separate islands of destruction, e.g., multiple lesions separated throughout the tissue region, may also be created over part of or the whole portion within tissue region-of-interest 3400. In addition, contiguous structures and/or overlapping structures 3416 may be provided from the controlled configuration of discrete lesions. For example, a series of one or more crossed-lesions 3418 can be generated along a tissue region to facilitate various types of treatment methods.

The specific configurations of controlled thermal injury are selected to achieve the desired tissue and therapeutic effect(s). For example, any tissue effect can be realized, including but not limited to thermal and non-thermal streaming, cavitational, hydrodynamic, ablative, hemostatic, diathermic, and/or resonance-induced tissue effects. Such effects can be suitably realized at treatment depths over a range of approximately 0-30000 μm within region of interest 2200 to provide a high degree of utility.

Figure 25A:
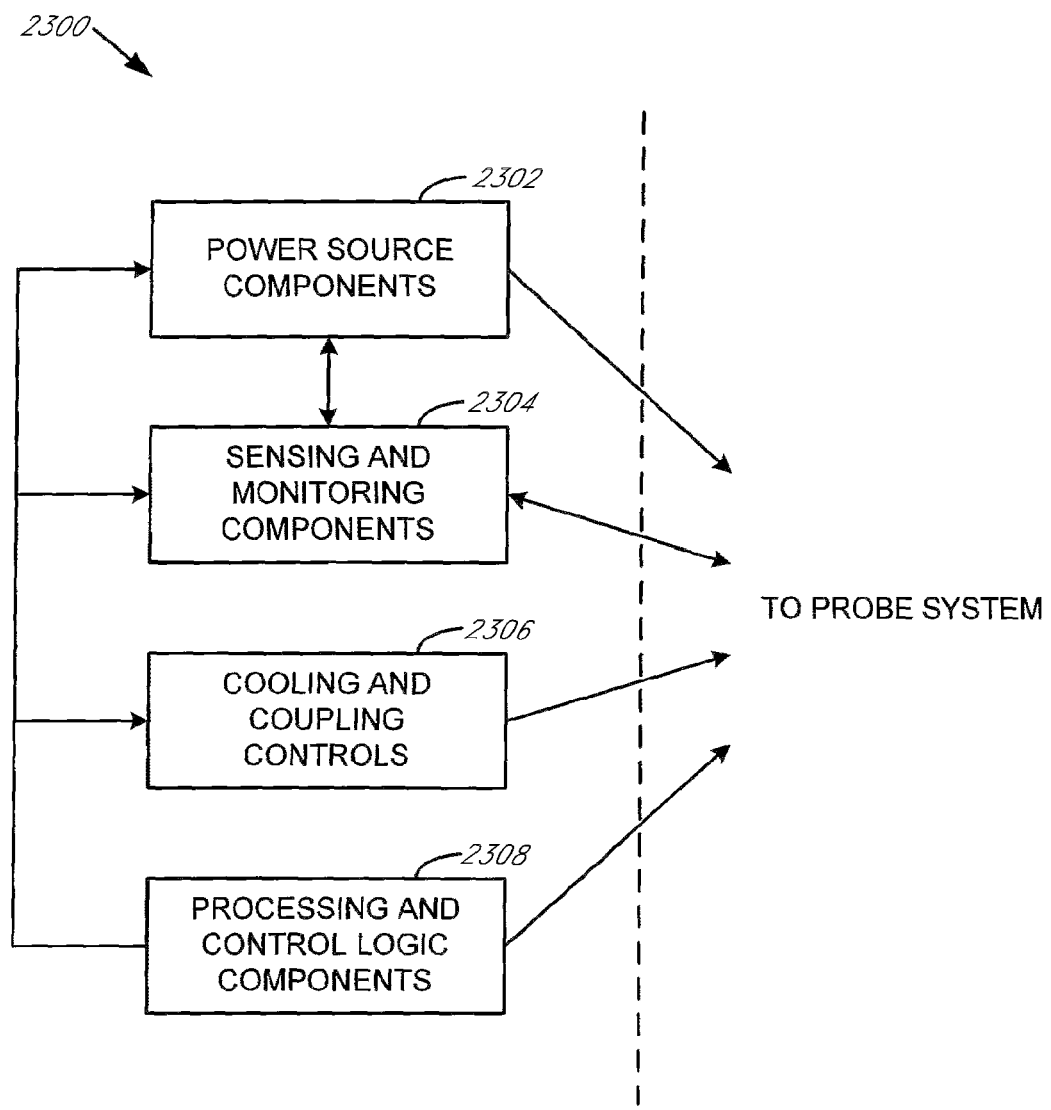
FIGS. 25A and 25B illustrate block diagrams of a control system in accordance with several embodiments.
Figure 25B:
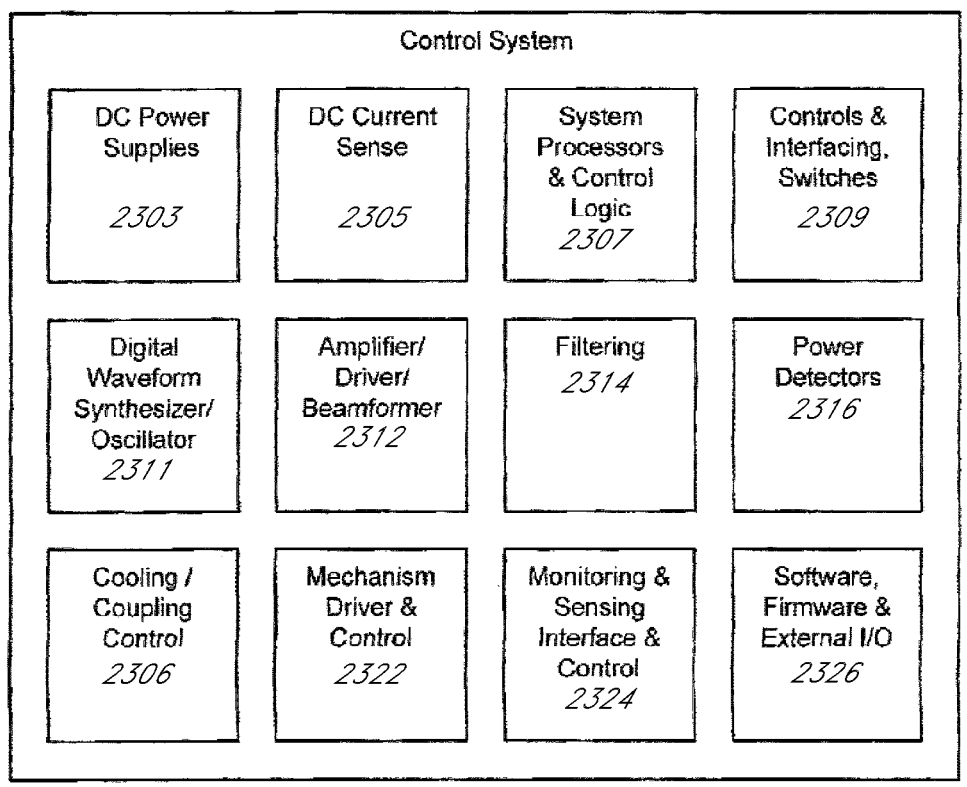

An embodiment of a control system 2202 and display system 2208 may be configured in various manners for controlling probe and system functionality. With reference again to FIGS. 25A and 25B, in accordance with embodiments, a control system 2300 can be configured for coordination and control of the entire therapeutic treatment process for noninvasive face lifts and deep tissue tightening. For example, control system 2300 can suitably comprise power source components 2302, sensing and monitoring components 2304, cooling and coupling controls 2306, and/or processing and control logic components 2308. Control system 2300 can be configured and optimized in a variety of ways with more or less subsystems and components to implement the therapeutic system for controlled thermal injury, and the embodiments in FIGS. 25A and 25B are merely for illustration purposes.

For example, for power sourcing components 2302, control system 2300 can comprise one or more direct current (DC) power supplies 2303 configured to provide electrical energy for entire control system 2300, including power required by a transducer electronic amplifier/driver 2312. A DC current sense device 2305 can also be provided to confirm the level of power going into amplifiers/drivers 2312 for safety and monitoring purposes.

Amplifiers/drivers 2312 can comprise multi-channel or single channel power amplifiers and/or drivers. In accordance with an embodiment for transducer array configurations, amplifiers/drivers 2312 can also be configured with a beamformer to facilitate array focusing. An embodiment of a beamformer can be electrically excited by an oscillator/digitally controlled waveform synthesizer 2310 with related switching logic.

The power sourcing components can also include various filtering configurations 2314. For example, switchable harmonic filters and/or matching may be used at the output of amplifier/driver 2312 to increase the drive efficiency and effectiveness. Power detection components 2316 may also be included to confirm appropriate operation and calibration. For example, electric power and other energy detection components 2316 may be used to monitor the amount of power going to an embodiment of a probe system.

Various sensing and monitoring components 2304 may also be suitably implemented within control system 2300. For example, in accordance with an embodiment, monitoring, sensing and interface control components 2324 may be configured to operate with various motion detection systems implemented within transducer probe 2204 to receive and process information such as acoustic or other spatial and temporal information from a region of interest. Sensing and monitoring components can also include various controls, interfacing and switches 2309 and/or power detectors 2316. Such sensing and monitoring components 2304 can facilitate open-loop and/or closed-loop feedback systems within treatment system 2200.

Still further, monitoring, sensing and interface control components 2324 may comprise imaging systems configured for one-dimensional, two-dimensional and/or three dimensional imaging functions. Such imaging systems can comprise any imaging modality based on at least one of photography and other visual optical methods, magnetic resonance imaging (MRI), computed tomography (CT), optical coherence tomography (OCT), electromagnetic, microwave, or radio frequency (RF) methods, positron emission tomography (PET), infrared, ultrasound, acoustic, or any other suitable method of visualization, localization, or monitoring of a region-of-interest 2106. Still further, various other tissue parameter monitoring components, such as temperature measuring devices and components, can be configured within monitoring, sensing and interface control components 2324, such monitoring devices comprising any modality now known or hereinafter devised.

Cooling/coupling control systems 2306 may be provided to remove waste heat from an embodiment of a probe 2204, provide a controlled temperature at the superficial tissue interface and deeper into tissue, and/or provide acoustic coupling from transducer probe 2204 to region-of-interest 2206. Such cooling/coupling control systems 2306 can also be configured to operate in both open-loop and/or closed-loop feedback arrangements with various coupling and feedback components.

Processing and control logic components 2308 can comprise various system processors and digital control logic 2307, such as one or more of microcontrollers, microprocessors, field-programmable gate arrays (FPGAs), computer boards, and associated components, including firmware and control software 2326, which interfaces to user controls and interfacing circuits as well as input/output circuits and systems for communications, displays, interfacing, storage, documentation, and other useful functions. System software and firmware 2326 controls all initialization, timing, level setting, monitoring, safety monitoring, and all other system functions required to accomplish user-defined treatment objectives. Further, various control switches 2308 can also be suitably configured to control operation.

An embodiment of a transducer probe 2204 can also be configured in various manners and comprise a number of reusable and/or disposable components and parts in various embodiments to facilitate its operation. For example, transducer probe 2204 can be configured within any type of transducer probe housing or arrangement for facilitating the coupling of transducer to a tissue interface, with such housing comprising various shapes, contours and configurations. Transducer probe 2204 can comprise any type of matching, such as for example, electric matching, which may be electrically switchable; multiplexer circuits and/or aperture/element selection circuits; and/or probe identification devices, to certify probe handle, electric matching, transducer usage history and calibration, such as one or more serial EEPROM (memories). Transducer probe 2204 may also comprise cables and connectors; motion mechanisms, motion sensors and encoders; thermal monitoring sensors; and/or user control and status related switches, and indicators such as LEDs. For example, a motion mechanism in probe 2204 may be used to controllably create multiple lesions, or sensing of probe motion itself may be used to controllably create multiple lesions and/or stop creation of lesions, e.g. for safety reasons if probe 2204 is suddenly jerked or is dropped. In addition, an external motion encoder arm may be used to hold the probe during use, whereby the spatial position and attitude of probe 2104 is sent to the control system to help controllably create lesions. Furthermore, other sensing functionality such as profilometers or other imaging modalities may be integrated into the probe in accordance with various embodiments. Moreover, the therapy contemplated herein can also be produced, for example, by transducers disclosed in U.S. application Ser. No. 10/944,499, and/or Ser. No. 10/944,500, both of which are hereby incorporated by reference in herein, in their entireties.

Figure 26A:
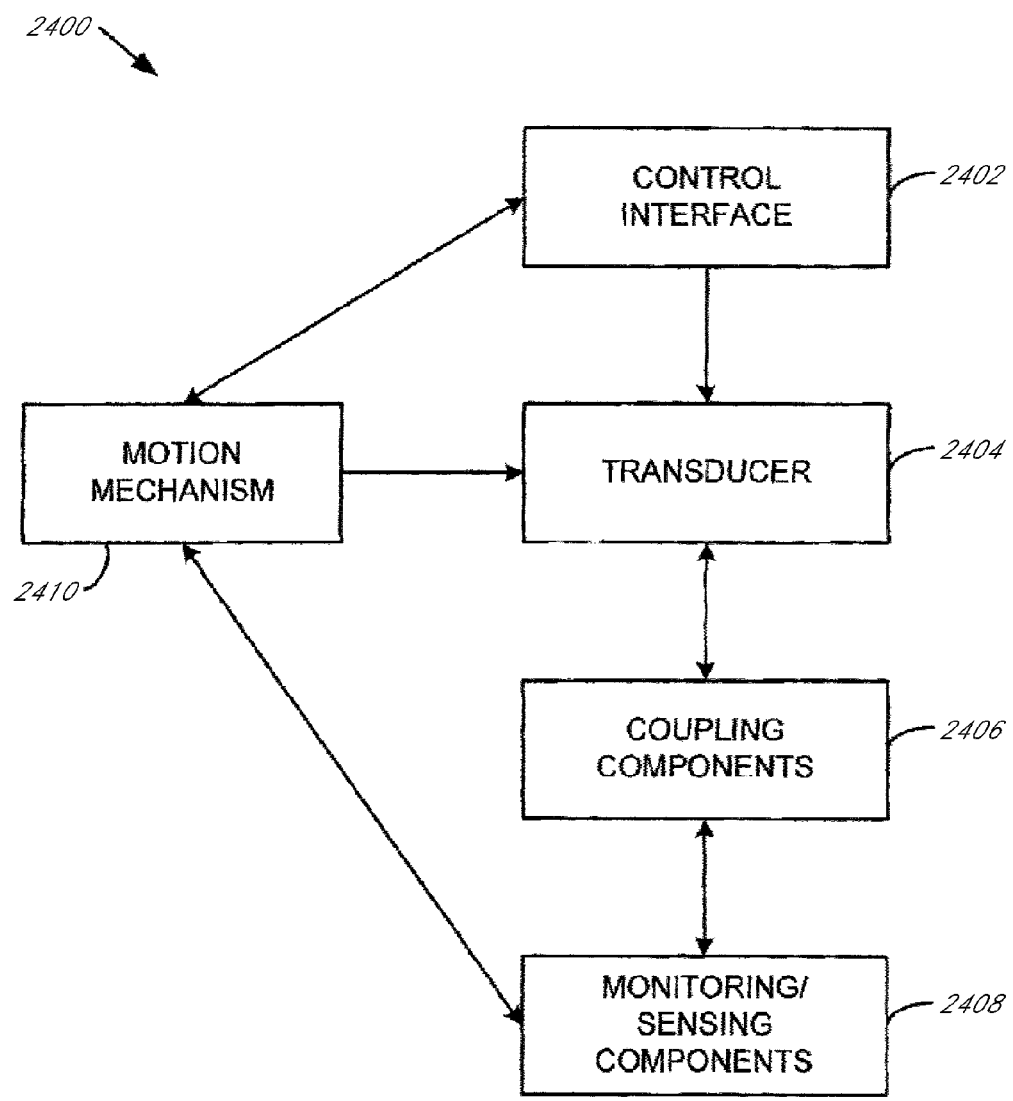
FIGS. 26A and 26B illustrate block diagrams of a probe system in accordance with several embodiments.
Figure 26B:
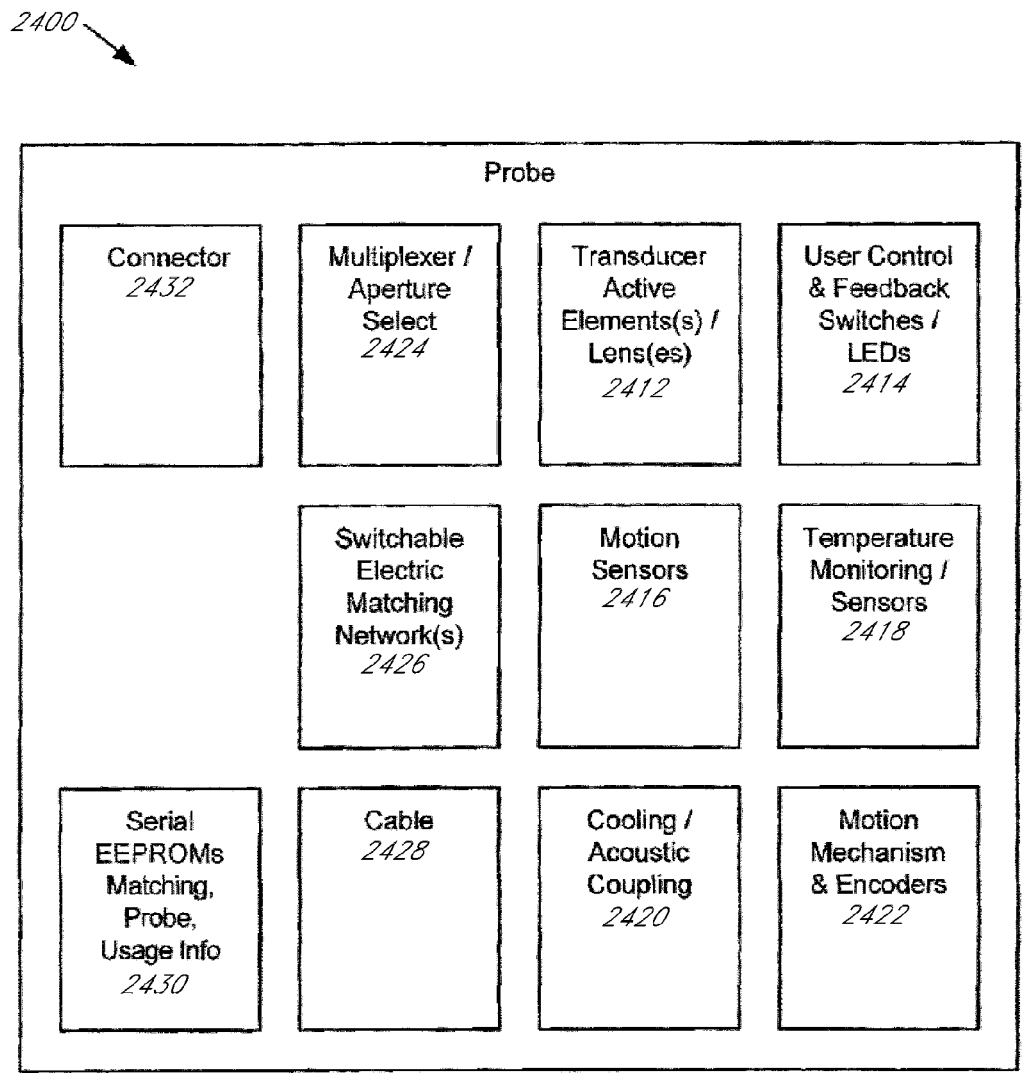

With reference to FIGS. 26A and 26B, in accordance with an embodiment, a transducer probe 2400 can comprise a control interface 2402, a transducer 2404, coupling components 2406, and monitoring/sensing components 2408, and/or motion mechanism 2410. However, transducer probe 2400 can be configured and optimized in a variety of ways with more or less parts and components to provide ultrasound energy for controlled thermal injury, and the embodiment in FIGS. 26A and 26B are merely for illustration purposes. Transducer 2404 can be any transducer configured to produce conformal lesions of thermal injury in superficial human tissue within a region of interest through precise spatial and temporal control of acoustic energy deposition.

Control interface 2402 is configured for interfacing with control system 2300 to facilitate control of transducer probe 2400. Control interface components 2402 can comprise multiplexer/aperture select 2424, switchable electric matching networks 2426, serial EEPROMs and/or other processing components and matching and probe usage information 2430 and interface connectors 2432.

Coupling components 2406 can comprise various devices to facilitate coupling of transducer probe 2400 to a region of interest. For example, coupling components 2406 can comprise cooling and acoustic coupling system 2420 configured for acoustic coupling of ultrasound energy and signals. Acoustic cooling/coupling system 2420 with possible connections such as manifolds may be utilized to couple sound into the region-of-interest, control temperature at the interface and deeper into tissue, provide liquid-filled lens focusing, and/or to remove transducer waste heat. Coupling system 2420 may facilitate such coupling through use of various coupling mediums, including air and other gases, water and other fluids, gels, solids, and/or any combination thereof, or any other medium that allows for signals to be transmitted between transducer active elements 2412 and a region of interest. In addition to providing a coupling function, in accordance with an embodiment, coupling system 2420 can also be configured for providing temperature control during the treatment application. For example, coupling system 2420 can be configured for controlled cooling of an interface surface or region between transducer probe 2400 and a region of interest and beyond by suitably controlling the temperature of the coupling medium. The suitable temperature for such coupling medium can be achieved in various manners, and utilize various feedback systems, such as thermocouples, thermistors or any other device or system configured for temperature measurement of a coupling medium. Such controlled cooling can be configured to further facilitate spatial and/or thermal energy control of transducer probe 2400.

Figure 33:
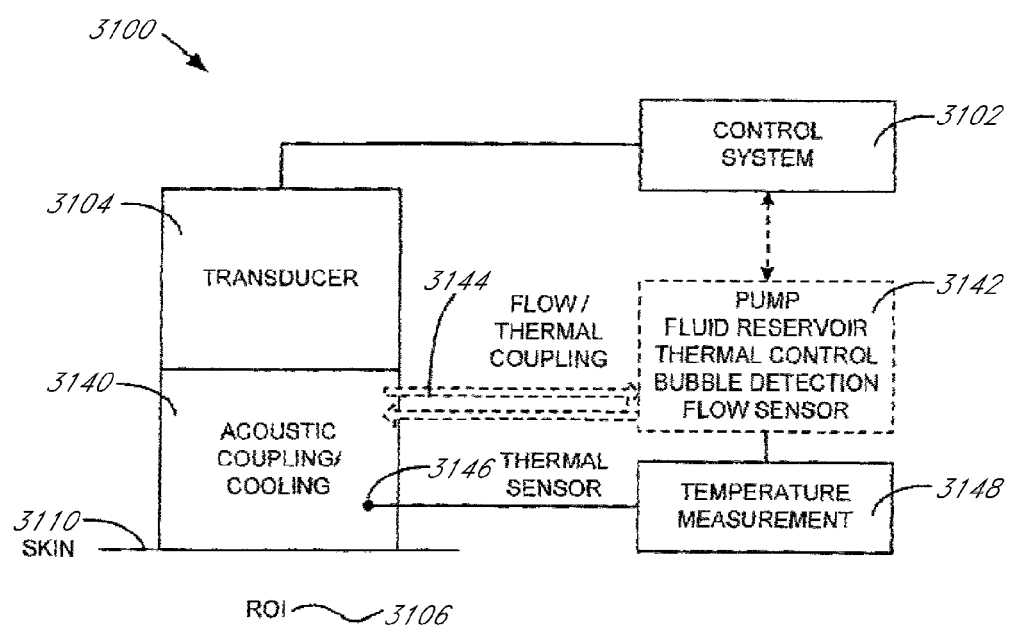
FIG. 33 illustrates a schematic diagram of an acoustic coupling and cooling system in accordance with an embodiment.

In accordance with an embodiment, with additional reference to FIG. 33, acoustic coupling and cooling 3140 can be provided to acoustically couple energy and imaging signals from transducer probe 3104 to and from the region of interest 3106, to provide thermal control at the probe to region-of-interest interface 3110 and deeper into tissue, and to remove potential waste heat from the transducer probe at region 3144. Temperature monitoring can be provided at the coupling interface via a thermal sensor 3146 to provide a mechanism of temperature measurement 3148 and control via control system 3102 and a thermal control system 3142. Thermal control may consist of passive cooling such as via heat sinks or natural conduction and convection or via active cooling such as with peltier thermoelectric coolers, refrigerants, or fluid-based systems comprised of pump, fluid reservoir, bubble detection, flow sensor, flow channels/tubing 3144 and thermal control 3142.

With continued reference to FIGS. 26A-26B, monitoring and sensing components 2408 can comprise various motion and/or position sensors 2416, temperature monitoring sensors 2418, user control and feedback switches 2414 and other like components for facilitating control by control system 2300, e.g., to facilitate spatial and/or temporal control through open-loop and closed-loop feedback arrangements that monitor various spatial and temporal characteristics.

Motion mechanism 2410 (or 400 as shown in FIG. 6, 10 or otherwise referred to as a movement mechanism, e.g., as shown in FIG. 7) can comprise manual operation, mechanical arrangements, or some combination thereof. For example, a motion mechanism 2422 can be suitably controlled by control system 2300, such as through the use of accelerometers, encoders or other position/orientation devices 2416 to determine and enable movement and positions of transducer probe 2400. Linear, rotational or variable movement can be facilitated, e.g., those depending on the treatment application and tissue contour surface.

Transducer 2404 (or 280 as shown in FIG. 6) can comprise one or more transducers configured for treating of SMAS layers and targeted regions. Transducer 2404 can also comprise one or more transduction elements and/or lenses 2412. The transduction elements can comprise a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. In addition to, or instead of, a piezoelectrically active material, transducer 2404 can comprise any other materials configured for generating radiation and/or acoustical energy. Transducer 2404 can also comprise one or more matching layers configured along with the transduction element such as coupled to the piezoelectrically active material. Acoustic matching layers and/or damping may be employed as necessary to achieve the desired electroacoustic response.

In accordance with an embodiment, the thickness of the transduction element of transducer 2404 can be configured to be uniform. That is, a transduction element 2412 can be configured to have a thickness that is substantially the same throughout. In accordance with another embodiment, the thickness of a transduction element 2412 can also be configured to be variable. For example, transduction element(s) 2412 of transducer 2404 can be configured to have a first thickness selected to provide a center operating frequency of approximately 2 kHz to 75 MHz (e.g., 500 kHz-15 MHz, 2 MHz-25 MHz, 1 MHz-10 MHz, 2-12 MHz, 3-10 MHz, 3.5-4.5 MHz, 4-5 MHz, 4.2-4.9 MHz, 4.3-4.7 MHz, 4.3 MHz, 4.7 MHz, 7-8 MHz, 7.2-7.8 MHz, 7.3-7.7 MHz, 7.3 MHz, 7.5 MHz, 8-12 MHz, 9-11 MHz, 9.5-10.5 MHz, or other frequencies), such as for imaging applications. Transduction element 2412 can also be configured with a second thickness selected to provide a center operating frequency of approximately 2 to 400 MHz, and typically between 4 MHz and 15 MHz for therapy application. In various embodiments, the frequency can be, e.g., 2 MHz-25 MHz, 1 MHz-10 MHz, 2-12 MHz, 3-10 MHz, 3.5-4.5 MHz, 4-5 MHz, 4.2-4.9 MHz, 4.3-4.7 MHz, 4.3 MHz, 4.7 MHz, 7-8 MHz, 7.2-7.8 MHz, 7.3-7.7 MHz, 7.3 MHz, 7.5 MHz, 8-12 MHz, 9-11 MHz, 9.5-10.5 MHz, or other frequencies. Transducer 2404 can be configured as a single broadband transducer excited with at least two or more frequencies to provide an adequate output for generating a desired response. Transducer 2404 can also be configured as two or more individual transducers, wherein each transducer comprises one or more transduction element. The thickness of the transduction elements can be configured to provide center-operating frequencies in a desired treatment range. For example, transducer 2404 can comprise a first transducer configured with a first transduction element having a thickness corresponding to a center frequency range of approximately 1 kHz to 3 MHz, and a second transducer configured with a second transduction element having a thickness corresponding to a center frequency of approximately 3 MHz to 100 MHz or more.

Figure 27:
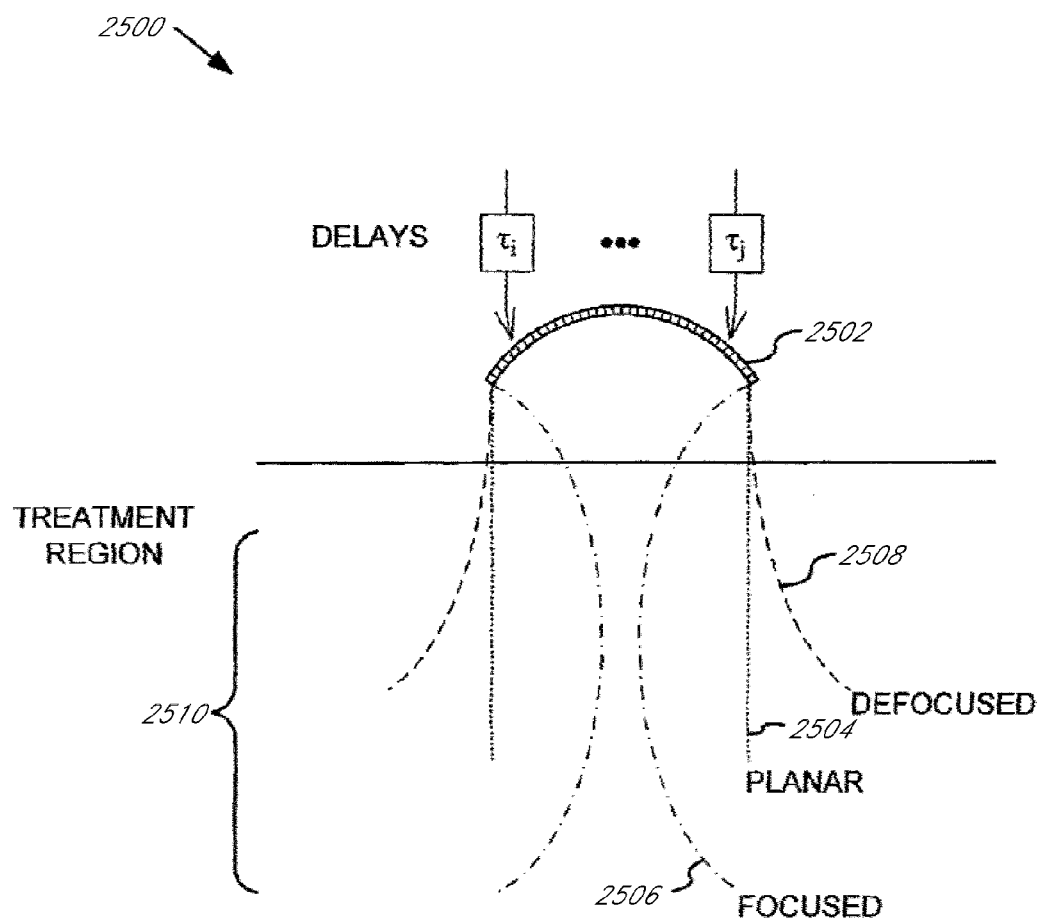
FIG. 27 illustrates a cross-sectional diagram of a transducer in accordance with an embodiment.

Transducer 2404 may be composed of one or more individual transducers in any combination of focused, planar, or unfocused single-element, multi-element, or array transducers, including 1-D, 2-D, and annular arrays; linear, curvilinear, sector, or spherical arrays; spherically, cylindrically, and/or electronically focused, defocused, and/or lensed sources. For example, with reference to an embodiment depicted in FIG. 27, transducer 2500 can be configured as an acoustic array to facilitate phase focusing. That is, transducer 2500 can be configured as an array of electronic apertures that may be operated by a variety of phases via variable electronic time delays. By the term "operated," the electronic apertures of transducer 2500 may be manipulated, driven, used, and/or configured to produce and/or deliver an energy beam corresponding to the phase variation caused by the electronic time delay. For example, these phase variations can be used to deliver defocused beams, planar beams, and/or focused beams, each of which may be used in combination to achieve different physiological effects in a region of interest 2510. Transducer 2500 may additionally comprise any software and/or other hardware for generating, producing and or driving a phased aperture array with one or more electronic time delays.

Transducer 2500 can also be configured to provide focused treatment to one or more regions of interest using various frequencies. In order to provide focused treatment, transducer 2500 can be configured with one or more variable depth devices to facilitate treatment. For example, transducer 2500 may be configured with variable depth devices disclosed in U.S. application Ser. No. 10/944,500, which is incorporated in its entirety by reference, herein. In addition, transducer 2500 can also be configured to treat one or more additional ROI 2510 (or 65 as shown in FIGS. 12-14) through the enabling of sub-harmonics or pulse-echo imaging, as disclosed in U.S. application Ser. No. 10/944,499, which is incorporated in its entirety by reference, herein.

Moreover, any variety of mechanical lenses or variable focus lenses, e.g. liquid-filled lenses, may also be used to focus and or defocus the sound field. For example, with reference to embodiments depicted in FIGS. 28A and 28B, transducer 2600 may also be configured with an electronic focusing array 2604 in combination with one or more transduction elements 2606 to facilitate increased flexibility in treating ROI 2610 (or 65 as shown in FIGS. 12-14). Array 2604 may be configured in a manner similar to transducer 2502. That is, array 2604 can be configured as an array of electronic apertures that may be operated by a variety of phases via variable electronic time delays, for example, $T_1$, $T_2 \ldots T_j$. By the term "operated," the electronic apertures of array 2604 may be manipulated, driven, used, and/or configured to produce and/or deliver energy in a manner corresponding to the phase variation caused by the electronic time delay. For example, these phase variations can be used to deliver defocused beams, planar beams, and/or focused beams, each of which may be used in combination to achieve different physiological effects in ROI 2610.

Transduction elements 2606 may be configured to be concave, convex, and/or planar. For example, in an embodiment depicted in FIG. 28A, transduction elements 2606 are configured to be concave in order to provide focused energy for treatment of ROI 2610. Additional embodiments of transduction elements are disclosed in U.S. application Ser. No. 10/944,500, which is incorporated in its entirety by reference, herein.

Figure 28A:
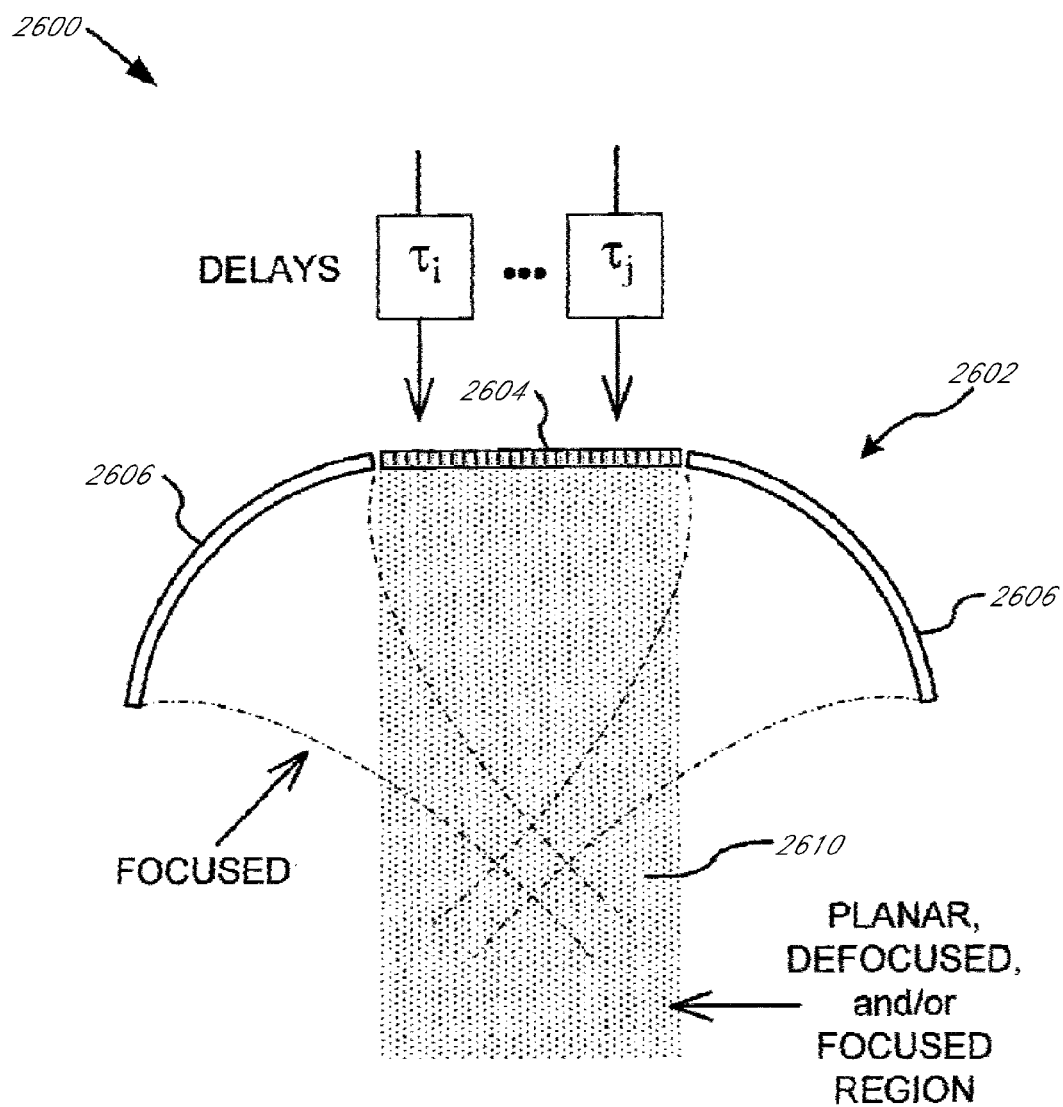
FIGS. 28A and 28B illustrate cross-sectional diagrams of a transducer in accordance with several embodiments.
Figure 28B:
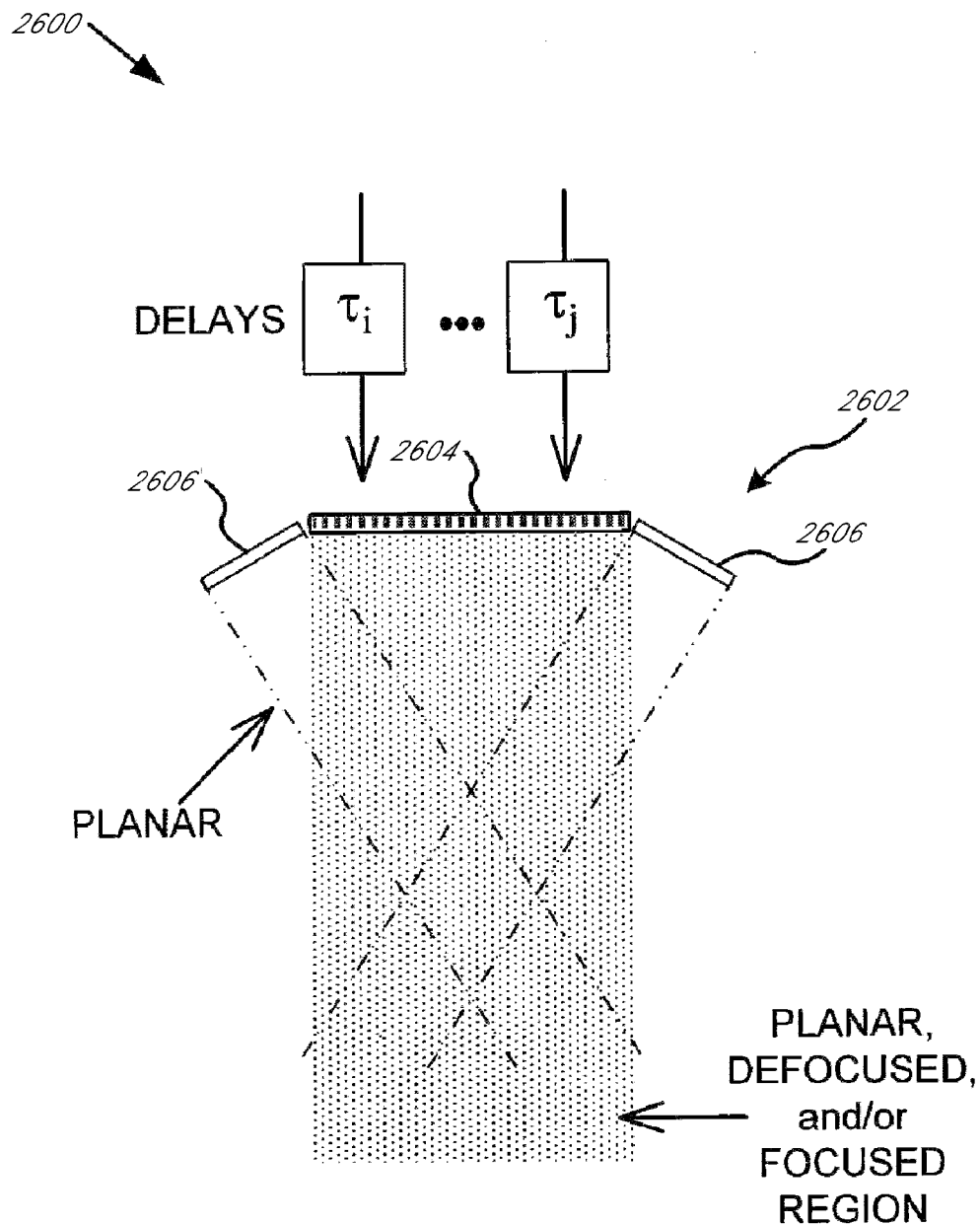

In another embodiment, depicted in FIG. 28B, transduction elements 2606 can be configured to be substantially flat in order to provide substantially uniform energy to ROI 2610. While FIGS. 28A and 28B depict embodiments with transduction elements 2604 configured as concave and substantially flat, respectively, transduction elements 2604 can be configured to be concave, convex, and/or substantially flat. In addition, transduction elements 2604 can be configured to be any combination of concave, convex, and/or substantially flat structures. For example, a first transduction element can be configured to be concave, while a second transduction element can be configured to be substantially flat.

Figure 30A:
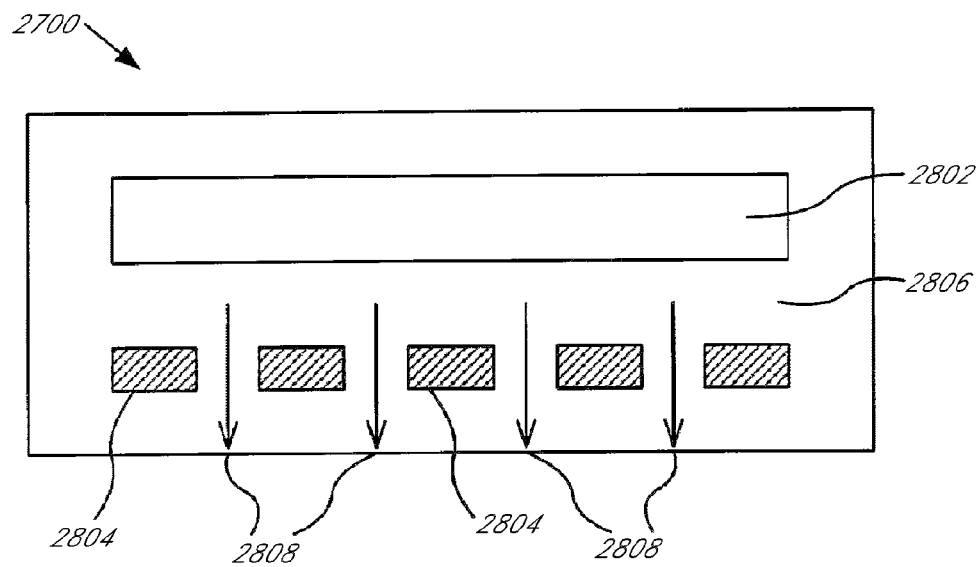
FIGS. 30A and 30B illustrate cross-sectional diagrams of a transducer in accordance with an embodiment.
Figure 30B:
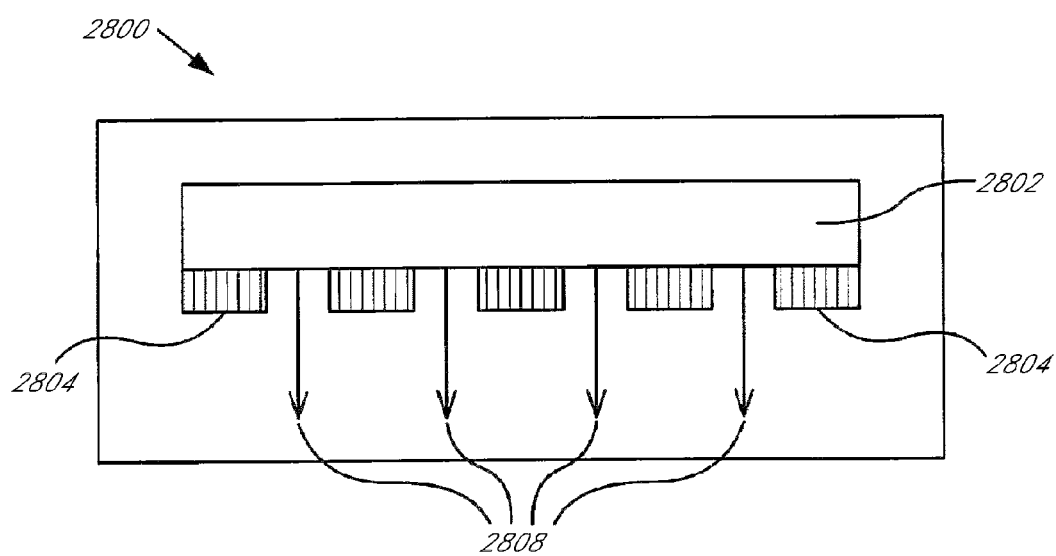

With reference to FIGS. 30A and 30B, transducer 2404 can be configured as single-element arrays, wherein a single-element 2802, e.g., a transduction element of various structures and materials, can be configured with a plurality of masks 2804, such masks comprising ceramic, metal or any other material or structure for masking or altering energy distribution from element 2802, creating an array of energy distributions 2808. Masks 2804 can be coupled directly to element 2802 or separated by a standoff 2806, such as any suitably solid or liquid material.

Figure 32A:
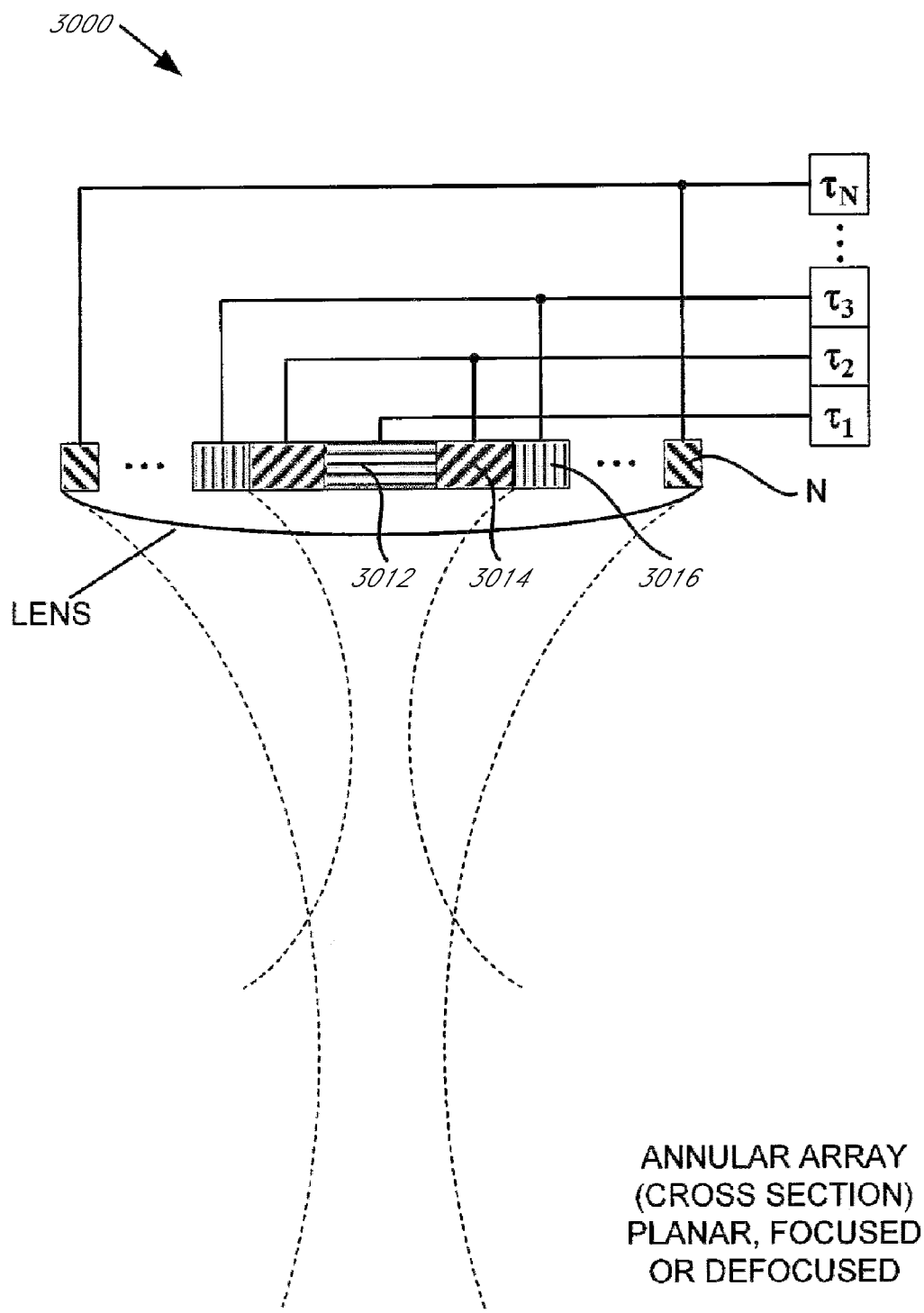
FIGS. 32A-32F illustrate cross-sectional diagrams of transducers in accordance with several embodiments.
Figure 32B:
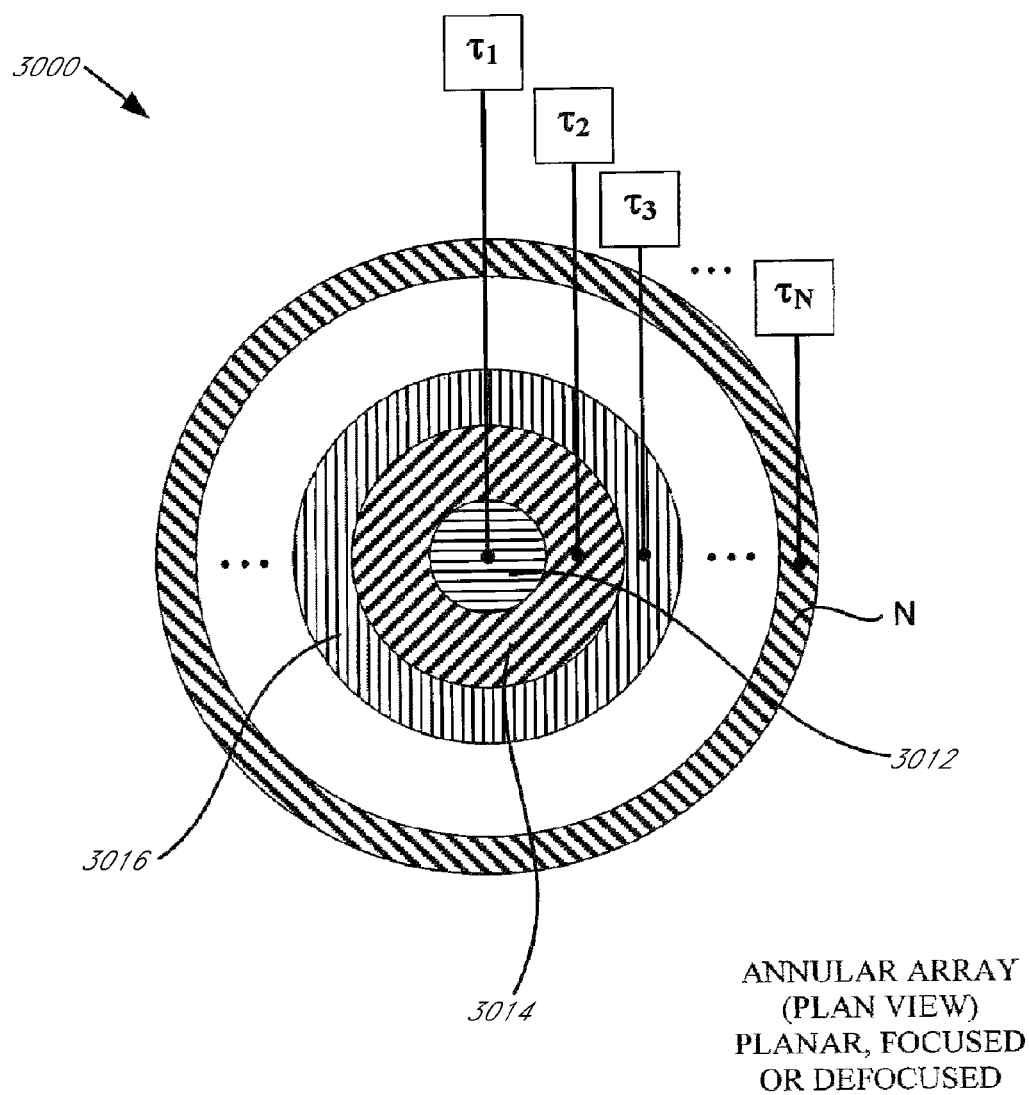
Figure 32C:
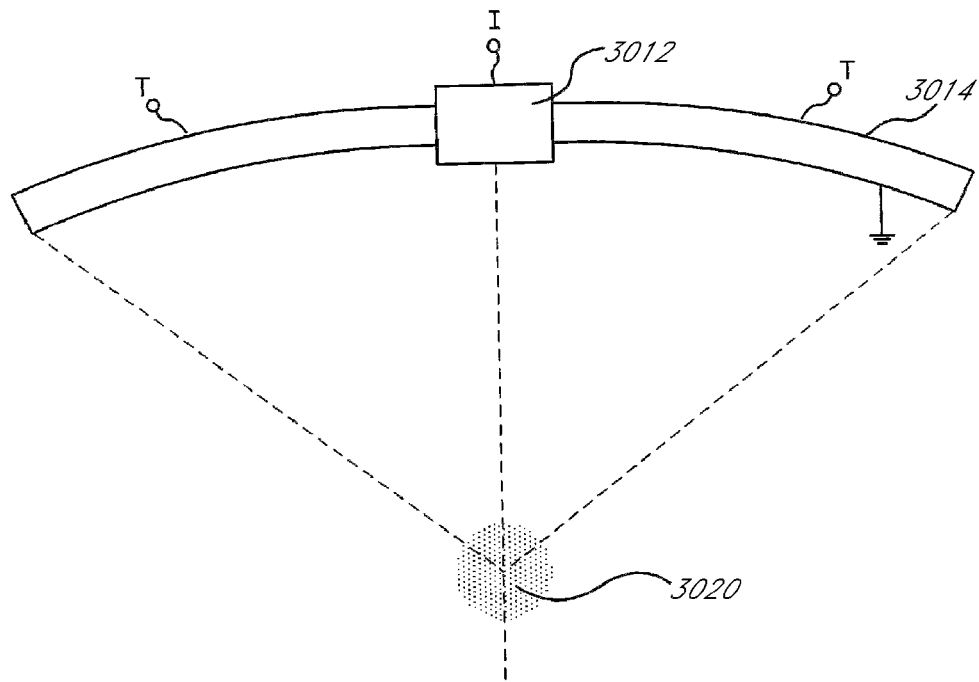
Figure 32D:
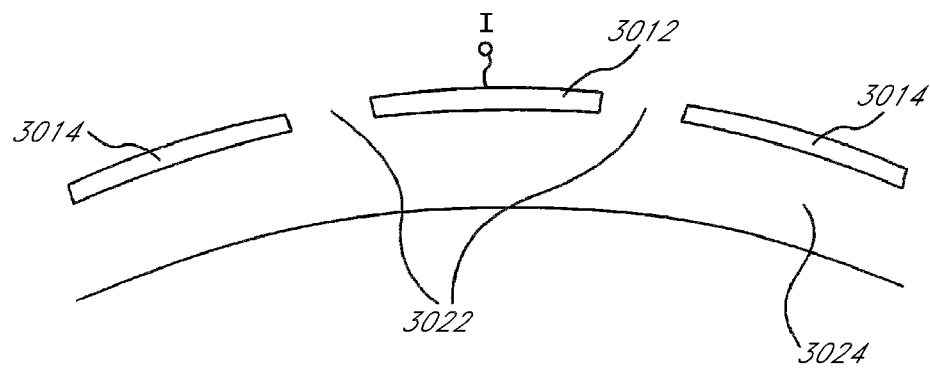
Figure 32E:
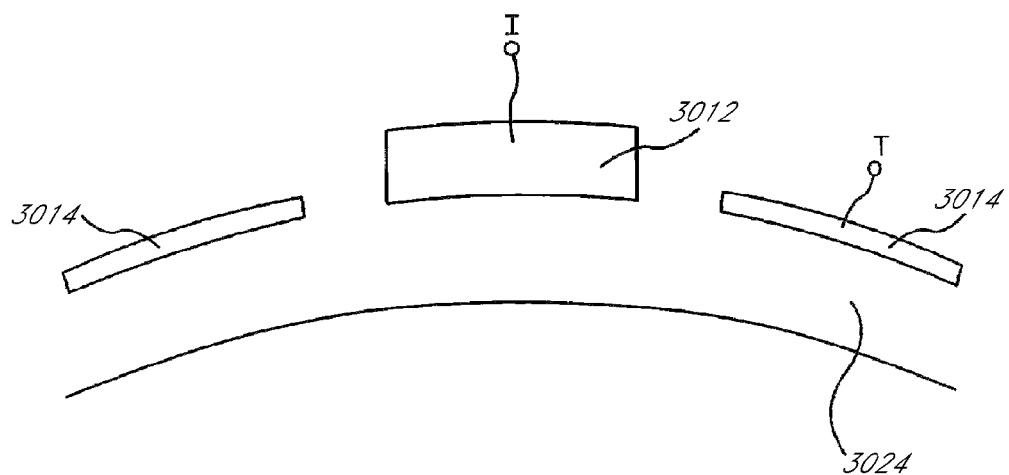

An embodiment of a transducer 2404 can also be configured as an annular array to provide planar, focused and/or defocused acoustical energy. For example, with reference to FIGS. 32A and 32B, in accordance with an embodiment, an annular array 3000 can comprise a plurality of rings 3012, 3014, 3016 to N. Rings 3012, 3014, 3016 to N can be mechanically and electrically isolated into a set of individual elements, and can create planar, focused, or defocused waves. For example, such waves can be centered on-axis, such as by methods of adjusting corresponding transmit and/or receive delays, $\tau 1, \tau 2, \tau 3 \ldots \tau N$. An electronic focus can be suitably moved along various depth positions, and can enable variable strength or beam tightness, while an electronic defocus can have varying amounts of defocusing. In accordance with an embodiment, a lens and/or convex or concave shaped annular array 3000 can also be provided to aid focusing or defocusing such that any time differential delays can be reduced. Movement of annular array 2800 in one, two or three-dimensions, or along any path, such as through use of probes and/or any conventional robotic arm mechanisms, may be implemented to scan and/or treat a volume or any corresponding space within a region of interest.

Transducer 2404 can also be configured in other annular or non-array configurations for imaging/therapy functions. For example, with reference to FIGS. 32C-32F, a transducer can comprise an imaging element 3012 configured with therapy element(s) 3014. Elements 3012 and 3014 can comprise a single-transduction element, e.g., a combined imaging/transducer element, or separate elements, can be electrically isolated 3022 within the same transduction element or between separate imaging and therapy elements, and/or can comprise standoff 3024 or other matching layers, or any combination thereof. For example, with particular reference to FIG. 32F, a transducer can comprise an imaging element 3012 having a surface 3028 configured for focusing, defocusing or planar energy distribution, with therapy elements 3014 including a stepped-configuration lens configured for focusing, defocusing, or planar energy distribution.

With a better understanding of the various transducer structures, and with reference again to FIG. 36, how the geometric configuration of the transducer or transducers that contributes to the wide range of lesioning effects can be better understood. For example, cigar-shaped lesions 3404 and 3406 may be produced from a spherically focused source, and/or planar lesions 3410 from a flat source. Concave planar sources and arrays can produce a "V-shaped" or ellipsoidal lesion 3414. Electronic arrays, such as a linear array, can produce defocused, planar, or focused acoustic beams that may be employed to form a wide variety of additional lesion shapes at various depths. An array may be employed alone or in conjunction with one or more planar or focused transducers. Such transducers and arrays in combination produce a very wide range of acoustic fields and their associated benefits. A fixed focus and/or variable focus lens or lenses may be used to further increase treatment flexibility. A convex-shaped lens, with acoustic velocity less than that of superficial tissue, may be utilized, such as a liquid-filled lens, gel-filled or solid gel lens, rubber or composite lens, with adequate power handling capacity; or a concave-shaped, low profile, lens may be utilized and composed of any material or composite with velocity greater than that of tissue. While the structure of transducer source and configuration can facilitate a particular shaped lesion as suggested above, such structures are not limited to those particular shapes as the other spatial parameters, as well as the temporal parameters, can facilitate additional shapes within any transducer structure and source.

In accordance with various embodiments of the present invention, transducer 2404 may be configured to provide one, two and/or three-dimensional treatment applications for focusing acoustic energy to one or more regions of interest. For example, as discussed above, transducer 2404 can be suitably diced to form a one-dimensional array, e.g., transducer 2602 comprising a single array of sub-transduction elements.

Figure 31:
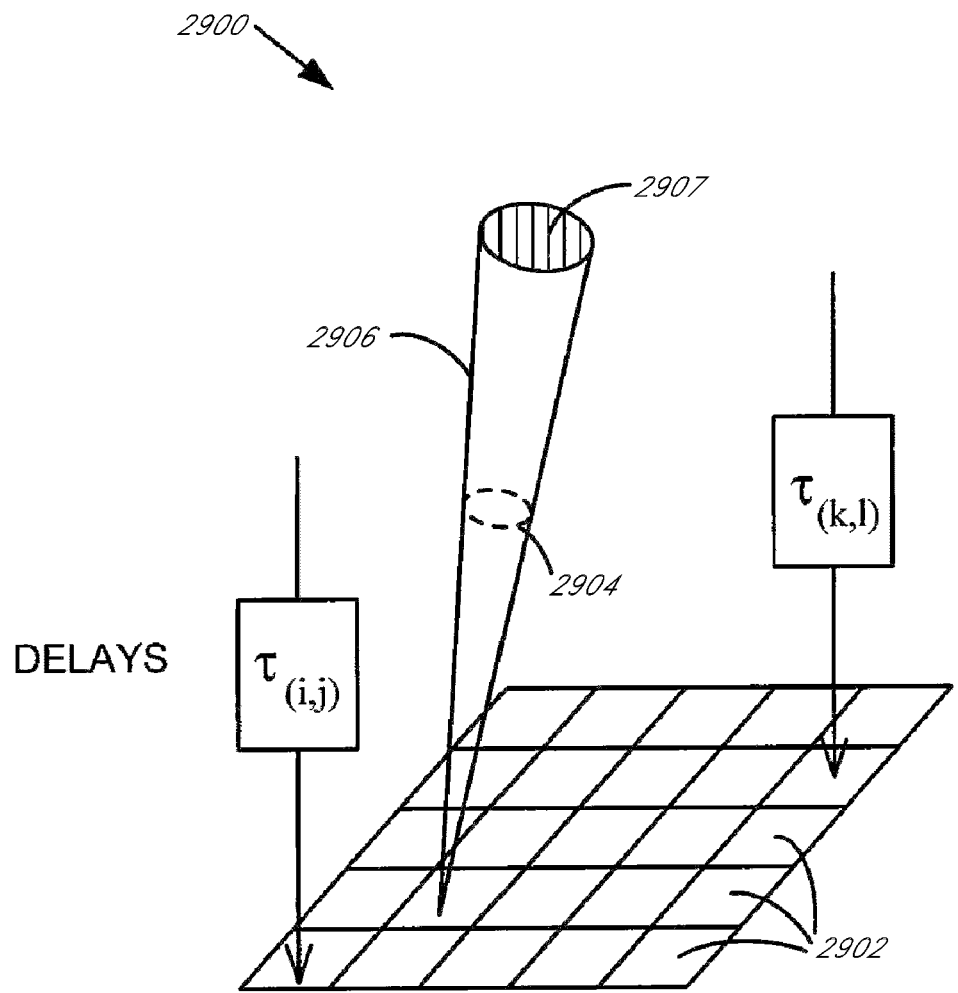
FIG. 31 illustrates a transducer configured as a two-dimensional array for ultrasound treatment in accordance with an embodiment.

In accordance with another embodiment, transducer 2404 may be suitably diced in two-dimensions to form a two-dimensional array. For example, with reference to FIG. 31, an embodiment with two-dimensional array 2900 can be suitably diced into a plurality of two-dimensional portions 2902. Two-dimensional portions 2902 can be suitably configured to focus on the treatment region at a certain depth, and thus provide respective slices 2904, 2907 of the treatment region. As a result, the two-dimensional array 2900 can provide a two-dimensional slicing of the image place of a treatment region, thus providing two-dimensional treatment.

In accordance with another embodiment, transducer 2404 may be suitably configured to provide three-dimensional treatment. For example, to provide-three dimensional treatment of a region of interest, with reference again to FIG. 23, a three-dimensional system can comprise a transducer within probe 104 configured with an adaptive algorithm, such as, for example, one utilizing three-dimensional graphic software, contained in a control system, such as control system 102. The adaptive algorithm is suitably configured to receive two-dimensional imaging, temperature and/or treatment or other tissue parameter information relating to the region of interest, process the received information, and then provide corresponding three-dimensional imaging, temperature and/or treatment information.

In accordance with an embodiment, with reference again to FIG. 31, a three-dimensional system can comprise a two-dimensional array 2900 configured with an adaptive algorithm to suitably receive 2904 slices from different image planes of the treatment region, process the received information, and then provide volumetric information 2906, e.g., three-dimensional imaging, temperature and/or treatment information. Moreover, after processing the received information with the adaptive algorithm, the two-dimensional array 2900 may suitably provide therapeutic heating to the volumetric region 2906 as desired.

In accordance with other embodiments, rather than utilizing an adaptive algorithm, such as three-dimensional software, to provide three-dimensional imaging and/or temperature information, a three-dimensional system can comprise a single transducer 2404 configured within a probe arrangement to operate from various rotational and/or translational positions relative to a target region.

Figure 29:
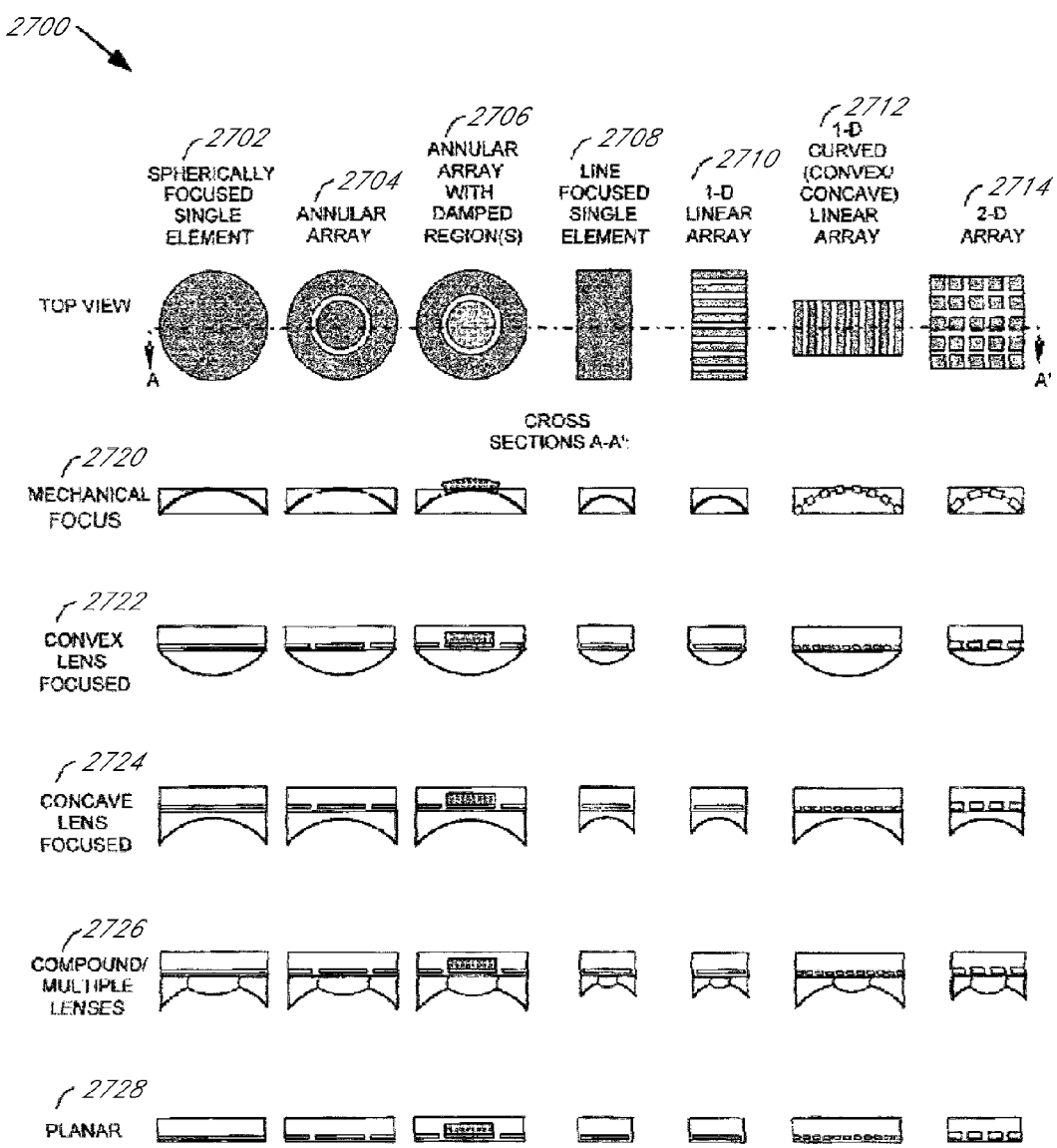
FIG. 29 illustrates transducer configurations for ultrasound treatment in accordance with various embodiments.
Figure 32F:
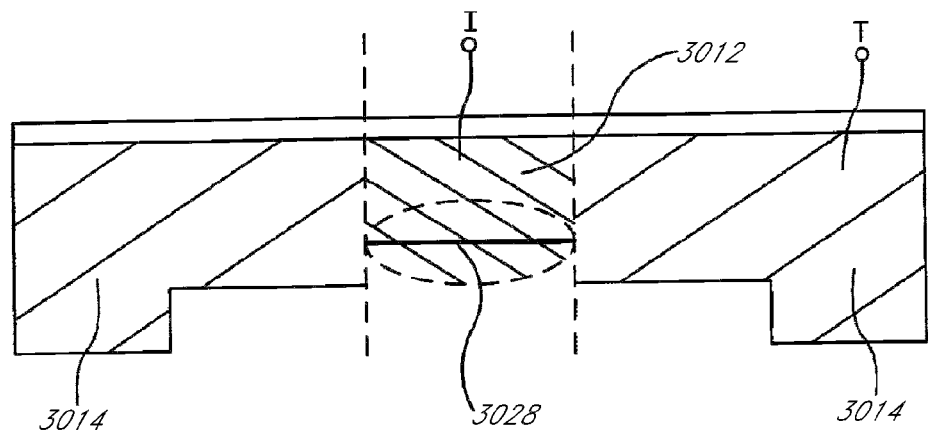

To further illustrate the various structures for transducer 2404, with reference to FIG. 29, ultrasound therapy transducer 2700 can be configured for a single focus, an array of foci, a locus of foci, a line focus, and/or diffraction patterns. Transducer 2700 can also comprise single elements, multiple elements, annular arrays, one-, two-, or three-dimensional arrays, broadband transducers, and/or combinations thereof, with or without lenses, acoustic components, and mechanical and/or electronic focusing. Transducers configured as spherically focused single elements 2702, annular arrays 2704, annular arrays with damped regions 2706, line focused single elements 2708, 1-D linear arrays 2710, 1-D curvilinear arrays in concave or convex form, with or without elevation focusing, 2-D arrays, and 3-D spatial arrangements of transducers may be used to perform therapy and/or imaging and acoustic monitoring functions. For any transducer configuration, focusing and/or defocusing may be in one plane or two planes via mechanical focus 2720, convex lens 2722, concave lens 2724, compound or multiple lenses 2726, planar form 2728, or stepped form, such as illustrated in FIG. 32F. Any transducer or combination of transducers may be utilized for treatment. For example, an annular transducer may be used with an outer portion dedicated to therapy and the inner disk dedicated to broadband imaging wherein such imaging transducer and therapy transducer have different acoustic lenses and design, such as illustrated in FIGS. 32C-32F.

Moreover, such transduction elements 2700 may comprise a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. Transduction elements 2700 may also comprise one or more matching layers configured along with the piezoelectrically active material. In addition to or instead of piezoelectrically active material, transduction elements 2700 can comprise any other materials configured for generating radiation and/or acoustical energy. A means of transferring energy to and from the transducer to the region of interest is provided.

Figure 34:
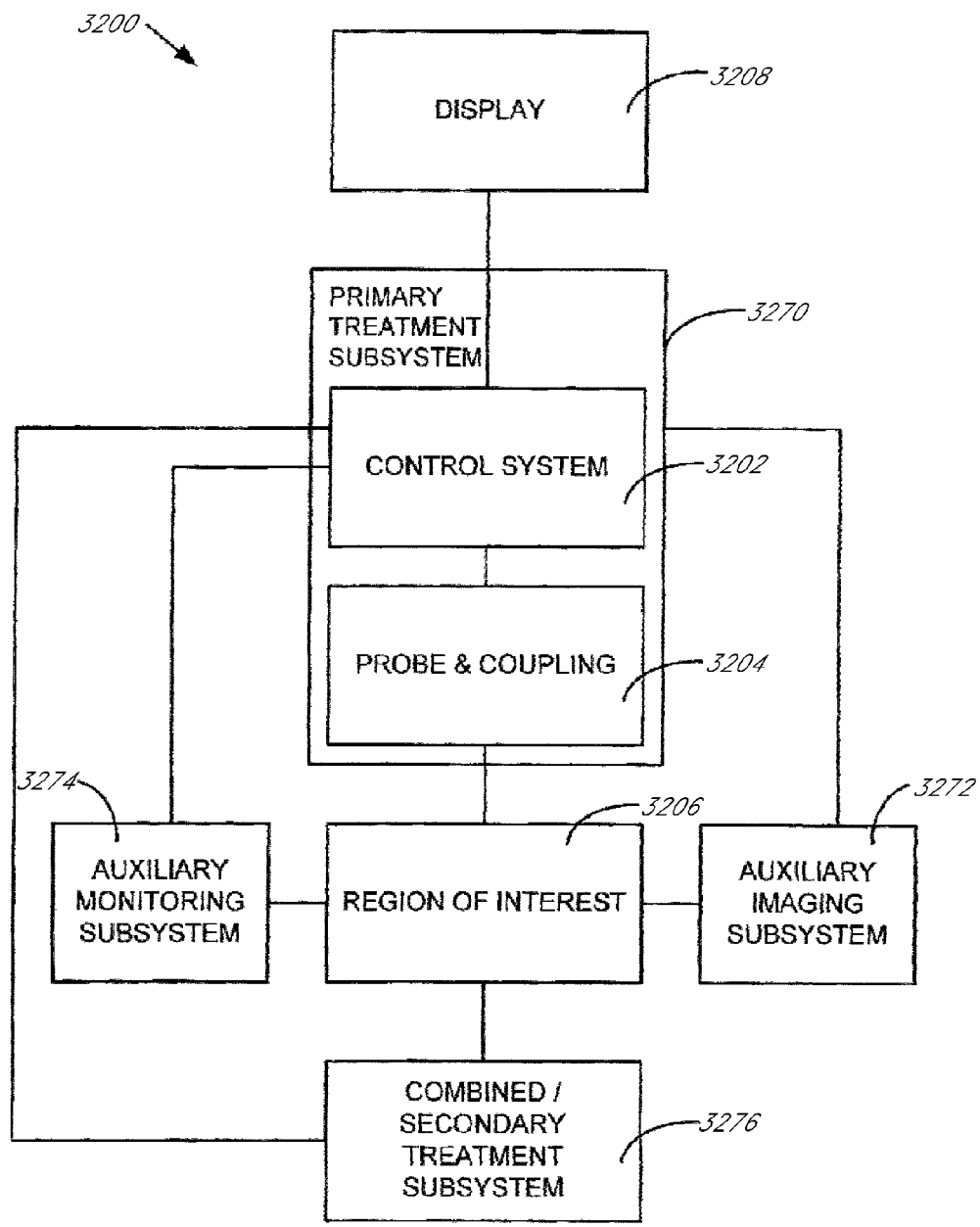
FIG. 34 illustrates a block diagram of a treatment system comprising an ultrasound treatment subsystem combined with additional subsystems and methods of treatment monitoring and/or treatment imaging as well as a secondary treatment subsystem in accordance with an embodiment.

In accordance with another embodiment, with reference to FIG. 34, a treatment system 2200 can be configured with and/or combined with various auxiliary systems to provide additional functions. For example, an embodiment of a treatment system 3200 for treating a region of interest 3206 can comprise a control system 3202, a probe 3204, and a display 3208. Treatment system 3200 further comprises an auxiliary imaging modality 3274 and/or auxiliary monitoring modality 3272 may be based upon at least one of photography and other visual optical methods, magnetic resonance imaging (MRI), computed tomography (CT), optical coherence tomography (OCT), electromagnetic, microwave, or radio frequency (RF) methods, positron emission tomography (PET), infrared, ultrasound, acoustic, or any other suitable method of visualization, localization, or monitoring of SMAS layers within region-of-interest 3206, including imaging/monitoring enhancements. Such imaging/monitoring enhancement for ultrasound imaging via probe 3204 and control system 3202 could comprise M-mode, persistence, filtering, color, Doppler, and harmonic imaging among others. Further, in several embodiments an ultrasound treatment system 3270, as a primary source of treatment, may be combined or substituted with another source of treatment 3276, including radio frequency (RF), intense pulsed light (IPL), laser, infrared laser, microwave, or any other suitable energy source.

Figure 35:
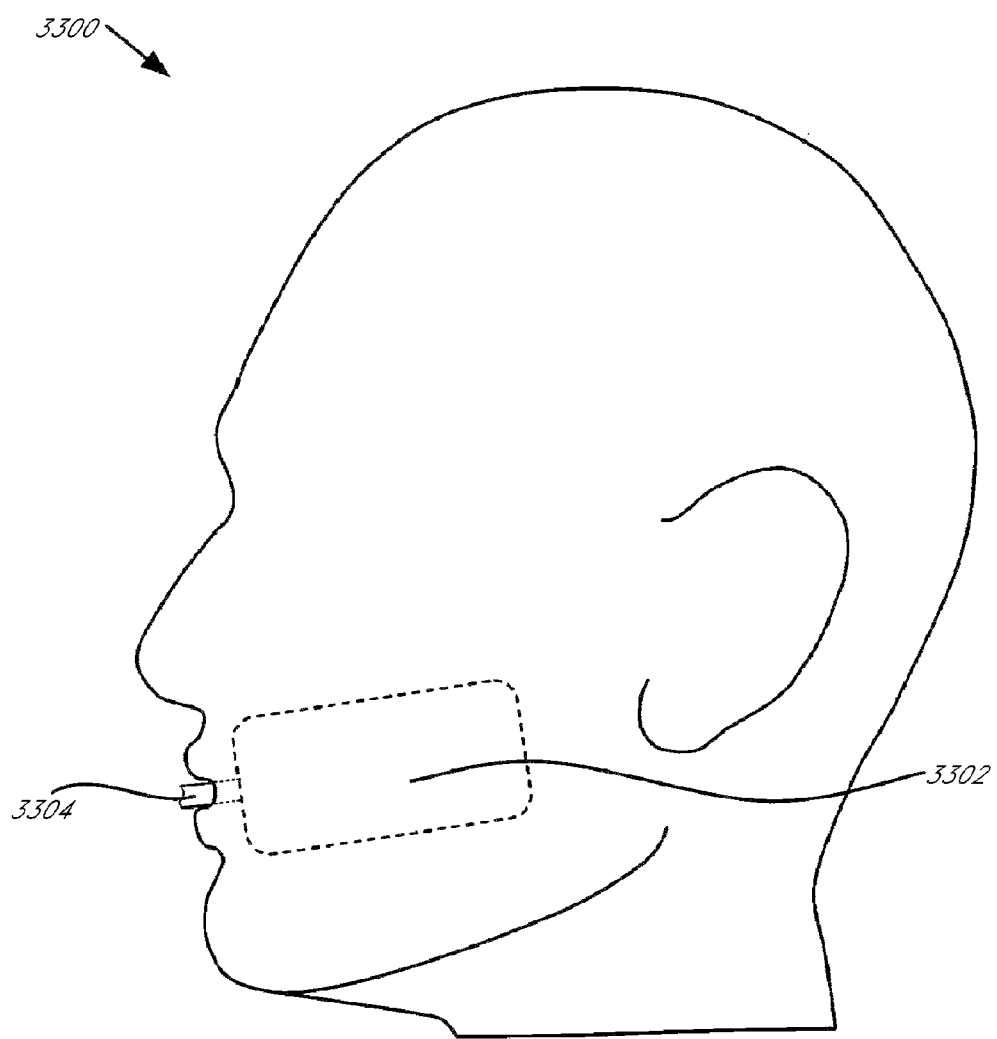
FIG. 35 illustrates a schematic diagram with imaging, therapy, or monitoring being provided with one or more active or passive oral inserts in accordance with an embodiment.

In accordance with another embodiment, with reference to FIG. 35, treatment composed of imaging, monitoring, and/or therapy to a region of interest may be further aided, augmented, and/or delivered with passive or active devices 3304 within the oral cavity. For example, if passive or active device 3304 is a second transducer or acoustic reflector acoustically coupled to the cheek lining it is possible to obtain through transmission, tomographic, or round-trip acoustic waves which are useful for treatment monitoring, such as in measuring acoustic speed of sound and attenuation, which are temperature dependent; furthermore such a transducer could be used to treat and/or image. In addition an active, passive, or active/passive object 3304 may be used to flatten the skin, and/or may be used as an imaging grid, marker, or beacon, to aid determination of position. A passive or active device 3304 may also be used to aid cooling or temperature control. Natural air in the oral cavity may also be used as passive device 3304 whereby it may be utilized to as an acoustic reflector to aid thickness measurement and monitoring function.

During operation of an embodiment of a treatment system, a lesion configuration of a selected size, shape, orientation is determined. Based on that lesion configuration, one or more spatial parameters are selected, along with suitable temporal parameters, the combination of which yields the desired conformal lesion. Operation of the transducer can then be initiated to provide the conformal lesion or lesions. Open and/or closed-loop feedback systems can also be implemented to monitor the spatial and/or temporal characteristics, and/or other tissue parameter monitoring, to further control the conformal lesions.

Figure 37:
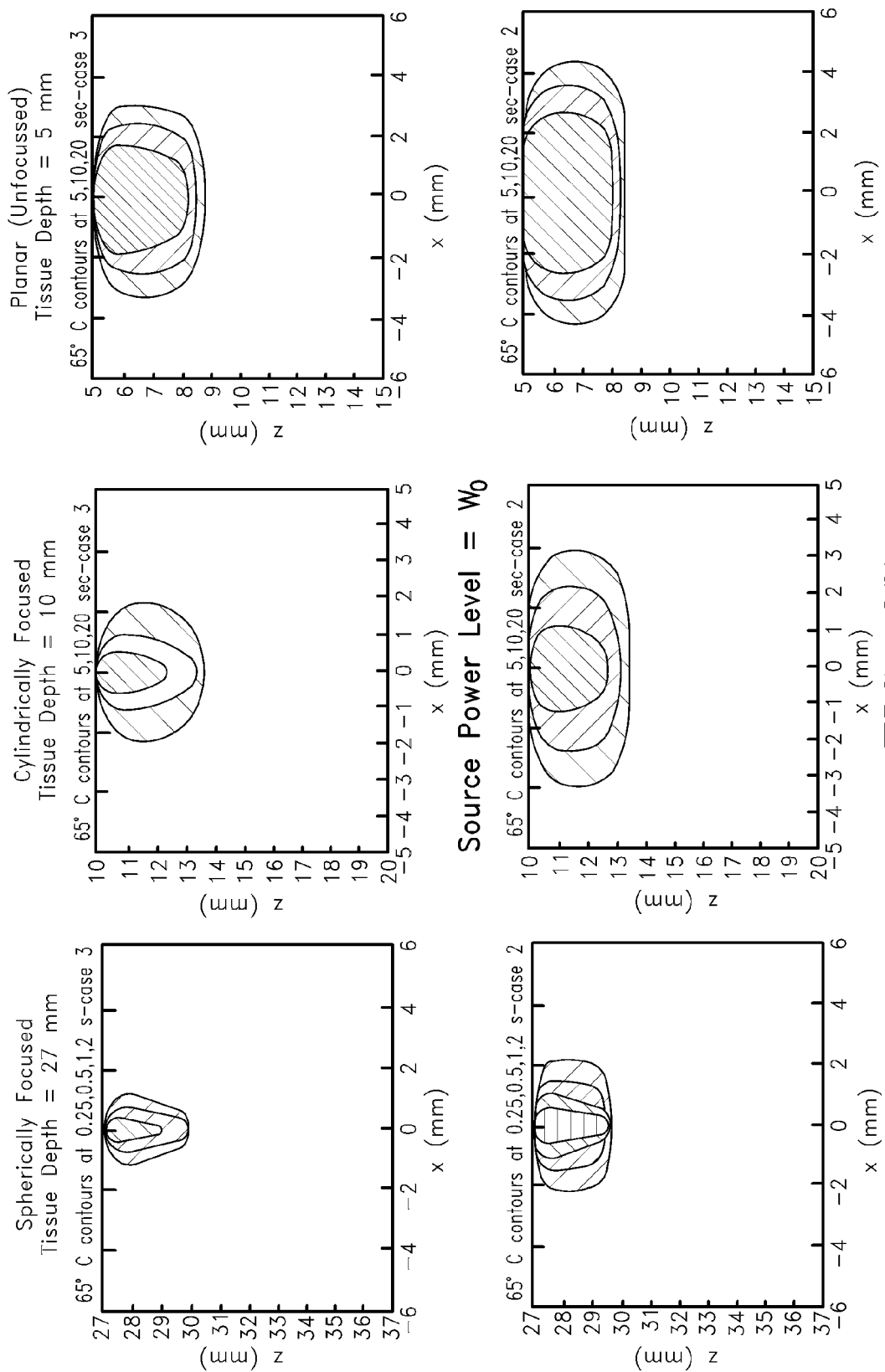
FIG. 37 illustrates a diagram of simulation results for various spatially controlled configurations in accordance with several embodiments.

With reference to FIG. 37, a collection of simulation results, illustrating thermal lesion growth over time are illustrated. Such lesion growth was generated with a spherically focused, cylindrically focused, and planar (unfocused) source at a nominal source acoustic power level, $W_0$ and twice that level, $2 W_0$, but any configurations of transducer can be utilized as disclosed herein. The thermal contours indicate where the tissue reached 65° C. for different times. The contour for the cylindrically focused source is along the short axis, or so-called elevation plane. The figure highlights the different shapes of lesions possible with different power levels and source geometries. In addition, with reference to FIG. 38, a pair of lesioning and simulation results is illustrated, showing chemically stained porcine tissue photomicrographs adjacent to their simulation results. In addition, with reference to FIG. 39, another pair of lesioning results is illustrated, showing chemically stained porcine tissue photomicrographs, highlighting a tadpole shaped lesion and a wedge shaped lesion.

Adjustment of the acoustic field spatial distribution via transducer type and distribution, such as size, element configuration, electronic or mechanical lenses, acoustic coupling and/or cooling, optionally combined with adjustment of the temporal acoustic field, such as through control of transmit power level and timing, transmit frequency and/or drive waveform can facilitate the achieving of controlled thermal lesions of variable size, shape, and depths. Moreover, the restorative biological responses of the human body can further cause the desired effects to the superficial human tissue.

Variable Depth Cosmetic Treatment

In various embodiments, a non-invasive treatment method and system comprises a transducer system configured for providing treatment (for example, ultrasound treatment) at one or more cosmetic treatment zones to a region of interest under a skin surface of a patient that can be used with any of the embodiments of the systems, devices, and/or methods described herein. One or more multiple points, created simultaneously or sequentially over time, can be placed for cosmetic treatment in any position in the region of interest. In various embodiments, the position can be varied by depth, height, width, along any axis, X, Y, Z, and/or any rotational position. In various embodiments, a position may be described as "variable depth" as an example. Other positions besides depth are also contemplated.

In various embodiments, a non-invasive variable depth treatment method and system comprises a variable depth transducer system configured for providing treatment to a patient that can be used with any of the embodiments of the systems, devices, and/or methods described herein. In one embodiment, a variable depth transducer system can comprise a transducer configured to provide treatment to more than one region of interest, such as between a deep treatment region of interest and a superficial region of interest, and/or a subcutaneous region of interest. In various embodiments, the variable depth transducer can comprise a transduction element having a piezoelectrically active layer, matching layers and/or other materials for generating radiation or acoustical energy. The variable depth transducer may be configured to operate at moderate frequencies within the range from approximately 750 kHz to 20 MHz or more. In addition, the transduction element may be configured with a variable depth device comprising one or more materials configured to allow for control and focusing/defocusing of the acoustic energy to more than one region of interest.

Figure 40:
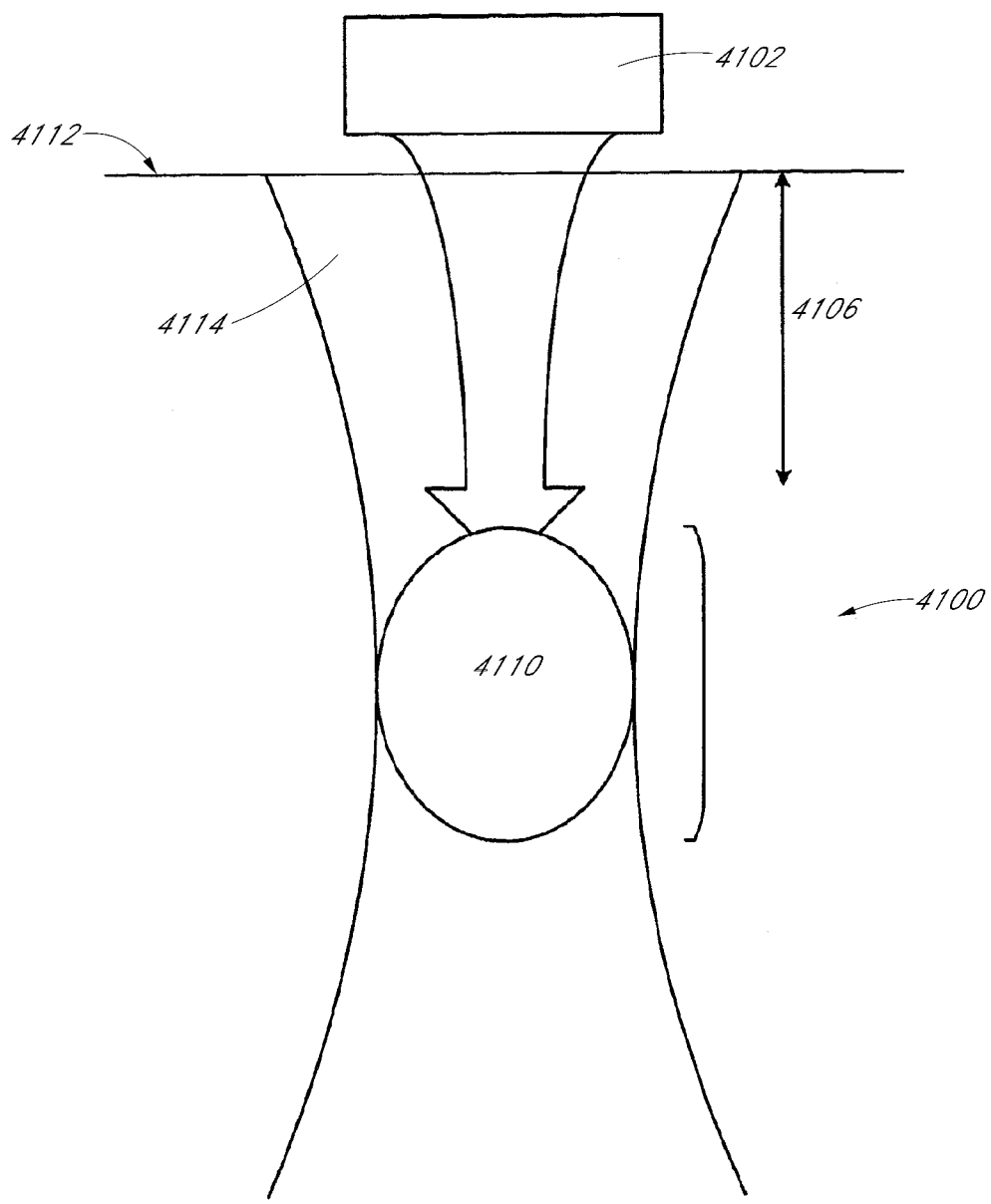
FIG. 40 illustrates a diagram of an ultrasound treatment system in accordance with an embodiment.

In some embodiments, therapeutic ultrasound treatment can employ low frequency transducers. Various embodiments of low frequency transducers have operational frequencies that typically range from 500 kHz to 1.5 MHz. Such low frequency transducers are often preferred because they allow for acoustical energy to be focused deep into the body, without harming the overlying tissue structures. In one embodiment, an application of non-invasive therapeutic ultrasound using a low frequency transducer is depicted in FIG. 40. The therapeutic system 4100 comprises a transducer 4102 that uses low frequency energy to treat a deep treatment region 4110. Deep treatment region 4110 is located at a deep depth 4106 below a superficial region 4112, e.g., tissue layers and structures, and a subcutaneous region 4114 of a patient. Deep depth 4106 may range from several millimeters to 5-7 centimeters or more. Some embodiments of a conventional system 4100 cannot treat superficial regions 4112 or subcutaneous regions 4114 through use of low-frequency transducer 4102, thus limiting the applications of such systems. For example, some cosmetic surgeries may also need to provide treatment to superficial and/or subcutaneous, as well as deep treatment regions, thus eliminating the use of lower frequency transducers.

One potential side effect of low-frequency therapy is that the acoustic energy must pass through intervening tissue layers before reaching the desired deep treatment area. The intervening layers tend to defocus the rays and absorb some of the acoustic energy. This causes the focal spot size to widen, making it difficult to control the location of the focal spot.

In accordance with various embodiments, a variable depth ultrasound treatment method and system are provided. In one embodiment, a method and system comprise a variable depth transducer system configured for providing ultrasound treatment to more than one region of interest, such as between at least two of a deep treatment region of interest, a superficial region of interest, and/or a subcutaneous region of interest.

In accordance with various embodiments, a variable depth transducer system can be configured for spatial control, such as by changing the distance from a transducer to a reflecting surface, or changing the angles of energy focused or unfocused to the region of interest, and/or configured for temporal control, such as by controlling changes in the frequency, drive amplitude and timing of the transducer. As a result, changes in the location of the treatment region, the shape and size and/or volume of the spot or region of interest, as well as the thermal conditions, can be dynamically controlled versus time.

In accordance with an embodiment, the variable depth transducer can comprise a transduction element having a piezoelectrically active layer, matching layers and/or other materials for generating radiation or acoustical energy. The variable depth transducer may be configured to operate at moderate frequencies to provide variable depth treatment. For example, an embodiment of a variable depth transducer system can be configured for providing treatment to a superficial region of interest, and/or to a subcutaneous region of interest utilizing moderate frequencies below 20 MHz, such as within a range from approximately 750 kHz to 20 MHz, or higher frequencies of 20 MHz to 35 MHz or more.

In accordance with another embodiment, the transduction element may be configured with a variable depth element comprising one or more materials configured to allow for control and focusing/defocusing of the acoustic energy to more than one region of interest, such as between a deep treatment region of interest and a superficial region of interest, and/or a subcutaneous region of interest. The materials utilized for the variable depth element for control and focusing/defocusing may be configured in a variety of manners and shapes, such as substantially flat, curved, or other arrangements for bending, reflecting and/or redirecting radiation and acoustical energy. In addition, the variable depth element may be configured within, or comprise a device coupled to, the transduction element in a variety of manners to provide for focusing/defocusing and control of the treatment energy.

In accordance with another embodiment, a transducer may be configured to enable energy deposition not only proximate a fundamental frequency of a piezoelectric material within the transduction element, but also at harmonic frequencies of the material, above a fundamental frequency, as well as resonances below a fundamental frequency. These multiple resonances may be controlled and enabled through various focusing techniques and transducer structures, including the adding of matching layers and/or backing layers to shape the resonant characteristics of the transducer.

In accordance with another embodiment, a variable depth acoustic transducer is configured for generating high acoustic power for treatment purposes, while also providing for good imaging capabilities. For example, to allow for the treatment spot size to be optimally controlled at various treatment depths, an embodiment may comprise a transducer configured into an array of sub-elements, each sub-element configured for processing acoustic waves with a sufficient bandwidth for good axial resolution.

In accordance with another embodiment, a variable depth transducer is configured in a probe arrangement to provide treatment. The variable depth transducer may also be configured with various mechanical devices to allow for optimal treatment and therapy, for example to provide controlled positioning of the variable depth transducer, such as through a non-invasive configuration. Further, the variable depth transducer may also be configured for one-dimensional, two-dimensional and annular arrays, and/or for three-dimensional treatment applications.

In accordance with another embodiment, an variable depth treatment system and method is configured to provide therapeutic heating, cooling and/or imaging of a treatment region as well as acoustically monitoring the temperature profile or other tissue parameter monitoring of the treatment region and the general vicinity thereof. For example, in accordance with an embodiment, a variable depth system is configured with a dynamic feedback arrangement based on monitoring of temperature or other tissue parameters, and/or based on imaging information to suitably adjust the spatial and/or temporal characteristics of the variable depth transducer.

Figure 41:
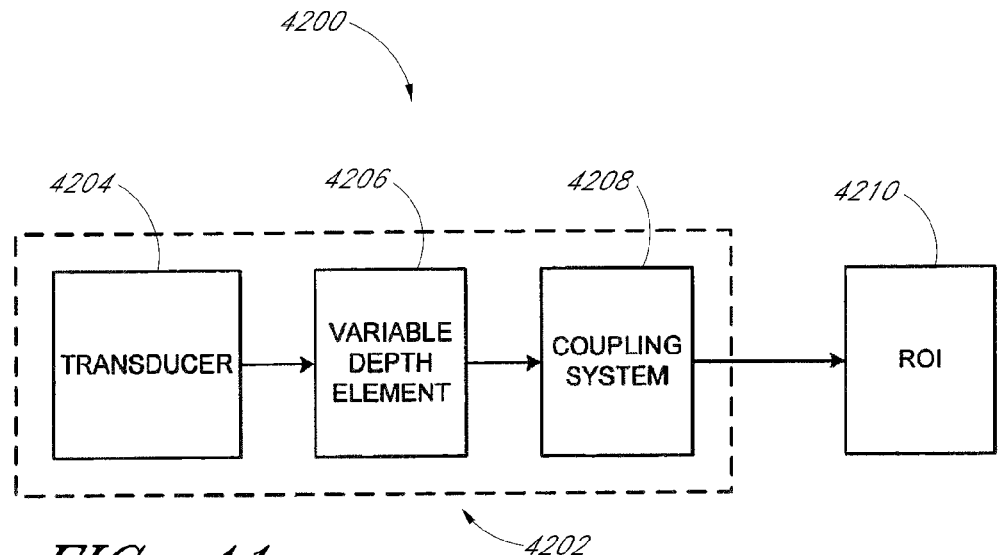
FIG. 41 illustrates a block diagram of an ultrasound treatment system in accordance with an embodiment.

In accordance with several embodiments, the invention comprises a variable depth acoustic transducer system configured for providing ultrasound treatment to more than one region of interest in a patient. For example, with reference to an embodiment illustrated in a block diagram of FIG. 41, a system 4200 for ultrasound treatment includes a variable depth transducer system 4202 that provides treatment to a region of interest 4210. Variable depth transducer system 4202 may comprise a transducer 4204 configured with a variable depth device 4206. In providing treatment, variable depth ultrasound system 4202 may provide therapy, imaging and/or temperature or other tissue parameter monitoring to region of interest 4210. Region of interest 4210 can comprise a deep treatment region, a superficial region, and/or a subcutaneous region of interest or any other region of interest located within a patient. To facilitate coupling of variable depth ultrasound system 4202 to region of interest 4210, variable depth ultrasound system 4202 can further comprise a coupling system 4208 configured for acoustic coupling of ultrasound energy and signals.

Figure 42:
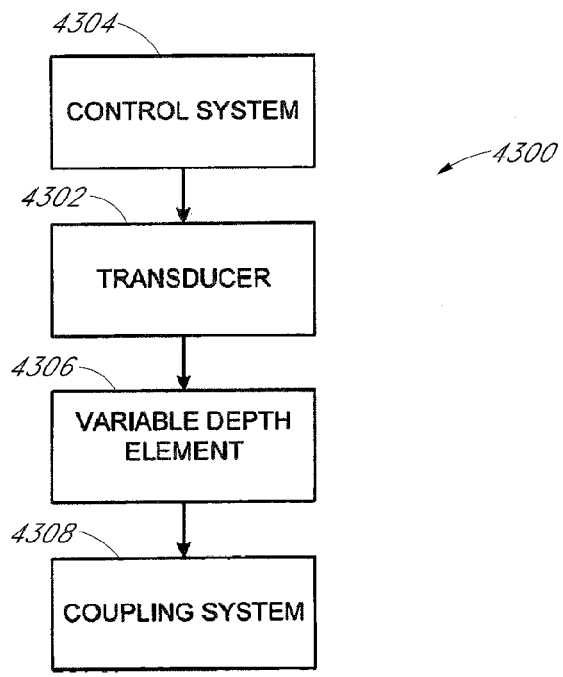
FIG. 42 illustrates a block diagram of a variable depth ultrasound treatment system in accordance with an embodiment.

In one embodiment, a variable depth transducer system 4300 is further exemplified in a block diagram illustrated in FIG. 42. Variable depth transducer system 4300 may comprise a control system 4304, a transducer 4302, a variable depth element 4306, and a coupling system 4308. Control system 4304 is configured for control and operation of transducer 4302 to provide treatment to more than one region of interest. Transducer 4302 and variable depth device 4306 are configured to provide variable depth ultrasound treatment to a treatment region. Coupling system 4308 is configured for coupling of transducer 4302 and variable depth device 4306 to a region of interest.

Control system 4304 may be configured for use within an ultrasound therapy system, an ultrasound imaging system, and/or an ultrasound imaging, therapy and/or treatment monitoring system, including motion control subsystems. In accordance with an embodiment, a control system 4304 comprises a processor, a display, and/or one or more input devices. The processor may comprise a personal computer, a Unix system, or any other conventional processing unit. The display may comprise a monitor, LCD screen, or any other device configured to display an image. An input/output device may comprise a keyboard, a mouse, a touch-screen, or any other device for inputting information. The information from the input device and images displayed may be received or transmitted in any format, such as manually, by analog device, by digital device, and/or by any other mechanisms. The processor, display, and/or input device may be coupled together in any manner. By coupling, the devices comprising control system 4304 may be directly connected to each other or may be connected through one or more other devices or components that allow a signal to travel to/from one component to another. The various coupling components for the devices comprising control system 4304 can include, but are not limited to, the internet, a wireless network, a conventional wire cable, an optical cable or connection through any other medium that conducts signals, and any other coupling device or communication medium.

In one embodiment, coupling system 4308 is configured for the coupling ultrasound energy and signals between transducer 4302 and variable depth device 4306 and a region of interest. Coupling system 4308 may facilitate such coupling through use of various coupling mediums, including air and other gases, water and other fluids, gels, solids, and/or any combination thereof, or any other medium that allows for signals to be transmitted between transducer 4302/variable depth device 4306 and the region of interest. In addition to providing a coupling function, in accordance with an embodiment, coupling system 4308 can also be configured for providing temperature control during the treatment application. For example, coupling system 4308 can be configured for controlled cooling of an interface surface or region between transducer 4302/variable depth device 4306 and the region of interest by suitably controlling the temperature of the coupling medium. The suitable temperature for such coupling medium can be achieved in various manners, and utilize various feedback systems, such as thermocouples, thermistors or any other device or system configured for temperature measurement of a coupling medium. Such controlled cooling can be configured to further facilitate spatial control of variable depth transducer system 4300.

In various embodiments, a variable depth transducer 4302 is configured for spatial control, such as by controlled changing of the distance from a transducer to a reflecting surface, or controlled changing of the angles of energy focused or unfocused to the region of interest, e.g., variable depth transducer 4302 can be configured with variable depth element 4306 comprising a frequency dependent lens configured for control of focal depth and position by changing the frequency of excitation of variable depth transducer 4302. In addition, variable depth transducer 4302 can also be configured for temporal control, such as by controlling changes in the frequency, drive amplitude and timing of the transducer. Thus, an embodiment of a variable depth transducer can be configured with spatial and/or temporal control. As a result, changes in the location of the treatment region, the shape and size and/or volume of the spot or region of interest, as well as the thermal conditions, can be dynamically controlled versus time.

Variable depth element 4306 can be suitably coupled to transducer 4302 to facilitate variable depth treatment. By coupling, transducer 4302 may be directly and/or movably connected to variable depth device 4306, or may be connected through one or more various components or elements that enable energy and/or signals to travel to/from one component to another. Transducer 4302 and variable depth element 4306 may also be combined into a single device, wherein variable depth device 4306 is configured within transducer 4302, e.g., as a part of a transduction element of transducer 4302.

Figure 43:
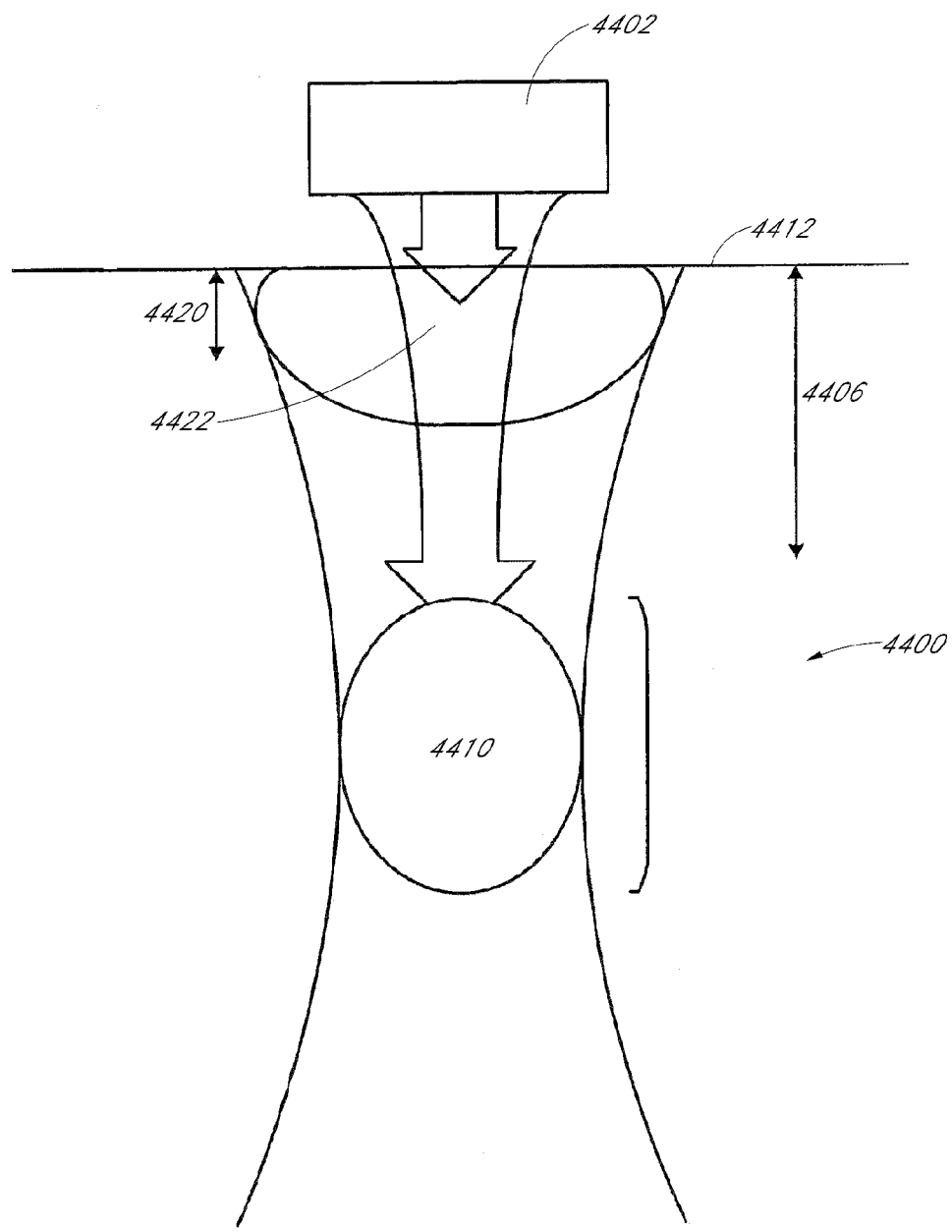
FIG. 43 illustrates a diagram of a variable depth ultrasound treatment system in accordance with an embodiment

In one embodiment, variable depth element 4306 is configured to enable variable depth treatment system 4300 to provide treatment to more than one region of interest, such as between a deep treatment region of interest, a superficial region of interest, and/or a subcutaneous region of interest, or other regions in between. Such treatment can occur within a single region of interest, or within more than one region of interest, at the same time. For example, with momentary reference to FIG. 43, an embodiment of a variable depth treatment system 4400 is shown. Variable depth treatment system 4400 may be configured for operating within moderate frequencies ranging from approximately 750 kHz to 20 MHz or more. Variable depth treatment system 4400 may be configured with a variable depth transducer system 4402 comprising a transducer configured with a variable depth device. Variable depth transducer system 4402 may be coupled to a control system for receiving and transmitting signals to/from a region of interest.

During operation, variable depth transducer system 4402 may be configured to transmit or receive signals to treat a deep treatment region 4410 located at deep depth 4406 within a patient. For example, depth 4406 for deep treatment region 4410 may range from approximately 50 mm to 7 cm or more.

Variable depth transducer system 4402 may also be configured to treat a second inner region 4422 of a patient. Inner region 4422 may comprise a superficial layer 4412 of a patient and/or a subcutaneous layer 4414 of patient. Inner region 4422 is located at a shorter depth 4420 within tissue layers of a patient. For example, depth 4420 may range from approximately 0 mm to 5 cm or more within a patient, wherein the 0 mm range comprises the outer surface of superficial layer 4412 of the patient. In other words, superficial layer 4412 of the patient may comprise any area on or near the surface of the patient. Treatment by variable depth treatment system 4400 may include treatment of both deep region 4410 and inner region 4422, or within only one region of interest.

Variable depth element 4306 can be configured in various manners to facilitate treatment of more than one region of interest, such as inner region 4422 and/or deep-seated region 4410. In accordance with an embodiment, transducer 4302 is configured with variable depth element 4306 comprising one or more materials configured to allow for control and focusing/defocusing of the acoustic energy to more than one region of interest. For example, with reference to embodiments illustrated in FIGS. 44A and 44B, a variable depth transducer system 4500 can comprise a transducer 4502, electrical leads 4510, and a variable depth device 4528 or 4530 suitably configured with transducer 4502 to facilitate treatment.

Transducer 4502 can include a transduction element comprising a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. In addition to or instead of a piezoelectrically active material, variable depth transducer 4502 may comprise any other materials configured for generating radiation and/or acoustical energy. Variable depth transducer 4502 may also comprise one or more matching layers and/or backing layers to suitably shape the resonant character of transducer 4502. For example, variable depth transducer 4502 may be configured, along with transduction element, with one or more matching layers and/or backing layers coupled to a piezoelectrically active material or any other material configured for generating radiation and/or acoustical energy.

For temporal control, the thickness of the transduction element of variable depth transducer 4502 may be selected to provide a center operating frequency of moderate range, for example from approximately 750 kHz to 30 MHz or more. Lower frequencies, e.g., between approximately 750 kHz and 8 MHz, can facilitate deeper penetration and higher frequencies, e.g., between approximately 8 to 20 MHz or more, can facilitate greater resolution. Selecting the frequency for operation can be based on the degree and balance of energy penetration and resolution that is desired for an application.

Figure 44B:
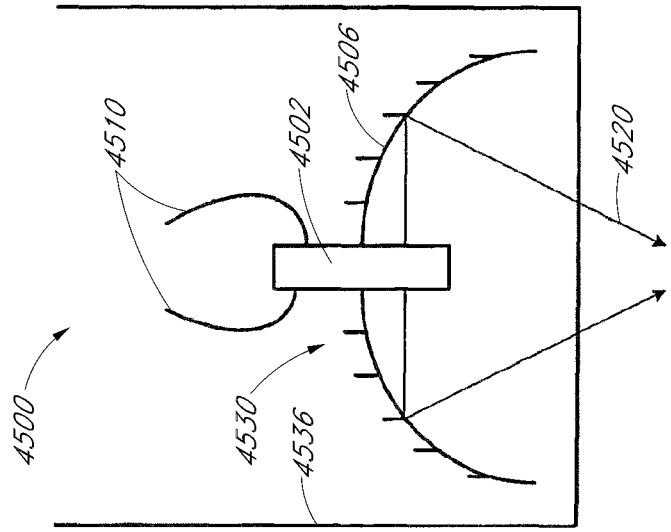
FIGS. 44A and 44B illustrate several embodiments for variable depth ultrasound transducers for treatment.
Figure 44A:
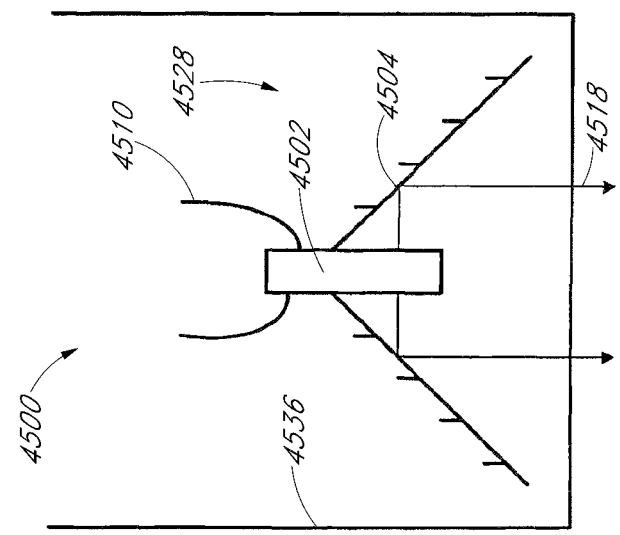

Electrical leads 4510 may be configured to enable power to be transmitted to and signals received from variable depth transducer 4502, and can comprise any wiring type, configuration and arrangement for use with ultrasound transducers. Variable depth transducer 4502 may also be coupled to electrical leads 4510 in various manners. For example, while FIGS. 44A and 44B depict electrical leads 4510 coupled to only one end of variable depth transducer 4502, electrical leads 4510 may also be coupled together on an opposite end, or any other location along variable depth transducer 4502.

To facilitate spatial control, in an embodiment, variable depth device 4528 can comprise one or more reflective materials 4504 configured to provide control and focusing of acoustic or radiation energy from variable depth transducer 4502 towards a region of interest 4518. In accordance with an embodiment, reflective materials 4504 can comprise acoustic mirrors, lenses, reflectors or prisms configured for focusing of acoustic or radiation energy. In some embodiments, the mirrors, reflectors or prisms may comprise any material for reflecting, bending or redirecting acoustic or radiated energy. For example, such materials may include stainless steel, aluminum, or any other metal alloy, glass, plastic, or any other material capable of bending, redirecting and/or reflecting back acoustical energy from a surface to another direction.

In accordance with one embodiment, reflective materials 4504 may be suitably inclined at approximately a 45 degree angle with respect to variable depth transducer 4502; however, reflective materials 4504 may be configured to be inclined at any angle with respect to variable depth transducer 4502 such that energy transmitted from variable depth transducer 4502 is bent, redirected or reflected from reflective materials 4504 towards a region of interest 4518. Changing the angle of inclination can, in one embodiment, suitably control the focusing of acoustic energy to any one region of interest 4518, such as to a deep treatment region of interest, a superficial region of interest, or a subcutaneous region of interest.

Variable depth devices 4528 and 4530 may be configured in a variety of manners, such as substantially flat, curved, or other suitable arrangements for reflecting, bending or redirecting acoustic or radiated energy. For example, with reference to FIG. 44A, variable depth device 4528 can comprise mirrors 4504 configured in a substantially flat manner. However, with reference to FIG. 44B, variable depth device 4530 can also comprise mirrors 4506 configured in a curved arrangement to allow for focusing of energy from variable depth transducer 4502 to a region of interest 4520. While FIG. 44B illustrates mirrors 4506 as substantially spherical and symmetric, mirrors 4506 may also be curved in an aspherical and/or asymmetric manner such that energy transmitted from variable depth transducer 4502 is bent, redirected, or reflected from mirrors 4506 towards a region of interest 4520. Still further, mirrors 4506 can also be configured in other shapes and arrangements, such as jagged, saw tooth, wavy or other non-planar surfaces, or any other surface or compound surfaces configured for reflecting, bending or redirecting acoustic or radiated energy.

Moreover, while FIG. 44A depicts variable depth device 4528 with mirrors 4504 configured to be substantially flat, and FIG. 44B depicts variable depth device 4530 with mirrors 4506 configured to be curved, variable depth devices

4528, 4530 may also be configured with any combination of substantially flat, curved mirrors, and/or other planar, non-planar or other arrangements for facilitating spatial control. In accordance with an embodiment utilizing spatial and temporal control, variable depth devices 4528 and 4530 can be configured with a frequency dependent mirror or lens configured for spatial control of the focal depth and position by changing the frequency of excitation of variable depth transducer 4502.

As a result, an embodiment of a transducer system 4500 can be configured for providing treatment to a superficial region of interest and/or to a subcutaneous region of interest utilizing moderate frequencies below approximately 20 MHz. For example, an embodiment of a transducer system 4500 can provide treatment to superficial regions and/or to subcutaneous regions that are more commonly addressed in cosmetic applications with an operating frequency range from approximately 750 kHz to 35 MHz or more.

Variable depth transducer system 4500 can be configured in various arrangements to provide non-invasive treatment. For example, in accordance with an embodiment, variable depth devices 4528, 4530 may be configured with variable depth transducer 4502 within a housing 4536. Housing 4536 can comprise any configuration of transducer housing for containing transducers and for interfacing with a patient to allow treatment, such as facilitate non-invasive treatment. Coupling of signals from transducer 4502 and variable depth devices 4528, 4530 through housing 4536 to a region of interest may be facilitated through any coupling medium, such as air and other gases, water and other fluids, gels, solids, any combination thereof, and/or any other medium that allows for signals to be transmitted from transducer 4502/variable depth devices 4528, 4530 to a region of interest.

In addition to comprising separate devices and components, variable depth transducer 4302 and variable depth element 4306 may also comprise the same device, e.g., variable depth element 4306 is configured within transducer 4302. For example, with reference to an embodiment illustrated in FIG. 45, a variable depth transducer system 4600 can comprise a variable depth transducer 4602 configured as a variable depth device to provide for control and focusing of acoustic energy 4620 towards a region of interest 4630.

Variable depth transducer 4602 may comprise a transduction element comprised of a piezoelectrically active material, such as lead zirconate titanate (PZT), or any other piezoelectrically active material, such as a piezoelectric ceramic, crystal, plastic, and/or composite materials, as well as lithium niobate, lead titanate, barium titante, and/or lead metaniobate. Variable depth transducer 4602 may also comprise one or more matching and/or backing layers configured along with the piezoelectrically active material. In addition to or instead of a piezoelectrically active material, variable depth transducer 4602 may comprise any other materials configured for generating radiation and/or acoustical energy.

In accordance with an embodiment, variable depth transducer 4602 is configured in a curved manner to enable focusing of acoustic energy 4620 to region of interest 4630. The curvature can be substantially spherical and/or symmetric manner, or curved in an aspherical and/or asymmetric manner. Furthermore, variable depth transducer 4602 can comprise any other configuration to enable focusing of acoustic energy 4620 to region of interest 4630, such as to a deep treatment region of interest, a superficial region of interest, and/or a subcutaneous region of interest. For example, variable depth transducer 4602 can be configured in any planar or non-planar arrangement.

For temporal control, according to one embodiment, the thickness of the transduction element of variable depth transducer 4602 may be selected to provide a center operating frequency of moderate range, for example from approximately 750 kHz to 20 MHz. Lower frequencies, e.g., between approximately 750 kHz and 8 MHz, can facilitate deeper penetration and higher frequencies, e.g., between approximately 8 to 30 MHz or more, facilitate greater resolution. As a result, an embodiment of a transducer system 4600 can be configured for providing treatment to a superficial region of interest and/or to a subcutaneous region of interest utilizing moderate frequencies below 20 MHz. For example, an embodiment of a transducer system 4600 can provide treatment to superficial regions and/or to subcutaneous regions that are more commonly addressed in cosmetic applications with an operating frequency range from approximately 750 kHz to 1.5 MHz or more.

Figure 45:
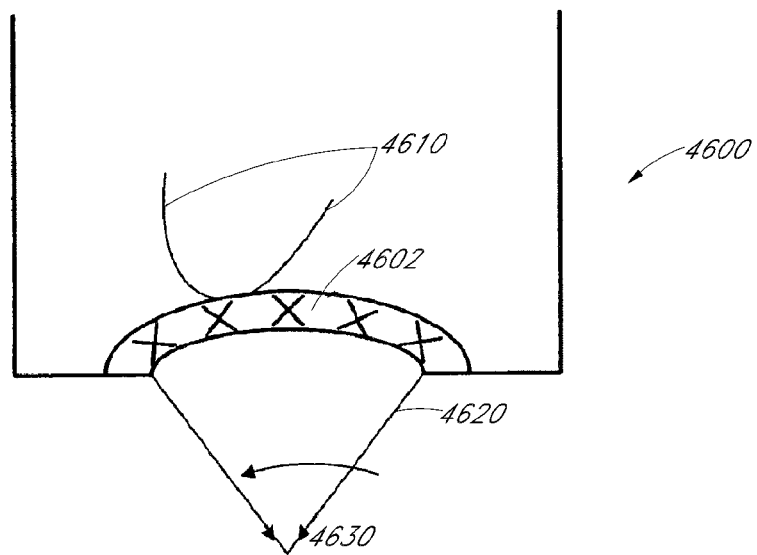
FIG. 45 illustrates another embodiment for a variable depth ultrasound transducer for treatment.

Electrical leads 4610 are configured to enable power to be transmitted to and signals received from variable depth transducer 4602, and can comprise any wiring type, configuration and arrangement for use with ultrasound transducers. Variable depth transducer 4602 may also be coupled to electrical leads 4610 in various manners. For example, while FIG. 45 depicts electrical leads 4610 coupled to only one side of variable depth transducer 4602, electrical leads 4610 may also be coupled together on an opposite end, or any other location along variable depth transducer 4602.

Figure 46:
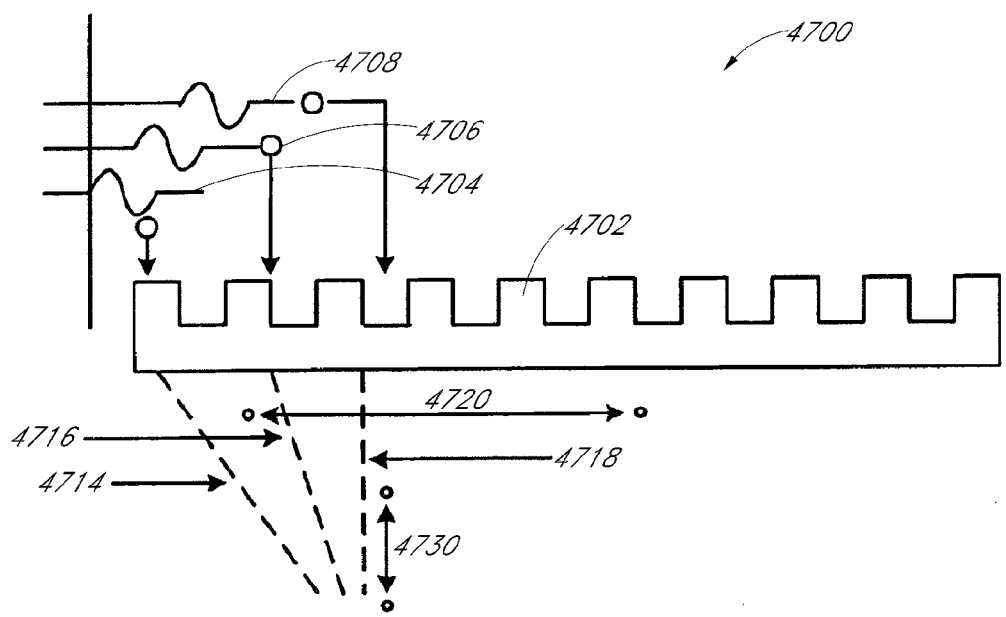
FIG. 46 illustrates an embodiment for electronic focusing of a transducer.

In addition to having a variable depth transducer 4602 configured as a variable depth device to provide for control and focusing of acoustic energy 4620 towards a region of interest 4630, in accordance with an embodiment, a variable depth transducer may also be configured electronically to provide for control and focusing of acoustic energy. For example, with reference to an embodiment depicted in FIG. 46, an electronic focusing transducer system 4700 is illustrated. Electronic focusing transducer system 4700 is configured with a variable depth transducer 4702. Like transducers 4502 and 4602, variable depth transducer 4702 may comprise a piezoelectrically active material, composite materials, one or more matching layers, and/or any other materials configured for generating radiation and/or acoustical energy. Variable depth transducer 4702 may also comprise a one-dimensional or two-dimensional array of transducers.

In accordance with an embodiment, variable depth transducer 4702 comprises one or more transducers and/or transduction elements that can be activated by various drive frequencies with suitable phase delay. For example, variable depth transducer 4702 can be activated by a first drive frequency 4704, and then subsequently activated by at least one or more delayed drive frequencies 4706 or 4708. The phase delay in drive frequencies allows for focusing of acoustical energy to occur both tangentially 4720 and axially 4730.

The drive frequencies 4704, 4706, 4708 transmitted to variable depth transducer 4702 may comprise substantially similar frequencies and/or different frequencies, wherein all frequencies are in the moderate range, e.g., between approximately 750 kHz to 20 MHz. The delay between drive frequencies 4704, 4706, 4708 may range from 0 ms to approximately a full period of the drive frequency. For example, the delay may comprise zero or approximately $\frac{1}{1000}$th of a drive frequency period up to $\frac{15}{16}$.sup.th, $\frac{31}{32}$.sup.nd or more of a drive frequency period, with variations comprising any fraction of a full wavelength in time delay.

Electronic phase delay focusing of variable depth transducer 4702 may be done tangentially and/or axially. For example, drive frequencies 4704, 4706, 4708 and/or the phase associated with drive frequencies 4704, 4706, 4708 may be varied to provide focusing tangentially and/or axially. In accordance with an embodiment, variable depth transducer 4702 may comprise subapertures that may be turned on and off to also provide focusing tangentially and/or axially. Phased focusing may prevent over-treatment of a region of interest by automating the focus and treatment times for a treatment region. Thus, for example, electronic control of variable depth transducer 4702 may be facilitated by shunting various subapertures together to control the effective acoustic size of the source/receiver.

Thus, an embodiment of a transducer system can comprise a variable depth transducer 4502, 4602, 4702 or any other transducer configuration for providing control and focus of acoustical and radiation energy to more than one region of interest within a patient. Such a transducer system can comprise a transducer configured with or coupled to a variable depth device or feature to provide energy to more than one region of interest. Moreover, a transducer system can provide treatment to superficial regions and/or to subcutaneous regions that are more commonly addressed in cosmetic applications with an operating frequency range below 30 MHz, or more, even from approximately 750 kHz to 8 MHz that is not attainable by prior art low-frequency transducers.

In accordance with another aspect, a variable depth acoustic transducer can also be configured for generating high acoustic power for treatment purposes, while also providing for good imaging capabilities. To allow for the treatment spot size to be optimally controlled at various treatment depths, an embodiment may comprise a transducer configured into an array of sub-elements.

For example, in accordance with an embodiment with reference again to FIG. 45, variable depth transducer 4602 can comprise a plurality of sub-transduction elements, wherein any of the plurality of sub-transduction elements may be configured to provide for focusing energy 4620, e.g., any of the plurality of sub-transduction elements can be configured for processing acoustic waves with a sufficient bandwidth for good axial resolution. The sub-transduction elements may be configured such that all are curved, e.g., with the same or varying curvatures, or with one or more sub-transduction elements being substantially flat, with the remaining sub-transduction elements being curved. Further, the sub-transduction elements can be configured in any other shapes configured to provide for control and focusing of acoustic energy 4620 towards a region of interest 4630.

In accordance with another embodiment, a variable depth transducer system 4300 may be configured to enable energy deposition not only proximate a fundamental frequency of a piezoelectric material within the transduction element, but also at other frequencies, such as harmonic frequencies of the material, above a fundamental frequency, as well as resonances below a fundamental frequency. These harmonic and below fundamental resonances may be controlled and enabled through various focusing techniques and transducer structures, including the adding of matching layers and/or backing layers to shape the resonant characteristics of the transducer.

For example, energy can be suitably provided to a treatment region at a frequency near the peak acoustic output or peak acoustic transmit efficiency of transducer 4302 when a piezoelectrically active material is driven near its fundamental frequency. Different sized and shaped piezoelectric materials have different fundamental frequencies for various electrode configurations. In accordance with an embodiment, energy can also be deposited when the piezoelectric material is driven above its fundamental frequency, e.g., at harmonics, or when driven below the fundamental frequency. The use of the multiple frequency characteristics of transducer 4302 may be controlled and enabled through various transducer configurations, acoustic control and/or focusing techniques.

Figure 47:
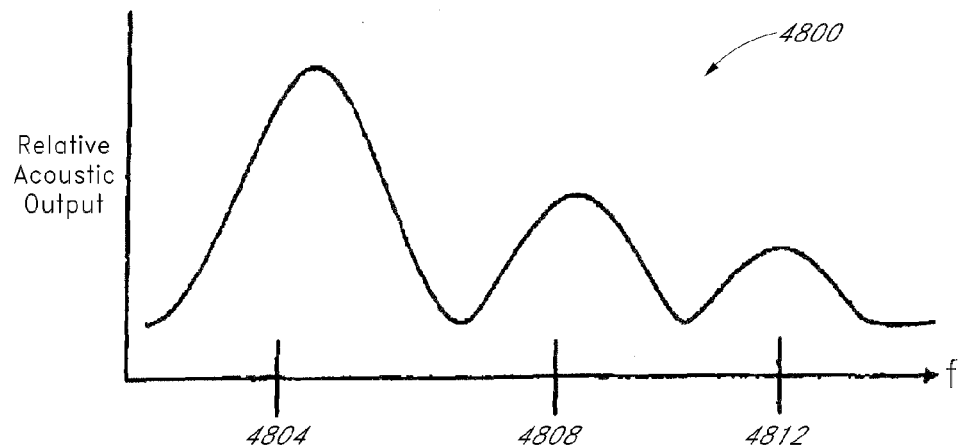
FIG. 47 illustrates a diagram of treatment characteristics of a transducer operating at the fundamental frequency and other frequencies and/or resonances above and below the fundamental in accordance with several embodiments.

In accordance with an embodiment, the multiple frequencies may be enabled through the concentration of acoustic energy through the variable depth device 4306. Enablement of the multiple frequencies allows for treatment at various depths corresponding to the different frequencies. For example, with additional reference to the acoustic output versus frequency curve illustrated in FIG. 47, variable depth transducer system 4300 may treat multiple regions, represented by curve 4800. Driving moderate frequencies through transducer 4302 and variable depth device 4306 may enable treatment of a first deep region 4804, treatment of a second shallower region 4808, and treatment of a third inner region 4812. With respect to treatment techniques, various therapy, imaging and/or temperature monitoring applications may be provided to regions 4804, 4808, and/or 4812. While three treatment regions are depicted in FIG. 47, variable depth transducer system 4300 may be configured to enable multiple frequencies for treatment of two, four, or more regions.

In accordance with another aspect of the invention, the variable depth transducer 4302 may be configured to provide one, two or three-dimensional treatment applications for focusing acoustic energy to one or more regions of interest. For example, as discussed above, variable depth transducer 4302 can be suitably diced to form a one-dimensional array, e.g., transducer 4602 comprising a single array of sub-transduction elements.

Figure 48:
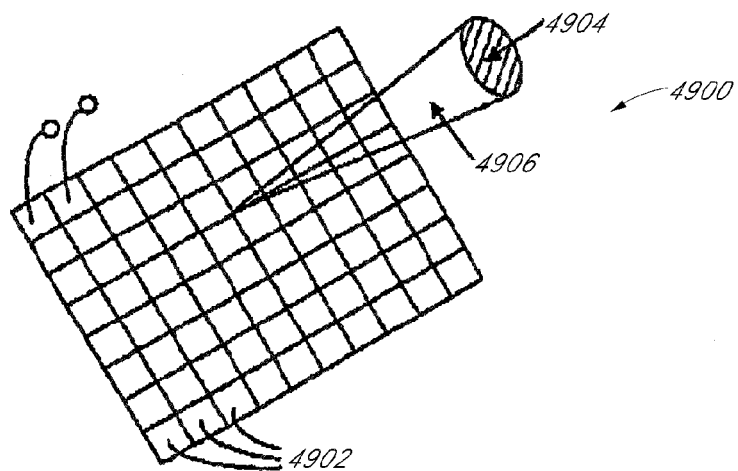
FIG. 48 illustrates an embodiment of a two-dimensional array.

In accordance with another embodiment, variable depth transducer 4302 may be suitably diced in two-dimensions to form a two-dimensional array. For example, with reference to FIG. 48, a two-dimensional array 4900 can be suitably diced into a plurality of two-dimensional portions 4902. Two-dimensional portions 4902 can be suitably configured to focus on the treatment region at a certain depth, and thus provide respective slices 4904 of the treatment region. As a result, the two-dimensional array 4900 can provide a two-dimensional slicing of the image place of a treatment region, thus providing two-dimensional treatment.

In accordance with another embodiment, variable depth transducer 4302 may be suitably configured to provide three-dimensional treatment. For example, to provide-three dimensional treatment of a region of interest, with reference again to FIG. 42, a three-dimensional system can comprise variable depth transducer 4302 configured with an adaptive algorithm, such as, for example, one utilizing three-dimensional graphic software, contained in a control system, such as control system 4304. The adaptive algorithm is suitably configured to receive two-dimensional imaging, temperature and/or treatment information relating to the region of interest, process the received information, and then provide corresponding three-dimensional imaging, temperature and/or treatment information.

In accordance with an embodiment, with reference again to FIG. 48, a three-dimensional system can comprise a two-dimensional array 4900 configured with an adaptive algorithm to suitably receive 4904 slices from different image planes of the treatment region, process the received information, and then provide volumetric information 4906, e.g., three-dimensional imaging, temperature and/or treatment information. Moreover, after processing the received information with the adaptive algorithm, the two-dimensional array 4900 may suitably provide therapeutic heating to the volumetric region 4906 as desired.

Alternatively, rather than utilizing an adaptive algorithm, such as three-dimensional software, to provide three-dimensional imaging and/or temperature information, an embodiment of a three-dimensional system can comprise a single variable depth transducer 4302 configured within a probe arrangement to operate from various rotational and/or translational positions relative to a target region.

Figure 49:
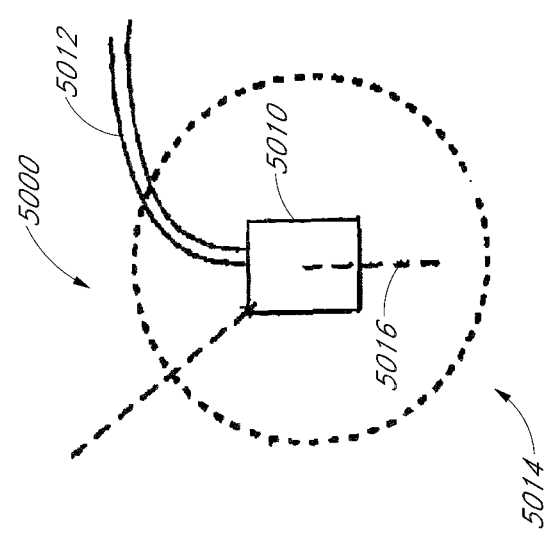
FIG. 49 illustrates an embodiment of a probe format for treatment

For example, with reference to FIG. 49, a probe 5010 can be configured to rotate around a perimeter of a treatment region 5014 to provide three-dimensional imaging and temperature information. Probe 5010 may comprise a variable depth transducer system, such as, for example with reference to FIG. 42, variable depth transducer 4302 configured with variable depth device 4306. In the embodiment, probe 5010 may be coupled to control system 4304 through a connector 5012. Connector 5012 may comprise a wire, optical cable, wireless connection, or any other device capable of sending and/or receiving information from control system 4304 to variable depth transducer 4302 and variable depth device 4306 housed within probe 5010.

Probe 5010 may be configured to rotate around an axis 5016 to provide three-dimensional information. The rotational movement can comprise movement in either a clockwise or counterclockwise direction, or both. Further, the rotational movement could include complete or partial rotations. Thus, the rotational movement could include movement between only two positions, or between any other number of rotational positions. Still further, probe 5010 can be configured to translate or sweep along axis 5016 to provide a larger field-of-view and thus facilitate additional three-dimensional information. Accordingly, the probe system 5000 may comprise rotational and/or translational movement suitably configured to provide three-dimensional information.

Figure 50:
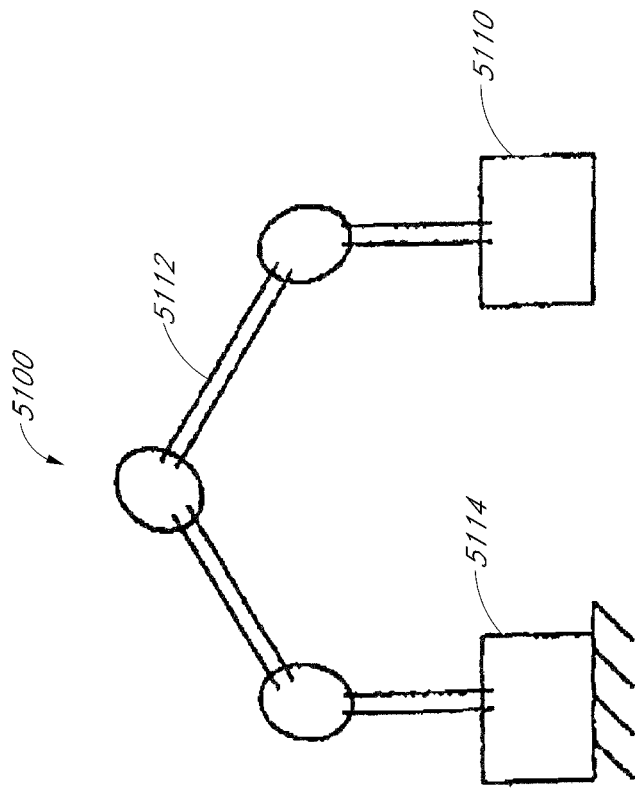
FIG. 50 illustrates an embodiment of a mechanism for treatment.

Rotational and/or translational movement of probe 5010 may be controlled by manually placing probe 5010 in various desired rotational positions around the treatment region 5014. The movement of variable depth transducer 4302 within probe 5010 in various rotational and/or translational positions can also be controlled by any mechanical scanning device now known or hereinafter devised for automated movement. For example, with reference to an embodiment illustrated in FIG. 50, automated rotational and/or translational movement may be achieved through use of a robotic arm mechanism 5100. Robotic arm mechanism 5100 comprises a manually and/or electromechanically actuated robotic arm 5112 coupled with a probe 5110 and a control 5114.

Probe 5110 may comprise a variable depth transducer system, such as variable depth transducer 4302 configured with variable depth device 4306. Movement of probe 5110 is mechanically provided through the operation of robotic arm 5112. Robotic arm 5112 may comprise one or more sub-segments that allow precise movement and precise measurement of position in one or more up to any direction. Robotic arm 5112 may be driven by control system 5114. Control system 5114 may comprise a drive box, gears or any other device for providing mechanical movement of robotic arm 5112. Control system 5114 may also comprise a processor, a display, and/or an input/output device. Probe 5110 may be further coupled to control system 5114 through a wire or optical cable configured alongside or within robotic arm 5112, a wireless connection, or any other device capable of sending and/or receiving information from control system 5114 to variable depth transducer 4302 and variable depth device 4306 housed within probe 5110.

Control system 5114 may provide movement and control of robotic arm 5112 with up to six degrees of freedom. Control system 5114 may allow for movement of robotic arm 5112 to be referenced with one or more fixed positions in space. Control system 5114 may also allow for movement of robotic arm 5112 to be referenced with one or more fixed positions on a patient.

While the three-dimensional systems may include a single acoustic transducer configured with a two-dimensional array 4900 and an adaptive algorithm to provide three-dimensional imaging, temperature monitoring and therapeutic heating to a treatment region; the three-dimensional system may also be configured to include both an adaptive algorithm and rotational and/or translational movement to provide additional information. As such, an even larger area of treatment may be obtained through the use of both the adaptive algorithm and the rotational and/or translational movement.

Continuing with this example, the three-dimensional system can be suitably configured to capture imaging and temperature information and provide therapeutic heating from variable depth transducer 4302 once variable depth transducer 4302 becomes fixedly maintained at various rotational positions. The three-dimensional system can also be suitably configured to capture imaging and temperature information and provide therapeutic heating just prior to, or just after, becoming fixedly positioned. The three-dimensional system can also be configured to capture imaging and temperature information and provide therapy during movement around the various rotational positions.

Figure 51A:
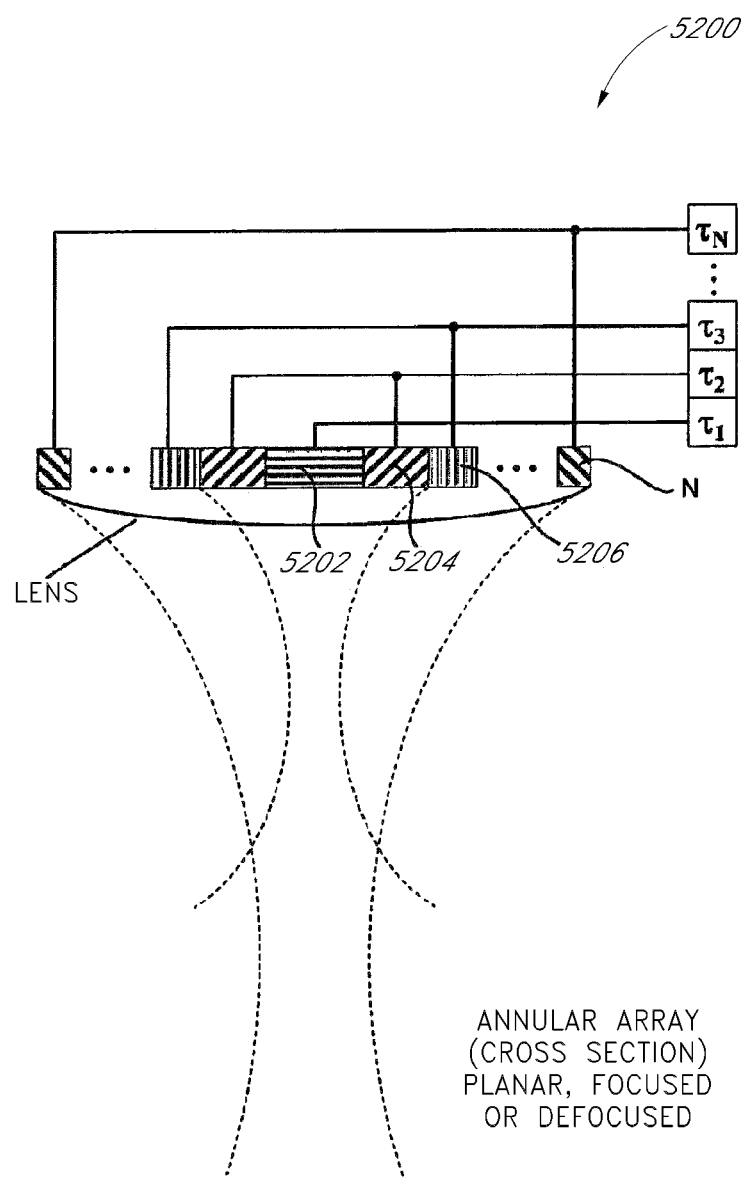
FIGS. 51A and 51B illustrate an embodiment of an annular array.
Figure 51B:
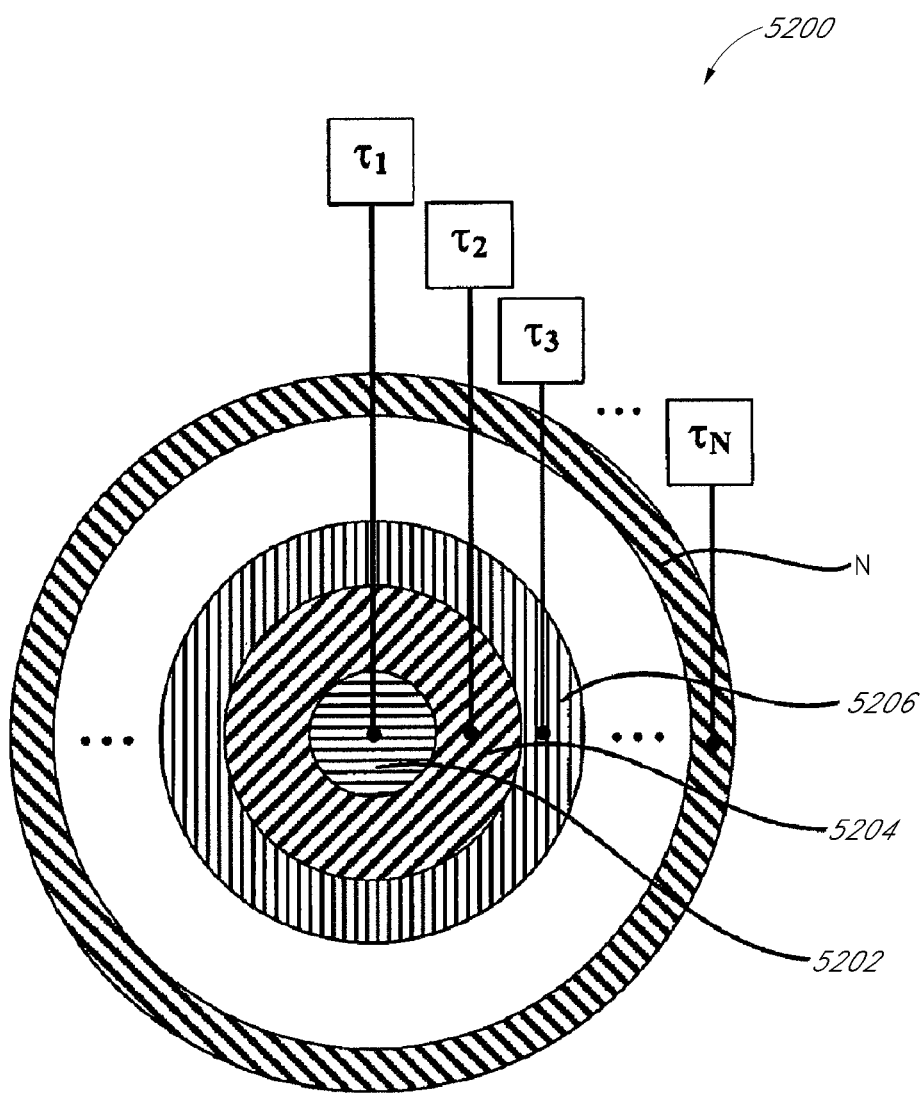

In addition to one, two or three-dimensional arrays, various embodiments of a variable depth transducer can also be configured within an annular array to provide planar, focused and/or defocused acoustical energy to more than one region of interest. For example, in accordance with an embodiment, with reference to FIGS. 51A and 51B, an annular array 5200 comprising a plurality of rings 5202, 5204, 5206 to N. Rings 5202, 5204, 5206 to N can be mechanically and electrically isolated into a set of individual elements, and can create planar, focused, or defocused waves. For example, such waves can be centered on-axis, such as by methods of adjusting corresponding transmit and/or receive delays, $\tau 1, \tau 2, \tau 3 \ldots \tau N$. An electronic focus can be suitably moved along various depth positions, and can enable variable strength or beam tightness, while an electronic defocus can have varying amounts of defocusing. In accordance with an embodiment, a lens can also be provided to aid focusing or defocusing such that any time differential delays can be reduced. Movement of annular array 5200 in one, two or three-dimensions, or along any path, such as through use of probe 5000 and/or robotic arm mechanism 5100, may be implemented to scan and/or treat a volume or any corresponding space within a region of interest.

In accordance with another embodiment, a variable depth treatment system and method may also be configured to provide therapeutic heating, cooling and/or imaging of a treatment region as well as acoustically monitoring the temperature profile or other tissue parameter monitoring of the treatment region and the general vicinity thereof. In accordance with an embodiment, a variable depth system may be configured with a dynamic feedback arrangement based on monitoring of temperature or other tissue parameters, and/or based on imaging information to suitably adjust the spatial and/or temporal characteristics of the variable depth transducer. Such imaging and other temperature or tissue parameter information can be suitably collected from ultrasound signals transmitted from a variable depth transducer, or from separate devices configured for collecting such information, e.g., a laser device configured with a receiver for profiling temperature, imaging or other such information.

For example, with reference again to FIG. 43, such feedback information can be utilized to dynamically adjust the height, e.g., with a standoff, or distance of a transduction element within variable depth transducer system 4402 from superficial layer 4412. Such adjustment of the distance and/or location of variable depth transducer system 4402 can be controlled either manually or mechanically. Changing the distance of variable depth transducer system 4402 can result in a change in the depth of penetration of the acoustical energy within a region of interest, for example, from an inner region 4422 to a deep region 4410. The depth of penetration of the acoustical energy can also be suitably changed by changing the temperature of any couplant configured between variable depth transducer system 4402 from superficial layer 4412, and/or the temperature of any coolant.

Feedback information may be suitably generated or provided by any one or more acoustical sources, such as B-scan images, A-lines, Doppler or color flow images, surface acoustic wave devices, hydrophones, elasticity measurement, or shear wave based devices. In addition, optical sources can also be utilized, such as video and/or infrared cameras, laser Doppler imagers, optical coherence tomography imagers, and temperature sensors. Further, feedback information can also be suitably provided by semiconductors, such as thermistors or solid state temperature sensors, by electronic and electromagnetic sensors, such as impedance and capacitance measurement devices and/or thermocouples, and by mechanical sensors, such as stiffness gages, strain gages or stress measurement sensors, or any suitably combination thereof. Moreover, various other switches, acoustic or other sensing mechanisms and methods may be suitably employed to enable transducer 4402 to be acoustically coupled to one or more regions of interest.

Cosmetic Treatment Transducers with Reflective Surfaces

In several embodiments described herein, transducer having one or more reflective surfaces are used. In various embodiments, a transducer can be used with any other embodiments of systems, devices, apparatus, and/or methods. In various embodiments, any of the transducers, such as transducer 6000, can be used for cosmetic treatment and/or therapy. In various embodiments, a transducer 6000 can include one or more transduction elements 6010. Some embodiments of transducers 6000 have a single transduction element 6010. In various embodiments, a transduction element 6010 can be an imaging element 6020. In various embodiments, a transduction element 6010 can be a therapy element 6030. In some embodiments, a transducer 6000 can include one or more imaging elements 6020 and/or one or more therapy elements 6030. In some embodiments, a transducer 6000 can both image and provide therapy with a single element 6010. In various embodiments, reference to a transducer 6000 may relate to a part of a transducer and/or an element 6010.

Various embodiments of the present invention relate to devices or methods of controlling the position of energy 6002 delivery to tissue. In some embodiments, position may relate to depth, or other dimension. In various embodiments, various forms of energy 6002 can include acoustic, ultrasound, light, laser, radio-frequency (RF), microwave, electromagnetic, radiation, thermal, cryogenic, electron beam, photon-based, magnetic, magnetic resonance, and/or other energy forms. Various embodiments of the present invention relate to devices or methods of controlling ultrasonic focal depth. In various embodiments, devices or methods can be used to alter the focal depth of ultrasound in any procedures such as, but not limited to, therapeutic ultrasound, diagnostic ultrasound, non-destructive testing (NDT) using ultrasound, ultrasonic welding, any application that involves coupling mechanical waves to an object, and other procedures. Generally, with therapeutic ultrasound, a tissue effect is achieved by concentrating the acoustic energy using focusing techniques from the aperture. In some instances, high intensity focused ultrasound (HIFU) is used for therapeutic purposes in this manner. The ability to focus the power from the aperture can be described with a parameter called "focal gain" It is through this focal gain that thermal and/or mechanical treatment, coagulation, ablation, or other effect on tissue can occur non-invasively or remotely. In some embodiments, a transducer 6000 includes a piezoelectric material. In some embodiments, a transducer 6000 includes a piezoelectric ceramic material. In some embodiments, a transducer 6000 includes a piezoelectric ceramic substrate.

In various embodiments, a transducer 6000 may be configured for delivering ultrasound energy 6002 for cosmetic therapy and/or treatment. In several of the embodiments described herein, the procedure is entirely cosmetic and not a medical act. In various embodiments, a static device or method may be used to control, alter, or vary focal depth, in order to effect tissue at a specific point for a desired cosmetic and/or therapeutic treatment. In various embodiments, target tissue is, but is not limited to, any of skin, eyelids, eye lash, eye brow, caruncula lacrimalis, crow's feet, wrinkles, eye, nose, mouth, tongue, teeth, gums, ears, brain, heart, lungs, ribs, abdomen, stomach, liver, kidneys, uterus, breast, vagina, prostrate, testicles, glands, thyroid glands, internal organs, hair, muscle, bone, ligaments, cartilage, fat, fat labuli, adipose tissue, subcutaneous tissue, implanted tissue, an implanted organ, lymphoid, a tumor, a cyst, an abscess, or a portion of a nerve, or any combination thereof.

In various embodiments, a transducer 6000 may be configured for delivering ultrasound energy 6002 to a focused zone, point, area, line, or region. In one embodiment, a transducer 6000 is configured for delivering ultrasound energy 6002 to a focused cosmetic treatment zone (CTZ) 6040 in tissue. In various embodiments, a cosmetic treatment zone may refer to a focused zone, point, area, line, or region. In various embodiments, delivery of ultrasound energy 6002 to a cosmetic treatment zone 6040 provides cosmetic treatment and/or cosmetic therapy to tissue, resulting in an improved cosmetic appearance and/or effect in the tissue. In various embodiments, a cosmetic treatment zone 6040 can be a point, a focal point, a lesion, a thermal lesion, an ablative lesion, a tightening point, a coagulation point, an ablation point, a thermal coagulation point, a thermal ablation point, a line, a discrete line, a zone, a discrete zone, region, and/or an area, or any other embodiment of a zone. In various embodiments, a cosmetic treatment zone 6040 can have different sizes, shapes, orientations, locations, depths, widths, and/or heights in tissue. In one embodiment, a transducer 6000 can create cosmetic treatment zone 6040 one at a time, with the transducer 6000 being electronically and/or mechanically moved to the next location where the next cosmetic treatment zone 6040 is created. In various embodiments, a process of mechanically and/or electronically moving the transducer 6000 to the next cosmetic treatment zone 6040 location and creating multiple cosmetic treatment zone 6040 along a linear path can be called a CTZ line. Curved lines and curved paths are also contemplated in various embodiments. In various embodiments, CTZ lines can be created along any skin surface, such as on a face or a body. In some embodiments, a transducer 6000 has a fixed focal depth. In some embodiments, a transducer 6000 has a variable focal depth. In some embodiments, a transducer 6000 can provide one or more focal points for forming one or more cosmetic treatment zones 6040.

In various embodiments, a transducer 6000 may be configured for delivering ultrasound energy 6002 to a cosmetic treatment zone 6040 for a tissue effect. In various embodiments, a transducer 6000 may be configured for non-invasive therapy and/or treatment. In various embodiments, a transducer 6000 may be configured for delivering high intensity focused ultrasound energy for cosmetic therapy or treatment. In various embodiments, a cosmetic treatment zone 6040 may result from the delivery of ultrasound energy from a transducer 6000 for a tissue effect, such as thermal treatment. In various embodiments, the thermal treatment may increase a tissue temperature at the cosmetic treatment zone 6040. In various embodiments, a thermal treatment may raise the tissue temperature at a cosmetic treatment zone 6040 to 35, 37, 39, 40, 45, 50, 55, 60, 65, 70, 75, 80, 85, 90, 95, 100, 105, 110, or over 110 degrees Celsius. In various embodiments, the tissue temperature at a cosmetic treatment zone 6040 is raised in a range of about 35-110, 35-40, 40-100, 40-55, 60-70, 60-65, 65-70, 65-75, 60-100, 65-100, 70-100, 55-70, 55-85 degrees Celsius, and any combinations, sub-combinations, and/or ranges therein.

Figure 52:
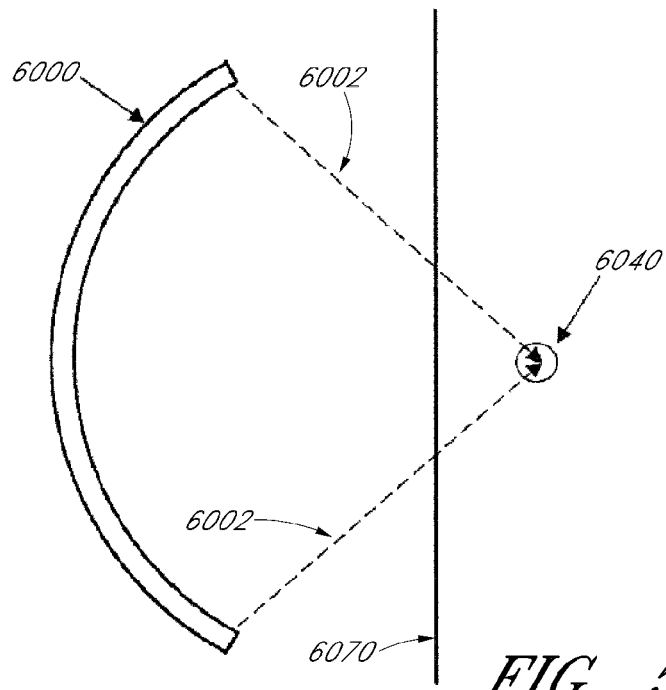
FIG. 52 illustrates a schematic cross-sectional side view of a transducer in a cosmetic treatment system according to an embodiment.

Reflective surfaces may be used to treat the face and body, including the brow, eye area, sweat glands, décolletage, and fat. In several embodiments, the transducers described herein can be flat, round, circular, cylindrical, annular, have rings, concave, convex, contoured, or have any shape. In various embodiments, a transduction element 6010 can be flat, round, circular, cylindrical, annular, concave, convex, contoured, have rings, and/or have any shape. With reference to the illustration in FIG. 52, an embodiment of a transducer 6000 can include a bowl with a diameter and one or more concave surfaces (with respective radii or diameters) geometrically focused to a cosmetic treatment zone 6040 at one or more focus depths below a tissue surface 6070. In one embodiment, a tissue surface 6070 is a skin surface. In one embodiment, a transducer 6000 may be radially symmetrical in three dimensions. For example, in one embodiment, transducer 6000 in FIG. 52 may be a radially symmetrical bowl. In one embodiment, a radially symmetric transducer can produce a focus point in a single point in space. In one embodiment, a transducer 6000 may extend linearly with a cross sectional shape. For example, in one embodiment, transducer 6000 in FIG. 52 may have a concave surface that extends like a cylinder. In one embodiment, a cylindrical transducer 6000 can produce a focus that extends along a line. In one embodiment, a cosmetic treatment zone 6040 as illustrated in FIG. 52 may be a single point. In one embodiment, a cosmetic treatment zone 6040 as illustrated in FIG. 52 may be a line extending in and/or out of the page. In one embodiment, a cosmetic treatment zone may refer to a single point focus. In one embodiment, a cosmetic treatment zone may refer to a linear focus, such as a focus line or a focus point that extends in one or more dimensions. In various embodiments, a concave surface directs ultrasound energy 6002 to a cosmetic treatment zone 6040. Multiple concave surfaces can direct ultrasound energy 6002 to multiple cosmetic treatment zones 6040. In one embodiment, when a transducer 6000 piezoelectric ceramic material is excited by an electrical stimulus, the material may expand or contract. The amount of expansion or contraction is related to boundary conditions in the ceramic as well as the magnitude of the electric field created in the ceramic. In some embodiments of conventional HIFU design, the front surface (e.g. subject side) is coupled to water and the back surface of a transducer 6000 is coupled to a low impedance medium which is typically air. In some embodiments, although the ceramic is free to expand at the back interface, essentially no mechanical energy is coupled from the ceramic to the air because of the significant acoustic impedance disparity. This results in this energy at the back of the ceramic reflecting and exiting the front (or subject side) surface. As illustrated in an embodiment in FIG. 52, the focus is created by machining the ceramic to the correct radius-of-curvature.

In various embodiments, a reflective surface 6100 can be used to reflect energy 6002 to create one or more focus points for the energy. In various embodiments, a reflective surface 6100 can be used to refract energy 6002 to create one or more focus points for the energy. In one embodiment, energy 6002 can be ultrasound energy from any embodiment of a transducer 6000. In one embodiment, a reflective surface 6100 can be used in conjunction with a flat transducer 6000. In one embodiment, a reflective surface 6100 can be used in conjunction with a cylindrical transducer 6000. In one embodiment, a reflective surface 6100 can be a parabolic reflector configured for one dimension that focuses acoustic energy 6002 from a cylindrical transducer 6000. In one embodiment, a reflective surface 6100 can be used to reflect energy 6002 to create one or more cosmetic treatment zones 6040. In various embodiments, one or more reflective surfaces 6100 can be used with one or more transducers 6000 with one or more therapy elements 6030. With reference to the illustration in FIG. 52, an embodiment of a transducer 6000 emitting energy 6002 is reflected off a reflective surface 6100 at a reflection point 6110. In one embodiment, the reflective surface 6100 is configured to reflect energy 6002 to at least one cosmetic treatment zone 6040. In one embodiment, a transducer 6000 is a flat transducer 6000.

In various embodiments, one or more reflective surfaces 6100 can be used with one or more transducers 6000 to create one, two, three, four, or more cosmetic treatment zones 6040. In various embodiments, one or more reflective surfaces 6100 can be used with one or more transducers 6000 to simultaneously create one, two, three, four, or more cosmetic treatment zones 6040. In various embodiments, one or more reflective surfaces 6100 can be used with one or more transducers 6000 to create one, two, three, four, or more cosmetic treatment zones 6040 at different times. In various embodiments, two or more cosmetic treatment zones 6040 can be produced on a beam axis, using the same axis, a parallel axis, a perpendicular axis, an angled axis, and/or an offset axis.

Figure 54:
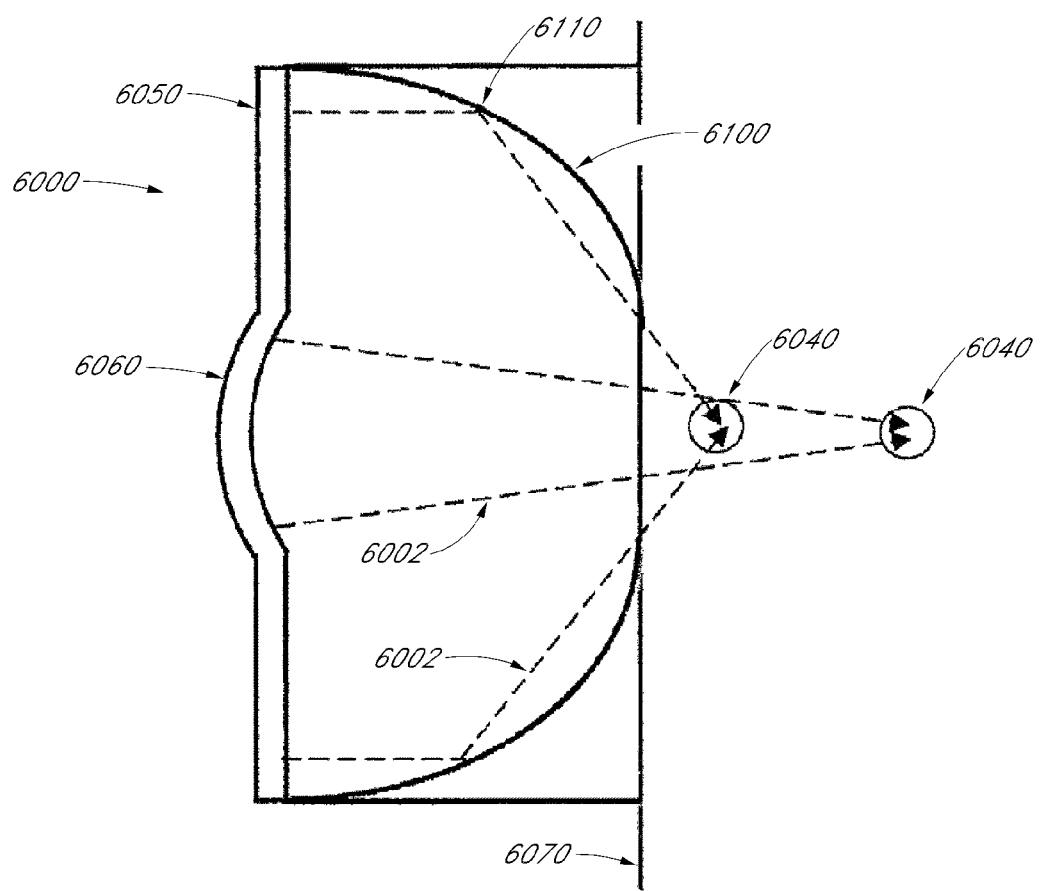
FIG. 54 illustrates a schematic cross-sectional side view of a transducer and a reflective surface in a cosmetic treatment system according to an embodiment.

With reference to the illustration in FIG. 54, in various embodiments, one or more transducers 6000 comprises one or more portions. In various embodiments, the portions can comprise an imaging transducer, an imaging element, a therapeutic transducer, a therapeutic element. In one embodiment, one or more transducers 6000 comprises a flat portion 6050 and/or a concave portion 6060. In some embodiments, the flat portion 6050 can be a flat transducer 6000 or a flat therapy element 6030. In some embodiments, the concave portion 6060 can be a concave transducer 6000 or a concave therapy element 6030. In some embodiments, the concave portion 6060 can be a radially symmetric bowl, a non-symmetric bowl, a cylinder, a partial cylinder, or other shape. In one embodiment, the flat portion 6050 is configured to reflect energy off a reflective surface 6100 to a first cosmetic treatment zone 6040. In one embodiment, the concave portion 6060 is configured to focus energy at a second cosmetic treatment zone 6040. In one embodiment, the first cosmetic treatment zone 6040 and the second cosmetic treatment zone 6040 are formed simultaneously. In one embodiment, the first cosmetic treatment zone 6040 and the second cosmetic treatment zone 6040 are formed at different times. In one embodiment, a reflective surface 6100 can reduce the amount of energy loss that may transpire if using a lens. In various embodiments, the amount of area that is focused using a reflection method is dependent on the focus location and the depth of the cosmetic treatment. In various embodiments, the amount of aperture area pointed to one focus or the other focus can be dependent on the focal gain differences between the two foci, the attenuation of the tissue, and the amount of energy to be transmitted to the cosmetic treatment zone 6040 location. In various embodiments, a concave portion 6060 may be used to increase the power in the vicinity of the cosmetic treatment zone(s) 6040 and/or can be configured to provide an appropriate intensity balance. In various embodiments, the one, two, or more cosmetic treatment zones 6040 can have various sizes, shapes, orientations, areas, heights, widths, depths, and/or other characteristics.

In various embodiments, one or more transducers 6000 and one or more reflective surfaces 6100 can be used to simultaneously create two, three, four, or more cosmetic treatment zones 6040. In various embodiments, one or more transducers 6000 and one or more reflective surfaces 6100 can be used to create two, three, four, or more cosmetic treatment zones 6040 at different times. Formation of multiple cosmetic treatment zones could reduce the overall treatment time and increase overall potential treatment region. In one embodiment, one transmission channel could be used to activate the transducer 6000. In one embodiment, multiple transmission channels could be used to activate the transducer 6000 or parts or portions of the transducer.

In various embodiments, the reflective surface 6100 can comprise a high or a low impedance material. In one embodiment the reflective surface 6100 may be of light acoustic impedance (such as, in one example, being air backed). In one embodiment the reflective surface 6100 may be of high acoustic impedance (such as, in one example, being stainless steel). In one embodiment, a curve can calculated with the offset from the transducer face, the focus, and the diameter of the therapy transducer. This curve may be used to determine the area of the hold for the flat disc.

In various embodiments, the impedance of a reflective surface 6100 may be based on a bulk impedance or through the creation of a highly reflective acoustic transmission line based on the operation frequency. In one embodiment, a reflective surface 6100 is configured to bend the acoustic beam toward an intended focus or cosmetic treatment zone 6040. The Law of Reflection states that the angle of incidence to a surface is equal to the angle of reflection. The angle of incidence and angle of reflection can be measured between the normal to the reflecting surface and the incoming and out-going ray respectively. The Law of Reflection can be used to calculate the required surface necessary to focus the beam at a particular cosmetic treatment zone 6040. The calculation input variables can include the intended focus, the diameter of the aperture, and the distance between a transducer 6000 (such as, in one example, a piezoelectric disc) and the reflective surface 6100.

Figure 55:
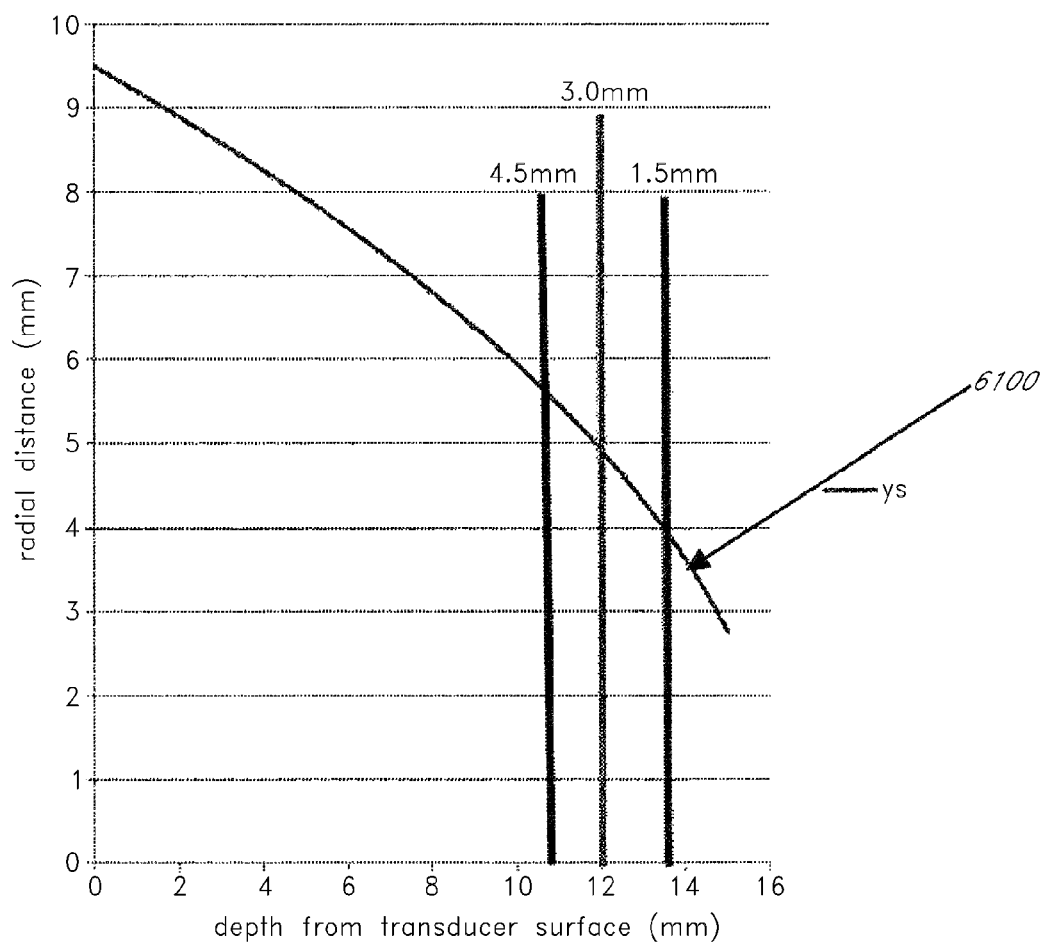
FIG. 55 is a chart illustrating a surface contour of a reflective surface according to several embodiments.

In various embodiments, as illustrated in FIG. 55, a surface contour for a reflective surface 6100 used with a flat transducer 6000 can be calculated with a 19 mm aperture, 15 mm focus, and a 0 mm offset between the reflective surface 6100 and transducer 6000. In one embodiment, the reflective surface 6100 is not used for the entire aperture. In one embodiment, the reflective surface 6100 is configured to couple to a skin surface, so the reflective surface can end where the skin surface begins. For illustrative purposes, a side view "skin line" can be used to illustrate the position or location of the reflector surface 6100—skin surface interface. FIG. 55 illustrates embodiments at three different focal depths below a skin surface, such as 4.5 mm, 3.0 mm and 1.5 mm. The transducer 6000 disc area is the least when focus is the deepest. In one embodiment, the transducer opening, which can be defined by the focal depth, determines the diameter of either a focused bowl or a lens that may be used to further contribute power to the intended foci at the cosmetic treatment zone(s) 6040. In various embodiments, FIG. 55 illustrates an aperture opening is 11.4 mm (5.7 mm in radial distance) for the 4.5 mm focal depth, 9.8 mm (4.9 mm in radial distance) for the 3.0 mm depth, and 8.0 mm (4.0 mm in radial distance) for the 1.5 mm depth.

Figure 56:
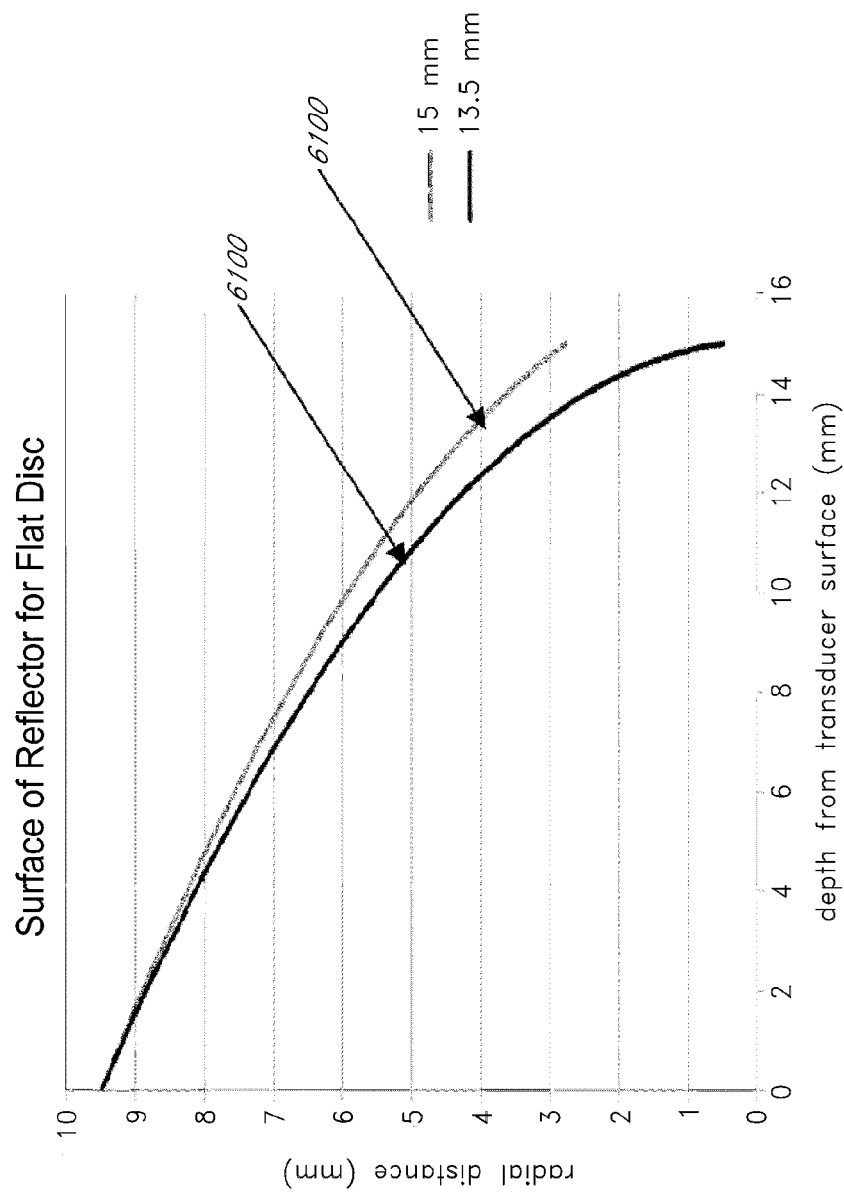
FIG. 56 is a chart illustrating surface contours of a reflective surface according to several embodiments.

In various embodiments, as illustrated in FIG. 56, a surface contour for a reflective surface 6100 can be designed to produce two different focal depths. For example, in FIG. 56, an embodiment of the reflective surface 6100 can change with respect to the respective focal depths or positions of the cosmetic treatment zones 6040. As shown in FIG. 56, in various embodiments, the contour of reflective surfaces 6100 for two different focal depths of two different cosmetic treatment zones 6040 is different depending on an aperture designed for various depth transducers 6000. In one embodiment, a 4.5 mm depth (below skin surface) transducer 6000 and a 3.0 mm depth (below skin surface) transducer 6000 have a 15 mm and 13.5 mm focus distance, respectively. In one embodiment, the phase difference between the two reflective surfaces 6100 can be determined if distance needs to be adjusted to correct for any phase differences, which can affect the intensity at the shallow and deep foci.

Figure 53:
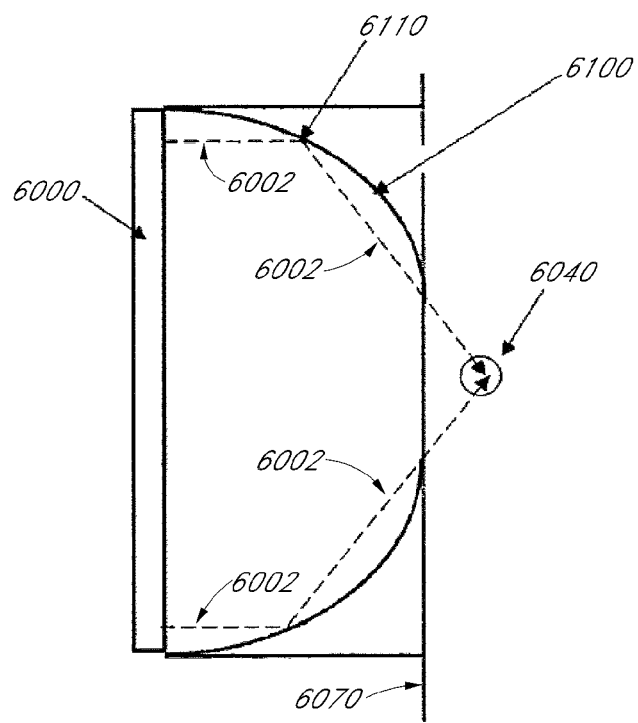
FIG. 53 illustrates a schematic cross-sectional side view of a transducer and a reflective surface in a cosmetic treatment system according to an embodiment.

FIGS. 52 and 54 illustrate some embodiments of a concave transducer 6000 in FIG. 52 and a hybrid flat/concave transducer 6000 with a flat portion 6050 and a concave portion 6060. For example, in one embodiment, the concave transducer 6000 in FIG. 52 is a uniformly curved surfaced with a focused depth at 15 mm. In various embodiments, the focus at 15 mm is a point or a line. In various embodiments, the frequency (e.g., ceramic thickness) varies depending on the dose depth. The reflective surface 6100 is adjacent a skin surface, shown as a vertical line in FIGS. 52-54. In one embodiment, transducer 6000 may include at least one imaging element. In one embodiment, an imaging element may be positioned in the concave portion 6060 for imaging. FIG. 54 illustrates an embodiment of a dual depth therapy transducer 6000. In various embodiments, a transducer 6000, element 6010, or a part of a transducer and/or element can be flat, curved, and/or shaped. In one embodiment, a transducer 6000, may be configured to reflect off one or more reflective surfaces 6100 to produce one, two, or more cosmetic treatment zones 6040 at one, two, or more focal depths. In various embodiments, combinations of a focus from any embodiment of a transducer and/or element surface with the focal effects of a reflector can produce various effects. For example, in various embodiments, a focal zone created by a transducer 6000 can be a point, line, plane, or other shape. In various embodiments, a reflective surface 6100 can be flat, planar, curved, and/or shaped to create a focal zone in a point, line, plane or other shape. Various combinations of various embodiments of transducers with reflective surfaces can produce one, two, three, four, or more cosmetic treatment zones 6040 at one, two, or more focal locations (e.g., depths, heights, positions, etc.). For example, in one embodiment, a flat portion 6050 and a concave portion 6060 of a transducer 6000 may be configured to reflect off one or more reflective surfaces 6100 to produce one, two, or more cosmetic treatment zones 6040 at one, two, or more focal depths.

In one embodiment, the flat portion 6050 and an optional concave portion 6060 (such as, in one example, provided as a small bowl) may be used to further balance the intensity at two or more foci. The acoustic energy from the flat portion of a transducer 6000 disc is directed toward a reflective surface 6100 that sends the energy toward one, two, or more focus or foci at cosmetic treatment zones 6040. In one embodiment, a flat portion 6050 is configured to focus at two foci: f1 and f2. In one embodiment, an optional concave portion 6060 bowl has a focus f3. As shown in FIG. 57, in one embodiment, a transducer 6000 can have a concave portion 6060 directed to one focus, F1. In one embodiment, the transducer can have one, two, or more imaging elements or transducers, Ix. As shown in FIG. 58, in one embodiment, a transducer 6000 can have a flat portion 6050 directed to two foci, F1 and F2, directed to a first cosmetic treatment zone 6040 and a second cosmetic treatment zone 6040. In one embodiment, a transducer 6000 can have a concave portion 6060 directed to a third foci, F3, directed to a third cosmetic treatment zone 6040. In one embodiment, the transducer can have one, two, or more imaging elements, Ix. In one embodiment, F2 is a shallow focus (e.g., in one example, 13.5 mm) and has the least area because of focal gain and reduced attenuation. In one embodiment, F1 is the deepest focus (e.g., in one example, 15 mm) and has the greatest area to overcome focal gain and any attenuation advantage of F1. In one embodiment, the intensity at the two foci F1 and F2 may be adjusted if the intensity is not intended to be equal. In one embodiment, focus F3 is directed at a focus depth that is between F1 and F2. In one embodiment, the aperture is used to further balance the power distribution between the two foci F1 and F2 and limit the overall power flux through the flat portion 6050 of the transducer 6000.

Returning to FIGS. 53 and 54, various embodiments of reflective surfaces 6100 can be used with any transducer 6000 to reflect energy in a desired direction. In some embodiments, the transducer can be flat, curved, cylindrical, planar, machined, and/or any shape. In one embodiment, a reflective surface 6100 is a parabolic reflector.

Figure 59:
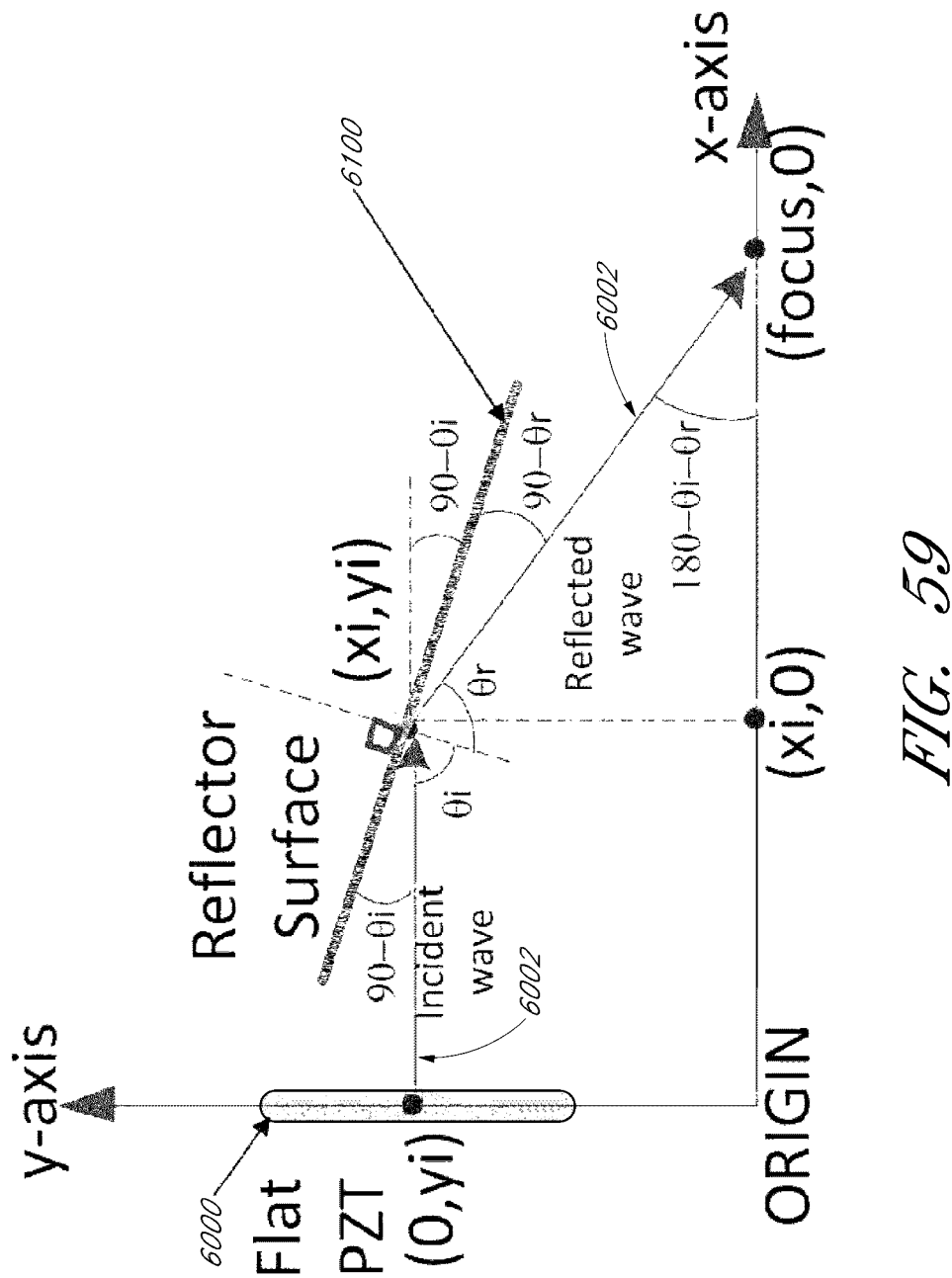
FIG. 59 illustrates a schematic side view of an energy wave from a transducer reflected off a reflective surface according to an embodiment.

In various embodiments, a transducer 6000 can have any shape. For example, in one embodiment, a transducer 6000 includes a flat portion 6050. In assuming an embodiment of a flat portion 6050 of a transducer 6000 is made up of point resonators, the slope of a reflective surface 6100 can be calculated to direct energy from the transducer 6000 to a focus at a cosmetic treatment zone 6040. Referring to FIG. 59, in one embodiment, a flat portion 6050 of a transducer 6000 emits energy in an incident wave. The incident wave makes an angle $\theta(i)$ relative to the normal of the reflective surface 6100. Since the normal is orthogonal to the reflective surface 6100, the angle between the incident wave and reflective surface 6100 is $90-\theta(i)$. A similar relationship can be expressed for the reflected wave which makes an angle $\theta(r)$ relative to the normal of the reflective surface 6100. The angle between the reflected wave and the reflective surface 6100 is $90-\theta(r)$. The slope of the reflective surface 6100 in this coordinate system is $$\text{slope}_{reflector} = \tan(\theta_t) \quad (1)$$

where $\theta(t)=90-\theta(i)$. The law of reflection simply states that the angle of incidence equals the angle of reflection:

$$\theta_i = \theta_r \quad (2)$$

Using this relationship, it is possible to show that the slope of the reflected wave is:

$$\text{slope}_{wave} = \tan(2\theta_t) = \frac{-y_i}{(\text{focus} - x_i)} \quad (3)$$

Equation (3) can be solved for $\theta_t$ and then placed in equation (1) to express the slope of the reflector (reflective surface 6100) in terms of a point on the flat portion 6050 (shown as flat portion PZT $(0, y_i)$), with the distance the reflector (reflective surface 6100) is from the point on the flat portion 6050 at flat portion PZT $(x_i)$ and the focus.

$$\text{slope}_{reflector} = \tan\left(\frac{\tan^{-1}\left(\frac{-y_i}{(\text{focus}-x_i)}\right)}{2}\right) = \frac{dy}{dx} \quad (4)$$

A trigonometric identity can be used to rewrite equation (4) in terms of cosecant and cotangent functions.

$$\tan\left(\frac{\theta}{2}\right) = \csc(\theta) - \cot(\theta) \quad (5)$$

Applying this trigonometric identity to equation (4):

$$\frac{dy}{dx} = \csc\left(\tan^{-1}\left(\frac{-y_i}{(\text{focus}-x_i)}\right)\right) - \cot\left(\tan^{-1}\left(\frac{-y_i}{(\text{focus}-x_i)}\right)\right) \quad (6)$$

Figures 60, 61:
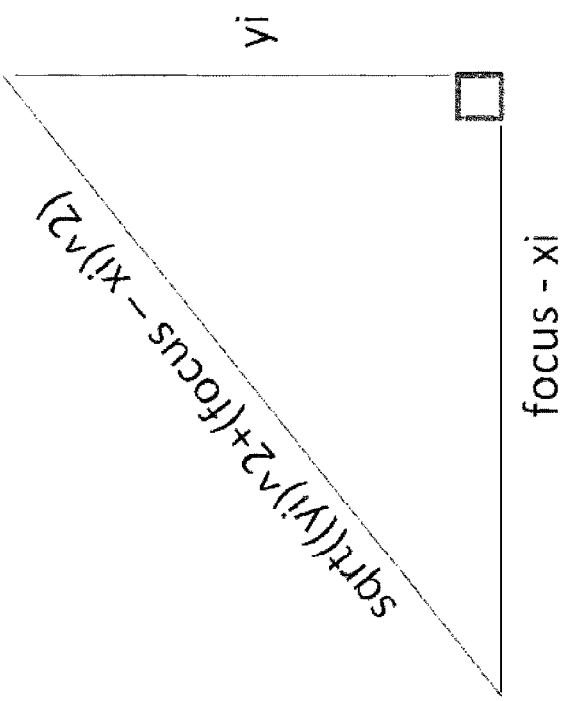
FIG. 60 illustrates a right triangle associated with an equation in relation to a reflection according to an embodiment.
FIG. 61 is a table listing calculations of certain points on a parabolic reflector surface according to an embodiment.

Equation (6) can be further rewritten using Pythagorean's theorem. FIG. 60 shows a right triangle associated with the arguments in Equation (6). Equation (7) has removed the trigonometric function such that the slope of the reflective surface 6100 is provided in terms of only the transducer 6000 surface height, distance to the reflective surface 6100 and focus.

$$\frac{dy}{dx} = \frac{-\sqrt{y_i^2 + u^2} + u}{y_i} \quad (7)$$

where $u = \text{focus} - x_i$. Numerical methods may be used to solve Equation (7). The slope is rewritten as an incremental ratio between two points on the reflective surface 6100:

$$\frac{dy}{dx} = \frac{y_{S+1} - y_S}{x_{S+1} - x_S} = \frac{-\sqrt{y_S^2 + (\text{focus} - x_S)^2} + (\text{focus} - x_S)}{y_S} \quad (8)$$

Equation 8 can be solved for the next point on the surface:

$$y_{S+1} = \left(\frac{-\sqrt{y_S^2 + (\text{focus} - x_S)^2} + (\text{focus} - x_S)}{y_S}\right)(x_{S+1} - x_S) + y_S \quad (9)$$

where s=0, 1, 2, 3, . . . N. Equation (9) shows a simple expression for the reflector surface. In order to solve this expression, initial conditions are determined. For example, $y_0$ is simply the outer most point on the transducer 6000. For example, if a transducer 6000 has a ring that has an outer diameter of 20 mm, then $y_0$ is 10 mm. The difference $(x_{s+1}-x_s)$ is the step size. In one embodiment, a step size of 50 μm is sufficient. The focus is the intended focus of the parabolic reflector on the x-axis relative to the coordinate system of the flat portion 6050.

Figure 62:
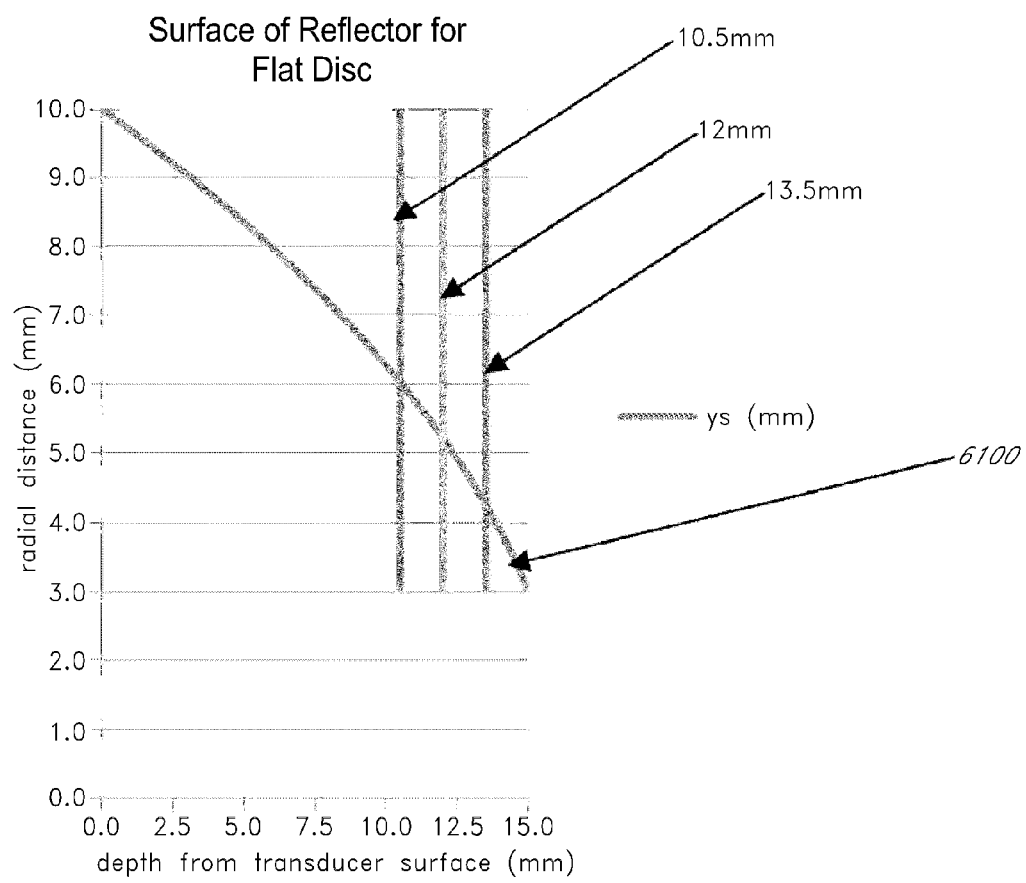
FIG. 62 is a chart illustrating a surface contour of a reflective surface according to several embodiments.

The table at FIG. 61 illustrates the first ten points in a calculation for one embodiment of a flat portion 6050 with a diameter of 20 mm and a focus goal of 15 mm. The step size is 50 μm. If the calculations are continued for multiple points, then the calculated parabolic reflector surface can be generated as shown in FIG. 62. The surface has been stopped at a radial distance ($y_s$) of 3 mm because this is the inner diameter of one embodiment of a flat portion 6050. In FIG. 62, potential skin line depths from the surface of the flat portion 6050 of the transducer 6000 show where some embodiments of reflective surface 6100 parabolic reflectors can end. For example, if the skin-line was 10.5 mm from the surface of the flat portion 6050 to meet a focus goal of 4.5 mm below the surface (with a parabolic reflector surface at 15 mm), then the parabolic reflective surface 6100 would end at an inner diameter (ID) of approximately 12.0 mm. In this example for one embodiment, this calculation suggests that in one embodiment, if the flat portion 6050 has an inner diameter ring of less than 12.0 mm in diameter, that energy would escape and pass through the opening in the reflective surface 6100. In relation to this example, in one embodiment, a flat portion 6050 ring could not have an inner diameter less than 12.0 mm, and in one embodiment, the inner diameter of the flat portion 6050 could be designed to exceed 12.0 mm to minimize acoustic energy escaping without hitting the reflector due to diffraction effects. In one embodiment, the inner diameter of the flat portion 6050 should be even greater than 6.0 mm to minimize acoustic energy escaping without hitting the reflector due to diffraction effects.

Figure 63:
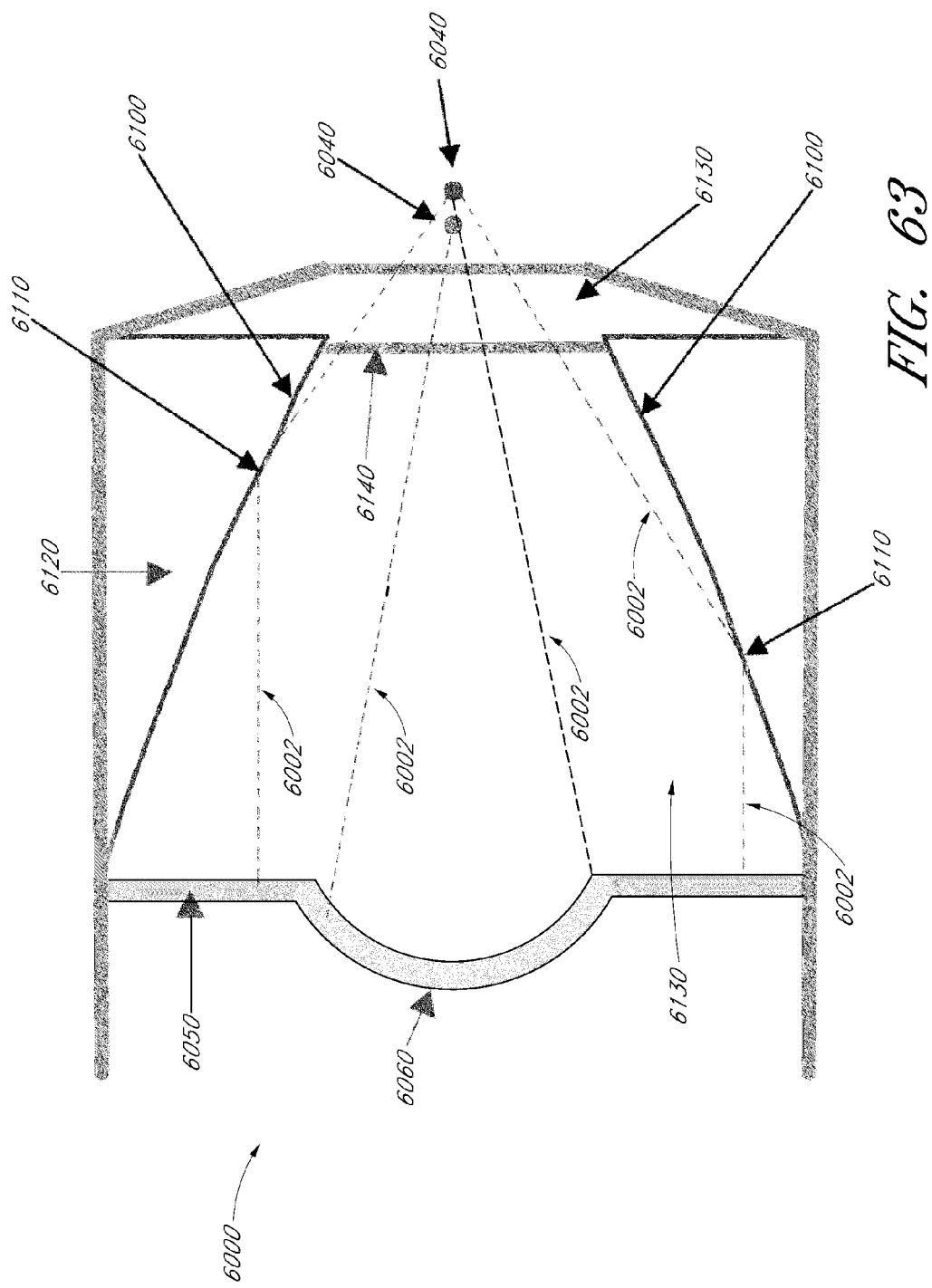
FIG. 63 illustrates a schematic cross-sectional side view of a transducer and a reflective surface in a cosmetic treatment system according to an embodiment.

In one embodiment, a three dimensional parabolic reflective surface 6100 is obtained by spinning the calculated surface as shown in FIG. 62 about an axis. With reference to the illustration in FIG. 63, in various embodiments, one or more transducers 6000 comprises a flat portion 6050 and/or a concave portion 6060. In one embodiment, the flat portion 6050 is configured to reflect energy off a reflective surface 6100 to a first cosmetic treatment zone 6040. In one embodiment, the concave portion 6060 is configured to focus energy at a second cosmetic treatment zone 6040. In one embodiment, the first cosmetic treatment zone 6040 and the second cosmetic treatment zone 6040 are formed simultaneously. In one embodiment, the first cosmetic treatment zone 6040 and the second cosmetic treatment zone 6040 are formed at different times. In one embodiment, the reflective surface 6100 is a parabolic reflector. In one embodiment, the reflective surface 6100 is shaped to place the focus at a specific location in tissue that creates an ultrasound therapeutic effect.

In various embodiments, a coupling medium 6130 provides for acoustic communication between a transducer 6000 and tissue. In various embodiments, a coupling medium 6130 can acoustically couple a transducer 6000, a reflective surface 6100, a module, a housing, a window, an acoustically transparent member 230, a probe 100, a skin surface, and/or any components and/or objects or tissue in a system for cosmetic treatment. In various embodiments, a coupling medium 6130 is a gel, liquid, fluid, solid, water, air, gas, non-gel and/or any combination thereof, or any other material for efficiently transmitting acoustic energy. In various embodiments, a coupling medium 6130 is used to transmit ultrasound energy between one or more devices and tissue with a transmission efficiency of 100%, 99% or more, 98% or more, 95% or more, 90% or more, 80% or more, 75% or more, 60% or more, 50% or more, 40% or more, 30% or more, 25% or more, 20% or more, 10% or more, and/or 5% or more.

In one embodiment, the reflective surface 6100 is a solid, such that a majority of ultrasound energy impinging on the surface is reflected toward the focus. In one embodiment, the reflective surface 6100 is a shell such that a majority of ultrasound energy is directed to the intended focus. In various embodiments, the reflective surface 6100 may include a material of a predetermined thickness based on the ultrasound frequency such that the boundary is highly reflective. In one embodiment, the reflective surface 6100 is backed by an ultrasound absorber 6120 that prevents or reduces the amount of re-radiation of ultrasound energy that is transmitted into the reflective surface 6100 back into the coupling fluid. In one embodiment, the reflective surface 6100 may have air holes and/or ports selectively added to various locations of the parabolic reflector to prevent the trapping of air bubbles or other bubbles in the coupling medium 6130. In one embodiment, the reflective surface 6100 can include an optional membrane 6140 that would also block the entry of bubbles into the cavity that contains the parabolic reflector. In one embodiment, the optional membrane 6140 is an acoustically transparent member.

In various embodiments, parabolic reflective surface 6100 methods may also apply to partially focused piezoelectric materials and/or tilted piezoelectric materials. Furthermore, the parabolic reflective surface 6100 may be combined with other resonating surfaces to create one single focus or multiple foci. In various embodiments, other resonating surfaces may or may not be independently excited and/or at a different frequency or phase relative to the transducer 6000 reflected off of the parabolic reflective surface 6100. For example, in one embodiment, a parabolic reflective surface 6100 may be integrated with a concave transducer 6000 bowl to create two or more foci at different depths or locations which may be used to increase the cosmetically treated area, and/or reduce overall cosmetic treatment time. In some embodiments, a parabolic reflective surface 6100 may also have multiple foci created in the same surface. For example, in one embodiment, a cylindrical transducer 6000 or cylindrical transduction element 6010, which is curved and focused in only one dimension could be focused in another dimension using a parabolic reflective surface 6100. In various embodiments, a cylindrical shape can refer to a partial cylindrical arc or portion of a curved surface along one dimension, such as a longitudinal axis.

Figure 64:
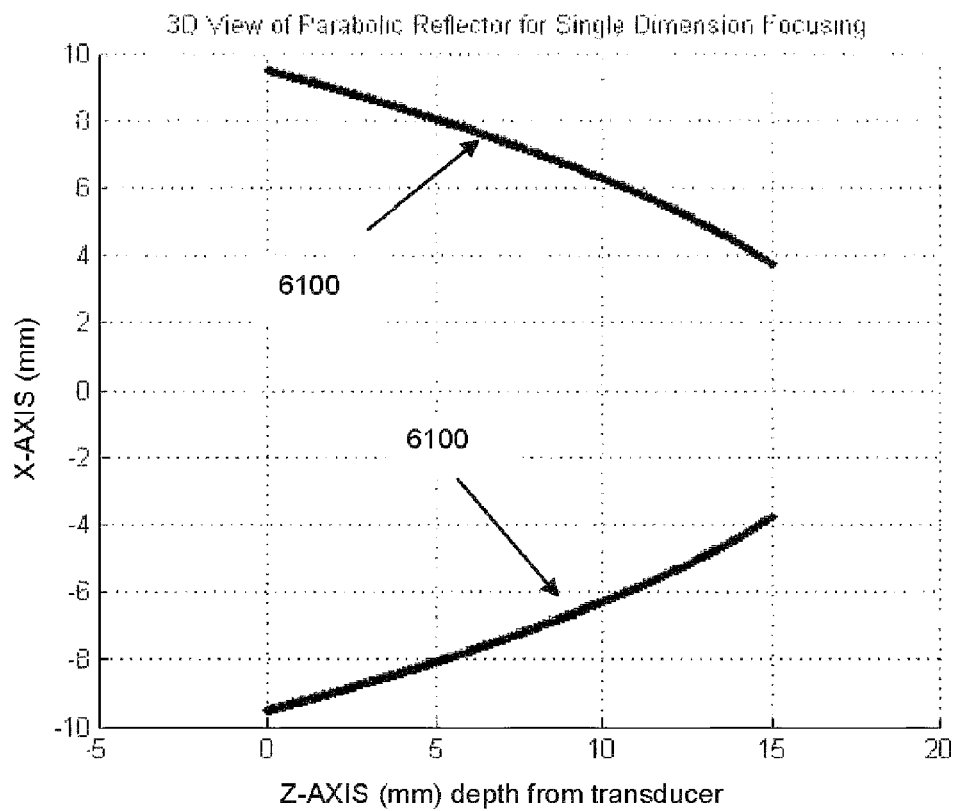
FIG. 64 is a chart illustrating a surface contour of a reflective surface with single dimension focusing according to several embodiments.
Figure 65:
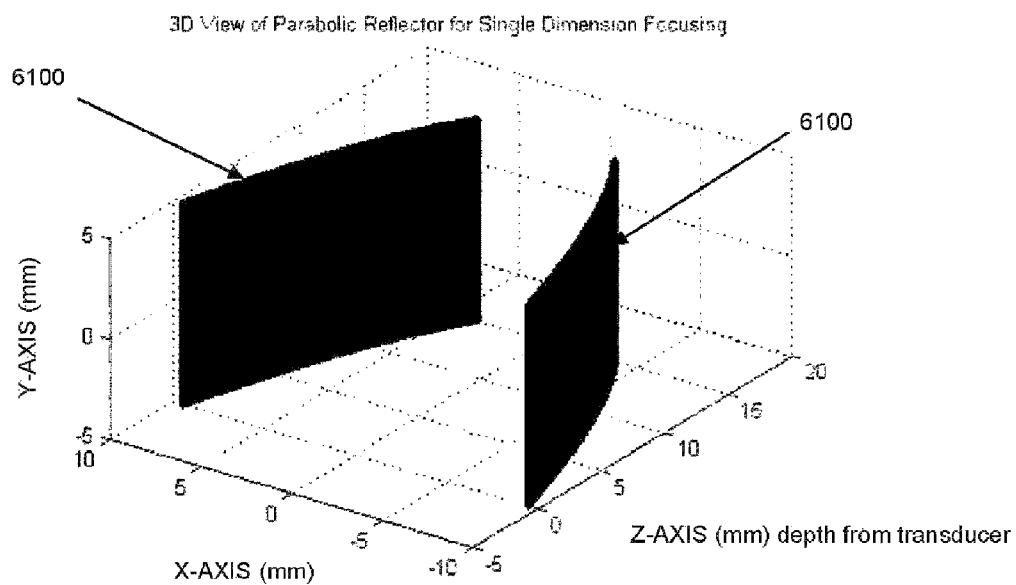
FIG. 65 is a three dimensional chart illustrating the surface contour of the reflective surfaces with single dimension focusing according to FIG. 64.

With reference to the charts in FIGS. 64 and 65, surface contours of a reflective surface 6100 with single dimension focusing according to several embodiments is illustrated. In various embodiments, a reflective surface 6100 can comprise a curved cross sectional surface that extends linearly.

In one embodiment, a reflective surface 6100 has a cross sectional shape that is extended along an axis. In one embodiment, a reflective surface 6100 is a parabolic surface that extends linearly along an axis. In one embodiment, a coordinate system is provided for reference. In one embodiment, a reflective surface 6100 with single dimension focusing extends linearly along a Y axis or a Y dimension. In one embodiment a Z axis or Z dimension extends as a depth from a transducer. In one embodiment a reflective surface 6100 varies with a curve along the Z axis.

In the illustrated embodiments at FIGS. 64-72, one or more single dimension cylindrical transducers 6000 direct energy to a focus zone that can be linear in shape, with the focus zone line extending along the X axis direction. In the illustrated embodiments at FIGS. 64-72, two parabolic reflective surfaces 6100 having a cross section that extend along the Y axis are configured to reflect at least part of the energy from the one or more transducers 6000. In the illustrated embodiment, the two reflective surfaces 6100 are symmetric with each other. In other embodiments, reflective surfaces can have different shapes, focus zones, etc.

Figure 66:
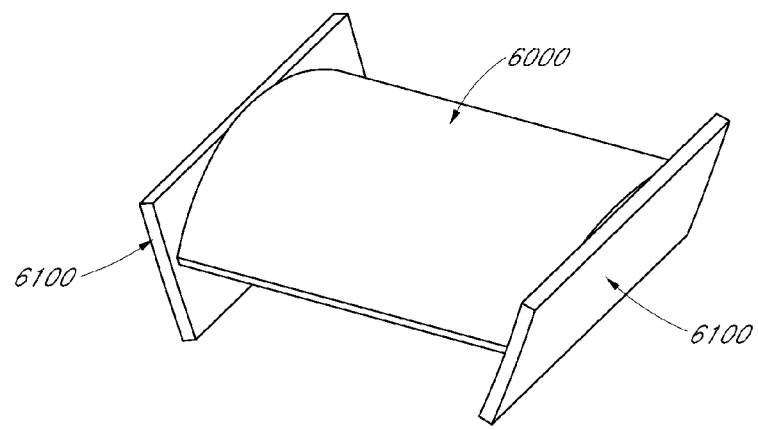
FIG. 66 illustrates a schematic isometric side view of a cylindrical transducer and two parabolic reflective surfaces in a cosmetic treatment system according to an embodiment.
Figures 67, 68:
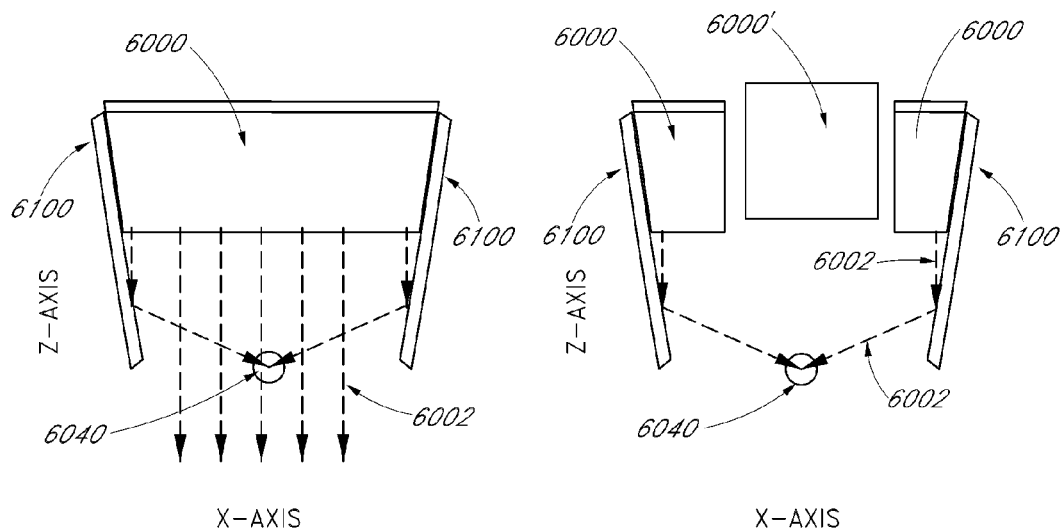
FIG. 67 illustrates a schematic side view of the cylindrical transducer and two parabolic reflective surfaces of FIG. 66.
FIG. 68 illustrates a schematic side view of two cylindrical transducers and two parabolic reflective surfaces in a cosmetic treatment system according to an embodiment.
Figure 69:
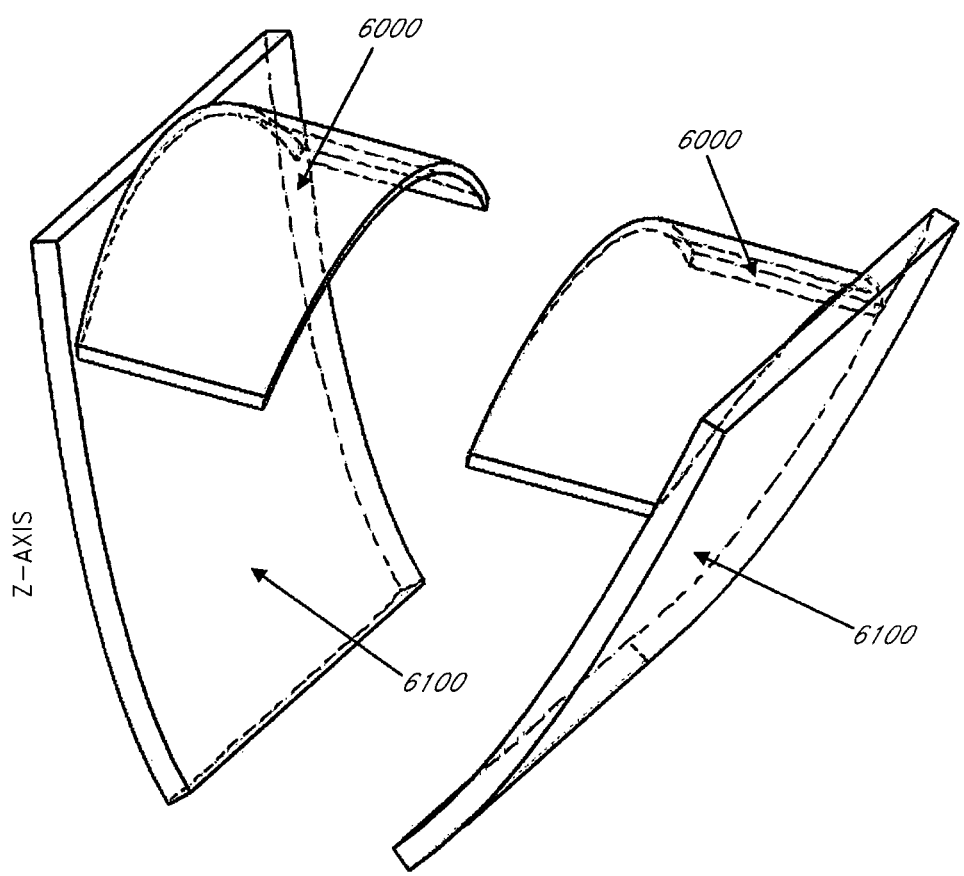
FIG. 69 illustrates a schematic isometric side view of two cylindrical transducers and two parabolic reflective surfaces in a cosmetic treatment system according to an embodiment.

With reference to the illustration in FIGS. 66-67, in various embodiments, a transducer 6000 can comprise a one dimensional focus. In various embodiments, the one dimensional transducer 6000 is curved and linearly extended with a constant, or changing, cross sectional shape. In one embodiment the transducer 6000 is cylindrical. In one embodiment, a cylindrical transducer 6000 comprises at least a part of a surface that provides a one dimensional focus, is curved and extends with a curved cross section along the X axis. In one embodiment, a cylindrical transducer 6000 focuses to a linear focus zone 6040, parallel to the X axis.

In various embodiments, one, two, three, or more transducers 6000 and/or transduction elements 6010 can be used together or separately. In various embodiments, the same or different types of transducers, elements (e.g., for therapy, imaging, single elements, multiple elements, arrays, linear arrays, grids, etc.) can be used together or separately. In some embodiments, an imaging transducer or element, Ix can be used. In one embodiment, as illustrated in FIG. 68, two or more cylindrical transducers 6000 can be used in a system. In one embodiment, another transducer 6000' may be placed in the gap or space between the two or more cylindrical transducers 6000. In various embodiments, an optional transducer 6000' is an imaging transducer, imaging element, single element, multiple element, array, linear array, concave, flat, therapeutic, or any other type of transducer or transduction element. In one embodiment, the two side transducers 6000 in FIG. 68 are similar to the transducer 6000 in FIG. 67 with a portion of the middle removed, thereby illustrating the focusing action of the portions of the transducers that reflect of the one or more reflective surfaces. In one embodiment, energy (e.g., ultrasound energy) is transmitted from a transducer 6000 off a reflective surface 6100 to a cosmetic treatment zone 6040. In one embodiment, one or more imaging elements or imaging transducers, Ix, can be placed in a gap or space between transducers 6000.

Figure 72:
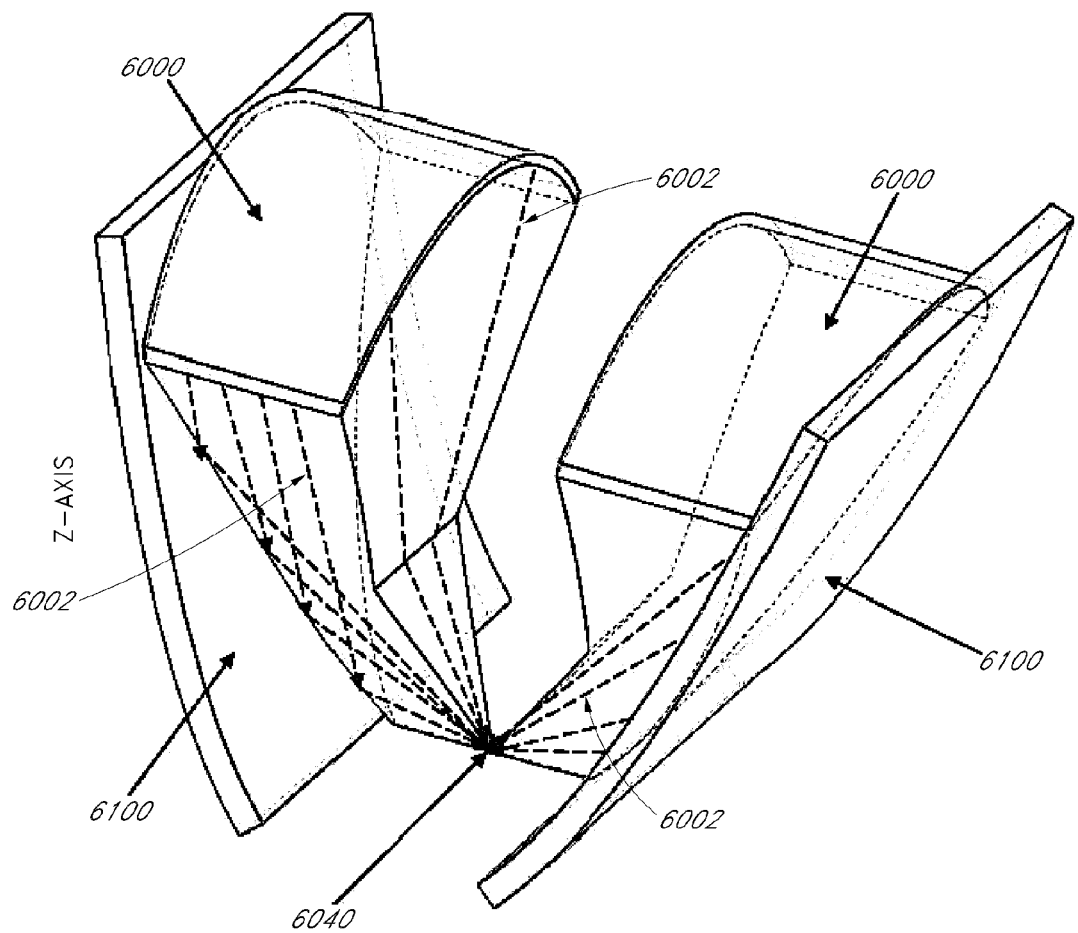
FIG. 72 illustrates a schematic isometric side view of the two cylindrical transducers and the two parabolic reflective surfaces of FIG. 69.

As illustrated in FIGS. 69-72, ultrasound energy (shown as dotted arrows) can be transmitted from one or more transducers 6000, reflected off one or more reflective surfaces 6100 to focus at one or more cosmetic treatment zones 6040. Although not illustrated, any transducer 6000 may be placed next to, between, in a space, in a gap or near other transducers 6000 (e.g., see embodiment in FIG. 68). FIG. 70 illustrates an embodiment of energy emitted from one or more cylindrical transducers 6000 to one or more linear cosmetic treatment zones 6040. FIG. 71 illustrates an embodiment of energy emitted from one or more reflective surfaces 6100 to one or more cosmetic treatment zones 6040. FIG. 72 illustrates an embodiment of energy from one or more cylindrical transducers 6000 reflected off one or more parabolic reflective surfaces 6100 to focus at one or more cosmetic treatment zones 6040. In one embodiment, the cosmetic treatment zone 6040 is a single point. In one embodiment, the cosmetic treatment zone 6040 is two or more points. In one embodiment, the cosmetic treatment zone 6040 is a line. In one embodiment, the cosmetic treatment zone 6040 is two or more lines. In one embodiment, the cosmetic treatment zone 6040 is a single shape. In one embodiment, the cosmetic treatment zone 6040 is two or more shapes. In various embodiments, a single cosmetic treatment zone 6040 can be formed by a single transducer 6000, a single transducer 6000 and a single reflective surface 6100, and/or one or more transducers 6000 and one or more reflective surfaces 6100. In various embodiments, multiple cosmetic treatment zones 6040 can be can be formed by a single transducer 6000, a single transducer 6000 and a single reflective surface 6100, and/or one or more transducers 6000 and one or more reflective surfaces 6100.

As shown in FIGS. 73-76, beam profile pressure plot experimental simulations on two cylindrical transducers 6000 with two parabolic reflective surfaces 6100 are shown according to various embodiments according to FIGS. 69-72. The contour plots in FIGS. 73-76 are shown in decibels, with a decibel value of the contour shown for one embodiment.

Figure 73:
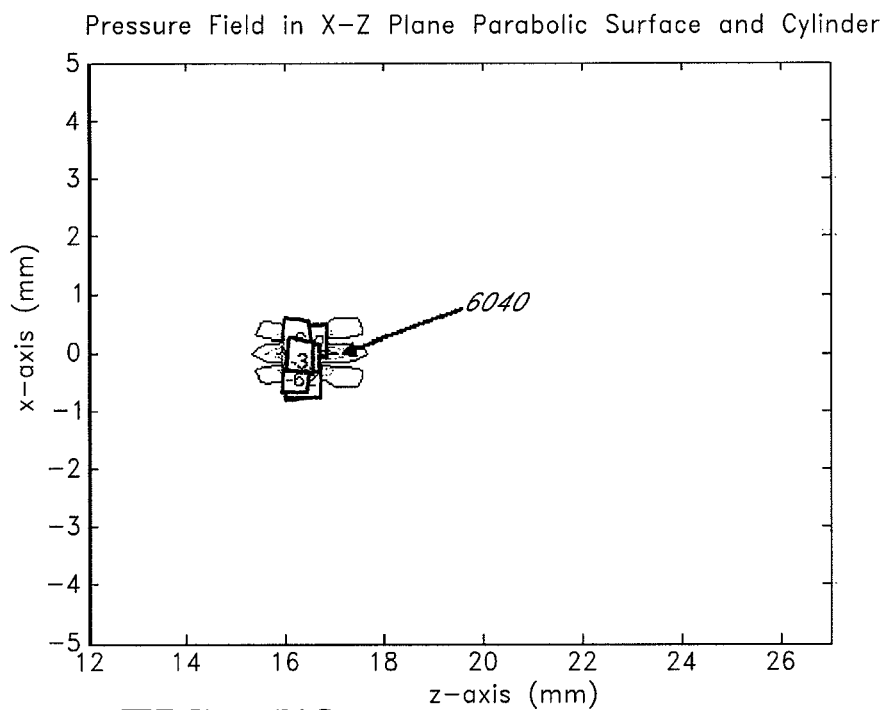
FIG. 73 is a chart illustrating a beam profile simulation of acoustic intensity across a plane of the embodiment of the cylindrical transducers and reflective surfaces of FIG. 72.
Figure 74:
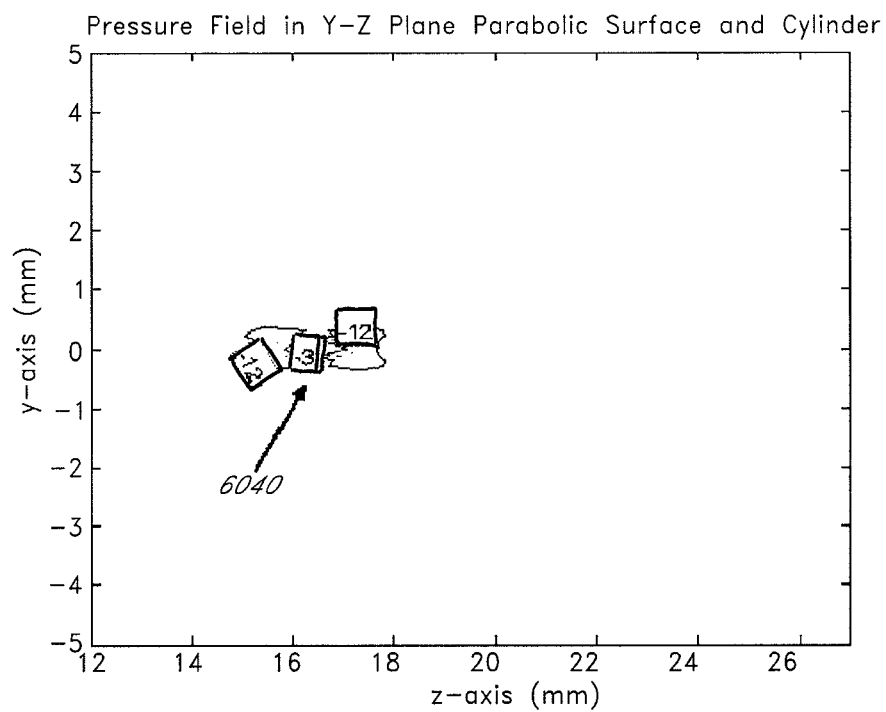
FIG. 74 is a chart illustrating a beam profile simulation of acoustic intensity across another plane of the embodiment of the cylindrical transducers and reflective surfaces of FIG. 72.

FIG. 73 shows a XZ plane pressure plot from a combined parabolic reflector and cylinder when they are focused to the same spatial point, e.g., when a cylindrical transducer 6000 and each reflective surface 6100 is focused to a single cosmetic treatment zone 6040 at a point. FIG. 74 shows a YZ plane pressure plot from the system of FIG. 73 when the transducer 6000 and each reflective surface 6100 is focused to a single cosmetic treatment zone 6040 at a point. As shown in FIGS. 73 and 74, the cosmetic treatment zone 6040 is focused to a single point.

Figure 75:
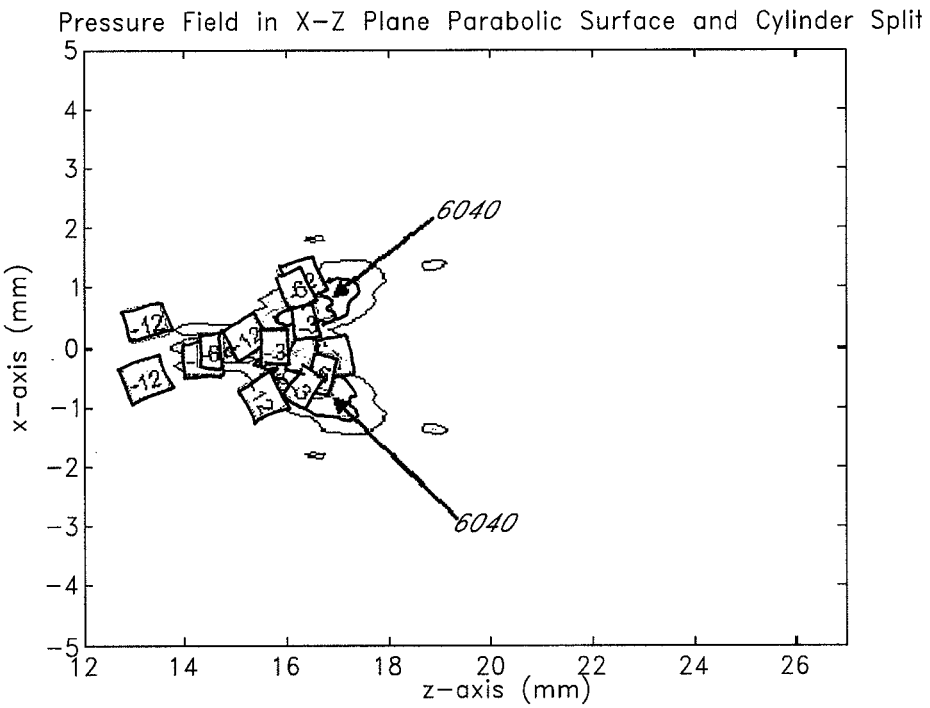
FIG. 75 is a chart illustrating a beam profile simulation of acoustic intensity across a plane of cylindrical transducers and reflective surfaces according to an embodiment.
Figure 76:
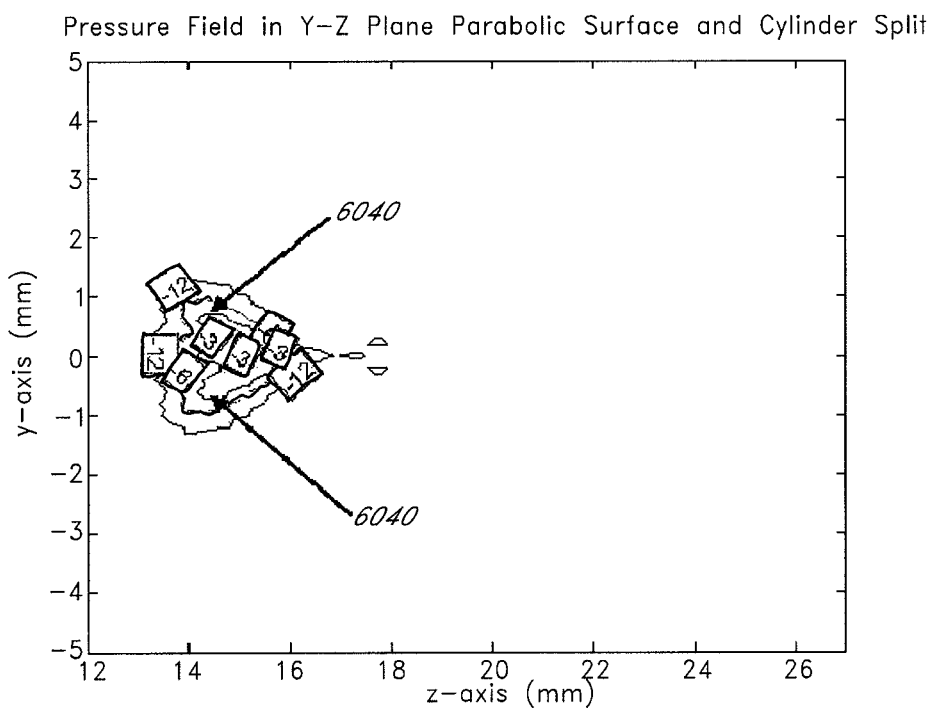
FIG. 76 is a chart illustrating a beam profile simulation of acoustic intensity across another plane of the cylindrical transducers and reflective surfaces of FIG. 75.
Figure 77:
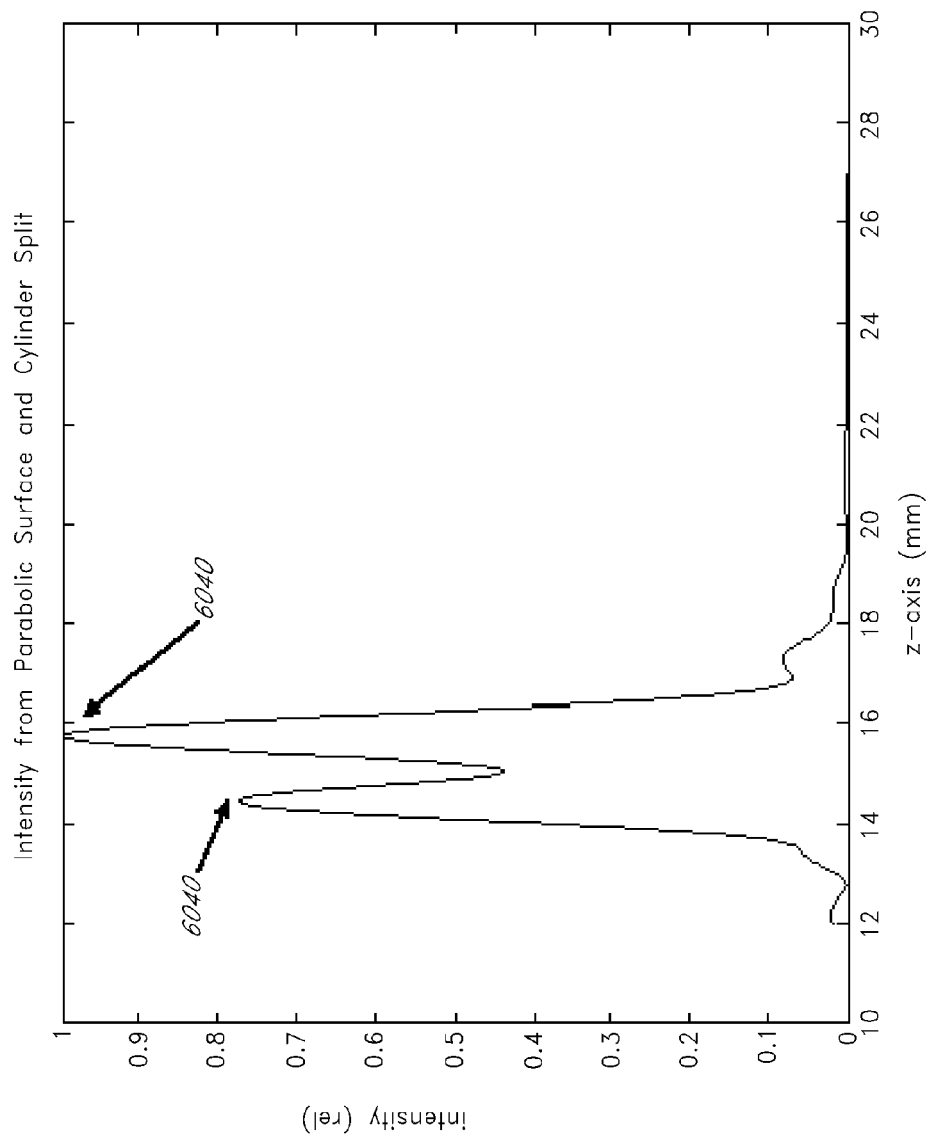
FIG. 77 is a chart illustrating a normalized intensity along a Z axis of the embodiment of the cylindrical transducers and reflective surfaces of FIG. 75.

FIG. 75 shows a XZ plane pressure plot from a combined parabolic reflector and cylinder when they are offset and focused to two different spatial points, e.g., when the cylindrical transducer 6000 and reflective surface(s) 6100 are focused to different cosmetic treatment zones 6040. FIG. 76 shows a YZ plane pressure plot from the system of FIG. 75 when the transducer 6000 and reflective surface(s) 6100 are focused to different cosmetic treatment zones 6040. As shown in FIGS. 75 and 76, the two cosmetic treatment zones 6040 are offset. FIG. 77 shows a normalized intensity along the z-axis with x=0 and y=0 from the embodiment of the system shown in FIGS. 75-76, in which the foci are slightly offset. As shown in FIG. 77, the two peaks indicate the offset reflective surfaces 6100 produce two offset cosmetic treatment zones 6040.

In various embodiments, a transducer 6000 is moveable within a probe hand wand, probe, housing, module, or cosmetic therapy device. In various embodiments, a reflective surface 6100 is moveable within a probe hand wand, probe, housing, module, or cosmetic therapy device. In one embodiment, a transducer 6000 and a reflective surface 6100 are fixed with respect to each other. In one embodiment, a transducer 6000 and a reflective surface 6100 are moveable with respect to each other. In various embodiments, a movement system 6200 can be used to generate a plurality of cosmetic treatment zones 6040 in one, two, or three dimensions. Multiple focal depths, heights, and widths can be achieved by mechanically moving the transducer 6000 and/or the reflective surface 6100 using one, two, three or more movement system actuators 6210. In various embodiments, one, two, three or more movement system actuators 6210 can be used to move the transducer 6000 and/or the reflective surface 6100 in linear, rotational, curved, or in any variety of directions.

Figure 78:
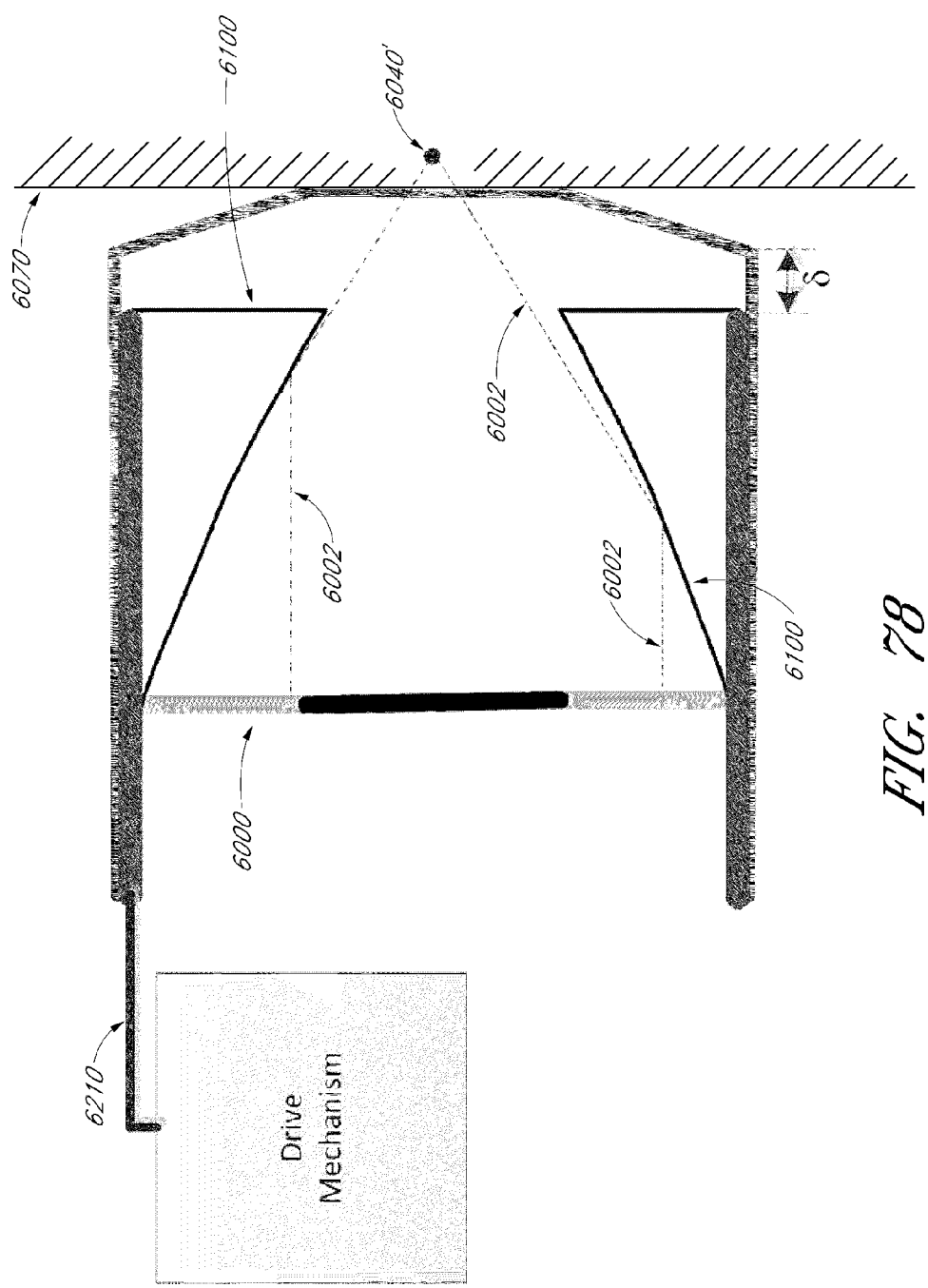
FIG. 78 illustrates a schematic cross-sectional side view of a movement system that moves a reflective surface in a cosmetic treatment system, in a first position, according to an embodiment.
Figure 79:
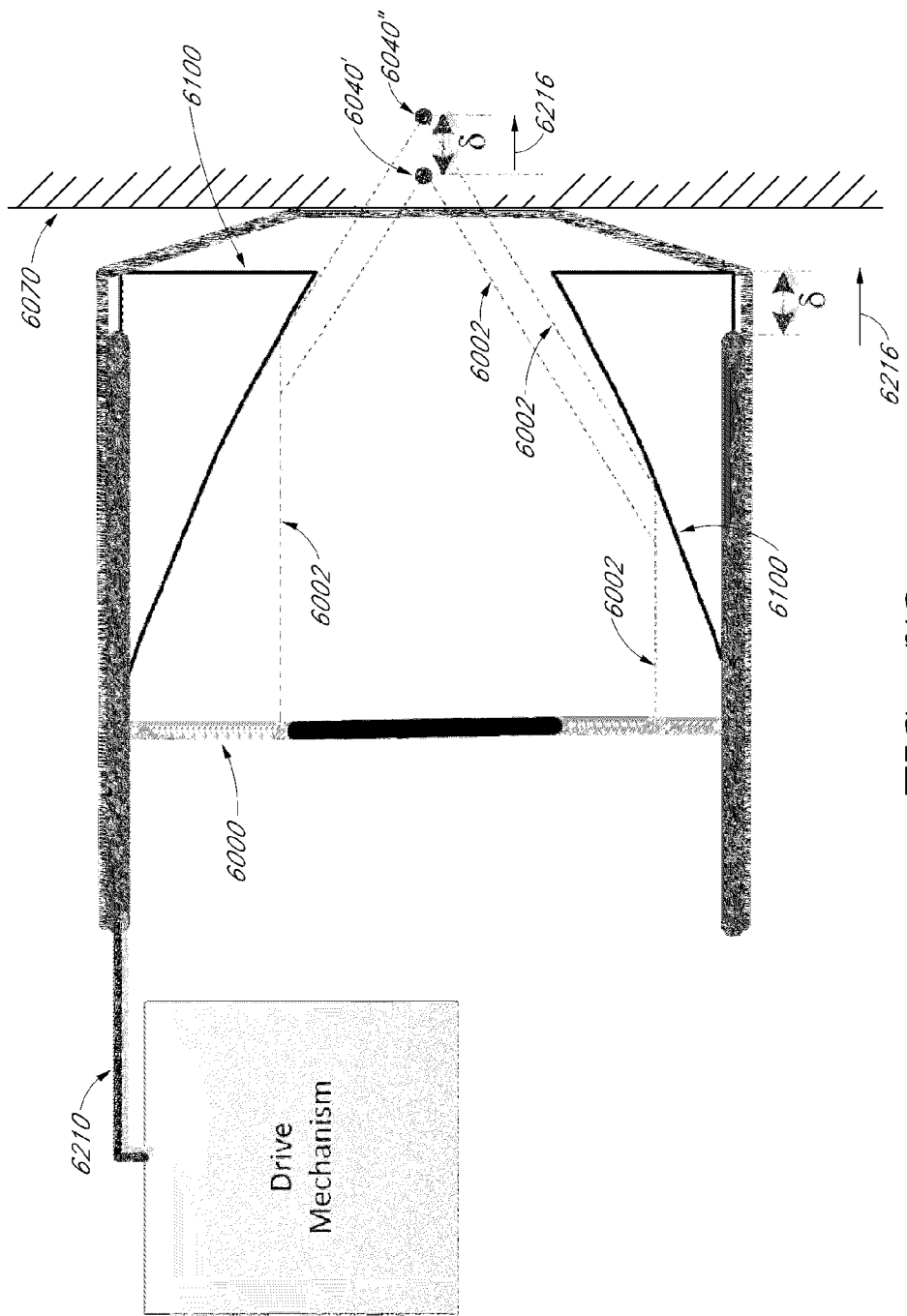
FIG. 79 illustrates a schematic cross-sectional side view of the movement system in a second position according to FIG. 78; that moves a reflective surface in a cosmetic treatment system according to an embodiment.

In one embodiment, a movement system 6200 is configured to automatically move a reflective surface 6100 in a controlled manner in one, two, three, four, five, or six directions or degrees of freedom. In various embodiments, a movement system 6200 can be any embodiment of a motion system or a movement mechanism. In one embodiment, a movement system 6200 is configured to move the reflective surface 6100 in an X, Y, and/or Z direction. In one embodiment, as shown in FIGS. 78-79, a movement system actuator 6210 moves the reflective surface 6100 in a direction 6216 up, down, closer or farther from the skin surface 6070 to adjust the treatment depth in tissue for placement of multiple cosmetic treatment zones 6040. In some embodiments, a transducer 6000 and a reflective surface 6100 produce multiple sets of cosmetic treatment zones 6040. In one embodiment, a transducer 6000 and a reflective surface 6100 produce a first set of cosmetic treatment zones 6040' from a first reflective surface position, and a second set of cosmetic treatment zones 6040" from a second reflective surface position. As shown in FIGS. 78-79, the movement system actuator 6210 moves the reflective surface 6100, and the relative position of cosmetic treatment zones 6040' to 6040" a distance δ. In one embodiment, multiple cosmetic treatment zones are produced simultaneously. In one embodiment, multiple cosmetic treatment zones are produced at different times.

Figure 80:
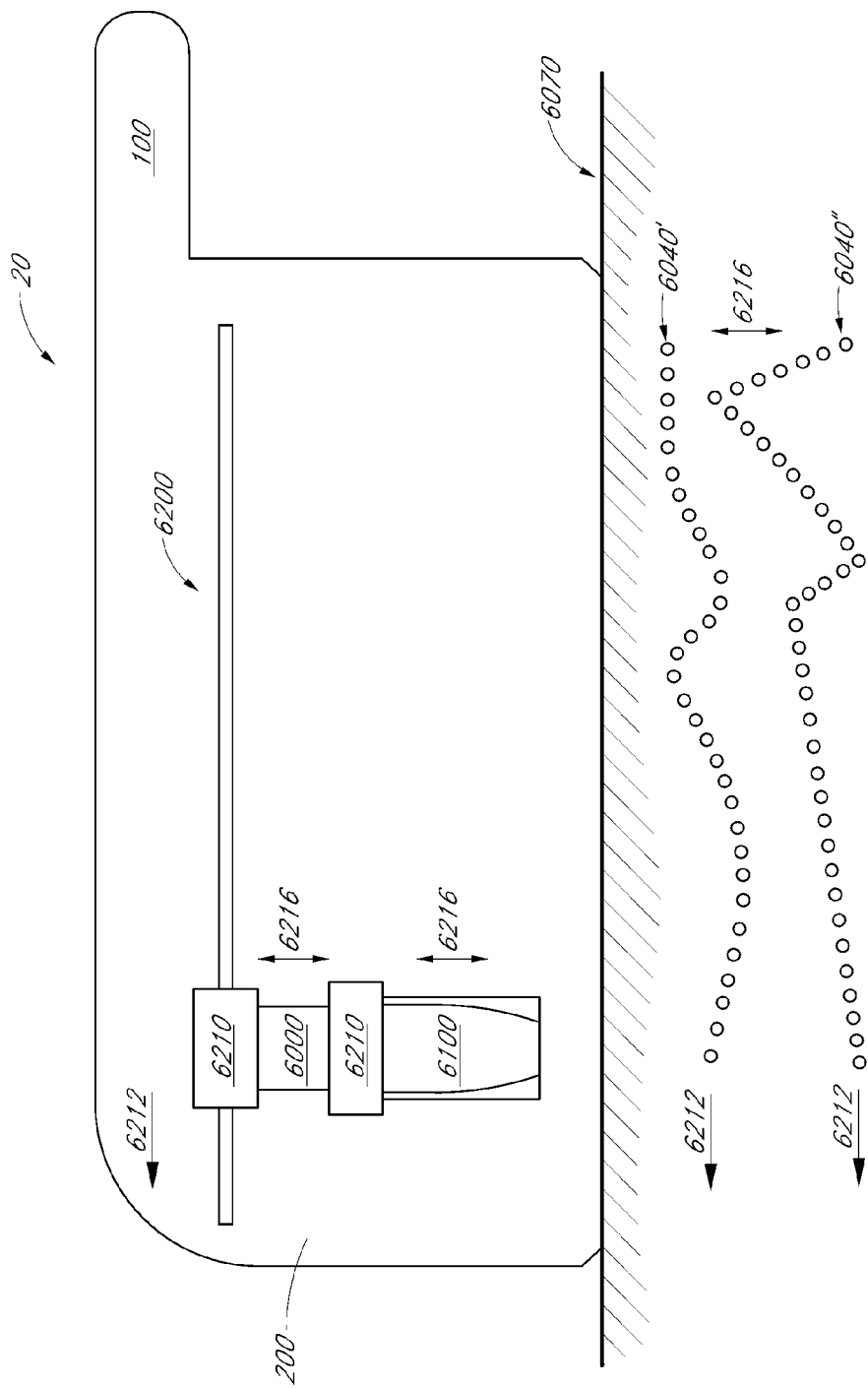
FIG. 80 illustrates a schematic cross-sectional side view of movement system that moves a transducer and/or a reflective surface in a cosmetic treatment system according to an embodiment.

In one embodiment, a movement system 6200 is configured to automatically move the transducer 6000 and/or the reflective surface 6100 in a controlled manner in one, two, three, four, five, or six directions or degrees of freedom. In various embodiments, a movement system 6200 can be any embodiment of a motion system or a movement mechanism. In one embodiment, a movement system 6200 is configured to move the transducer 6000 and/or the reflective surface 6100 in an X, Y, and/or Z direction. In one embodiment, a movement system actuator 6210 moves the transducer 6000 and/or the reflective surface 6100 in a direction 6212 parallel to the surface of the skin so multiple cosmetic treatment zones 6040 can be made along a particular focal depth. In one embodiment, a movement system actuator 6210 moves the transducer 6000 and/or the reflective surface 6100 in a direction 6214 perpendicular to direction 6212 and parallel to the surface of the skin so multiple cosmetic treatment zones 6040 can be made along a particular focal depth. In one embodiment, a movement system actuator 6210 moves the transducer 6000 and/or the reflective surface 6100 in a direction 6216 up, down, closer or farther from the skin surface to adjust the treatment depth in tissue for placement of multiple cosmetic treatment zones 6040. As shown in FIG. 80, various embodiments of a cosmetic treatment system 20 include a movement system 6200 that moves a transducer 6000 and/or a reflective surface 6100. In some embodiments, a transducer 6000 and a reflective surface 6100 simultaneously produce multiple sets of cosmetic treatment zones 6040. In one embodiment, a transducer 6000 and a reflective surface 6100 simultaneously produce a first set of cosmetic treatment zones 6040' and a second set of cosmetic treatment zones 6040". As shown in FIG. 80, in one embodiment, a movement system 6200 can use one or more movement system actuators 6210 to move the transducer 6000, the reflective surface 6100, and/or both the transducer 6000 and the reflective surface 6100 to create a plurality of cosmetic treatment zones 6040 that can be moved independently or in conjunction with each other.

The embodiments and the examples described herein are examples and not intended to be limiting in describing the full scope of the systems and methods described herein. Any method steps described herein need not be performed in the order described. Any headings used are for convenience only, and should not be used to limit the scope of embodiments. Several embodiments of the present invention may be described herein in terms of various components and processing steps. It should be appreciated that such components and steps may be realized by any number of hardware components configured to perform the specified functions. For example, some embodiments may employ various medical treatment devices, visual imaging and display devices, input terminals and the like, which may carry out a variety of functions under the control of one or more control systems or other control devices. The various operational steps, as well as the components for carrying out the operational steps, may be implemented in alternate ways depending upon the particular application or in consideration of any number of cost functions associated with the operation of the system, e.g., various of the steps may be deleted, modified, or combined with other steps. Further, it should be noted that while the method and system for ultrasound treatment with a variable depth transducer as described above is suitable for use by a medical and/or cosmetic practitioner proximate the patient, the system can also be accessed remotely, for example, the medical and/or cosmetic practitioner can view through a remote display having imaging information transmitted in various manners of communication, such as by satellite/wireless or by wired connections such as IP or digital cable networks and the like, and can direct a local practitioner as to the suitable placement for the transducer. Equivalent changes, modifications and variations of some embodiments, materials, compositions and methods can be made within the scope of the present invention, with substantially similar results.

The citation of references herein does not constitute admission that those references are prior art or have relevance to the patentability of the teachings disclosed herein. All references cited in the Description section of the specification are hereby incorporated by reference in their entirety for all purposes. In the event that one or more of the incorporated references, literature, and similar materials differs from or contradicts this application, including, but not limited to, defined terms, term usage, described techniques, or the like, this application controls.

Some embodiments and the examples described herein are examples and not intended to be limiting in describing the full scope of compositions and methods of these invention. Equivalent changes, modifications and variations of some embodiments, materials, compositions and methods can be made within the scope of the present invention, with substantially similar results.

What is claimed is:

1. An aesthetic imaging and treatment system with a reflective surface to produce multiple cosmetic treatment zones for use in cosmetic treatment, the system comprising:
   an ultrasonic probe comprising:
      a first switch operably controlling an ultrasonic imaging function for providing an ultrasonic imaging;

a second switch operably controlling an ultrasonic treatment function for providing an ultrasonic treatment; and a movement mechanism configured to direct ultrasonic treatment in at least one sequence of individual thermal cosmetic treatment zones; and a transducer module, wherein the transducer module is configured for both ultrasonic imaging and ultrasonic treatment, wherein the transducer module is configured for interchangeable coupling to the ultrasonic probe, wherein the transducer module comprises an ultrasound transducer and a reflective surface, wherein the ultrasound transducer comprises a flat portion and a concave portion;

wherein the ultrasound transducer is configured to apply ultrasonic therapy to tissue at least at a cosmetic treatment zone at a first depth with the concave portion, wherein the flat portion of the ultrasound transducer is configured to apply ultrasound energy to a reflection point on the reflective surface, wherein the reflective surface is configured to reflect energy from the reflection point to apply ultrasonic therapy to tissue at least at cosmetic treatment zone at a second depth, wherein the transducer module is configured to be operably coupled to at least one of the first switch, the second switch and the movement mechanism; and a control module, wherein the control module comprises a processor for controlling the transducer module, and a display configured to display an image from the ultrasonic imaging, wherein the display is also configured to display a graphical user interface, wherein the graphical user interface is connected the control module.

2. The aesthetic imaging and treatment system according to claim 1, wherein the first depth and the second depth are located at different depths below a single region of a skin surface to increase the overall volume of tissue treated below the skin surface, thereby providing an enhanced overall cosmetic result.

3. The aesthetic imaging and treatment system according to claim 1, wherein the reflective surface is a parabolic reflector.

4. The aesthetic imaging and treatment system according to claim 1, wherein the reflective surface comprises an absorber configured to reduce the amount of re-radiation of ultrasound energy that is transmitted into the reflective surface.

5. The aesthetic imaging and treatment system according to claim 1, wherein the reflective surface comprises a membrane and a reflective surface cavity, the reflective surface cavity comprising a coupling medium configured for transmission of the ultrasound energy between the transducer, reflective surface, and the membrane.

6. The aesthetic imaging and treatment system according to claim 1, wherein the transducer comprises a flat portion configured to direct energy to the reflective surface to focus ultrasound energy to the second depth in tissue.

7. The aesthetic imaging and treatment system according to claim 1, wherein the transducer comprises a concave portion configured to focus ultrasound energy to the first depth in tissue.

8. The aesthetic imaging and treatment system according to claim 1, wherein the transducer comprises a concave portion configured to direct energy to the reflective surface to focus ultrasound energy to the second depth in tissue.

9. The aesthetic imaging and treatment system according to claim 1, wherein the treatment function is at least one of a face lift, a brow lift, a chin lift, an eye treatment, a wrinkle reduction, a scar reduction, a burn treatment, a tattoo removal, a skin tightening, a vein removal, a vein reduction, a treatment on a sweat gland, a treatment of hyperhidrosis, a sun spot removal, a fat treatment, a vaginal rejuvenation, and an acne treatment.

10. An aesthetic imaging and treatment system comprising:

an ultrasonic probe comprising:

a first ultrasound transducer configured for ultrasonic treatment;

a second ultrasound transducer configured for ultrasonic treatment a first reflective surface inside the ultrasonic probe, a second reflective surface inside the ultrasonic probe, wherein the first reflective surface is acoustically coupled to the first ultrasound transducer;

wherein the second reflective surface is acoustically coupled to the second ultrasound transducer;

a movement mechanism inside the ultrasonic probe, wherein the movement mechanism is operable to move the first ultrasound transducer and the second ultrasound transducer within the ultrasonic probe and the first reflective surface and the second reflective surface within the ultrasonic probe; and a control module coupled to the ultrasonic probe and comprising a graphical user interface on a display, wherein the control module is configured for controlling the first ultrasound transducer, the second ultrasound transducer, and the movement mechanism;

wherein at least one of the first and the second ultrasound transducers is configured to apply ultrasonic therapy to tissue at least at a first cosmetic treatment zone at a first depth, wherein the at least one of the first and the second reflective surfaces is configured to reflect energy from at least one of the first the second ultrasound transducers to apply ultrasonic therapy to tissue at least at a second cosmetic treatment zone at a second depth, wherein the first depth is different from the second depth.

11. The aesthetic imaging and treatment system according to claim 10, wherein the at least one of the first and the second transducers is configured to provide an acoustic power in a range of between about 1 W to about 100 W and a frequency of about 1 MHz to about 10 MHz to thermally heat the tissue to cause coagulation.

12. The aesthetic imaging and treatment system according to claim 10, wherein the movement mechanism is configured to move the at least one of the first and the second transducers to change the first depth.

13. The aesthetic imaging and treatment system according to claim 10, wherein the movement mechanism is configured to move the at least one of the first and the second reflective surfaces to change the second depth.

14. The aesthetic imaging and treatment system according to claim 10, wherein the treatment function is at least one of a face lift, a brow lift, a chin lift, an eye treatment, a wrinkle reduction, a scar reduction, a burn treatment, a tattoo removal, a skin tightening, a vein removal, a vein reduction, a treatment on a sweat gland, a treatment of hyperhidrosis, a sun spot removal, a fat treatment, a vaginal rejuvenation, and an acne treatment.

15. A treatment system, the system comprising:
   a controlling device operably controlling an ultrasonic treatment function for providing an ultrasonic treatment; and
   a hand wand configured to direct ultrasonic treatment in a sequence of individual thermal cosmetic treatment zones, the hand wand comprising:
      a transducer comprising a flat portion and a concave portion;
      wherein the flat portion is configured to emit ultrasound energy to a reflection point on the reflective surface, and
      wherein the reflective surface is a parabolic reflective surface configured to direct ultrasound energy from the flat portion to the reflection point, and from the reflection point to a first cosmetic treatment zone at a first depth from a skin surface;
      wherein the concave portion is configured to direct a concave portion ultrasound energy to a second cosmetic treatment zone at a second depth from the skin surface without reflectin the concave portion ultrasound energy off the parabolic reflective surface.

16. The treatment system according to claim 15, wherein the first depth and the second depth are located at different depths below a single region of a skin surface to increase the overall volume of tissue treated below the skin surface, thereby providing an enhanced overall cosmetic result.

17. The treatment system according to claim 15, wherein the reflective surface comprises an absorber configured to reduce the amount of re-radiation of ultrasound energy that is transmitted into the reflective surface.

18. The treatment system according to claim 15, wherein the reflective surface comprises a membrane and a reflective surface cavity, the reflective surface cavity comprising a coupling medium configured for transmission of the ultrasound energy between the transducer, reflective surface, and the membrane.

19. The treatment system according to claim 15, wherein the transducer comprises a flat portion configured to direct energy to the reflective surface.

20. The treatment system according to claim 15, wherein the transducer comprises a concave portion configured to focus ultrasound energy to the first depth in tissue.

* * * * *